US012442045B2

(12) United States Patent
Williams

(10) Patent No.: US 12,442,045 B2
(45) Date of Patent: Oct. 14, 2025

(54) METHODS OF DETECTING SPATIAL HETEROGENEITY OF A BIOLOGICAL SAMPLE

(71) Applicant: 10x Genomics, Inc., Pleasanton, CA (US)

(72) Inventor: Stephen R. Williams, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 18/640,645

(22) Filed: Apr. 19, 2024

(65) Prior Publication Data

US 2024/0279747 A1 Aug. 22, 2024

Related U.S. Application Data

(60) Division of application No. 17/538,406, filed on Nov. 30, 2021, now Pat. No. 11,965,213, which is a continuation of application No. PCT/US2020/035337, filed on May 29, 2020.

(60) Provisional application No. 62/854,959, filed on May 30, 2019.

(51) Int. Cl.
*C12Q 1/6886* (2018.01)
*C12Q 1/6874* (2018.01)

(52) U.S. Cl.
CPC ......... *C12Q 1/6886* (2013.01); *C12Q 1/6874* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,514,388 | A | 4/1985 | Psaledakis |
| 4,683,195 | A | 7/1987 | Mullis |
| 4,683,202 | A | 7/1987 | Mullis |
| 4,800,159 | A | 1/1989 | Mullis |
| 4,883,867 | A | 11/1989 | Lee |
| 4,965,188 | A | 10/1990 | Mullis |
| 4,968,601 | A | 11/1990 | Jacobson et al. |
| 4,988,617 | A | 1/1991 | Landegren et al. |
| 5,002,882 | A | 3/1991 | Lunnen |
| 5,130,238 | A | 7/1992 | Malek |
| 5,308,751 | A | 5/1994 | Ohkawa |
| 5,321,130 | A | 6/1994 | Yue |
| 5,410,030 | A | 4/1995 | Yue |
| 5,436,134 | A | 7/1995 | Haugland |
| 5,455,166 | A | 10/1995 | Walker |
| 5,472,881 | A | 12/1995 | Beebe et al. |
| 5,494,810 | A | 2/1996 | Barany et al. |
| 5,503,980 | A | 4/1996 | Cantor |
| 5,512,439 | A | 4/1996 | Hornes |
| 5,512,462 | A | 4/1996 | Cheng |
| 5,582,977 | A | 12/1996 | Yue |
| 5,599,675 | A | 2/1997 | Brenner |
| 5,610,287 | A | 3/1997 | Nikiforov et al. |
| 5,641,658 | A | 6/1997 | Adams |
| 5,648,245 | A | 7/1997 | Fire et al. |
| 5,658,751 | A | 8/1997 | Yue |
| 5,695,940 | A | 12/1997 | Drmanac et al. |
| 5,750,341 | A | 5/1998 | Macevicz |
| 5,763,175 | A | 6/1998 | Brenner |
| 5,807,522 | A | 9/1998 | Brown et al. |
| 5,830,711 | A | 11/1998 | Barany et al. |
| 5,837,832 | A | 11/1998 | Chee et al. |
| 5,837,860 | A | 11/1998 | Anderson et al. |
| 5,854,033 | A | 12/1998 | Lizardi |
| 5,863,753 | A | 1/1999 | Haugland |
| 5,871,921 | A | 2/1999 | Landegren et al. |
| 5,912,148 | A | 6/1999 | Eggerding |
| 5,919,626 | A | 7/1999 | Shi et al. |
| 5,925,545 | A | 7/1999 | Reznikoff et al. |
| 5,928,906 | A | 7/1999 | Koester et al. |
| 5,958,775 | A | 9/1999 | Wickstrrom |
| 5,962,271 | A | 10/1999 | Chenchik et al. |
| 5,962,272 | A | 10/1999 | Chenchik et al. |
| 5,965,443 | A | 10/1999 | Reznikoff et al. |
| 6,013,440 | A | 1/2000 | Lipshutz |
| 6,027,889 | A | 2/2000 | Barany et al. |
| 6,054,274 | A | 4/2000 | Sampson et al. |
| 6,060,240 | A | 5/2000 | Kamb et al. |
| 6,130,073 | A | 10/2000 | Eggerding |
| 6,143,496 | A | 11/2000 | Brown |
| 6,153,389 | A | 11/2000 | Haarer |
| 6,159,736 | A | 12/2000 | Reznikoff et al. |
| 6,165,714 | A | 12/2000 | Lane et al. |
| 6,172,218 | B1 | 1/2001 | Brenner |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Glasgow et al.Int J Mol Sci. 20, 2131, p. 1-6 and Supplemental Table S11 (Year: 2019).*
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).

(Continued)

*Primary Examiner* — Carla J Myers
(74) *Attorney, Agent, or Firm* — Fish & Richardson P.C.

(57) ABSTRACT

Provided herein are methods of characterizing tumors or a region of interest in a biological sample.

20 Claims, 36 Drawing Sheets

(56) References Cited

U.S. PATENT DOCUMENTS 6,210,891 B1 4/2001 Nyren
6,210,894 B1 4/2001 Brennan
6,214,587 B1 4/2001 Dattagupta
6,251,639 B1 6/2001 Kurn
6,258,568 B1 7/2001 Nyren
6,265,552 B1 7/2001 Schatz
6,266,459 B1 7/2001 Walt
6,268,148 B1 7/2001 Barany et al.
6,274,320 B1 8/2001 Rothberg
6,291,180 B1 9/2001 Chu
6,291,187 B1 9/2001 Kingsmore et al.
6,300,063 B1 10/2001 Lipshutz et al.
6,306,597 B1 10/2001 Macevicz
6,309,824 B1 10/2001 Drmanac
6,323,009 B1 11/2001 Lasken et al.
6,344,316 B1 2/2002 Lockhart
6,344,329 B1 2/2002 Lizardi et al.
6,355,431 B1 3/2002 Chee
6,368,801 B1 4/2002 Faruqi
6,401,267 B1 6/2002 Drmanac
6,404,907 B1 6/2002 Gilchrist
6,432,360 B1 8/2002 Church et al.
6,503,713 B1 1/2003 Rana
6,506,561 B1 1/2003 Cheval et al.
6,534,266 B1 3/2003 Singer
6,544,732 B1 4/2003 Chee
6,573,043 B1 6/2003 Cohen et al.
6,579,695 B1 6/2003 Lambalot
6,620,584 B1 9/2003 Chee
6,632,641 B1 10/2003 Brennan
6,699,710 B1 3/2004 Kononen
6,737,236 B1 5/2004 Pieken et al.
6,770,441 B2 8/2004 Dickinson
6,773,886 B2 8/2004 Kaufman
6,787,308 B2 9/2004 Balasubramanian
6,797,470 B2 9/2004 Barany et al.
6,800,453 B2 10/2004 Labaer
6,812,005 B2 11/2004 Fan et al.
6,828,100 B1 12/2004 Ronaghi
6,833,246 B2 12/2004 Balasubramanian
6,852,487 B1 2/2005 Barany et al.
6,859,570 B2 2/2005 Walt
6,864,052 B1 3/2005 Drmanac
6,867,028 B2 3/2005 Janulaitis
6,872,816 B1 3/2005 Hall et al.
6,875,572 B2 4/2005 Prudent et al.
6,878,515 B1 4/2005 Landegren
6,890,741 B2 5/2005 Fan et al.
6,897,023 B2 5/2005 Fu
6,913,881 B1 7/2005 Aizenstein et al.
6,942,968 B1 9/2005 Dickinson et al.
6,969,488 B2 11/2005 Bridgham
6,969,589 B2 11/2005 Patil
7,001,792 B2 2/2006 Sauer et al.
7,011,944 B2 3/2006 Prudent et al.
7,057,026 B2 6/2006 Barnes
7,083,980 B2 8/2006 Reznikoff et al.
7,115,400 B1 10/2006 Adessi
7,118,883 B2 10/2006 Inoue
7,166,431 B2 1/2007 Chee et al.
7,192,735 B2 3/2007 Lambalot
7,211,414 B2 5/2007 Hardin
7,255,994 B2 8/2007 Lao
7,258,976 B2 8/2007 Mitsuhashi
7,259,258 B2 8/2007 Kozlov et al.
7,264,929 B2 9/2007 Rothberg
7,282,328 B2 10/2007 Kong et al.
7,297,518 B2 11/2007 Quake
7,329,492 B2 2/2008 Hardin
7,358,047 B2 4/2008 Hafner et al.
7,361,488 B2 4/2008 Fan et al.
7,375,234 B2 5/2008 Sharpless et al.
7,378,242 B2 5/2008 Hurt
7,393,665 B2 7/2008 Brenner
7,405,281 B2 7/2008 Xu
7,407,757 B2 8/2008 Brenner
7,427,678 B2 9/2008 Pieken et al.
7,473,767 B2 1/2009 Dimitrov
7,499,806 B2 3/2009 Kermani et al.
7,537,897 B2 5/2009 Brenner
7,563,576 B2 7/2009 Chee
7,579,153 B2 8/2009 Brenner
7,582,420 B2 9/2009 Oliphant et al.
7,601,498 B2 10/2009 Mao
7,608,434 B2 10/2009 Reznikoff et al.
7,611,869 B2 11/2009 Fan
7,635,566 B2 12/2009 Brenner
7,666,612 B2 2/2010 Johnsson
7,674,752 B2 3/2010 He
7,700,286 B2 4/2010 Stroun et al.
7,709,198 B2 5/2010 Luo et al.
7,776,547 B2 8/2010 Roth
7,776,567 B2 8/2010 Mao
7,785,869 B2 8/2010 Belgrader et al.
7,803,943 B2 9/2010 Mao
7,888,009 B2 2/2011 Barany et al.
7,892,747 B2 2/2011 Barany et al.
7,910,304 B2 3/2011 Drmanac
7,914,981 B2 3/2011 Barany et al.
7,955,794 B2 6/2011 Shen et al.
7,960,119 B2 6/2011 Chee
7,985,565 B2 7/2011 Mayer et al.
8,003,354 B2 8/2011 Shen et al.
8,076,063 B2 12/2011 Fan
8,092,784 B2 1/2012 Mao
8,148,068 B2 4/2012 Brenner
8,206,917 B2 6/2012 Chee
8,268,554 B2 9/2012 Schallmeiner
8,288,103 B2 10/2012 Oliphant
8,288,122 B2 10/2012 O'Leary et al.
8,337,851 B2 12/2012 Aukerman
8,383,338 B2 2/2013 Kitzman
8,431,691 B2 4/2013 McKernan et al.
8,460,865 B2 6/2013 Chee
8,481,257 B2 7/2013 Van Eijk
8,481,258 B2 7/2013 Church et al.
8,481,292 B2 7/2013 Casbon
8,481,698 B2 7/2013 Lieberman et al.
8,507,204 B2 8/2013 Pierce et al.
8,519,115 B2 8/2013 Webster et al.
8,551,710 B2 10/2013 Bernitz et al.
8,568,979 B2 10/2013 Stuelpnagel et al.
RE44,596 E 11/2013 Stroun et al.
8,586,310 B2 11/2013 Mitra
8,597,891 B2 12/2013 Barany et al.
8,603,743 B2 12/2013 Liu et al.
8,604,182 B2 12/2013 Luo et al.
8,614,073 B2 12/2013 Van Eijk
8,624,016 B2 1/2014 Barany et al.
8,685,889 B2 4/2014 Van Eijk
8,741,564 B2 6/2014 Seligmann
8,741,606 B2 6/2014 Casbon
8,748,103 B2 6/2014 Faham et al.
8,771,950 B2 7/2014 Church et al.
8,785,353 B2 7/2014 Van Eijk
8,790,873 B2 7/2014 Namsaraev et al.
8,809,238 B2 8/2014 Livak et al.
8,815,512 B2 8/2014 Van Eijk
8,835,358 B2 9/2014 Fodor
8,865,410 B2 10/2014 Shendure
8,906,626 B2 12/2014 Oliphant et al.
8,911,945 B2 12/2014 Van Eijk
8,936,912 B2 1/2015 Mitra
8,951,726 B2 2/2015 Luo et al.
8,951,728 B2 2/2015 Rasmussen
8,986,926 B2 3/2015 Ferree et al.
9,005,891 B2 4/2015 Sinicropi et al.
9,005,935 B2 4/2015 Belyaev
9,023,768 B2 5/2015 Van Eijk
9,062,348 B1 6/2015 Van Eijk
9,080,210 B2 7/2015 Van Eijk
9,121,069 B2 9/2015 Lo
9,194,001 B2 11/2015 Brenner
9,201,063 B2 12/2015 Sood et al.

(56) References Cited

U.S. PATENT DOCUMENTS 9,217,176 B2 12/2015 Faham
9,273,349 B2 3/2016 Nguyen et al.
9,290,808 B2 3/2016 Fodor
9,290,809 B2 3/2016 Fodor
9,328,383 B2 5/2016 Van Eijk
9,334,536 B2 5/2016 Van Eijk
9,340,830 B2 5/2016 Lipson
9,371,563 B2 6/2016 Geiss et al.
9,371,598 B2 6/2016 Chee
9,376,716 B2 6/2016 Van Eijk
9,376,717 B2 6/2016 Gao et al.
9,376,719 B2 6/2016 Eijk
9,416,409 B2 8/2016 Hayden
9,447,459 B2 9/2016 Van Eijk
9,453,256 B2 9/2016 Van Eijk
9,493,820 B2 11/2016 Van Eijk
9,506,061 B2 11/2016 Brown et al.
9,512,422 B2 12/2016 Barnard et al.
9,512,487 B2 12/2016 Faham et al.
9,574,230 B2 2/2017 Van Eijk
9,593,365 B2 3/2017 Frisen et al.
9,598,728 B2 3/2017 Barany et al.
9,624,538 B2 4/2017 Church et al.
9,644,204 B2 5/2017 Hindson et al.
9,657,335 B2 5/2017 Van Eijk
9,670,542 B2 6/2017 Eijk
9,694,361 B2 7/2017 Bharadwaj
9,702,004 B2 7/2017 Van Eijk
9,714,446 B2 7/2017 Webster et al.
9,714,937 B2 7/2017 Dunaway
9,727,810 B2 8/2017 Fodor et al.
9,745,627 B2 8/2017 Van Eijk
9,777,324 B2 10/2017 Van Eijk
9,783,841 B2 10/2017 Nolan et al.
9,790,476 B2 10/2017 Gloeckner et al.
9,816,134 B2 11/2017 Namsaraev
9,834,814 B2 12/2017 Peter et al.
9,850,536 B2 12/2017 Oliphant et al.
9,856,521 B2 1/2018 Stevens et al.
9,868,979 B2 1/2018 Chee et al.
9,879,313 B2 1/2018 Chee et al.
9,896,721 B2 2/2018 Van Eijk
9,898,576 B2 2/2018 Van Eijk
9,898,577 B2 2/2018 Van Eijk
9,902,991 B2 2/2018 Sinicropi et al.
9,909,167 B2 3/2018 Samusik et al.
9,938,566 B2 4/2018 Shepard et al.
9,957,550 B2 5/2018 Yeakley et al.
10,002,316 B2 6/2018 Fodor et al.
10,023,907 B2 7/2018 Van Eijk
10,030,261 B2 7/2018 Frisen et al.
10,035,992 B2 7/2018 Gloeckner et al.
10,041,949 B2 8/2018 Bendall et al.
10,049,770 B2 8/2018 Madabhushi et al.
10,059,989 B2 8/2018 Giresi et al.
10,059,990 B2 8/2018 Boyden et al.
10,078,895 B2 9/2018 Madabhushi et al.
10,095,832 B2 10/2018 Van Eijk
10,138,509 B2 11/2018 Church et al.
10,144,966 B2 12/2018 Cantor
10,179,932 B2 1/2019 Church et al.
10,196,691 B2 2/2019 Harkin et al.
10,221,461 B2 3/2019 Robins et al.
10,227,639 B2 3/2019 Levner et al.
10,246,752 B2 4/2019 Faham et al.
10,273,541 B2 4/2019 Hindson et al.
10,308,982 B2 6/2019 Chee
10,357,771 B2 7/2019 Bharadwaj
10,370,698 B2 8/2019 Nolan et al.
10,415,080 B2 9/2019 Dunaway et al.
10,465,235 B2 11/2019 Gullberg et al.
10,472,669 B2 11/2019 Chee
10,480,022 B2 11/2019 Chee
10,480,029 B2 11/2019 Bent et al.
10,494,667 B2 12/2019 Chee
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,544,403 B2 1/2020 Gloeckner et al.
10,550,429 B2 2/2020 Harada et al.
10,590,244 B2 3/2020 Delaney et al.
10,633,648 B2 4/2020 Seelig et al.
10,640,816 B2 5/2020 Beechem et al.
10,640,826 B2 5/2020 Church et al.
10,662,468 B2 5/2020 Chee
10,669,569 B2 6/2020 Gullberg et al.
10,724,078 B2 7/2020 Van Driel et al.
10,725,027 B2 7/2020 Bell
10,774,372 B2 9/2020 Chee et al.
10,774,374 B2 9/2020 Frisen et al.
10,787,701 B2 9/2020 Chee
10,815,519 B2 10/2020 Husain et al.
10,829,803 B2 11/2020 Terbrueggen et al.
10,844,426 B2 11/2020 Daugharthy et al.
10,858,698 B2 12/2020 Church et al.
10,858,702 B2 12/2020 Lucero et al.
10,913,975 B2 2/2021 So et al.
10,914,730 B2 2/2021 Chee et al.
10,927,403 B2 2/2021 Chee et al.
10,961,566 B2 3/2021 Chee
11,001,879 B1 5/2021 Chee
11,008,607 B2 5/2021 Chee
11,046,996 B1 6/2021 Chee et al.
11,067,567 B2 7/2021 Chee
11,104,936 B2 8/2021 Zhang et al.
11,118,216 B2 9/2021 Koshinsky et al.
11,156,603 B2 10/2021 Chee
11,162,132 B2 11/2021 Frisen et al.
11,208,684 B2 12/2021 Chee
11,214,796 B2 1/2022 Shirai et al.
11,286,515 B2 3/2022 Chee et al.
11,293,917 B2 4/2022 Chee
11,299,774 B2 4/2022 Frisen et al.
11,313,856 B2 4/2022 Chee
11,332,790 B2 5/2022 Chell et al.
11,352,659 B2 6/2022 Frisen et al.
11,352,667 B2 6/2022 Hauling et al.
11,359,228 B2 6/2022 Chee et al.
11,365,442 B2 6/2022 Chee
11,371,086 B2 6/2022 Chee
11,384,386 B2 7/2022 Chee
11,390,912 B2 7/2022 Frisen et al.
11,401,545 B2 8/2022 Chee
11,407,992 B2 8/2022 Dadhwal
11,408,029 B2 8/2022 Katiraee et al.
11,434,524 B2 9/2022 Ramachandran Iyer et al.
11,459,607 B1 10/2022 Terry et al.
11,479,809 B2 10/2022 Frisen et al.
11,479,810 B1 10/2022 Chee
11,492,612 B1 11/2022 Dadhwal
11,501,440 B2 11/2022 Weisenfeld et al.
11,505,828 B2 11/2022 Chell et al.
11,512,308 B2 11/2022 Gallant et al.
11,519,022 B2 12/2022 Chee
11,519,033 B2 12/2022 Schnall-Levin et al.
11,530,438 B2 12/2022 Persson et al.
11,535,887 B2 12/2022 Gallant et al.
11,542,543 B2 1/2023 Chee
11,549,138 B2 1/2023 Chee
11,560,587 B2 1/2023 Chee
11,560,592 B2 1/2023 Chew et al.
11,560,593 B2 1/2023 Chell et al.
11,592,447 B2 2/2023 Uytingco et al.
11,608,498 B2 3/2023 Gallant et al.
11,608,520 B2 3/2023 Galonska et al.
11,613,773 B2 3/2023 Frisen et al.
11,618,897 B2 4/2023 Kim et al.
11,618,918 B2 4/2023 Chee et al.
11,624,063 B2 4/2023 Dadhwal
11,624,086 B2 4/2023 Uytingco et al.
11,634,756 B2 4/2023 Chee
11,649,485 B2 5/2023 Yin et al.
11,661,626 B2 5/2023 Katiraee et al.

(56) References Cited

U.S. PATENT DOCUMENTS 11,680,260 B2 6/2023 Kim et al.
11,692,218 B2 7/2023 Engblom et al.
11,702,693 B2 7/2023 Bharadwaj
11,702,698 B2 7/2023 Stoeckius
11,713,480 B2 8/2023 Lee
11,732,292 B2 8/2023 Chee
11,732,299 B2 8/2023 Ramachandran Iyer
11,732,300 B2 8/2023 Bava
11,733,238 B2 8/2023 Chee
11,739,372 B2 8/2023 Frisen et al.
11,739,381 B2 8/2023 Chew et al.
11,753,673 B2 9/2023 Chew et al.
11,753,674 B2 9/2023 Chee et al.
11,753,675 B2 9/2023 Ramachandran Iyer
11,761,030 B2 9/2023 Chee
11,761,038 B1 9/2023 Stoeckius
11,767,550 B2 9/2023 Chee
11,768,175 B1 9/2023 Kim et al.
11,773,433 B2 10/2023 Gallant et al.
11,781,130 B2 10/2023 Dadhwal
11,788,122 B2 10/2023 Frisen et al.
11,795,498 B2 10/2023 Frisen et al.
11,795,507 B2 10/2023 Chell et al.
11,808,769 B2 11/2023 Uytingco et al.
11,821,024 B2 11/2023 Chee et al.
11,821,035 B1 11/2023 Bent et al.
11,827,935 B1 11/2023 Ramachandran Iyer et al.
11,835,462 B2 12/2023 Bava
11,840,687 B2 12/2023 Gallant et al.
11,840,724 B2 12/2023 Chew et al.
11,845,979 B2 12/2023 Engblom et al.
11,859,178 B2 1/2024 Gallant et al.
11,866,767 B2 1/2024 Uytingco et al.
11,866,770 B2 1/2024 Chee
11,873,482 B2 1/2024 Kim et al.
11,891,654 B2 2/2024 Alvarado Martinez et al.
11,898,205 B2 2/2024 Bava
11,926,822 B1 3/2024 Gohil et al.
11,926,863 B1 3/2024 Boutet
11,926,867 B2 3/2024 Yin et al.
11,933,957 B1 3/2024 Tentori et al.
11,952,627 B2 4/2024 Stoeckius
11,959,076 B2 4/2024 Kim et al.
11,959,130 B2 4/2024 Galonska et al.
11,965,213 B2 4/2024 Williams
11,970,739 B2 4/2024 Chew et al.
11,981,958 B1 5/2024 Galonska
11,981,960 B1 5/2024 Lin et al.
11,981,965 B2 5/2024 Chell et al.
RE50,065 E 7/2024 Frisen et al.
12,024,741 B2 7/2024 Tentori et al.
12,031,177 B1 7/2024 Tentori et al.
12,060,604 B2 8/2024 Katiraee et al.
12,071,655 B2 8/2024 Sukovich et al.
12,076,701 B2 9/2024 Bava
12,098,417 B2 9/2024 Engblom et al.
12,098,985 B2 9/2024 Cox et al.
12,110,541 B2 10/2024 Bava
12,117,439 B2 10/2024 Delaney et al.
12,128,403 B2 10/2024 Kim et al.
12,129,516 B2 10/2024 Tentori et al.
12,157,124 B2 12/2024 Cox et al.
12,180,543 B2 12/2024 Uytingco et al.
12,195,790 B2 1/2025 Sukovich et al.
12,203,134 B2 1/2025 Nagendran et al.
12,209,280 B1 1/2025 Mignardi et al.
12,223,751 B2 2/2025 Li et al.
12,228,544 B2 2/2025 Kim et al.
12,234,505 B2 2/2025 Chee
12,241,060 B2 3/2025 Kim et al.
12,241,890 B2 3/2025 Delaney et al.
12,249,085 B2 3/2025 Tentori et al.
12,265,079 B1 4/2025 Bent
12,270,077 B2 4/2025 Schnall-Levin et al.
12,275,988 B2 4/2025 Galonska et al.
12,281,357 B1 4/2025 Tentori et al.
12,286,673 B2 4/2025 Bava
12,287,264 B2 4/2025 Cox et al.
12,297,486 B2 5/2025 Patterson et al.
12,297,487 B2 5/2025 Chee
12,297,488 B2 5/2025 Chee
2001/0055764 A1 12/2001 Empendocles et al.
2002/0006477 A1 1/2002 Shishido et al.
2002/0040275 A1 4/2002 Cravatt
2002/0051986 A1 5/2002 Baez et al.
2002/0055100 A1 5/2002 Kawashima
2002/0058250 A1 5/2002 Firth
2002/0086441 A1 7/2002 Baranov et al.
2002/0132246 A1 9/2002 Kallioniemi et al.
2002/0164611 A1 11/2002 Bamdad
2003/0017451 A1 1/2003 Wang et al.
2003/0022207 A1 1/2003 Balasubramanian
2003/0064398 A1 4/2003 Barnes
2003/0092624 A1 5/2003 Wang et al.
2003/0134279 A1 7/2003 Isola et al.
2003/0138879 A1 7/2003 Lambalot
2003/0148335 A1 8/2003 Shen et al.
2003/0162216 A1 8/2003 Gold
2003/0165948 A1 9/2003 Alsmadi et al.
2003/0170637 A1 9/2003 Pirrung et al.
2003/0211489 A1 11/2003 Shen et al.
2003/0224419 A1 12/2003 Corcoran
2003/0232348 A1 12/2003 Jones et al.
2003/0232382 A1 12/2003 Brennan
2003/0235854 A1 12/2003 Chan et al.
2004/0002090 A1 1/2004 Mayer et al.
2004/0019005 A1 1/2004 Van Ness
2004/0033499 A1 2/2004 Ilsley et al.
2004/0067492 A1 4/2004 Peng et al.
2004/0067493 A1 4/2004 Matsuzaki
2004/0082059 A1 4/2004 Webb et al.
2004/0096853 A1 5/2004 Mayer
2004/0106110 A1 6/2004 Balasubramanian
2004/0235103 A1 11/2004 Reznikoff et al.
2004/0241660 A1 12/2004 Wojtowicz et al.
2004/0248325 A1 12/2004 Bukusoglu et al.
2004/0259105 A1 12/2004 Fan et al.
2005/0003431 A1 1/2005 Wucherpfennig
2005/0014203 A1 1/2005 Darfler et al.
2005/0019776 A1 1/2005 Callow et al.
2005/0026188 A1 2/2005 Van Kessel
2005/0037362 A1 2/2005 Remacle et al.
2005/0037393 A1 2/2005 Gunderson et al.
2005/0048535 A1* 3/2005 Santin ..................... A61P 35/00
702/20
2005/0048580 A1 3/2005 Labaer
2005/0064460 A1 3/2005 Holliger et al.
2005/0079518 A1* 4/2005 Baker .................. C12Q 1/6886
435/6.14
2005/0095627 A1 5/2005 Kolman et al.
2005/0100900 A1 5/2005 Kawashima et al.
2005/0130173 A1 6/2005 Leamon et al.
2005/0136414 A1 6/2005 Gunderson et al.
2005/0164292 A1 7/2005 Farooqui
2005/0170373 A1 8/2005 Monforte
2005/0191656 A1 9/2005 Drmanac et al.
2005/0191698 A1 9/2005 Chee et al.
2005/0202433 A1 9/2005 Van Beuningen
2005/0227271 A1 10/2005 Kwon
2005/0239119 A1 10/2005 Tsukada et al.
2005/0260653 A1 11/2005 LaBaer
2005/0266417 A1 12/2005 Barany et al.
2006/0041385 A1 2/2006 Bauer et al.
2006/0046313 A1 3/2006 Roth
2006/0084078 A1 4/2006 Zhao
2006/0105352 A1 5/2006 Qiao et al.
2006/0110739 A1 5/2006 Heyduk
2006/0154286 A1 7/2006 Kong et al.
2006/0188875 A1 8/2006 Cox et al.
2006/0188901 A1 8/2006 Barnes et al.
2006/0199183 A1 9/2006 Valat et al.
2006/0211001 A1 9/2006 Yu et al.
2006/0216775 A1 9/2006 Burkart et al.
2006/0228758 A1 10/2006 Muchhal et al.

(56) References Cited

U.S. PATENT DOCUMENTS

2006/0240439 A1 10/2006 Smith et al.
2006/0263789 A1 11/2006 Kincaid
2006/0275782 A1 12/2006 Gunderson et al.
2006/0281109 A1 12/2006 Barr Ost et al.
2007/0020640 A1 1/2007 McCloskey et al.
2007/0020669 A1 1/2007 Ericsson
2007/0026430 A1 2/2007 Andersen et al.
2007/0054288 A1 3/2007 Su et al.
2007/0087360 A1 4/2007 Boyd
2007/0099208 A1 5/2007 Drmanac et al.
2007/0128624 A1 6/2007 Gormley et al.
2007/0128656 A1 6/2007 Agrawal
2007/0134723 A1 6/2007 Kozlov et al.
2007/0161020 A1 7/2007 Luo et al.
2007/0161029 A1 7/2007 Li et al.
2007/0166705 A1 7/2007 Milton et al.
2007/0172873 A1 7/2007 Brenner et al.
2007/0178503 A1 8/2007 Jiang
2007/0207482 A1 9/2007 Church et al.
2007/0254305 A1 11/2007 Paik et al.
2007/0269805 A1 11/2007 Hogers
2008/0003586 A1 1/2008 Hyde et al.
2008/0009420 A1 1/2008 Schroth et al.
2008/0108082 A1 5/2008 Rank et al.
2008/0108804 A1 5/2008 Hayashizaki et al.
2008/0132429 A1 6/2008 Perov et al.
2008/0153086 A1 6/2008 Wong
2008/0160580 A1 7/2008 Adessi et al.
2008/0220434 A1 9/2008 Thomas
2008/0261204 A1 10/2008 Lexow
2008/0280773 A1 11/2008 Fedurco et al.
2008/0286795 A1 11/2008 Kawashima et al.
2008/0293046 A1 11/2008 Allawi et al.
2009/0005252 A1 1/2009 Drmanac et al.
2009/0006002 A1 1/2009 Honisch et al.
2009/0018024 A1 1/2009 Church et al.
2009/0026082 A1 1/2009 Rothberg et al.
2009/0036323 A1 2/2009 van Eijk et al.
2009/0082212 A1 3/2009 Williams
2009/0099041 A1 4/2009 Church et al.
2009/0105959 A1 4/2009 Braverman et al.
2009/0117573 A1 5/2009 Fu et al.
2009/0127589 A1 5/2009 Rothberg et al.
2009/0155781 A1 6/2009 Drmanac et al.
2009/0170713 A1 7/2009 van Eijk et al.
2009/0202998 A1 8/2009 Schlumpberger et al.
2009/0215633 A1 8/2009 van Eijk et al.
2009/0233802 A1 9/2009 Bignell et al.
2009/0253581 A1 10/2009 van Eijk et al.
2009/0270273 A1 10/2009 Burns et al.
2009/0283407 A1 11/2009 Shah et al.
2009/0286249 A1 11/2009 Becker et al.
2009/0291854 A1 11/2009 Weisinger-Mayr et al.
2009/0312193 A1 12/2009 Kim et al.
2010/0035249 A1 2/2010 Hayashizaki et al.
2010/0069263 A1 3/2010 Shendure et al.
2010/0105052 A1 4/2010 Drmanac et al.
2010/0105112 A1 4/2010 Heltze et al.
2010/0120097 A1 5/2010 Matz et al.
2010/0120098 A1 5/2010 Grunenwald et al.
2010/0129874 A1 5/2010 Mitra et al.
2010/0137143 A1 6/2010 Rothberg et al.
2010/0145037 A1 6/2010 Brive et al.
2010/0173384 A1 7/2010 Johnsson et al.
2010/0184618 A1 7/2010 Namsaraev et al.
2010/0210475 A1 8/2010 Lee et al.
2010/0216137 A1* 8/2010 Bankaitis-Davis .. C12Q 1/6886 435/6.14
2010/0227329 A1 9/2010 Cuppens
2010/0273219 A1 10/2010 May et al.
2010/0282617 A1 11/2010 Rothberg et al.
2011/0028685 A1 2/2011 Purkayastha et al.
2011/0033854 A1 2/2011 Drmanac et al.
2011/0045462 A1 2/2011 Fu et al.
2011/0059436 A1 3/2011 Hardin et al.
2011/0059865 A1 3/2011 Smith et al.
2011/0111409 A1 5/2011 Sinicropi et al.
2011/0152111 A1 6/2011 Fan et al.
2011/0165178 A1 7/2011 Wasylyk et al.
2011/0207134 A1 8/2011 Faham et al.
2011/0245101 A1 10/2011 Chee et al.
2011/0245111 A1 10/2011 Chee
2011/0287435 A1 11/2011 Grunenwald et al.
2012/0021930 A1 1/2012 Schoen et al.
2012/0046175 A1 2/2012 Rodesch et al.
2012/0046178 A1 2/2012 Van Den Boom et al.
2012/0065081 A1 3/2012 Chee
2012/0135871 A1 5/2012 van Eijk et al.
2012/0202698 A1 8/2012 van Eijk et al.
2012/0202704 A1 8/2012 Fan et al.
2012/0220479 A1 8/2012 Ericsson et al.
2012/0245053 A1 9/2012 Shirai et al.
2012/0252702 A1 10/2012 Muratani et al.
2012/0258871 A1 10/2012 Kozlov et al.
2012/0270305 A1 10/2012 Reed et al.
2012/0289414 A1 11/2012 Mitra et al.
2012/0301925 A1 11/2012 Belyaev
2013/0005594 A1 1/2013 Terbrueggen et al.
2013/0005600 A1 1/2013 Olek
2013/0023433 A1 1/2013 Luo et al.
2013/0035239 A1 2/2013 Kong et al.
2013/0040842 A1 2/2013 Lim et al.
2013/0065768 A1 3/2013 Zheng et al.
2013/0079232 A1 3/2013 Kain et al.
2013/0202718 A1 8/2013 Pepin et al.
2013/0244884 A1 9/2013 Jacobson et al.
2013/0260372 A1 10/2013 Buermann et al.
2013/0261019 A1 10/2013 Lin et al.
2013/0302801 A1 11/2013 Asbury et al.
2013/0338042 A1 12/2013 Shen et al.
2014/0066318 A1 3/2014 Frisen et al.
2014/0080715 A1 3/2014 Lo et al.
2014/0121118 A1 5/2014 Warner
2014/0155295 A1 6/2014 Hindson et al.
2014/0270435 A1 9/2014 Dunn
2014/0274731 A1 9/2014 Raymond et al.
2014/0296081 A1 10/2014 Diehn et al.
2014/0323330 A1 10/2014 Glezer et al.
2014/0342921 A1 11/2014 Weiner
2014/0378345 A1 12/2014 Hindson et al.
2014/0378350 A1 12/2014 Hindson et al.
2015/0051085 A1 2/2015 Vogelstein et al.
2015/0292988 A1 10/2015 Bharadwaj et al.
2015/0344942 A1 12/2015 Frisen et al.
2015/0376609 A1 12/2015 Hindson et al.
2016/0019337 A1 1/2016 Roberts et al.
2016/0024576 A1 1/2016 Chee
2016/0041159 A1 2/2016 Labaer et al.
2016/0060687 A1 3/2016 Zhu et al.
2016/0108458 A1 4/2016 Frei et al.
2016/0122817 A1 5/2016 Jarosz et al.
2016/0138091 A1 5/2016 Chee et al.
2016/0145677 A1 5/2016 Chee et al.
2016/0194692 A1 7/2016 Gore et al.
2016/0201125 A1 7/2016 Samuels et al.
2016/0253584 A1 9/2016 Fodor et al.
2016/0289740 A1 10/2016 Fu et al.
2016/0298180 A1 10/2016 Chee
2016/0305856 A1 10/2016 Boyden et al.
2016/0333403 A1 11/2016 Chee
2016/0376642 A1 12/2016 Landegren et al.
2017/0009278 A1 1/2017 Söderberg et al.
2017/0016053 A1 1/2017 Beechem et al.
2017/0058339 A1 3/2017 Chee
2017/0058340 A1 3/2017 Chee
2017/0058345 A1 3/2017 Chee
2017/0088881 A1 3/2017 Chee
2017/0159109 A1 6/2017 Zheng et al.
2017/0166962 A1 6/2017 van Eijk et al.
2017/0220733 A1 8/2017 Zhuang et al.
2017/0233722 A1 8/2017 Seelig et al.
2017/0275669 A1 9/2017 Weissleder et al.
2017/0283860 A1 10/2017 Kool et al.
2017/0335297 A1 11/2017 Ha et al.

(56) References Cited

U.S. PATENT DOCUMENTS

2017/0335410 A1 11/2017 Driscoll et al.
2017/0342405 A1 11/2017 Fu et al.
2017/0343545 A1 11/2017 Hadrup et al.
2017/0349940 A1 12/2017 Morin et al.
2018/0057873 A1 3/2018 Zhou et al.
2018/0080019 A1 3/2018 Blainey et al.
2018/0088112 A1 3/2018 Fan et al.
2018/0094316 A1 4/2018 Oliphant et al.
2018/0105808 A1 4/2018 Mikkelsen et al.
2018/0112209 A1 4/2018 Eshoo
2018/0112261 A1 4/2018 Van Driel et al.
2018/0127817 A1 5/2018 Borchert et al.
2018/0156784 A1 6/2018 Usmani et al.
2018/0163265 A1 6/2018 Zhang et al.
2018/0179591 A1 6/2018 van Eijk
2018/0180601 A1 6/2018 Pedersen et al.
2018/0201925 A1 7/2018 Steemers et al.
2018/0201980 A1 7/2018 Chee et al.
2018/0208967 A1 7/2018 Larman et al.
2018/0216161 A1 8/2018 Chen et al.
2018/0216162 A1 8/2018 Belhocine et al.
2018/0237864 A1 8/2018 Imler et al.
2018/0245142 A1 8/2018 So et al.
2018/0247017 A1 8/2018 van Eijk et al.
2018/0274039 A1 9/2018 Zhang et al.
2018/0291427 A1 10/2018 Edelman
2018/0291439 A1 10/2018 van Eijk et al.
2018/0305681 A1 10/2018 Jovanovich et al.
2018/0312822 A1 11/2018 Lee et al.
2018/0320226 A1 11/2018 Church et al.
2018/0334670 A1 11/2018 Bharadwaj et al.
2019/0032121 A1 1/2019 Daugharthy et al.
2019/0055594 A1 2/2019 Samusik et al.
2019/0064173 A1 2/2019 Bharadwaj et al.
2019/0071656 A1 3/2019 Chang et al.
2019/0119735 A1 4/2019 Deisseroth et al.
2019/0135774 A1 5/2019 Orbai
2019/0145982 A1 5/2019 Chee et al.
2019/0161796 A1 5/2019 Hauling et al.
2019/0177777 A1 6/2019 Chee
2019/0177778 A1 6/2019 Chee
2019/0177789 A1 6/2019 Hindson et al.
2019/0177800 A1 6/2019 Boutet et al.
2019/0203275 A1 7/2019 Frisen et al.
2019/0218276 A1 7/2019 Regev et al.
2019/0218608 A1 7/2019 Daugharthy et al.
2019/0233878 A1 8/2019 Delaney et al.
2019/0233880 A1 8/2019 Mir
2019/0249226 A1 8/2019 Bent et al.
2019/0262831 A1 8/2019 West et al.
2019/0264268 A1 8/2019 Frisen et al.
2019/0271028 A1 9/2019 Khafizov et al.
2019/0271030 A1 9/2019 Chee
2019/0271031 A1 9/2019 Chee
2019/0300943 A1 10/2019 Chee et al.
2019/0300944 A1 10/2019 Chee et al.
2019/0300945 A1 10/2019 Chee et al.
2019/0309353 A1 10/2019 Chee
2019/0309354 A1 10/2019 Chee
2019/0309355 A1 10/2019 Chee
2019/0323071 A1 10/2019 Chee
2019/0323088 A1 10/2019 Boutet et al.
2019/0338353 A1 11/2019 Belgrader et al.
2019/0360034 A1 11/2019 Zhou et al.
2019/0360043 A1 11/2019 Pham et al.
2019/0367969 A1 12/2019 Belhocine et al.
2019/0367982 A1 12/2019 Belhocine et al.
2019/0367997 A1 12/2019 Bent et al.
2020/0002763 A1 1/2020 Belgrader et al.
2020/0010891 A1 1/2020 Beechem et al.
2020/0024641 A1 1/2020 Nolan et al.
2020/0047010 A1 2/2020 Lee et al.
2020/0048690 A1 2/2020 Chee
2020/0063191 A1 2/2020 Kennedy-Darling et al.
2020/0063195 A1 2/2020 Chee
2020/0063196 A1 2/2020 Chee
2020/0071751 A1 3/2020 Daugharthy et al.
2020/0080136 A1 3/2020 Zhang et al.
2020/0109443 A1 4/2020 Chee
2020/0123597 A1 4/2020 Daniel
2020/0140920 A1 5/2020 Pierce et al.
2020/0173985 A1 6/2020 Dong et al.
2020/0199565 A1 6/2020 Chen et al.
2020/0199572 A1 6/2020 Kuersten et al.
2020/0224244 A1 7/2020 Nilsson et al.
2020/0239874 A1 7/2020 Mikkelsen
2020/0256867 A1 8/2020 Hennek et al.
2020/0277663 A1 9/2020 Iyer
2020/0277664 A1 9/2020 Frenz
2020/0283852 A1 9/2020 Oliphant et al.
2020/0299757 A1 9/2020 Chee et al.
2020/0325531 A1 10/2020 Chee
2020/0362398 A1 11/2020 Kishi et al.
2020/0370095 A1 11/2020 Farmer et al.
2020/0399687 A1 12/2020 Frisen et al.
2020/0407781 A1 12/2020 Schnall-Levin
2021/0010068 A1 1/2021 Chee et al.
2021/0010070 A1 1/2021 Schnall-Levin et al.
2021/0017587 A1 1/2021 Cai et al.
2021/0095331 A1 4/2021 Fan et al.
2021/0115504 A1 4/2021 Cai et al.
2021/0123040 A1 4/2021 Macosko et al.
2021/0130881 A1 5/2021 Cox
2021/0140982 A1 5/2021 Uytingco et al.
2021/0150707 A1 5/2021 Weisenfeld et al.
2021/0155982 A1 5/2021 Yin et al.
2021/0158522 A1 5/2021 Weisenfeld et al.
2021/0172007 A1 6/2021 Chee et al.
2021/0180141 A1 6/2021 Li et al.
2021/0189475 A1 6/2021 Tentori et al.
2021/0190770 A1 6/2021 Delaney et al.
2021/0198741 A1 7/2021 Williams
2021/0199660 A1 7/2021 Williams et al.
2021/0207202 A1 7/2021 Chee
2021/0214785 A1 7/2021 Stoeckius
2021/0222235 A1 7/2021 Chee
2021/0222241 A1 7/2021 Bharadwaj
2021/0222242 A1 7/2021 Ramachandran Iyer
2021/0222253 A1 7/2021 Uytingco
2021/0223227 A1 7/2021 Stoeckius
2021/0230584 A1 7/2021 Mikkelsen et al.
2021/0230681 A1 7/2021 Patterson et al.
2021/0230692 A1 7/2021 Daugharthy et al.
2021/0237022 A1 8/2021 Bava
2021/0238581 A1 8/2021 Mikkelsen et al.
2021/0238664 A1 8/2021 Bava et al.
2021/0238675 A1 8/2021 Bava
2021/0238680 A1 8/2021 Bava
2021/0247316 A1 8/2021 Bava
2021/0255175 A1 8/2021 Chee et al.
2021/0262018 A1 8/2021 Bava et al.
2021/0262019 A1 8/2021 Alvarado Martinez et al.
2021/0269864 A1 9/2021 Chee
2021/0270822 A1 9/2021 Chee
2021/0285036 A1 9/2021 Yin et al.
2021/0285046 A1 9/2021 Chell et al.
2021/0292748 A1 9/2021 Frisen et al.
2021/0292822 A1 9/2021 Frisen et al.
2021/0317510 A1 10/2021 Chee et al.
2021/0317524 A1 10/2021 Lucero et al.
2021/0324457 A1 10/2021 Ramachandran Iyer et al.
2021/0332424 A1 10/2021 Schnall-Levin
2021/0332425 A1 10/2021 Pfeiffer et al.
2021/0348221 A1 11/2021 Chell et al.
2022/0002791 A1 1/2022 Frisen et al.
2022/0003755 A1 1/2022 Chee
2022/0010367 A1 1/2022 Ramachandran Iyer et al.
2022/0017951 A1 1/2022 Ramachandran Iyer et al.
2022/0025446 A1 1/2022 Shah
2022/0025447 A1 1/2022 Tentori et al.
2022/0033888 A1 2/2022 Schnall-Levin et al.
2022/0049293 A1 2/2022 Frenz et al.
2022/0049294 A1 2/2022 Uytingco et al.
2022/0064630 A1 3/2022 Bent et al.

(56) References Cited

U.S. PATENT DOCUMENTS

| | | | |
|---|---|---|---|
| 2022/0081728 | A1 | 3/2022 | Williams |
| 2022/0090058 | A1 | 3/2022 | Frisen et al. |
| 2022/0090175 | A1 | 3/2022 | Uytingco et al. |
| 2022/0090181 | A1 | 3/2022 | Gallant et al. |
| 2022/0098576 | A1 | 3/2022 | Dadhwal |
| 2022/0098661 | A1 | 3/2022 | Chew et al. |
| 2022/0106632 | A1 | 4/2022 | Galonska et al. |
| 2022/0106633 | A1 | 4/2022 | Engblom et al. |
| 2022/0112486 | A1 | 4/2022 | Ramachandran Iyer et al. |
| 2022/0112545 | A1 | 4/2022 | Chee |
| 2022/0119869 | A1 | 4/2022 | Ramachandran Iyer et al. |
| 2022/0127659 | A1 | 4/2022 | Frisen et al. |
| 2022/0127666 | A1 | 4/2022 | Katiraee et al. |
| 2022/0127672 | A1 | 4/2022 | Stoeckius |
| 2022/0145361 | A1 | 5/2022 | Frenz et al. |
| 2022/0154255 | A1 | 5/2022 | Chee et al. |
| 2022/0170083 | A1 | 6/2022 | Khaled et al. |
| 2022/0195422 | A1 | 6/2022 | Gallant et al. |
| 2022/0195505 | A1 | 6/2022 | Frisen et al. |
| 2022/0196644 | A1 | 6/2022 | Chee |
| 2022/0213526 | A1 | 7/2022 | Frisen et al. |
| 2022/0220544 | A1 | 7/2022 | Ach et al. |
| 2022/0241780 | A1 | 8/2022 | Tentori et al. |
| 2022/0267844 | A1 | 8/2022 | Ramachandran Iyer et al. |
| 2022/0282329 | A1 | 9/2022 | Chell et al. |
| 2022/0290217 | A1 | 9/2022 | Frenz et al. |
| 2022/0290219 | A1 | 9/2022 | Chee |
| 2022/0298560 | A1 | 9/2022 | Frisen et al. |
| 2022/0325325 | A1 | 10/2022 | Chee et al. |
| 2022/0326251 | A1 | 10/2022 | Uytingco et al. |
| 2022/0333171 | A1 | 10/2022 | Chee |
| 2022/0333191 | A1 | 10/2022 | Mikkelsen et al. |
| 2022/0333192 | A1 | 10/2022 | Uytingco |
| 2022/0333195 | A1 | 10/2022 | Schnall-Levin et al. |
| 2022/0334031 | A1 | 10/2022 | Delaney et al. |
| 2022/0348905 | A1 | 11/2022 | Dadhwal |
| 2022/0348992 | A1 | 11/2022 | Stoeckius et al. |
| 2022/0356464 | A1 | 11/2022 | Kim et al. |
| 2022/0364163 | A1 | 11/2022 | Stahl et al. |
| 2022/0389491 | A1 | 12/2022 | Chee |
| 2022/0389503 | A1 | 12/2022 | Mikkelsen et al. |
| 2022/0389504 | A1 | 12/2022 | Chew et al. |
| 2022/0403455 | A1 | 12/2022 | Ramachandran Iyer et al. |
| 2022/0404245 | A1 | 12/2022 | Chell et al. |
| 2023/0002812 | A1 | 1/2023 | Stoeckius et al. |
| 2023/0014008 | A1 | 1/2023 | Shastry |
| 2023/0017773 | A1 | 1/2023 | Kim et al. |
| 2023/0031305 | A1 | 2/2023 | Neuta et al. |
| 2023/0033960 | A1 | 2/2023 | Gallant et al. |
| 2023/0034039 | A1 | 2/2023 | Shahjamali |
| 2023/0034216 | A1 | 2/2023 | Bava |
| 2023/0040363 | A1 | 2/2023 | Chee |
| 2023/0042088 | A1 | 2/2023 | Chee |
| 2023/0042817 | A1 | 2/2023 | Mignardi |
| 2023/0047782 | A1 | 2/2023 | Tentori et al. |
| 2023/0056549 | A1 | 2/2023 | Dadhwal |
| 2023/0064372 | A1 | 3/2023 | Chell et al. |
| 2023/0069046 | A1 | 3/2023 | Chew et al. |
| 2023/0077364 | A1 | 3/2023 | Patterson et al. |
| 2023/0080543 | A1 | 3/2023 | Katiraee et al. |
| 2023/0081381 | A1 | 3/2023 | Chew et al. |
| 2023/0100497 | A1 | 3/2023 | Frisen et al. |
| 2023/0107023 | A1 | 4/2023 | Chee |
| 2023/0111225 | A1 | 4/2023 | Chew et al. |
| 2023/0113230 | A1 | 4/2023 | Kim et al. |
| 2023/0126825 | A1 | 4/2023 | Nagendran et al. |
| 2023/0129552 | A1 | 4/2023 | Ramachandran Iyer |
| 2023/0135010 | A1 | 5/2023 | Tentori et al. |
| 2023/0143569 | A1 | 5/2023 | Iyer et al. |
| 2023/0145575 | A1 | 5/2023 | Gallant et al. |
| 2023/0147726 | A1 | 5/2023 | Hadrup et al. |
| 2023/0151412 | A1 | 5/2023 | Chee |
| 2023/0159994 | A1 | 5/2023 | Chee |
| 2023/0159995 | A1 | 5/2023 | Iyer et al. |
| 2023/0160008 | A1 | 5/2023 | Chell et al. |
| 2023/0175045 | A1 | 6/2023 | Katsori et al. |
| 2023/0183684 | A1 | 6/2023 | Gallant et al. |
| 2023/0183785 | A1 | 6/2023 | Frisen et al. |
| 2023/0194469 | A1 | 6/2023 | Tentori et al. |
| 2023/0194470 | A1 | 6/2023 | Kim et al. |
| 2023/0203478 | A1 | 6/2023 | Kim et al. |
| 2023/0212650 | A1 | 7/2023 | Chew et al. |
| 2023/0212655 | A1 | 7/2023 | Chee |
| 2023/0212656 | A1 | 7/2023 | Chow et al. |
| 2023/0220368 | A1 | 7/2023 | Kim |
| 2023/0220454 | A1 | 7/2023 | Bent et al. |
| 2023/0220455 | A1 | 7/2023 | Galonska et al. |
| 2023/0227811 | A1 | 7/2023 | Dadhwal |
| 2023/0228762 | A1 | 7/2023 | Uytingco et al. |
| 2023/0242973 | A1 | 8/2023 | Frisen et al. |
| 2023/0242976 | A1 | 8/2023 | Tentori et al. |
| 2023/0265488 | A1 | 8/2023 | Gohil et al. |
| 2023/0265489 | A1 | 8/2023 | Uytingco et al. |
| 2023/0265491 | A1 | 8/2023 | Tentori et al. |
| 2023/0267625 | A1 | 8/2023 | Tentori et al. |
| 2023/0279474 | A1 | 9/2023 | Katiraee |
| 2023/0279477 | A1 | 9/2023 | Kvastad et al. |
| 2023/0279481 | A1 | 9/2023 | Marrache et al. |
| 2023/0287399 | A1 | 9/2023 | Gallant et al. |
| 2023/0287475 | A1 | 9/2023 | Chell et al. |
| 2023/0287481 | A1 | 9/2023 | Katsori et al. |
| 2023/0295699 | A1 | 9/2023 | Sukovich et al. |
| 2023/0295722 | A1 | 9/2023 | Bharadwaj |
| 2023/0304072 | A1 | 9/2023 | Gohil et al. |
| 2023/0304074 | A1 | 9/2023 | Chee et al. |
| 2023/0304078 | A1 | 9/2023 | Frisen et al. |
| 2023/0313279 | A1 | 10/2023 | Giacomello et al. |
| 2023/0323340 | A1 | 10/2023 | Dadhwal |
| 2023/0323434 | A1 | 10/2023 | Yin et al. |
| 2023/0323436 | A1 | 10/2023 | Chee |
| 2023/0323447 | A1 | 10/2023 | Schnall-Levin et al. |
| 2023/0323453 | A1 | 10/2023 | Stoeckius |
| 2023/0332138 | A1 | 10/2023 | Kim et al. |
| 2023/0332211 | A1 | 10/2023 | Chee |
| 2023/0332212 | A1 | 10/2023 | Chew et al. |
| 2023/0332227 | A1 | 10/2023 | Ramachandran Iyer |
| 2023/0332247 | A1 | 10/2023 | Singh et al. |
| 2023/0351619 | A1 | 11/2023 | Tentori et al. |
| 2023/0358733 | A1 | 11/2023 | Chee |
| 2023/0366008 | A1 | 11/2023 | Chew et al. |
| 2023/0383285 | A1 | 11/2023 | Kim et al. |
| 2023/0383344 | A1 | 11/2023 | Stoeckius |
| 2023/0392204 | A1 | 12/2023 | Chell et al. |
| 2023/0393071 | A1 | 12/2023 | Bava |
| 2023/0407404 | A1 | 12/2023 | Baumgartner et al. |
| 2023/0416807 | A1 | 12/2023 | Chee |
| 2023/0416808 | A1 | 12/2023 | Sukovich et al. |
| 2023/0416850 | A1 | 12/2023 | Singh et al. |
| 2024/0002931 | A1 | 1/2024 | Bava |
| 2024/0011081 | A1 | 1/2024 | Chee |
| 2024/0011090 | A1 | 1/2024 | Chew et al. |
| 2024/0018572 | A1 | 1/2024 | Mignardi |
| 2024/0018575 | A1 | 1/2024 | Gallant et al. |
| 2024/0018589 | A1 | 1/2024 | Schnall-Levin et al. |
| 2024/0026445 | A1 | 1/2024 | Ramachandran Iyer et al. |
| 2024/0033743 | A1 | 2/2024 | Tentori et al. |
| 2024/0035937 | A1 | 2/2024 | Cox et al. |
| 2024/0043908 | A1 | 2/2024 | Chew et al. |
| 2024/0043925 | A1 | 2/2024 | Bent et al. |
| 2024/0052343 | A1 | 2/2024 | Gallant et al. |
| 2024/0053351 | A1 | 2/2024 | Uytingco et al. |
| 2024/0060115 | A1 | 2/2024 | Chee et al. |
| 2024/0067953 | A1 | 2/2024 | Mikkelsen et al. |
| 2024/0068016 | A1 | 2/2024 | Frisen et al. |
| 2024/0068017 | A1 | 2/2024 | Lundeberg et al. |
| 2024/0076723 | A1 | 3/2024 | Mignardi |
| 2024/0080346 | A1 | 3/2024 | Engblom et al. |
| 2024/0084365 | A1 | 3/2024 | Frisen et al. |
| 2024/0084366 | A1 | 3/2024 | Chee |
| 2024/0084383 | A1 | 3/2024 | Ramachandran Iyer et al. |
| 2024/0093274 | A1 | 3/2024 | Frisen et al. |
| 2024/0093290 | A1 | 3/2024 | Stahl et al. |
| 2024/0110228 | A1 | 4/2024 | Uytingco et al. |
| 2024/0124933 | A1 | 4/2024 | Chell et al. |

(56) References Cited

U.S. PATENT DOCUMENTS

| | | | |
|---|---|---|---|
| 2024/0125772 | A1 | 4/2024 | Delaney et al. |
| 2024/0141327 | A1 | 5/2024 | Kim et al. |
| 2024/0158838 | A1 | 5/2024 | Alvarado Martinez et al. |
| 2024/0175080 | A1 | 5/2024 | Galonska et al. |
| 2024/0182968 | A1 | 6/2024 | Bava |
| 2024/0191286 | A1 | 6/2024 | Boutet et al. |
| 2024/0200121 | A1 | 6/2024 | Boutet |
| 2024/0209425 | A1 | 6/2024 | Yin et al. |
| 2024/0218427 | A1 | 7/2024 | Sukovich et al. |
| 2024/0218432 | A1 | 7/2024 | Mielinis |
| 2024/0219701 | A1 | 7/2024 | Tentori et al. |
| 2024/0253036 | A1 | 8/2024 | Kim et al. |
| 2024/0263218 | A1 | 8/2024 | Katiraee et al. |
| 2024/0271190 | A1 | 8/2024 | Stoeckius et al. |
| 2024/0271195 | A1 | 8/2024 | Mikhaiel et al. |
| 2024/0287600 | A1 | 8/2024 | Iyer et al. |
| 2024/0294971 | A1 | 9/2024 | Galonska |
| 2024/0294974 | A1 | 9/2024 | Galonska et al. |
| 2024/0294975 | A1 | 9/2024 | Lin et al. |
| 2024/0301488 | A1 | 9/2024 | Stoeckius |
| 2024/0301489 | A1 | 9/2024 | Chew et al. |
| 2024/0360494 | A1 | 10/2024 | Costa et al. |
| 2024/0368711 | A1 | 11/2024 | Giacomello et al. |
| 2024/0377297 | A1 | 11/2024 | Cox et al. |
| 2024/0385088 | A1 | 11/2024 | Kim et al. |
| 2024/0392349 | A1 | 11/2024 | Frisen et al. |
| 2024/0392351 | A1 | 11/2024 | Chee |
| 2024/0392352 | A1 | 11/2024 | Stahl et al. |
| 2024/0392353 | A1 | 11/2024 | Engblom et al. |
| 2024/0401109 | A1 | 12/2024 | Kim et al. |
| 2024/0401117 | A1 | 12/2024 | Bava |
| 2024/0401118 | A1 | 12/2024 | Tentori et al. |
| 2024/0404301 | A1 | 12/2024 | Li et al. |
| 2024/0408593 | A1 | 12/2024 | Kim et al. |
| 2024/0416315 | A1 | 12/2024 | Bava |
| 2024/0417783 | A1 | 12/2024 | Chew et al. |
| 2024/0417784 | A1 | 12/2024 | Sukovich et al. |
| 2025/0002980 | A1 | 1/2025 | Tentori et al. |
| 2025/0002982 | A1 | 1/2025 | Stoeckius et al. |
| 2025/0003956 | A1 | 1/2025 | Delaney et al. |
| 2025/0019689 | A1 | 1/2025 | Galonska et al. |
| 2025/0019749 | A1 | 1/2025 | Katiraee et al. |
| 2025/0066762 | A1 | 2/2025 | Man et al. |
| 2025/0066770 | A1 | 2/2025 | Costa |
| 2025/0073719 | A1 | 3/2025 | Cox et al. |
| 2025/0075261 | A1 | 3/2025 | Kim |
| 2025/0101501 | A1 | 3/2025 | Chee |
| 2025/0101502 | A1 | 3/2025 | Chee |
| 2025/0101504 | A1 | 3/2025 | Nagendran et al. |
| 2025/0122564 | A1 | 4/2025 | Mignardi et al. |
| 2025/0122565 | A1 | 4/2025 | Schnall-Levin et al. |
| 2025/0129412 | A1 | 4/2025 | Uytingco et al. |
| 2025/0129421 | A1 | 4/2025 | Schnall-Levin et al. |
| 2025/0137043 | A1 | 5/2025 | Tentori |
| 2025/0145984 | A1 | 5/2025 | Ma et al. |
| 2025/0146057 | A1 | 5/2025 | Schnall-Levin et al. |
| 2025/0146058 | A1 | 5/2025 | Tentori |
| 2025/0146071 | A1 | 5/2025 | Schnall-Levin et al. |
| 2025/0146072 | A1 | 5/2025 | Schnall-Levin et al. |
| 2025/0154565 | A1 | 5/2025 | Chee |
| 2025/0154566 | A1 | 5/2025 | Chee |
| 2025/0154567 | A1 | 5/2025 | Chee |
| 2025/0154568 | A1 | 5/2025 | Frisen et al. |
| 2025/0154569 | A1 | 5/2025 | Stoeckius et al. |
| 2025/0154571 | A1 | 5/2025 | Ramachandran Iyer et al. |
| 2025/0154588 | A1 | 5/2025 | Ramachandran Iyer et al. |
| 2025/0155446 | A1 | 5/2025 | Uytingco et al. |
| 2025/0163501 | A1 | 5/2025 | Singh et al. |
| 2025/0163509 | A1 | 5/2025 | Daugharthy et al. |
| 2025/0171833 | A1 | 5/2025 | Frisen et al. |
| 2025/0171848 | A1 | 5/2025 | Chell et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2130913 | 12/2009 |
| EP | 2292788 | 3/2011 |
| EP | 2302070 | 3/2011 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| RU | 2145635 | 2/2000 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/017390 | 3/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/055159 | 7/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/065814 | 7/2005 |
| WO | WO 2005/113804 | 12/2005 |
| WO | WO 2006/020515 | 2/2006 |
| WO | WO 2006/064199 | 6/2006 |
| WO | WO 2006/124771 | 11/2006 |
| WO | WO 2007/010251 | 1/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2009/032167 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |

(56) References Cited

FOREIGN PATENT DOCUMENTS

| | | |
|---|---|---|
| WO | WO 2010/053587 | 5/2010 |
| WO | WO 2010/088517 | 8/2010 |
| WO | WO 2010/126614 | 11/2010 |
| WO | WO 2011/008502 | 1/2011 |
| WO | WO 2011/019964 | 2/2011 |
| WO | WO 2011/062933 | 5/2011 |
| WO | WO 2011/068088 | 6/2011 |
| WO | WO 2011/094669 | 8/2011 |
| WO | WO 2011/127099 | 10/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/140224 | 10/2012 |
| WO | WO 2012/159089 | 11/2012 |
| WO | WO 2012/168003 | 12/2012 |
| WO | WO 2013/022807 | 2/2013 |
| WO | WO 2013/033271 | 3/2013 |
| WO | WO 2013/090390 | 6/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2013/155119 | 10/2013 |
| WO | WO 2013/158936 | 10/2013 |
| WO | WO 2013/025952 | 12/2013 |
| WO | WO 2014/044724 | 3/2014 |
| WO | WO 2014/060483 | 4/2014 |
| WO | WO 2014/071361 | 5/2014 |
| WO | WO 2014/085725 | 6/2014 |
| WO | WO 2014/130576 | 8/2014 |
| WO | WO 2014/144713 | 9/2014 |
| WO | WO 2014/152397 | 9/2014 |
| WO | WO 2014/163886 | 10/2014 |
| WO | WO 2014/210223 | 12/2014 |
| WO | WO 2014/210225 | 12/2014 |
| WO | WO 2014/210233 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2016/007839 | 1/2016 |
| WO | WO 2016/057552 | 4/2016 |
| WO | WO 2016/077763 | 5/2016 |
| WO | WO 2016/100196 | 6/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/027367 | 2/2017 |
| WO | WO 2017/027368 | 2/2017 |
| WO | WO 2017/044993 | 3/2017 |
| WO | WO 2017/075293 | 5/2017 |
| WO | WO 2017/096158 | 7/2017 |
| WO | WO 2017/143155 | 8/2017 |
| WO | WO 2017/144338 | 8/2017 |
| WO | WO 2017/147483 | 8/2017 |
| WO | WO 2017/156336 | 9/2017 |
| WO | WO 2017/177308 | 10/2017 |
| WO | WO 2017/184984 | 10/2017 |
| WO | WO 2017/192633 | 11/2017 |
| WO | WO 2017/222453 | 12/2017 |
| WO | WO 2018/022809 | 2/2018 |
| WO | WO 2018/023068 | 2/2018 |
| WO | WO 2018/026873 | 2/2018 |
| WO | WO 2018/045181 | 3/2018 |
| WO | WO 2018/045186 | 3/2018 |
| WO | WO 2018/057999 | 3/2018 |
| WO | WO 2018/064640 | 4/2018 |
| WO | WO 2018/075436 | 4/2018 |
| WO | WO 2018/075693 | 4/2018 |
| WO | WO 2018/085599 | 5/2018 |
| WO | WO 2018/089550 | 5/2018 |
| WO | WO 2018/091676 | 5/2018 |
| WO | WO 2018/107054 | 6/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/075091 | 4/2019 |
| WO | WO 2019/104337 | 5/2019 |
| WO | WO 2019/113457 | 6/2019 |
| WO | WO 2019/113533 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047004 | 3/2020 |
| WO | WO 2020/047005 | 3/2020 |
| WO | WO 2020/047007 | 3/2020 |
| WO | WO 2020/047010 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/142490 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |

(56) References Cited

FOREIGN PATENT DOCUMENTS

| | | |
|---|---|---|
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/015913 | 11/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |

OTHER PUBLICATIONS

[No Author Listed], "Proseek® Multiplex 96×96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.

Abaan et al., "The exomes of the NCI-60 panel: a genomic resource for cancer biology and systems pharmacology," Cancer Res., Jul. 2013, 73(14):4372-82.

Abels et al., "Glioblastoma-Associated Microglia Reprogramming Is Mediated by Functional Transfer of Extracellular miR-21," Cell Reports, Sep. 2019, 28(12):3105-3119.

Adessi et al., "Solid phase DNA amplification: characterisation of primer attachment and amplification mechanisms," Nucl. Acids Res., 2000, 28(20):E87, 8 pages.

Adiconis et al., "Comparative analysis of RNA sequencing methods for degraded or low-input samples," Nat Methods, Jul. 2013, 10(7):623-9.

Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.

Affymetrix, "Human Genome U95Av2," Internet Citation, retrieved from the internet: on the World Wide Web affymetrix.com, retrieved on Oct. 2, 2002, 1 page.

Ahern, "Biochemical, Reagents Kits Offer Scientists Good Return on Investment," The Scientist, Jul. 1995, 9(15):20, 7 pages.

Ahlfen et al., "Determinants of RNA quality from FFPE samples," PLoS One, Dec. 2007, 2(12):e1261, 7 pages.

Alam, "Proximity Ligation Assay (PLA)," Curr Protoc Immunol., Nov. 2018, 123(1):e58, 8 pages.

Albretsen et al., "Applications of magnetic beads with covalently attached oligonucleotides in hybridization: Isolation and detection of specific measles virus mRNA from a crude cell lysate," Anal. Biochem., 1990, 189(1):40-50.

Algayer et al., "Novel pH Selective, Highly Lytic Peptides Based on a Chimeric Influenza Hemagglutinin Peptide/Cell Penetrating Peptide Motif," Molecules, May 2019, 24(11):2079, 23 pages.

Ali et al., "Patterns of Immune Infiltration in Breast Cancer and Their Clinical Implications: A Gene-Expression-Based Retrospective Study," PLoS Med., Dec. 2016, 13(12):e1002194, 24 pages.

Allawi et al., "Thermodynamics and NMR of Internal G.T Mismatches in DNA," Biochemistry, 1996, 36(34):10581-10594.

(56) References Cited

OTHER PUBLICATIONS

Amgad et al., "Report on computational assessment of Tumor Infiltrating Lymphocytes from the International Immuno-Oncology Biomarker Working Group," Nature Partner Journals Breast Cancer, May 2020, 6:16, 13 pages.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Deciphering the Antibodyome—Peptide Arrays for Serum Antibody Biomarker Diagnostics," Current Proteomics, 6(1):1-12, 2009.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "A spatiotemporal organ-wide gene expression and cell atlas of the developing human heart," Cell, Dec. 12, 2019, 179(7): 1647-1660.
Asp et al., "Spatial detection of fetal marker genes expressed at low level in adult human heart tissue," Scientific Reports, 2017, 7(1):12941, 10 pages.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Ayers et al., "IFN-γ-related mRNA profile predicts clinical response to PD-1 blockade," J Clin. Invest., Aug. 2017, 127(8):2930-2940.
Azab et al., "Potential Molecular Biomarkers for Prediction of Coronary Artery Disease, its Severity and Extent," Bulletin of Egyptian Society for Physiological Sciences, Jun. 1, 2017, 37(2), 110-128.
Bailey et al., "Comprehensive Characterization of Cancer Driver Genes and Mutations," Cell, Apr. 2018, 173(2):371-385, 38 pages.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Banerjee et al., "Viral glycoproteins: biological role and application in diagnosis," Virusdisease, Mar. 2016, 27(1):1-11.
Barbie et al., "Systematic RNA interference reveals that oncogenic KRAS-driven cancers require TBK1," Nature, Nov. 2009, 462(7269):108-12.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Bechara et al., "Cell-penetrating peptides: 20 years later, where do we stand?," FEBS Lett., Jun. 2013, 587(12):1693-702.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Behan et al., "Prioritization of cancer therapeutic targets using CRISPR-Cas9 screens," Nature, Apr. 2019, 568:511-516.
Beier et al., "Versatile derivatisation of solid support media for covalent bonding on DNA- microchips," Nucleic Acids Res., May 1999, 27(9):1970-7.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Bell, "A simple way to treat PCR products prior to sequencing using ExoSAP-IT," Biotechniques, 2008, 44(6):834, 1 page.
Belton et al., "Hi-C: A comprehensive technique to capture the conformation of genomes," Methods, Nov. 2012, 58(3):268-276, 16 pages.
Bentley et al., "Accurate whole human genome sequencing using reversible terminator chemistry," Nature, 2008, 456(7218):53-59.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Bibikova et al., "Quantitative gene expression profiling in formalin-fixed paraffin-embedded tissues using universal bead arrays," The American Journal of Pathology, Nov. 1, 2004, 165(5):1799-1807.
Bielas et al., "Human cancers express a mutator phenotype," Proc. Natl. Acad. Sci. USA, 2006, 103(48): 18238-18242.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blandini et al., "Animal models of Parkinson's disease," Febs J., Apr. 2012, 279(7):1156-66.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Bowtell, "The genesis and evolution of high-grade serous ovarian cancer," Nat. Rev. Cancer, 2010, (11 ):803-808 Abstract.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.

(56) References Cited

OTHER PUBLICATIONS

Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bugada et al., "Inflammation-based scores: a new method for patient-targeted strategies and improved perioperative outcome in cancer patients," Biomed Res Int., 2014, 2014:142425, 12 pages.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Cai et al., "Tenascin-c mediated vasculogenic mimicry formation via regulation of MMP2/MMP9 in glioma," Cell Death and Disease, Nov. 21, 2019, 10(879):1-14.
Caliari et al., "A practical guide to hydrogels for cell culture," Nat Methods., Apr. 2016, 13(5):405-14.
Cancernetwork.com, [online], Allison et al., "Heterogeneity and cancer," Oncology (Williston Park), Sep. 15, 2014, 28(9):772-8, via Internet Archive: Wayback Machine URL<The Wayback Machine—https://web.archive.org/web/20190129000357/http://www.cancernetwork.com:80/oncology-journal/heterogeneity-and-cancer>, retrieved on Oct. 21, 2021, URL<http://www.cancernetwork.com:80/oncology-journal/heterogeneity-and-cancer>, 3 pages.
Cao et al., "Homozygous EEF1A2 mutation causes dilated cardiomyopathy, failure to thrive, global developmental delay, epilepsy and early death," Hum Mol Genet., Sep. 2017, 26(18):3545-3552.
Carter et al., "Stabilization of an optical microscope to 0.1 nm in three dimensions," Applied Optics, 2007, 46:421-427.
Ceci et al., "Targeting Tumor-Associated Marcrophages to Increase the Efficacy of Immune Checkpoint Inhibitors: A Glimpse into Novel Therapeutic Approaches for Metastatic Melanoma," Cancers (Basal), Nov. 2020, 12(11):3401.
Cerutti et al., "Generation of sequence-specific, high affinity anti-DNA antibodies," Journal of Biological Chemistry, 2001, 276(16): 12769-12773.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al. "Arrayed profiling of multiple glycans on whole living cell surfaces." Analytical chemistry, Oct. 15, 2013, 85(22):11153-11158.
Chen et al., "A Homogeneous, Ligase-mediated DNA diagnostic test," Genome research, 1998, 8(5):549-556.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "High PLTP activity is associated with depressed left ventricular systolic function," Atherosclerosis, Jun. 2013, 228(2):438-42.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "μCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Chiang et al., "NFkappaB translocation in human microvessel endothelial cells using a four-compartment subcellular protein redistribution assay," J Biochem Biophys Methods, Nov. 2000, 46(1-2):53-68.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Choi et al., "Multiplexed detection of mRNA using porosity-tuned hydrogel microparticles," Analytical chemistry, Sep. 28, 2012, 84(21):9370-9378.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Co et al., "Factors affecting the under-diagnosis of atypical ductal hyperplasia diagnosed by core needle biopsies—A 10-year retrospective study and review of the literature," Int J Surg., Jan. 2018, 49:27-31.
Cockroft et al., "A single-molecule nanopore device detects DNA polymerase activity with single-nucleotide resolution," J Am Chem Soc., Jan. 2008, 130(3):818-20.
Codeluppi et al., "Spatial organization of the somatosensory cortex revealed by osmFISH," Nature Methods, Nov. 2018, 15:932-935.
Constantine et al., "Use of genechip high-density oligonucleotide arrays for gene expression monitoring," Life Science News, Amersham Life Science, 1998, pp. 11-14.
Copeland et al., "Mitochondrial DNA Alterations in Cancer," Cancer Invest., 2002, 557-569.
Corces et al., "An improved ATAC-seq protocol reduces background and enables interrogation of frozen tissues," Nat. Methods, 2017, 14(10):959-962.
Cox et al., "Tissue subcellular fractionation and protein extraction for use in mass-spectrometry-based proteomics," Nat Protoc., 2006, 1(4):1872-8.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.

(56) References Cited

OTHER PUBLICATIONS

Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Dalmeijer et al., "Matrix Gla Protein Species and Risk of Cardiovascular Events in Type 2 Diabetic Patients," Diabetes Care, Nov. 2013, 36(11):3766-71.
Darmanis et al., "ProteinSeq: High-Performance Proteomic Analyses by Proximity, Ligation and Next Generation Sequencing," PLos One, 2011, 6(9): e25583, 10 pages.
Darnell, Jr., "Reflections on the history of pre-mRNA processing and highlights of current knowledge: A unified picture," RNA, Feb. 2013, 19:443-460, 19 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Davis et al., "Glioblastoma: Overview of Disease and Treatment," Clin J Oncol Nurs, Oct. 2016, 20(5):S2-S8.
Dawson et al., "Animal models of neurodegenerative diseases," Nat Neurosci., Oct. 2018, 21(10):1370-1379.
Dawson et al., "Genetic animal models of Parkinson's disease," Neuron, Jun. 2010, 66(5):646-661.
Deamer et al., "Characterization of nucleic acids by Nanopore analysis," Acc Chem Res., Oct. 2002, 35(10):817-25.
Deamer et al., "Nanopores and nucleic acids: prospects for ultrarapid sequencing," Trends Biotechnol., Apr. 2000, 18(4):147-51.
Dean et al., "Comprehensive human genome amplification using multiple displacement amplification," Proc Natl. Acad. Sci. USA, 2002, 99(8):5261-66.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Deininger et al., "Allograft inflammatory factor-1 defines a distinct subset of infiltrating macrophages/microglial cells in rat and human gliomas," Acta Neuropathol, Dec. 2000, 100(6):673-680.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "Accurate sequencing by hybridization for DNA diagnostics and individual genomics," Nature Biotechnology, 16:54-58, 1998.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Drum et al., "Thymosin Beta-4 Is Elevated in Women With Heart Failure With Preserved Ejection Fraction," Journal of the American Heart Association, Jun. 2017, 6(6):e005586, 20 pages.
Dtp.cancer.gov, [online], "A Catalog of in Vitro Cell Lines, Transplantable Animal and Human Tumors and Yeast," The Division of Cancer Treatment and Diagnosis (DCTD), National Cancer Institute, May 5, 2020, retrieved on Jun. 7, 2021, retrieved from URL<https://dtp.cancer.gov/organization/btb/docs/DCTDTumorRepositoryCatalog.pdf>, 77 pages.
Duncan et al., "Affinity chromatography of a sequence-specific DNA binding protein using Teflon-linked oligonucleotides," Anal. Biochem., 1988, 169(1):104-108.
Eagen, "Principles of Chromosome Architecture Revealed by Hi-C," Trends in Biochemical Sciences, Jun. 2018, 43(6):469-478.
Eastburn et al., "Identification of Genetic Analysis of Cancer Cells with PCT-activated Cell Sorting," Nucleic Acids Research, Jul. 16, 2014, 42(16):e128, 10 pages.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Ertsey et al., "Coverslip Mounted-Immersion Cycled in Situ RT-PCR for the Localization of mRNA in Tissue Sections," Biotechniques, 1998, 24(1):92-100.
Evers et al., "The effect of formaldehyde fixation on RNA: optimization of formaldehyde adduct removal," J Mol Diagn., May 2011, 13(3):282-8.
Fahy et al., "Design and synthesis of polyacrylamide-based oligonucleotide supports for use in nucleic acid diagnostics," Nucleic Acids Res., Apr. 1993, 21(8):1819-26.
Fan et al., "A versatile assay for high-throughput gene expression profiling on universal array matrices," Genome Research, May 1, 2004, 14(5):878-885.
Fan et al., "Illumina Universal Bead Arrays," Methods in Enzymology, 2006, 410:57-73.
Fang et al., "A genetics-led approach defines the drug target landscape of 30 immune-related traits," Nature Genetics, Jun. 2019, 51(7):1082-1091, 15 pages.
Fang et al., "Ferroptosis as a target for protection against cardiomyopathy," Proc Natl Acad Sci USA, Feb. 2019, 116(7):2672-2680.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Faruqi et al., "High-throughput genotyping of single nucleotide polymorphisms with rolling circle amplification," BMC Genomics, Aug. 2001, 2:4, 10 pages.
Fehlmann et al., "cPAS-based sequencing on the BGISEQ-500 to explore small non-coding RNAs," Clin Epigenetics, Nov. 2016, 8:123, 11 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fluidigm, "Hyperion Imaging System: Visualize a new path forward," Feb. 2018, retrieved from URL <https://www.fluidigm.com/binaries/content/documents/fluidigm/search/hippo%3Aresultset/hyperion-imaging-system-br-400326/fluidigm%3Afile>, 27 pages.
Fluidigm, "Immuno-Oncology Research with the Hyperion Imaging System: A high-parameter imaging solution at subcellular resolution to characterize the immune repertoire in the tumor microenvironment," Apr. 2018, retrieved from URL <https://www.fluidigm.com/binaries/content/documents/fluidigm/search/hippo%3Aresultset/application-note-immuno-oncology-research-with-the-hyperion%E2%84%A2-imaging-system/fluidigm%3Afile>, 6 pages.
Fluidigm, "Immuno-Oncology Research with the Hyperion Imaging System: A high-parameter imaging solution at subcellular resolution to characterize the immune repertoire in the tumor microenvironment," Aug. 2018, retrieved from URL <https://www.fluidigm.com/binaries/content/documents/fluidigm/marketing/immuno-oncology-research-with-the-hyperion-imaging-system-appnote-400332/immuno-oncology-research-with-the-hyperion-imaging-system-appnote-400332/fluidigm%3Afile>, 6 pages.

(56) References Cited

OTHER PUBLICATIONS

Fluidigm, "Maxpar Antibodies for Imaging Mass Cytometry," Mar. 2018, retrieved from URL <https://www.fluidigm.com/binaries/content/documents/fluidigm/search/hippo%3Aresultset/hyperion-antibodies-for-imaging-mass-cytometry-br-101-7115/fluidigm%3Afile>, 2 pages.
Fodor et al., "Light-directed, spatially addressable parallel chemical synthesis," Science, 1995, 251(4995):767-773.
Forcucci et al., "All-plastic miniature fluorescence microscope for point-of-care readout of bead-based bioassays.," J. Biomed Opt., 2015, 20(10):105010, 15 pages.
Forster et al., "A human gut bacterial genome and culture collection for improved metagenomic analyses," Nature Biotechnology, 2019, 37(2):186-192.
Fredriksson et al., "Multiplexed protein detection by proximity ligation for cancer detection," Nature Methods, 4(4): 327-29, 2007.
Fredriksson et al., "Multiplexed proximity ligation assays to profile putative plasma biomarkers relevant to pancreatic and ovarian cancer," Clin. Chem., 5(3): 582-89, 2008.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Galleri.com [online], "Multi-cancer early detection through a simple blood draw," 2022, retrieved on Jan. 21, 2022, retrieved from URL<https://www.galleri.com/hcp/the-galleri-test>, 5 pages.
Galon et al., "The immune score as a new possible approach for the classification of cancer," J Transl Med., Jan. 2012, 10: 1, 4 pages.
Ganguli et al., "Pixelated spatial gene expression analysis from tissue," Nat Commun., Jan. 2018, 9(1):202, 9 pages.
Gans et al., "Inkjet Printing of Polymers: State of the Art and Future Developments," Advanced Materials, Feb. 2004, 16(3):203-213.
Gansauge et al., "Single-stranded DNA library preparation from highly degraded DNA using T4 DNA ligase," Nucleic Acids Res., Jun. 2017, 45(10):e79, 10 pages.
Gao et al., "A highly homogeneous expansion microscopy polymer composed of tetrahedron-like monomers," bioRxiv, Oct. 22, 2019, 23 pages (Preprint).
Gao et al., "Q&A: Expansion microscopy," BMC Biology, 15:50, 9 pages, 2017.
Gao et al., "Shaping Polarization of Tumor-Associated Macrophages in Cancer Immunotherapy," Frontiers in Immunology, Jun. 2022, 13:888713, 12 pages.
Gaucherand et al., "The Influenza A Virus Endoribonuclease PA-X Usurps Host mRNA Processing Machinery to Limit Host Gene Expression," Cell Reports, Apr. 2019, 27(3):776-792.
Genbank Accession No. AC009495.1, "*Homo sapiens* clone NH0490102, * Sequencing in Progress * , 12 unordered pieces," Aug. 24, 1999, 53 pages.
Genbank Accession No. AC009495.5, "*Homo sapiens* BAC clone RP11-49012 from 2, complete sequence," Apr. 21, 2005, 32 pages.
Genbank Accession No. AL445433.14, "Human DNA sequence from clone RP11-234N17 on chromosome 1, complete sequence," Jan. 24, 2013, 32 pages.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Genecards, "CA1 Gene—Carbonic Anhydrase 1," genecards.org, Nov. 9, 2022, retrieved from URL <genecards.org/cgi-bin/carddisp.pl?gene-CA1>, 30 pages.
Genecards, "ENSG00000227034," genecards.org, retrieved on Sep. 7, 2023, retrieved from URL <https://www.genecards.org/cgi-bin/carddisp.pl?gene=ENSG00000227034>, 13 pages.
Gerard et al., "Excess dNTPs minimize RNA hydrolysis during reverse transcription," Biotechniques, Nov. 2002, 33(5):984, 986, 988, 990.
Giacomello et al., "Spatially resolved transcriptome profiling in model plant species", Nature Plants 3, 17061, 11 pages, 2017.
Gibson-Corley et al., "Principles for valid histopathologic scoring in research," Vet Pathol., Nov. 2013, 50(6):1007-15.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Gilles et al., "Single nucleotide polymorphic discrimination by an electronic dot blot assay on semiconductor microchips," Nat Biotechnol, Apr. 1999, 17(4):365-70.
Glass et al., "SIMPLE: a sequential immunoperoxidase labeling and erasing method," J. Histochem. Cytochem., Oct. 2009, 57(10):899-905.
Gloor, "Gene targeting in *Drosophila,*" Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goh et al., "Highly Specific Multiplexed RNA Imaging In Tissues With Split-FISH," Nat Methods, Jun. 15, 2020, 17(7):689-693, 21 pages.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Goltsev et al., "Deep Profiling of Mouse Splenic Architecture with CODEX Multiplexed Imaging," Cell, 2018, 174(4):968-981.
Gong et al., "Secretory vimentin is associated with coronary artery disease in patients and induces atherogenesis in ApoE −/− mice," Int J Cardiol., May 2019, 283:9-16.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gotz et al., "Animal models of Alzheimer's disease and frontotemporal dementia," Nat Rev Neurosci., Jul. 2008, 9(7):532-44.
Gould et al., "Selective lysis of breast carcinomas by simultaneous stimulation of sodium channels and blockade of sodium pumps," Oncotarget, Feb. 2018, 9(21):15606-15615.
Gracia Villacampa et al., "Genome-wide Spatial Expression Profiling in FFPE Tissues," bioRxiv, 2020, p. 38 pages.
Gray et al., "A tail of translational regulation," Elife, Jun. 2017, 6:e29104, 4 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.

(56) References Cited

OTHER PUBLICATIONS

Guo et al., "The Role of Tumor-Infiltrating B Cells in Tumor Immunity," J. Oncol., Sep. 24, 2019, 2019:2592419, 10 pages.
Gupta et al., "Single-cell isoform RNA sequencing characterizes isoforms in thousands of cerebellar cells," Nature Biotechnol., Oct. 2018, 36:1197-1202.
Hadley et al., "Determining composition of micron-scale protein deposits in neurodegenerative disease by spatially targeted optical microproteomics," ELIFE, 2015, 4(e09579):21 pages.
Hadrup et al., "Parallel detection of antigen-specific T-cell responses by multidimensional encoding of MHC multimers," Nat. Methods., Jul. 2009, 6(7), 520-526.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Han et al., "3C and 3C-based techniques: the powerful tools for spatial genome organization deciphering", Molecular Cytogenetics (2018) 11: 21, 10 pages, 2018.
Han et al., "Isolation of intact bacteria from blood by selective cell lysis in a microfluidic porous silica monolith," Microsyst Nanoeng., Jun. 2019, 5:30, 11 pages.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4): 1939-1946.
Hernandez et al., "Solution-phase and solid-phase sequential, selective modification of side chains in KDYWEC and KDYWE as models for usage in single-molecule protein sequencing," New J Chem., Jan. 2017, 41(2):462-469.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Hipp et al., "A novel BCMA/CD3 bispecific T-cell engager for the treatment of multiple myeloma induces selective lysis in vitro and in vivo," Leukemia, Oct. 2017, 31(10):2278, 31 pages.
Hlubek et al., "Heterogeneous expression of Wnt/b-catenin target genes within colorectal cancer," 2007, Int. J. Cancer: 2017, 1941-1948.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoadley et al., "Cell-of-Origin Patterns Dominate the Molecular Classification of 10,000 Tumors from 33 Types of Cancer," Cell, Apr. 2018, 173(2):291-304, 21 pages.
Hobro et al., "An evaluation of fixation methods: Spatial and compositional cellular changes observed by Raman imaging," Vibrational Spectroscopy, Jul. 2017, 91:31-45.
Hoffman et al., "Formaldehyde crosslinking: a tool for the study of chromatin complexes," J Biol Chem., Oct. 2015, 290(44):26404-11.
Holmstrøm et al., "A highly sensitive and fast nonradioactive method for detection of polymerase chain reaction products," Anal Biochem, Mar. 1993, 209(2):278-83.
Hou et al., "NDUFABI confers cardio-protection by enhancing mitochondrial bioenergetics through coordination of respiratory complex and supercomplex assembly," Cell Res., Sep. 2019, 29(9):754-766.
Howell et al., "iFRET: An Improved Fluorescence System for DNA-Melting Analysis," Genome Research, 2002, 12:1401-1407.
Hoyer et al., "Electrostatic spraying: a novel technique for preparation of polymer coatings on electrodes," Anal Chem, Nov. 1996, 68(21):3840-4.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1): 121-4.
Hua et al., "Multi-level transcriptome sequencing identifies COL 1Al as a candidate marker in human heart failure progression," BMC Med., Jan. 2020, 18(1):2, 16 pages.
Hughes et al., "Highly Efficient, Massively-Parallel Single-Cell RNA-Seq Reveals Cellular States and Molecular Features of Human Skin Pathology," bioRxiv, Jul. 2019, 51 pages.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Im et al., "An Introduction to Performing Immunofluorescence Staining," Biobanking: Methods and Protocols, Method in Molecular Biology, Yong (ed.), 2019, 1897, Chapter 26, 299-311.
Inoue and Wittbrodt, "One for All—A Highly Efficient and Versatile Method for Fluorescent Immunostaining in Fish Embryos," PLoS One 6, e19713, 2011.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Ji et al., "Multimodal Analysis of Composition and Spatial Architecture in Human Squamous Cell Carcinoma," Cell, Jul. 2020, 182(2):497-514.e22.
Joos et al., "Covalent attachment of hybridizable oligonucleotides to glass supports," Anal Biochem., Apr. 1997, 247(1):96-101.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.

(56) References Cited

OTHER PUBLICATIONS

Kandoth et al., "Mutational landscape and significance across 12 major cancer types," Nature, Oct. 2013, 502(7471):333-339, 20 pages.
Kansal et al., "The use of cerebrospinal fluid and neuropathologic studies in neuropsychiatry practice and research," Psychiatr Clin North Am., Jun. 2015, 38(2):309-22.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kashyap et al., "Selective local lysis and sampling of live cells for nucleic acid analysis using a microfluidic probe," Sci Rep., Jul. 2016, 6:29579, 10 pages.
Kawachi et al., "Tumor-associated CD204 + M2 macrophages are unfavorable prognostic indicators in uterine cervical adenocarcinoma," Cancer Sci., Mar. 2018, 109(3):863-870.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kim et al., "Microarray Analysis in Pulmonary Hypertensive Rat Heart after Simvastatin Treatment," The Ewha Medical Journal, Jul. 31, 2018, 41(3), 53-62.
Kirby et al., "Cryptic plasmids of *Mycobacterium avium:* Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Koch et al., "Photochemical immobilization of anthraquinone conjugated oligonucleotides and PCR amplicons on solid surfaces," Bioconjugate Chem., Jul. 2000, 11(4):474-483.
Kokkat et al., "Archived formalin-fixed paraffin-embedded (FFPE) blocks: A valuable underexploited resource for extraction of DNA, RNA, and protein," Apr. 2013, 11(2):101-6.
Kolbert et al., "Ribosomal DNA sequencing as a tool for identification of bacterial pathogens," Curr Opin Microbiol, Jun. 1999, 2(3):299-305.
Kolovos et al., "Investigation of the spatial structure and interactions of the genome at sub-kilobasepair resolution using T2C," Nat. Protoc., 2018, 13:459-477.
Korbel et al., "Paired-end mapping reveals extensive structural variation in the human genome," Science, 2007, 318(5849):420-426.
Korlach et al., "Selective aluminum passivation for targeted immobilization of single DNA polymerase molecules in zero-mode waveguide nanostructures," Proc. Natl. Acad. Sci. USA, 2008, 105:1176-1181.
Kourou et al., "Machine learning applications in cancer prognosis and prediction," Computational and Structural Biotechnology Journal, Jan. 2015, 13:8-17.
Kozlov et al., "A highly scalable peptide-based assay system for proteomics," PloS ONE, 2012, 7(6): e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kuhn et al., "A novel, high-performance random array platform for quantitative gene expression profiling," Genome Res, 2004, 14:2347-2356.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
LaFerla et al., "Animal models of Alzheimer disease," Cold Spring Harb Perspect Med., Nov. 2012, 2(11):a006320, 14 pages.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Lamture et al., "Direct detection of nucleic acid hybridization on the surface of a charge coupled device," Nucleic Acid Res., Jun. 1994, 22(11):2121-5.
Landegren et al., "A Ligase-Mediated Gene Detection Technique," Science, 1988, 241(4869):1077-1080.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Autoantigen discovery with a synthetic human peptidome," Nature Biotechnology, May 2011, 29(6):535-541.
Larman et al., "Sensitive, multiplex and direct quantification of RNA sequences using a modified RASL assay," Nucleic Acids Research, 2014, 42(14):9146-9157.
Lassmann et al., A Novel Approach for Reliable Microarray Analysis of Microdissected Tumor Cells From Formalin-Fixed and Paraffin-Embedded Colorectal Cancer Resection Specimens, J Mol Med, 87, 211-224, 2009.
Lee et al., "A novel COL3A1 gene mutation in patient with aortic dissected aneurysm and cervical artery dissections," Heart Vessels, Mar. 2008, 23(2):144-8.
Lee et al., "Assembly of metallic nanoparticle arrays on glass via nanoimprinting and thin-film dewetting," Beilstein J Nanotechnol., May 2017, 8:1049-1055.
Lee et al., "Cytokines in cancer immunotherapy," Cancers (Basel), Oct. 2011, 3(4):3856-3893.
Lee et al., "Fluorescent in situ sequencing (FISSEQ) of RNA for gene expression profiling in intact cells and tissues," Nature Protocols, 2015, 10(3):442-458.
Lee et al., "Highly multiplexed subcellular RNA sequencing in situ", Science, 2014, 343(6177):1360-1363.
Lee et al., "Improving the efficiency of genomic loci capture using oligonucleotide arrays for high throughput resequencing," BMC Genomics, Dec. 2009, 10:646, 12 pages.
Lein et al., "The promise of spatial transcriptomics for neuroscience in the era of molecular cell typing", Science 358, 64-69, 2017.
Leriche et al., "Cleavable linkers in chemical biology," Bioorganic & Medicinal Chemistry, 2012, 20:571-582.
Levene et al., "Zero-Mode Waveguides for Single-Molecule Analysis at High Concentrations," Science, 2003, 299:682-686.
Lewczuk et al., "Cerebrospinal fluid and blood biomarkers for neurodegenerative dementias: An update of the Consensus of the Task Force on Biological Markers in Psychiatry of the World

(56) References Cited

OTHER PUBLICATIONS

Federation of Societies of Biological Psychiatry," World J Biol Psychiatry, Jun. 2018, 19(4):244-328.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "DNA molecules and configurations in a solid-state nanopore microscope," Nat Mater., Sep. 2003, 2(9):611-5.
Li et al., "Long non-coding RNA linc00645 promotes TGF-β-induced epithelial-mesenchymal transition by regulating miR-205-3p-ZEB1 axis in glioma," Cell Death Dis, Sep. 2019, 10(10):717, 17 pages.
Li et al., "Methylation extends the reach of liquid biopsy in cancer detection," Nat Rev Clin Oncol., Nov. 2020, 17(11):655-656.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Li et al., "RNase H-dependent PCR-enabled T-cell receptor sequencing for highly speci!c and ef!cient targeted sequencing of T-cell receptor mRNA for single-cell and repertoire analysis," Nature Protocols, Aug. 2019, 14:2571-2594.
Lin et al., "Highly multiplexed imaging of single cells using a high-throughput cyclic immunofluorescence method," Nat Commun., Sep. 2015, 6:8390, 7 pages.
Lin et al., "Histopathological assessment of inflammation and expression of inflammatory markers in patients with ketamine-induced cystitis," Mol Med Rep., Apr. 2015, 11(4):2421-2428.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Locke et al., "DNA Methylation Cancer Biomarkers: Translation to the Clinic," Front Genet., Nov. 2019, 10:1150, 22 pages.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lu et al., "A microfluidic electroporation device for cell lysis," Lab Chip., Jan. 2005, 5(1):23-29.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lundquist et al., "Parallel confocal detection of single molecules in real time," Opt. Lett., 2008, 33:1026-1028.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Macosko et al., "Highly Parallel Genome-wide Expression Profiling of Individual Cells Using Nanoliter Droplets," Cell, 2015, 161:1202-1214.
Magaki et al., "An introduction to Performance of Immunohistochemistry," Biobanking: Methods and Protocols, Method in Molecular Biology, Yong (ed.), 2019, 1897, Chapter 25, 289-298.
Mamedov et al., "Preparing unbiased T-cell receptor and antibody cDNA libraries for the deep next generation sequencing profiling," Frontiers in Immunol., Dec. 23, 2013, 4(456):1-10.
Maniatis et al., "Spatiotemporal Dynamics of Molecular Pathology in Amyotrophic Lateral Sclerosis," bioRxiv, Science, 2018, 364(6435), 54 pages.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
Matias et al., "Microglia-glioblastoma interactions: New role for Wnt signaling," Biochim Biophys Acta Rev Cancer, Aug. 2017, 1868(1):333-340.
May, "Catching cancer extremely early," Science, Mar. 2021, 8 pages.
McCloskey et al., "Encoding PCR products with batch-stamps and barcodes," Biochem. Genet., 2007, 45(11-12):761-767.
McKernan et al., "Sequence and structural variation in a human genome uncovered by short-read, massively parallel ligation sequencing using two-base encoding," Genome Res., 19: 1527-41, 2009.
Meers et al., "Improved CUT&RUN chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.

(56) References Cited

OTHER PUBLICATIONS

Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mitra et al., "Fluorescent in situ sequencing on polymerase colonies," Anal Biochem, Sep. 2003, 320(1):55-65.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mlecinik et al., "Histopathologic-based prognostic factors of colorectal cancers are associated with the state of the local immune reaction," J Clin Oncol., Feb. 2011, 29(6):610-8.
Moffitt et al., "RNA Imaging with Multiplexed Error-Robust Fluorescence In Situ Hybridization (MERFISH)," Methods Enzymol., 2016, 572:1-49.
Mohsen et al., "The Discovery of Rolling Circle Amplification and Rolling Circle Transcription," Acc Chem Res., Nov. 15, 2016, 49(11):2540-2550, 25 pages.
Moncada et al., "Building a tumor atlas: integrating single-cell RNA-Seq data with spatial transcriptomics in pancreatic ductal adenocarcinoma", Institute for Computational Medicine, bioRxiv, 28 pages, 2018.
Moor et al., "Spatial transcriptomics: paving the way for tissue-level systems biology", Science Direct, Current Opinion in Biotechnology, 46: 126-133, 2017.
Morlan et al., "Selective depletion of rRNA enables whole transcriptome profiling of archival fixed tissue," PLoS One, Aug. 2012, 7(8):e42882, 8 pages.
Mortazavi et al., "Mapping and quantifying mammalian transcriptomes by RNA-Seq," Nature Methods, 5(7): 621-8, 2008.
Moshrefzadeh et al., "Nonuniform photobleaching of dyed polymers for optical waveguides," Applied Physics Letters, 1993, 62:16-18.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nagahara et al., "Neuroprotective effects of brain-derived neurotrophic factor in rodent and primate models of Alzheimer's disease," Nat Med., Mar. 2009, 15(3):331-337.
Nakagawa et al., "Significance of the inflammation-based prognostic score in recurrent pancreatic cancer," Pancreatology, Jul. 2019, 19(5):722-728.
Nakao et al., "Myosin heavy chain gene expression in human heart failure," J Clin Invest., Nov. 1997, 100(9):2362-70.
Nallur et al., "Signal amplification by rolling circle amplification on DNA microarrays," Nucleic Acids Res., Dec. 1, 2001, 29(23):e118, 9 pages.
Nam et al., "Nanoparticle-Based Bio-Bar Codes for the Ultrasensitive Detection of Proteins," Science, Sep. 26, 2003, 301(5641):1884-1886.
Nam et al., "Somatic mutations and cell identity linked by Genotyping of Transcriptomes," Nature, Jul. 2019, 571(7765):355-360.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Nassiri et al., "Detection and discrimination of intracranial tumors using plasma cell-free DNA methylomes," Nat Med., Jul. 2020, 26(7):1044-1047.
NCBI Database, Search result of NCBI nucleotide database at URL <ncbi.nlm.nih.gov/nuccore/?term=a1445433.1> for AL44533.1, NIH, National Library of Medicine, retrieved on Sep. 7, 2023, 1 page.
NCBI Gene ID: 101927056, "LINC02614 long intergenic non-protein coding RNA 2614 [ *Homo sapiens* (human) ]," Last Updated on Nov. 23, 2021, 6 pages.
NCBI Gene ID: 101927740, "LINC02202 long intergenic non-protein coding RNA 2202 *Homo sapiens* (human)," Last Updated on Nov. 23, 2021, 5 pages.
NCBI Gene ID: 225689, "MAPK15 mitogen-activated protein kinase 15 [ *Homo sapiens* (human) ]," Last Updated on Nov. 25, 2021, 11 pages.
NCBI Gene ID: 2709, "GJB5 gap junction protein beta 5 [ *Homo sapiens* (human) ]," Last Updated on Nov. 23, 2021, 8 pages.
NCBI Gene ID: 286133, "SCARA5 scavenger receptor class A member 5 [ *Homo sapiens* (human) ]," Last Updated on Nov. 23, 2021, 9 pages.
NCBI Gene ID: 2921, "CXCL3 C-X-C motif chemokine ligand 3 [ *Homo sapiens* (human) ]," Last Updated on Nov. 23, 2021, 8 pages.
NCBI Gene ID: 3047, "HBG1 hemoglobin subunit gamma 1 [ *Homo sapiens* (human) ]," Last Updated on Nov. 28, 2021, 9 pages.
NCBI Gene ID: 369, "ARAF A-Raf proto-oncogene, serine/threonine kinase [ *Homo sapiens* (human) ]," Last Updated on Nov. 25, 2021, 13 pages.
NCBI Gene ID: 4321, "MMP12 matrix metallopeptidase 12 [ *Homo sapiens* (human) ]," Last Updated on Nov. 23, 2021, 10 pages.
NCBI Gene ID: 5648, "MASP1 MBL associated serine protease 1 [ *Homo sapiens* (human) ]," Last Updated on Nov. 28, 2021, 16 pages.
NCBI Gene ID: 692109, "SNORD69 small nucleolar RNA, C/D box 69 [ *Homo sapiens* (human) ]," Last Updated on Nov. 23, 2021, 5 pages.
NCBI Gene ID: 759, "CA1 carbonic anhydrase 1 [ *Homo sapiens* (human) ]," Last Updated on Nov. 23, 2021, 12 pages.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmi p/>, retrieved on Jun. 16, 2021, retrieved from URL<https://www.ncbi.nlm.nih.gov/probe/docs/techmip/>, 2 pages.
Neb.com [online], "*E. coli* Poly(A) Polymerase," 2022, retrieved on Aug. 4, 2022, retrieved from URL<https://www.neb.com/products/m0276-ecoli-poly-a-polymerase#Product%20Information>, 5 pages.
Nederlof et al., "Comprehensive evaluation of methods to assess overall and cell-specific immune infiltrates in breast cancer," Breast Cancer Res, Dec. 2019, 21(1):151, 13 pages.
Newman et al., "Robust enumeration of cell subsets from tissue expression profiles," Nature Methods, May 2015, 12(5):453-457.
Ng et al., "Gene identification signature (GIS) analysis for transcriptome characterization and genome annotation," Nature Methods, 2005, 2(2):105-111.
Ng et al., "Massively parallel sequencing and rare disease," Human Malec. Genetics, 19(2): R119-R124, 2010.
Ng et al., "Multiplex sequencing of paired-end ditags (MS-PET): a strategy for the ultra-high-throughput analysis of transcriptomes and genomes," Nucleic Acids Research, Jul. 2006, 34(12): e84, 10 pages.
Nguyen et al., "Two-photon polymerization for biological applications," Materials Today, Jul. 2017, 20(6):314-322.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
NIH National Cancer Institute, "Tumor Markers in Common Use," cancer.gov, reviewed May 11, 2021, retrieved on Jun. 2, 2023, retrieved from URL <https://www.cancer.gov/about-cancer/diagnosis-staging/diagnosis/tumor-markers-list>, 12 pages.

(56) References Cited

OTHER PUBLICATIONS

Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
nist.gov, "Researchers Fully Sequence the Y Chromosome for the First Time," National Institute of Standards and Technology, Aug. 23, 2023, retrieved on Feb. 1, 2024, retrieved from URL <https://www.nist.gov/news-events/news/2023/08/researchers-fully-sequence-y-chromosome-first-time>, pp. 1-4.
Nowak, "Entering the Postgenome Era," Science, 1995, 270(5235):368-71.
Nuzzo et al., "Detection of renal cell carcinoma using plasma and urine cell-free DNA methylomes," Nat Med., Jul. 2020, 26(7):1041-1043.
Ohtsubo et al., "Bacterial insertion sequences," Curr Top Microbiol Immunol., 1996, 204:1-26.
Oksuz et al., "Systematic evaluation of chromosome conformation capture assays," Nature Methods, Sep. 2021, 18:1046-1055.
Olivier, "The Invader assay for SNP genotyping," Mutat. Res., Jun. 2005, 573(1-2):103-110.
Oren et al., "Selective lysis of bacteria but not mammalian cells by diastereomers of melittin: structure-function study," Biochemistry, Feb. 1997, 36(7):1826-35.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Park et al., "The Estimation of Breast Cancer Disease-Probability by Difference of Individual Susceptibility," Cancer Res. Treat., Feb. 2003, 35(1):35-51, Abstract.
Passow et al., "RNAlater and flash freezing storage methods nonrandomly influence observed gene expression in RNAseq experiments," bioRxiv, Jul. 2018, 28 pages.
Paterson et al., "Cerebrospinal fluid in the differential diagnosis of Alzheimer's disease: clinical utility of an extended panel of biomarkers in a specialist cognitive clinic," Alzheimers Res Ther., Mar. 2018, 10(1):32, 11 pages.
Pathak et al., "Present and Future Prospect of Small Molecule & Related Targeted Therapy Against Human Cancer," Vivechan Int J Res., 2018, 9(1):36-49.
PCT International Preliminary Report on Patentability in International Appln. No. PCT/US2020/035337, dated Nov. 16, 2021, 9 pages.
PCT International Search Report and Written Opinion in International Appln. No. PCT/US2020/035337, dated Aug. 11, 2020, 11 pages.
Pellegrino et al., "High-throughput Single-cell DNA Sequencing of Acut Myeloid Leukemia Tumors with Droplet Microfluidics," Genome Research, Aug. 7, 2018, 28(9):1345-1352.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gene," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Piek et al., "Novel heart failure biomarkers: why do we fail to exploit their potential?," Critical Reviews in Clinical Laboratory Sciences, Jun. 2018, 55(4):246-263.
Piepenburg et al., "DNA detection using recombination proteins," PLoS Biol., Jul. 2006, 4(7):e204, 7 pages.
Pilewskie et al., "Margins in breast cancer: How much is enough?," Cancer, Apr. 2018, 124(7):1335-1341.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Rajeswari et al., "Multiple pathogen biomarker detection using an encoded bead array in droplet PCR," J. Microbial Methods, Aug. 2017, 139:22-28.
Ranki et al., "Sandwich hybridization as a convenient method for the detection of nucleic acids in crude samples," Gene, 1983, 21(1-2):77-85.
Rao et al., "Spontaneous development of Alzheimer's disease-associated brain pathology in a Shugoshin-1 mouse cohesinopathy model," Aging Cell, Aug. 2018, 17(4):e12797, 11 pages.
Redmond et al., "Single-cell TCRseq: paired recovery of entire T-cell alpha and beta chain transcripts in T-cell receptors from single-cell RNAseq," Genome Med, 2016, 8:80, 12 pages.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ripoli et al., "A Comparison of Fresh Frozen vs. Formalin-Fixed, Paraffin-Embedded Specimens of Canine Mammary Tumors via Branched-DNA Assay," Int. J. Mol. Sci., May 2016, 17(5):724, 11 pages.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.

(56) References Cited

OTHER PUBLICATIONS

Rogers et al., "Immobilization of oligonucleotides onto a glass support via disulfide bonds: A method for preparation of DNA microarrays," Anal Biochem., Jan. 1999, 266(1):23-30.
Rogers et al., "Use of a novel cross-linking method to modify adenovirus tropism," Gene Ther., Dec. 1997, 4(12):1387-92.
Rohland et al., "Partial uracil-DNA-glycosylase treatment for screening of ancient DNA," Phil. Trans. R. Soc. B, Jan. 19, 2015, 370(1660): 20130624, 11 pages.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Rubin et al., "Whole-genome resequencing reveals loci under selection during chicken domestication.," Nature, Mar. 2010, 464: 587-591.
Running et al., "A procedure for productive coupling of synthetic oligonucleotides to polystyrene microtiter wells for hybridization capture," Biotechniques, Mar. 1990, 8(3):276-279.
Salmén et al., "Barcoded solid-phase RNA capture for Spatial Transcriptomics profiling in mammalian tissue sections," Nature Protocols, Oct. 2018, 13(11):2501-2534.
Salmen et al., "Multidimensional transcriptomics provides detailed information about immune cell distribution and identity in HER2+ breast tumors," bioRxiv, 2018, 41 pages.
Sanchez-Vega et al., "Oncogenic Signaling Pathways in the Cancer Genome Atlas," Cell, Apr. 2018, 173(2):321-337.e10, 28 pages.
Sasagawa et al., "Comparative Transcriptome Analysis Identifies CCDC80 as a Novel Gene Associated with Pulmonary Arterial Hypertension," Front Pharmacol., Jun. 2016, 7:142, 13 pages.
Satija et al., "Spatial reconstruction of single-cell gene expression data," Nature, Apr. 13, 2015, 33(5):495-402, 14 pages.
Saxonov et al., "10x Genomics, Mastering Biology to Advance Human Health," PowerPoint, 10x, 2020, 41 pages.
Scheideler et al., "Recapitulating complex biological signaling environments using a multiplexed, DNA-patterning approach," Sci. Adv., 2020, 6:eay5696.
Schellings et al., "Absence of SPARC results in increased cardiac rupture and dysfunction after acute myocardial infarction," J Exp Med., Jan. 2009, 206(1):113-23.
Schena et al., "Quantitative monitoring of gene expression patterns with a complementary DNA microarray," Science, Oct. 1995, 270(5235):467-470.
Schmidl et al., "ChIPmentation: fast, robust, low-input ChIP-seq for histones and transcription factors," Nature Methods, Oct. 2015, 12:963-965.
Schmidt et al., "Cerebrospinal fluid melanin-concentrating hormone (MCH) and hypocretin-1 (HCRT-1, orexin-A) in Alzheimer's disease," PloS one, May 2013, 8(5):e63136, 6 pages.
Schmitt et al., "Detection of ultra-rare mutations by next-generation sequencing," PNAS (2012) 109:14508-14523.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Segaliny et al., "Functional TCR T cell screening using single-cell droplet microfluidics†," Lab Chip, 2018, 3733-3749.
Sergeeva et al., "Display technologies: Application for the discovery of drug and gene delivery agents," Advanced Drug Delivery Reviews, 2006, 58(15):1622-1654.
Shalon et al., "A DNA microarray system for analyzing complex DNA samples using two-color fluorescent probe hybridization," Genome Res., Jul. 1996, 6(7):639-45.
Sharma, "Self-Assembly of Colloidal Particles," Resonance, 2018, 23:263-275.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Sheth et al., "Spatial metagenomic characterization of microbial biogeography in the gut," Nature Biotechnology, Aug. 2019, 37:877-883.
Shi, "Enabling large-scale pharmacogenetic studies by high-throughput mutation detection and genotyping technologies," Clin. Chem., Feb. 2001, 47(2):164-172.
Shoemaker et al., "Quantitative phenotypic analysis of yeast deletion mutants using a highly parallel molecular bar-coding strategy," Nature genetics (1996) 14:450-456.
Sievertzon et al., "Transcriptome analysis in primary neural stem cells using a tag cDNA amplification method," BMC Neuroscience, Dec. 2005, 6: 28.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Slomovic et al., "Addition of poly(A) and poly(A)-rich tails during RNA degradation in the cytoplasm of human cells," Proc Natl Acad Sci USA, Apr. 2010, 107(16):7407-12.
Smejkal et al., "Microfluidic isotachophoresis: a review," Electrophoresis, Jun. 2013, 34(11):1493-1509.
Smolock et al., "Ribosomal Protein L17, RpL 17, is an Inhibitor of Vascular Smooth Muscle Growth and Carotid Intima Formation," Circulation, Nov. 2012, 126(20):2418-2427.
Söderberg et al., "Characterizing proteins and their interactions in cells and tissues using the in situ proximity ligation assay," Methods, Jul. 2008, 45(3):227-32.
Soen et al., "Detection and Characterization of Cellular Immune Responses Using Peptide-MHC Microarrays," PLOS Biology, Dec. 22, 2003, 1(3):429-438.
Soni and Meller, "Progress toward ultrafast DNA sequencing using solid-state nanopores," Clin Chem., 2007, 53:1996-2001.
Sorensen et al., "Tumour-associated microglia/macrophages predict poor prognosis in high-grade gliomas and correlate with an aggressive tumour subtype," Neuropathology and Applied Neurobiology, Feb. 2018, 44:185-206.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stanton et al., "Altered patterns of gene expression in response to myocardial infarction," Circulation research, May 12, 2000, 86(9), 939-945.

(56) References Cited

OTHER PUBLICATIONS

Steponaitis et al., "High CHI3L 1 expression is associated with glioma patient survival," Diagnostic Pathology, Apr. 27, 2016, 11(42):1-8.
Stevens Jr. et al., "Enhancement of phosphoprotein analysis using a fluorescent affinity tag and mass spectrometry," Rapid Commun Mass Spectrom, 2005, 19(15):2157-62.
Stewart et al., "Spatially-resolved quantification of proteins in triple negative breast cancers reveals differences in the immune microenvironment associated with prognosis," Sci Rep., Apr. 2020, 10(1):6598, 8 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Su et al., "Restriction enzyme selection dictates detection range sensitivity in chromatin conformation capture-based variant-to-gene mapping approaches," bioRxiv, Dec. 15, 2020, 22 pages.
Subramanian et al., "Gene set enrichment analysis: a knowledge-based approach for interpreting genome-wide expression profiles," PNAS, Oct. 2005, 102(43):15545-15550.
Sumida et al., "Complement C1q-induced activation of β-catenin signalling causes hypertensive arterial remodelling," Nat Commun., Feb. 2015, 6:6241, 12 pages.
Sun et al., "Statistical Analysis of Spatial Expression Pattern for Spatially Resolved Transcriptomic Studies," Nature Methods, Jan. 27, 2020, 17(2): 193-200.
Sutherland et al., "Utility of formaldehyde cross-linking and mass spectrometry in the study of protein-protein interactions," J. Mass Spectrom., Jun. 2008, 43(6):699-715.
Svensson et al., "SpatialDE: identification of spatially variable genes," Nature Methods, May 2018, 15:343-346, 15 pages.
Takei et al., "Integrated Spatial Genomics Reveals Global Architecture of Single Nuclei," Nature, Jan. 27, 2021, 590(7845):344-350, 53 pages.
Tan et al., "Parylene peel-off arrays to probe the role of cell-cell interactions in tumour angiogenesis," Integr Biol (Camb), Oct. 2009, 1(10):587-594.
Taylor et al., "Mitochondrial DNA mutations in human disease," Nature Reviews Genetics, May 2005, 6(5):389-402.
Tegtmeyer et al., "Alternative Interactions of the SV40 A Protein with DNA," Virology, 1981, 115:75-87.
Tentori et al., "Detection of Isoforms Differing by a Single Charge Unit in Individual Cells," Chem. Int. Ed., 2016, 55(40):12431-5.
Thi Be Tu et al., "The serum/PDGF-dependent "melanogenic" role of the minute level of the oncogenic kinase PAK1 in melanoma cells proven by the highly sensitive kinase assay," Drug Discov Ther., Jan. 2017, 10(6):314-322.
Thorsson et al., "The Immune Landscape of Cancer," Immunity, Apr. 2018, 48(4):812-830, 37 pages.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tilstam et al., "MIF family cytokines in cardiovascular diseases and prospects for precision-based therapeutics," Expert Opin Ther Targets, Jul. 2017, 21(7):671-683.
Timofeev et al., "Regioselective immobilization of short oligonucleotides to acrylic copolymer gels," Nucleic Acids Res., Aug. 1996, 24(16):3142-8.
Tolbert et al., "New methods for proteomic research: preparation of proteins with N-terminal cysteines for labeling and conjugation," Angewandte Chemie International Edition, Jun. 2002, 41(12):2171-4.
Tomita et al., "Attention-Based Deep Neural Networks for Detection of Cancerous and Precancerous Esophagus Tissue on Histopathological Slides," JAMA Network Open. Nov. 6, 2019, 2(11): e1914645, 13 pages.
Toss et al., "Breast conservation in ductal carcinoma in situ (DCIS): what defines optimal margins?," Histopathology, Apr. 2017, 70(5):681-692.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Useast.ensenbl.org, [online], "Ensembl Gene ID: ENSG00000227034," May 2021, retrieved on Dec. 8, 2021, retrieved from URL<https://useast.ensembl.org/Homo_sapiens/Gene/Summary?db=core;g=ENSG00000227034;r=1:99008218-99008474;t=ENST00000457507>, 2 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Varma et al., "Abstract 13455: Translational Control of Y-Box Binding Protein 1 (Yb-1) During Pathological Cardiac Hypertrophy," Circulation, Nov. 2018, 138:A13455, 5 pages, Abstract.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Verywell Health, "A Timeline of COVID-19 Variants," Team Verywell Health, Dec. 19, 2023, pp. 1-12.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Wade et al., "Genome sequence, comparative analysis, and population genetics of the domestic horse.," Science., 326: 865-7, 2009.

(56) References Cited

OTHER PUBLICATIONS

Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Mutations in NEXN, a Z-disc gene, are associated with hypertrophic cardiomyopathy," Am J Hum Genet., Nov. 2010, 87(5):687-93.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang et al., "Three-dimensional intact-tissue sequencing of single-cell transcriptional states," Science, Jul. 2018, 361(6400):eaat5691, 22 pages.
Wang, "RNA amplification for successful gene profiling analysis," J Transl Med., Jul. 2005, 3:28, 11 pages.
Waxman et al., "De-regulation of common housekeeping genes in hepatocellular carcinoma," BMC Genomics, Jul. 18, 2007, 8:243, pp. 1-9.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Willi-Monnerat et al., "Comprehensive spatiotemporal transcriptomic analyses of the ganglionic eminences demonstrate the uniqueness of its caudal subdivision," Molecular and Cellular Nueorsciences 37: 845-856, 2008.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Xiao et al., "Direct determination of haplotypes from single DNA molecules," Nature Methods, 2009, 6(3):199-01.
Yamauchi et al., "Subcellular western blotting of single cells," Microsyst Nanoeng., 2017, 3:16079, 9 pages.
Yan et al., "Decorin gene delivery inhibits cardiac fibrosis in spontaneously hypertensive rats by modulation of transforming growth factor-beta/Smad and p38 mitogen-activated protein kinase signaling pathways," Hum Gene Ther., Oct. 2009, 20(10):1190-200.
Yang et al., "The role of tumor-associated macrophages in breast carcinoma invasion and metastasis," Int J Clin Exp Pathol., Jun. 2015, 8(6):6656-64.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Ye et al., "Triggered self-assembly of magnetic nanoparticles," Sci Rep., Mar. 2016, 6:23145, 9 pages.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yet et al., "Cardiac-specific expression of heme oxygenase-1 protects against ischemia and reperfusion injury in transgenic mice," Circ Res., Jul. 2001, 89(2):168-73.
Yin et al., "Genetically encoded short peptide tag for versatile protein labeling by Sfp phosphopantetheinyl transferase," PNAS, 2005, 102(44):15815-20.
Yoosuf et al., "Identification and transfer of spatial transcriptomics signatures for cancer diagnosis," Breast Cancer Res., Jan. 2020, 22(1):6, 10 pages.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Long Non-Coding RNA and Breast Cancer," Technol Cancer Res Treat., Jan. 2019, 18:1-10.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhang et al., "Prognostic Significance of Tumor-Infiltrating Natural Killer Cells in Solid Tumors: A Systematic Review and Meta-Analysis," Front. Immunol. Jul. 2, 2020, 11:1242, 11 pages.
Zhang et al., "Single-base mutational analysis of cancer and genetic diseases using membrane bound modified oligonucleotides," Nucleic Acids Res., Jul. 1991, 19(14):3929-33.
Zhang et al., "Stripping custom microRNA microarrays and the lessons learned about probe-slide interactions," Anal Biochem., Mar. 2009, 386(2):222-7.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Analysis of the expression profile of Dickkopf-1 gene in human glioma and the associate with tumor malignancy," Journal of Experimental & Clinical Cancer Research, Oct. 28, 2010, 29(138):1-7.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.

(56) References Cited

OTHER PUBLICATIONS

Zilberman et al., “Genome-wide analysis of DNA methylation patterns,” Development (2007) 134: 3959-3965.
Zlobec et al., “Next-generation tissue microarray (ngTMA) increases the quality of biomarker studies: an example using CD3, CD8, and CD45RO in the tumor microenvironment of six different solid tumor types,” Journal of Translational Medicine, 2013 11(104):1-7.
10xGenomics.com, [online], “Visium Spatial Gene Expression Reagent Kits—User Guide,” Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.
Jonczyk et al., “Living cell microarrays: An overview of concepts,” Microarrays, 2016, 5(11):1-29.
Lemire et al., “Alkaline hydrolysis to remove potentially infectious viral RNA contaminants from DNA,” Virology Journal, 2016, 13:88, 12 pages.
Loessner et al., “Hydrogel microwell arrays allow the assessment of protease-associated enhancement of cancer cell aggregation and survival,” Microarrays, 2013, 2:208-227.

* cited by examiner

FIG. 22E
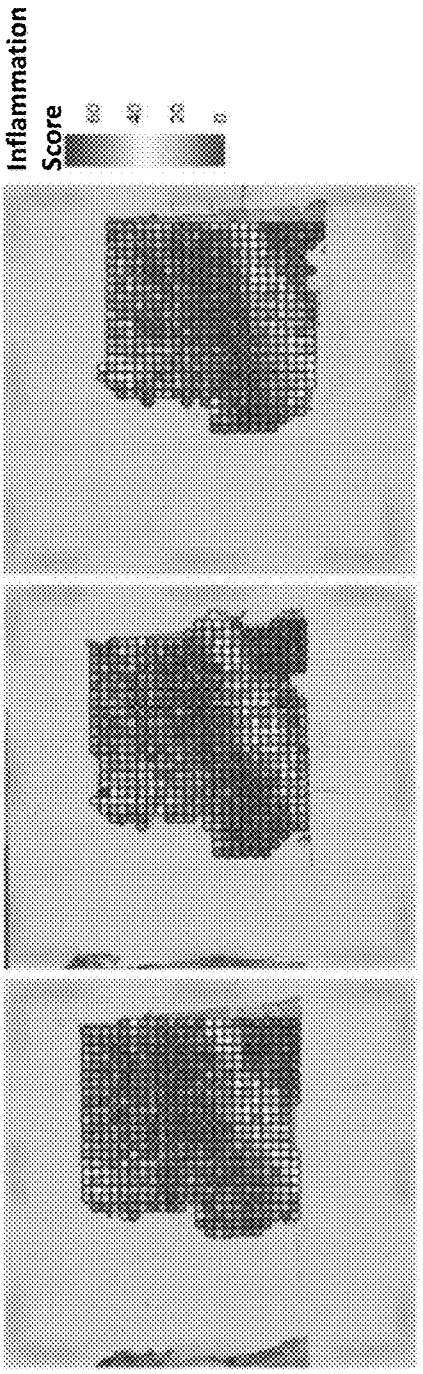
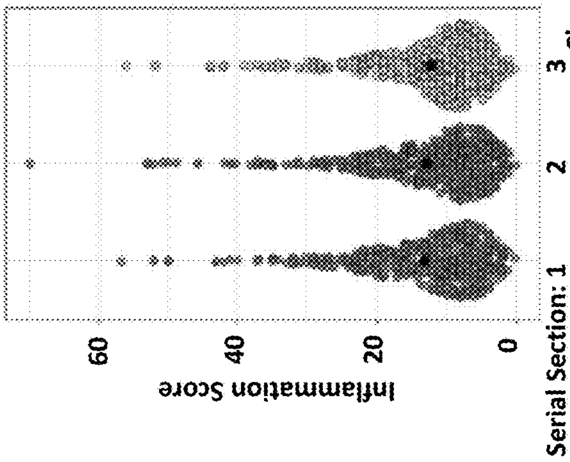
FIG. 22F
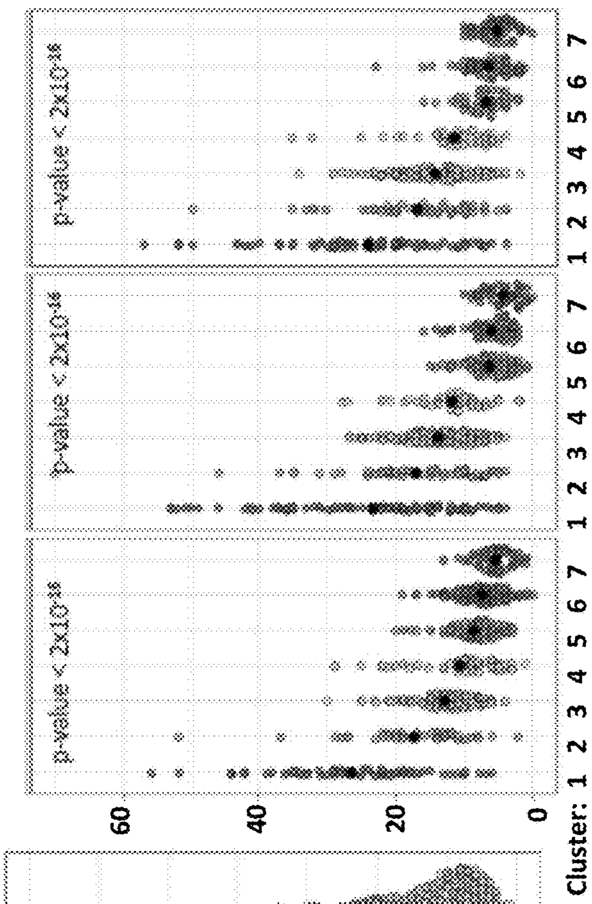
FIG. 22G

METHODS OF DETECTING SPATIAL HETEROGENEITY OF A BIOLOGICAL SAMPLE

CROSS-REFERENCE TO RELATED APPLICATIONS

This application is a divisional of U.S. application Ser. No. 17/538,406, filed Nov. 30, 2021, which is a continuation of International Application PCT/US2020/035337, with an international filing date of May 30, 2019, which claims priority to U.S. Provisional Patent Application No. 62/854,959, filed May 30, 2019, which is incorporated by reference in its entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

Correlating the location of one or more analytes to a location of a biological sample can help aid in identification of the cellular types and cellular structures in the sample. This becomes important in the setting of various cancer samples, where a sample includes certain regions of cellular and genetic heterogeneity compared to other regions of a tissue. In the United States approximately 22,000 women receive a new diagnosis and 14,000 women die from ovarian cancer (OC) each year, making the disease the fifth most deadly cancer among women. Like many cancers, OC can be genetically heterogeneous making studies difficult to plan, execute, and interpret. Bulk methods such as whole-genome and whole-transcriptome sequencing are limited in their ability to resolve fine grain molecular signatures which limit their utility in dissecting the underlying biology of individual tumors.

Understanding the regions of cellular and genetic heterogeneity could aid in development of individual treatments in patients that otherwise appear similar. At the same time, it is also important to identify immunological infiltrates are disparately expressed in certain areas of a tumor. Tumors can be heterogeneous (cellularly or genetically), with different regions within a tumor sample demonstrating different gene expression. However, identifying and characterizing the genetic and cellular regions of heterogeneity in a sample while having the capability to correlate the heterogeneity to a region of a sample remains a challenge. Thus, there remains a need to develop ways to identify and characterize regions of heterogeneity in a biological sample.

SUMMARY

This disclosure related to methods of characterizing a tumor sample (e.g., regions of interest within a tumor sample) that include the use of any of the spatial transcriptomics methods described herein. The characterization of the tumor sample can allow for, e.g., the selection of appropriate treatment for the subject (e.g., immune-based therapies, e.g., IO therapeutic regimens, e.g., checkpoint inhibitors) and can also for the diagnosis of a particular type of subtype of cancer in the subject. The characterization can also be used to predict the efficacy of a treatment (e.g., immune-based therapies, e.g., IO therapeutic regimens, e.g., checkpoint inhibitors) of cancer in a subject. The characterization can also be used to determine the prognosis of the cancer in the subject. The characterization can be used to determine the relative aggressiveness and/or stage of the tumor (e.g., the entire tumor or a region of interest in the tumor) in the subject. The resulting characterization can also be used to identify a gene signature (e.g., inflammatory gene signature, e.g., a gene signature including one or more of CCL5, CD27, CD274, CD276, CD8A, CMKLR1, CXCL9, CXCR6, HLA-DQA1, HLA-DRB1, HLA-E, IDO1, LAG3, NKG7, PDCD1LG2, PSMB10, STAT1, and TIGIT) or a tumor culture profile of a tumor (e.g., across the entire tumor or a region of interest in the tumor), heterogeneity (e.g., protein expression heterogeneity, immune cell heterogeneity, inflammatory status/level/score/cluster profile heterogeneity, gene expression heterogeneity, and/or genetic mutation heterogeneity) of a tumor (e.g., across the entire tumor or a region of interest in a tumor), immune status of a tumor (e.g., across the entire tumor or a region of a tumor), inflammatory status of a tumor (e.g., across the entire tumor or a region of interest in a tumor), and an inflammatory score of a tumor (e.g., across the entire tumor or a region of interest in a tumor). Non-limiting methods and aspects of determining an inflammation score are described in Bugada et al., *BioMed. Res. Int. Article ID* 142425, 2014. Non-limiting methods and aspects of determining an inflammatory culture profile are described in Newman et al., *Nature Methods* 12:453-457, 2018 (CIBERSORT); Aran et al., *Genome Res.* 18(1):220, 2017 (xCell); and Ayers et al., *J. Clin. Invest.* 127(8):2930-2940, 2017 (Inflammation and Immune Scoring). Non-limiting methods and aspects of determining an tumor cluster profile are described in, e.g., Subramanian et al., *PNAS* 102:15545-15550, 2005 (GSEA tumor cluster profile) and qiagenbioinformatics website (Einter 18 Release) (IPA tumor cluster profile). In some embodiments of any of the methods described herein, the tumor is an ovarian cancer tumor (e.g., a serous ovarian cancer tumor).

Thus, in one instance, provided herein is a method of defining an area of a biological sample as having a tumor or a region of interest comprising: (a) contacting the biological sample with a plurality of probes, wherein a probe of the plurality of probes comprises a spatial barcode and a capture domain that binds specifically to a nucleic acid in the biological sample, wherein the nucleic acid is associated with an immune cell or a cancer cell; (b) determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample; and (c) defining the area of the biological sample as having the tumor or the region of interest based on the location of the nucleic acid associated with the immune cell or the cancer cell in the biological sample.

In another instance, provided herein is a method of determining heterogeneity of a tumor or a region of interest in a biological sample comprising: (a) contacting the biological sample with a plurality of probes, wherein a probe of the plurality of probes comprises a spatial barcode and a capture domain that binds specifically to a nucleic acid in the biological sample, wherein the nucleic acid is associated with an immune cell or a cancer cell; (b) determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample; and (c) determining the heterogeneity of the tumor or the region of interest in the biological sample based on the location of the nucleic acid associated with the immune cell or the cancer cell in the biological sample.

In another instance, provided herein is a method of identifying a subject having cancer as having an increased likelihood of being responsive to a treatment for cancer using a method comprising: (a) contacting a biological sample obtained from the subject with a plurality of probes, wherein a probe of the plurality of probes comprises a spatial barcode and a capture domain that binds specifically to a nucleic acid in the biological sample, wherein the nucleic acid is associated with an immune cell or a cancer cell; (b) determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample; and (c) identifying a subject having the nucleic acid associated with an immune cell or a cancer cell in the biological sample as having an increased likelihood of being responsive to the treatment for cancer.

In another instance, provided herein is a method of selecting a treatment for cancer for a subject previously identified as having an increased likelihood of being responsive to the treatment for cancer using a method comprising the steps of: (a) contacting a biological sample obtained from the subject with a plurality of probes, wherein a probe of the plurality of probes comprises a spatial barcode and a capture domain that binds specifically to a nucleic acid in the biological sample, wherein the nucleic acid is associated with an immune cell or a cancer cell; (b) determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample; and (c) identifying a subject having the nucleic acid associated with an immune cell or a cancer cell in the biological sample as having an increased likelihood of being responsive to the treatment for cancer.

In another instance, provided herein is a method of selecting a treatment for cancer for a subject previously identified as having an increased likelihood of being responsive to the treatment for cancer using a method comprising the steps of: (a) contacting a biological sample obtained from the subject with a plurality of probes, wherein a probe of the plurality of probes comprises a spatial barcode and a capture domain that binds specifically to a nucleic acid in the biological sample, wherein the nucleic acid is associated with an immune cell or a cancer cell; (b) determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample; (c) determining heterogeneity of a tumor or a region of interest in the biological sample based on the location of the nucleic acid associated with the immune cell or the cancer cell in the biological sample; and (d) identifying a subject determined to have heterogeneity of the tumor or the region of interest in the biological sample as having an increased likelihood of being responsive to the treatment for cancer.

In some instances, the heterogeneity comprises heterogeneity in gene expression. In some instances, the heterogeneity comprises heterogeneity in one or more genomic mutations. In some instances, the heterogeneity comprises heterogeneity in immune status. In some instances, the heterogeneity comprises heterogeneity in inflammatory score. In some instances, the heterogeneity comprises heterogeneity in local inflammatory cell concentration. In some instances, the heterogeneity comprises heterogeneity in inflammatory gene expression. In some instances, the region of interest is an area of the biological sample comprising the immune cell. In some instances, the nucleic acid associated with the immune cell or the cancer cell is CCL5, HLA-DRB1, CD27, HLA-E, CD274, IDO1, CD276, LAG3, CD8A, NKG7, CMKLR1, PDCD1LG2, CXCL9, PSMB10, CXCR6, STAT1, HLA-DQA1, TIGIT, MASP1, HBG1, CA1, SCARA5, AC009495.1, MAPK15, SNORD69, CXCL3, RNA 2202, RNA 2614, GJB5, MMP12, AL445433.1, ARAF, or any combination thereof.

In some instances, the nucleic acids associated with the immune cell or the cancer cell are CCL5, HLA-DRB1, CD27, HLA-E, CD274, IDO1, CD276, LAG3, CD8A, NKG7, CMKLR1, PDCD1LG2, CXCL9, PSMB10, CXCR6, STAT1, HLA-DQA1, TIGIT, or any combination thereof. In some instances, the nucleic acids associated with the immune cell or the cancer cell are MASP1 and HBG1. In some instances, the nucleic acids associated with the immune cell or the cancer cell are CA1 and SCARA5. In some instances, the nucleic acids associated with the immune cell or the cancer cell are AC009495.1 and MAPK15. In some instances, the nucleic acids associated with the immune cell or the cancer cell are SNORD69 and CXCL3. In some instances, the nucleic acids associated with the immune cell or the cancer cell are RNA 2202 and RNA 2614. In some instances, the nucleic acids associated with the immune cell or the cancer cell are GJB5 and MMP12. In some instances, the nucleic acids associated with the immune cell or the cancer cell are AL445433.1 and ARAF.

In some instances, the immune cell is selected from a naïve B cell, a memory B cell, a plasma cell, a CD8+ T cell, a CD4+ naïve T cell, a CD4+ memory-resting T cell, a CD4+ memory-activated T cell, a follicular helper T cell, a regulatory T cell (Tregs), a gamma-delta T cell, a resting NK cell, an activated NK cell, a monocyte, an M0 macrophage, an M1 macrophage, an M2 macrophage, a resting dendritic cell, an activated dendritic cell, a resting mast cell, an activated mast cell, an eosinophil, or a neutrophil. In some instances, the immune cell is selected from an M0 macrophage, an M1 macrophage, or an M2 macrophage.

In some instances, the region of interest or the tumor is an area of the biological sample comprising the cancer cell. In some instances, the cancer cell is selected from a breast cancer cell, an ovarian cancer cell, a colon cancer cell, a pancreatic cancer cell, a prostate cancer cell, a squamous cell cancer cell, a cervical cancer cell, a lung cancer cell, a small cell lung cancer cell, a kidney cancer cell, a liver cancer cell, a brain tumor cell, a skin cancer cell, or a bladder cancer cell. In some instances, the cancer cell is an ovarian cancer cell. In some instances, the cancer cell is a breast cancer cell.

In some instances, the methods further include comparing expression of the nucleic acid in the biological sample to expression of the nucleic acid in a control cell.

In some instances, the control cell is a cancer cell. In some instances, the cancer cell is a breast cancer cell, an ovarian cancer cell, a colon cancer cell, a pancreatic cancer cell, a prostate cancer cell, a squamous cell cancer cell, a cervical cancer cell, a lung cancer cell, a small cell lung cancer cell, a kidney cancer cell, a liver cancer cell, a brain cancer cell, a skin cancer cell, or a bladder cancer cell.

In some instances, the control cell is an immune cell. In some instances, the immune cell is selected from a naïve B cell, a memory B cell, a plasma cell, a CD8+ T cell, a CD4+ naïve T cell, a CD4+ memory-resting T cell, a CD4+ memory-activated T cell, a follicular helper T cell, a regulatory T cell (Tregs), a gamma-delta T cell, a resting NK cell, an activated NK cell, a monocyte, an M0 macrophage, an M1 macrophage, an M2 macrophage, a resting dendritic cell, an activated dendritic cell, a resting mast cell, an activated mast cell, an eosinophil, and a neutrophil.

In some instances, the nucleic acid associated with the cancer cell comprises at least one genomic mutation selected from the group consisting of a substitution, a deletion, a translocation, and an insertion. In some instances, the at least one genomic mutation results in a gene amplification, a gene deletion, a gene inactivation, a mutation that results in increased transcription of a gene, a mutation that results in the expression of an protein having increased activity, a mutation that results in decreased transcription of a gene, or a mutation that results in the expression of an protein having decreased activity, as compared to a corresponding wildtype nucleic acid. In some instances, the at least one genomic mutation comprises a mutation that contributes to resistance of the tumor or the region of interest to treatment. In some instances, the method further comprises determining a location of one or more additional nucleic acids associated with one or more additional immune cells in the biological sample.

In some instances, the method further comprises determining a location of one or more additional nucleic acids associated with one or more additional cancer cells in the biological sample. In some instances, the one or more additional nucleic acids is mRNA. In some instances, the one or more additional nucleic acids is genomic DNA. In some instances, the one or more additional nucleic acids include at least two additional nucleic acids that encode proteins in the same or a similar cellular pathway. In some instances, the one or more additional nucleic acids include at least two additional nucleic acids that encode proteins associated with two or more additional immune cells.

In some instances, the method further comprises identifying or diagnosing a cancer in the subject based on the location of the nucleic acid in the biological sample. In some instances, the cancer is ovarian cancer. In some instances, the cancer is breast cancer.

In some instances, the method further comprises determining a prognosis of the cancer in the subject based on the heterogeneity of the tumor or the region of interest in the biological sample. In some instances, the method further comprises scoring or determining the severity of the cancer in the subject based on the heterogeneity of the tumor or the region of interest in the biological sample. In some instances, the method further comprises determining an inflammatory score based on the heterogeneity of the tumor or the region of interest in the biological sample.

In some instances, the nucleic acid in the biological sample is RNA. In some instances, the RNA is mRNA.

Non-limiting aspects of performing spatial transcriptomics methods are described herein. Additional aspects and methods of performing spatial transcriptomics methods are described in, e.g., WO 2011/127099, WO 2014/210223, WO 2014/210225, U.S. Ser. No. 61/321,124, U.S. Ser. No. 13/080,616, U.S. Ser. No. 61/839,320, U.S. Ser. No. 61/879,313, U.S. Ser. No. 61/839,313, U.S. Ser. No. 61/839,320, WO 2012/140224, WO 2014/060483, GB 1218654.0, GB 1304585.1, GB 1106254.4, WO 2016/162309, U.S. Ser. No. 62/145,874, WO 2018/091676, GB 1619458.1, U.S. Pat. Nos. 9,371,598, 10,030,261, 9,593,365, 9,868,979, 9,879,313, US 2017/0016053, WO 2016/007839, WO 2018/045181, WO 2014/163886, WO 2018/045186, PCT/US2016/043385, PCT/US2019/065077, PCT/US2019/065048, PCT/US2019/064987, PCT/US2019/065013, PCT/US2019/065100, PCT/US2019/065072, PCT/US2019/065081, PCT/US2019/065096, and PCT/US2019/065041, (each of which is incorporated herein by reference in its entirety).

Additional aspects of the methods provided herein are described in the claims and the Examples.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 22E shows the relative tissue inflammation score (IS or TIS) in the biological samples in FIG. 22A.

FIG. 22F shows spatially-resolved-per-spot TIS across each serial section in FIG. 22A.

FIG. 22G shows spatially-resolved-per-spot TIS statistical analysis across each Cluster in each serial section. Left window corresponds to serial section 1; middle window corresponds to serial section 2; right window corresponds to serial section 3. ANOVA p-value shown.

DETAILED DESCRIPTION

I. Introduction

Figure 1:
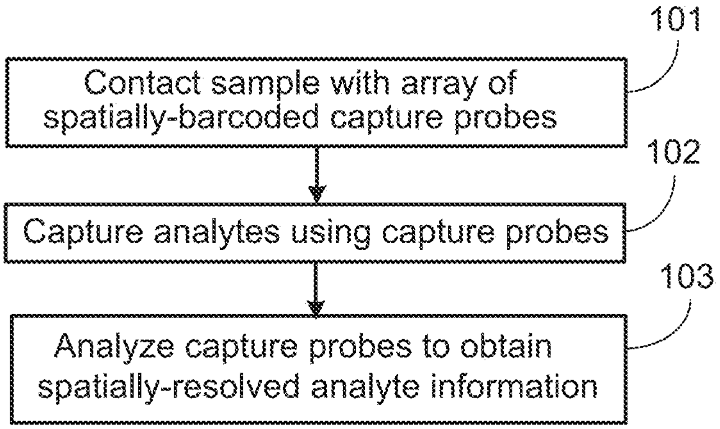
FIG. 1 shows an exemplary spatial analysis workflow.

This disclosure describes apparatus, systems, methods, and compositions for spatial analysis of biological samples. This section describes certain general terminology, analytes, sample types, and preparative steps that are referred to in later sections of the disclosure.

Apparatuses, systems, methods, and compositions for spatial analysis of biological samples are disclosed in WO 2020/047010 A2; WO 2020/047004 A2; WO 2020/047007 A2; WO 2020-047005 A2; WO 2020/047002 A1; PCT/US2019/065077, PCT/US2019/065048, PCT/US2019/064987, PCT/US2019/065013, PCT/US2019/065100, PCT/US2019/065072, PCT/US2019/065081, PCT/US2019/065096, and PCT/US2019/065041; each of which is herein incorporated by reference in its entirety.

(a) Spatial Analysis

Tissues and cells can be obtained from any source. For example, tissues and cells can be obtained from single-cell or multicellular organisms (e.g., a mammal). Tissues and cells obtained from a mammal, e.g., a human, often have varied analyte levels (e.g., gene and/or protein expression) which can result in differences in cell morphology and/or function. The position of a cell or a subset of cells (e.g., neighboring cells and/or non-neighboring cells) within a tissue can affect, e.g., the cell's fate, behavior, morphology, and signaling and cross-talk with other cells in the tissue. Information regarding the differences in analyte levels (gene and/or protein expression) within different cells in a tissue of a mammal can also help physicians select or administer a treatment that will be effective and can allow researchers to identify and elucidate differences in cell morphology and/or cell function in the single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop. Differences in analyte levels within different cells in a tissue of a mammal can also provide information of different mechanisms of disease pathogenesis in a tissue and mechanism of action of a therapeutic treatment within a tissue. Differences in analyte levels within different cells in a tissue of a mammal can also provide information on drug resistance mechanisms and the development of the same in a tissue of a mammal. Differences in the presence or absence of analytes within different cells in a tissue of a multicellular organism (e.g., a mammal) can provide information on drug resistance mechanisms and the development of the same in a tissue of a multicellular organism.

The spatial analysis methodologies herein provide for the detection of differences in an analyte level (e.g., gene and/or protein expression) within different cells in a tissue of a mammal or within a single cell from a mammal. For example, spatial analysis methodologies can be used to detect the differences in analyte levels (e.g., gene and/or protein expression) within different cells in histological slide samples, the data from which can be reassembled to generate a three-dimensional map of analyte levels (e.g., gene and/or protein expression) of a tissue sample obtained from a mammal, e.g., with a degree of spatial resolution (e.g., single-cell resolution).

Spatial heterogeneity in developing systems has typically been studied via RNA hybridization, immunohistochemistry, fluorescent reporters, or purification or induction of pre-defined subpopulations and subsequent genomic profiling (e.g., RNA-seq). Such approaches, however, rely on a relatively small set of pre-defined markers, therefore introducing selection bias that limits discovery. These prior approaches also rely on a priori knowledge. RNA assays traditionally relied on staining for a limited number of RNA species. In contrast, single-cell RNA-sequencing allows for deep profiling of cellular gene expression (including non-coding RNA), but the established methods separate cells from their native spatial context.

Spatial analysis methodologies described herein provide a vast amount of analyte level and/or expression data for a variety of multiple analytes within a sample at high spatial resolution, e.g., while retaining the native spatial context. Spatial analysis methods include, e.g., the use of a capture probe including a spatial barcode (e.g., a nucleic acid sequence that provides information as to the position of the capture probe within a cell or a tissue sample (e.g., mammalian cell or a mammalian tissue sample) and a capture domain that is capable of binding to an analyte (e.g., a protein and/or nucleic acid) produced by and/or present in a cell. As described herein, the spatial barcode can be a nucleic acid that has a unique sequence, a unique fluorophore or a unique combination of fluorophores, a unique amino acid sequence, a unique heavy metal or a unique combination of heavy metals, or any other unique detectable agent. The capture domain can be any agent that is capable of binding to an analyte produced by and/or present in a cell (e.g., a nucleic acid that is capable of hybridizing to a nucleic acid from a cell (e.g., an mRNA, genomic DNA, mitochondrial DNA, or miRNA), a substrate including an analyte, a binding partner of an analyte, or an antibody that binds specifically to an analyte). A capture probe can also include a nucleic acid sequence that is complementary to a sequence of a universal forward and/or universal reverse primer. A capture probe can also include a cleavage site (e.g., a cleavage recognition site of a restriction endonuclease), a photolabile bond, a thermosensitive bond, or a chemical-sensitive bond.

The binding of an analyte to a capture probe can be detected using a number of different methods, e.g., nucleic acid sequencing, fluorophore detection, nucleic acid amplification, detection of nucleic acid ligation, and/or detection of nucleic acid cleavage products. In some examples, the detection is used to associate a specific spatial barcode with a specific analyte produced by and/or present in a cell (e.g., a mammalian cell).

Capture probes can be, e.g., attached to a surface, e.g., a solid array, a bead, or a coverslip. In some examples, capture probes are not attached to a surface. In some examples, capture probes can be encapsulated within, embedded within, or layered on a surface of a permeable composition (e.g., any of the substrates described herein). For example, capture probes can be encapsulated or disposed within a permeable bead (e.g., a gel bead). In some examples, capture probes can be encapsulated within, embedded within, or layered on a surface of a substrate (e.g., any of the exemplary substrates described herein, such as a hydrogel or a porous membrane).

In some examples, a cell or a tissue sample including a cell are contacted with capture probes attached to a substrate (e.g., a surface of a substrate), and the cell or tissue sample is permeabilized to allow analytes to be released from the cell and bind to the capture probes attached to the substrate. In some examples, analytes released from a cell can be actively directed to the capture probes attached to a substrate using a variety of methods, e.g., electrophoresis, chemical gradient, pressure gradient, fluid flow, or magnetic field.

In other examples, a capture probe can be directed to interact with a cell or a tissue sample using a variety of methods, e.g., inclusion of a lipid anchoring agent in the capture probe, inclusion of an agent that binds specifically to, or forms a covalent bond with a membrane protein in the capture probe, fluid flow, pressure gradient, chemical gradient, or magnetic field.

Non-limiting aspects of spatial analysis methodologies are described in WO 2011/127099, WO 2014/210233, WO 2014/210225, WO 2016/162309, WO 2018/091676, WO 2012/140224, WO 2014/060483, U.S. Pat. Nos. 10,002,316, 9,727,810, U.S. Patent Application Publication No. 2017/0016053, Rodriques et al., *Science* 363(6434):1463-1467, 2019; WO 2018/045186, Lee et al., *Nat. Protoc.* 10(3):442-458, 2015; WO 2016/007839, WO 2018/045181, WO 2014/163886, Trejo et al., *PLoS ONE* 14(2):e0212031, 2019, U.S. Patent Application Publication No. 2018/0245142, Chen et al., *Science* 348(6233):aaa6090, 2015, Gao et al., *BMC Biol.* 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, and Gupta et al., *Nature Biotechnol.* 36:1197-1202, 2018, and can be used herein in any combination. Further non-limiting aspects of spatial analysis methodologies are described herein.

(b) General Terminology

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

(i) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include non-random, semi-random, and/or random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode (e.g., a polynucleotide barcode). For example, a polynucleotide barcode can include two or more polynucleotide sequences (e.g., sub-barcodes) that may be separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g., found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, or honey bee; an arachnid such as a spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum.*

(vi) Genome

A "genome" generally refers to genomic information from a subject, which can be, for example, at least a portion of, or the entirety of, the subject's gene-encoded hereditary information. A genome can include coding regions (e.g., that code for proteins) as well as non-coding regions. A genome can include the sequences of some or all of the subject's chromosomes. For example, the human genome ordinarily has a total of 46 chromosomes. The sequences of some or all of these can constitute the genome.

(vii) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(viii) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(ix) Primer

A "primer" is a single-stranded nucleic acid sequence having a 3' end that can be used as a chemical substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases.

(x) Primer Extension

A "primer extension" refers to any method where two nucleic acid sequences (e.g., a constant region from each of two distinct capture probes) become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(xi) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(xii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(xiii) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including derivatives of naturally-occurring DNA polymerase enzymes. For instance, in some embodiments, the DNA polymerase is modified to remove 5'-3' exonuclease activity. Sequence-modified derivatives or mutants of DNA polymerase enzymes that can be used include, but are not limited to, mutants that retain at least some of the functional, e.g., DNA polymerase activity of the wild-type sequence. Mutations can affect the activity profile of the enzymes, e.g., enhance or reduce the rate of polymerization, under different reaction conditions, e.g., temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase® (available from Lucigen, Middleton, WI). Derivatives, e.g., sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes (i.e., RNA dependent DNA polymerases), suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g., reverse transcriptase, activity of the wild-type sequence. The reverse transcriptase enzyme can be provided as part of a composition that includes other components, e.g., stabilizing components that enhance or improve the activity of the reverse transcriptase enzyme, such as RNase inhibitor(s), inhibitors of DNA-dependent DNA synthesis, e.g., actinomycin D. Many sequence-modified derivative or mutants of reverse transcriptase enzymes, e.g., M-MLV, and compositions including unmodified and modified enzymes are commercially available, e.g., ArrayScript™, MultiScribe™, ThermoScript™, and SuperScript® I, II, III, and IV enzymes.

Certain reverse transcriptase enzymes (e.g., Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g., an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™", or dyes such as "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xiv) Antibody

An "antibody" is a polypeptide molecule that recognizes and binds to a complementary target antigen. Antibodies typically have a molecular structure shape that resembles a Y shape, or polymers thereof. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also include single domain antibodies ($V_H$H domains and VNAR domains), scFvs, and Fab fragments.

(xvi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a capture probe or analyte. The detectable label can be directly detectable by itself (e.g., radioisotope labels or fluorescent labels) or, in the case of an enzymatic label, can be indirectly detectable, e.g., by catalyzing chemical alterations of a chemical substrate compound or composition, which chemical substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18(5)), DIDS, Dil (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate chemical substrates (e.g., an oxidizing reagent plus a chemiluminescent compound). A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters.

(xvii) Template Switching Oligonucleotide

A "template switching oligonucleotide" is an oligonucleotide that hybridizes to untemplated nucleotides added by a reverse transcriptase (e.g., enzyme with terminal transferase activity) during reverse transcription. In some embodiments, a template switching oligonucleotide hybridizes to untemplated poly(C) nucleotides added by a reverse transcriptase. In some embodiments, the template switching oligonucleotide adds a common 5' sequence to full-length cDNA that is used for cDNA amplification.

In some embodiments, the template switching oligonucleotide adds a common sequence onto the 5' end of the RNA being reverse transcribed. For example, a template switching oligonucleotide can hybridize to untemplated poly(C) nucleotides added onto the end of a cDNA molecule and provide a template for the reverse transcriptase to continue replication to the 5' end of the template switching oligonucleotide, thereby generating full-length cDNA ready for further amplification. In some embodiments, once a full-length cDNA molecule is generated, the template switching oligonucleotide can serve as a primer in a cDNA amplification reaction.

In some embodiments, a template switching oligonucleotide is added before, contemporaneously with, or after a reverse transcription, or other terminal transferase-based reaction. In some embodiments, a template switching oligonucleotide is included in the capture probe. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target. In some embodiments, the hybridization region can, e.g., include a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In other embodiments, the hybridization region can include at least one base in addition to at least one G base. In other embodiments, the hybridization can include bases that are not a G base. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxylnosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 1, 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

(xviii) Splint Oligonucleotide

A "splint oligonucleotide" is an oligonucleotide that, when hybridized to other polynucleotides, acts as a "splint" to position the polynucleotides next to one another so that they can be ligated together. In some embodiments, the splint oligonucleotide is DNA or RNA. The splint oligonucleotide can include a nucleotide sequence that is partially complimentary to nucleotide sequences from two or more different oligonucleotides. In some embodiments, the splint oligonucleotide assists in ligating a "donor" oligonucleotide and an "acceptor" oligonucleotide. In general, an RNA ligase, a DNA ligase, or another other variety of ligase is used to ligate two nucleotide sequences together In some embodiments, the splint oligonucleotide is between 10 and 50 oligonucleotides in length, e.g., between 10 and 45, 10 and 40, 10 and 35, 10 and 30, 10 and 25, or 10 and 20 oligonucleotides in length. In some embodiments, the splint oligonucleotide is between 15 and 50, 15 and 45, 15 and 40, 15 and 35, 15 and 30, 15 and 30, or 15 and 25 nucleotides in length.

(c) Analytes

The apparatus, systems, methods, and compositions described in this disclosure can be used to detect and analyze a wide variety of different analytes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte can be an organelle (e.g., nuclei or mitochondria).

Cell surface features corresponding to analytes can include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

Additional examples of analytes include mRNA and cell surface features (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D)J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein). In some embodiments, a perturbation agent can be a small molecule, an antibody, a drug, an aptamer, a miRNA, a physical environmental (e.g., temperature change), or any other known perturbation agents.

Analytes can include a nucleic acid molecule with a nucleic acid sequence encoding at least a portion of a V(D)J sequence of an immune cell receptor (e.g., a TCR or BCR). In some embodiments, the nucleic acid molecule is cDNA first generated from reverse transcription of the corresponding mRNA, using a poly(T) containing primer. The generated cDNA can then be barcoded using a capture probe, featuring a barcode sequence (and optionally, a UMI sequence) that hybridizes with at least a portion of the generated cDNA. In some embodiments, a template switching oligonucleotide hybridizes to a poly(C) tail added to a 3'end of the cDNA by a reverse transcriptase enzyme. The original mRNA template and template switching oligonucleotide can then be denatured from the cDNA and the barcoded capture probe can then hybridize with the cDNA and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described in PCT Patent Application PCT/US2017/057269, filed Oct. 18, 2017, and U.S. patent application Ser. No. 15/825,740, filed Nov. 29, 2017, both of which are incorporated herein by reference in their entireties. V(D)J analysis can also be completed with the use of one or more labelling agents that bind to particular surface features of immune cells and associated with barcode sequences. The one or more labelling agents can include an MHC or MHC multimer.

As described above, the analyte can include a nucleic acid capable of functioning as a component of a gene editing reaction, such as, for example, clustered regularly interspaced short palindromic repeats (CRISPR)-based gene editing. Accordingly, the capture probe can include a nucleic acid sequence that is complementary to the analyte (e.g., a sequence that can hybridize to the CRISPR RNA (crRNA), single guide RNA (sgRNA), or an adapter sequence engineered into a crRNA or sgRNA).

In general, the systems, apparatus, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate. Methods for performing multiplexed assays to analyze two or more different analytes will be discussed in a subsequent section of this disclosure.

(d) Biological Samples (i) Types of Biological Samples

A "biological sample" is obtained from the subject for analysis using any of a variety of techniques including, but not limited to, biopsy, surgery, and laser capture microscopy (LCM), and generally includes cells and/or other biological material from the subject. In addition to the subjects described above, a biological sample can be obtained from non-mammalian organisms (e.g., a plants, an insect, an arachnid, a nematode (e.g., *Caenorhabditis elegans*), a fungi, an amphibian, or a fish (e.g., zebrafish)). A biological sample can be obtained from a prokaryote such as a bacterium, e.g., *Escherichia coli*, Staphylococci or *Mycoplasma pneumoniae*; an archaea; a virus such as Hepatitis C virus or human immunodeficiency virus; or a viroid. A biological sample can be obtained from a eukaryote, such as a patient derived organoid (PDO) or patient derived xenograft (PDX). The biological sample can include organoids, a miniaturized and simplified version of an organ produced in vitro in three dimensions that shows realistic micro-anatomy. Organoids can be generated from one or more cells from a tissue, embryonic stem cells, and/or induced pluripotent stem cells, which can self-organize in three-dimensional culture owing to their self-renewal and differentiation capacities. In some embodiments, an organoid is a cerebral organoid, an intestinal organoid, a stomach organoid, a lingual organoid, a thyroid organoid, a thymic organoid, a testicular organoid, a hepatic organoid, a pancreatic organoid, an epithelial organoid, a lung organoid, a kidney organoid, a gastruloid, a cardiac organoid, or a retinal organoid. Subjects from which biological samples can be obtained can be healthy or asymptomatic individuals, individuals that have or are suspected of having a disease (e.g., cancer) or a pre-disposition to a disease, and/or individuals that are in need of therapy or suspected of needing therapy.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include immune cells. Sequence analysis of the immune repertoire of such cells, including genomic, proteomic, and cell surface features, can provide a wealth of information to facilitate an understanding the status and function of the immune system. By way of example, determining the status (e.g., negative or positive) of minimal residue disease (MRD) in a multiple myeloma (MM) patient following autologous stem cell transplantation is considered a predictor of MRD in the MM patient (see, e.g., U.S. Patent Application Publication No. 2018/0156784, the entire contents of which are incorporated herein by reference).

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

Cell-free biological samples can include extracellular polynucleotides. Extracellular polynucleotides can be isolated from a bodily sample, e.g., blood, plasma, serum, urine, saliva, mucosal excretions, sputum, stool, and tears.

As discussed above, a biological sample can include a single analyte of interest, or more than one analyte of interest. Methods for performing multiplexed assays to analyze two or more different analytes in a single biological sample is discussed in a subsequent section of this disclosure.

(ii) Preparation of Biological Samples

A variety of steps can be performed to prepare a biological sample for analysis. Except where indicated otherwise, the preparative steps include tissue sectioning, freezing, fixation, including formalin fixation, embedding, staining, hydrogel embedding, biological sample transfer, isometric expansion, substrate attachment, preparation of suspended and adherent cells, tissue permeabilization. Exemplary methods of biological sample preparation is disclosed in WO 2020/047010 A2; WO 2020/047004 A2; WO 2020/047007 A2; WO 2020/047005 A2; WO 2020/047002 A1; PCT/US2019/065077; PCT/US2019/065048; PCT/US2019/064987; PCT/US2019/065013; PCT/US2019/065100; PCT/US2019/065072; PCT/US2019/065081; PCT/US2019/065096; and PCT/US2019/065041; each of which is incorporated by reference in its entirety.

(1) Tissue Permeabilization

In some embodiments, a biological sample can be permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution). In some embodiments, the biological sample can be permeabilized using any of the methods described herein (e.g., using any of the detergents described herein, e.g., SDS and/or N-lauroylsarcosine sodium salt solution) before or after enzymatic treatment (e.g., treatment with any of the enzymes described herein, e.g., trypin, proteases (e.g., pepsin and/or proteinase K)).

In some embodiments, a biological sample can be permeabilized by exposing the sample to greater than about 1.0 w/v % (e.g., greater than about 2.0 w/v %, greater than about 3.0 w/v %, greater than about 4.0 w/v %, greater than about 5.0 w/v %, greater than about 6.0 w/v %, greater than about 7.0 w/v %, greater than about 8.0 w/v %, greater than about 9.0 w/v %, greater than about 10.0 w/v %, greater than about 11.0 w/v %, greater than about 12.0 w/v %, or greater than about 13.0 w/v %) sodium dodecyl sulfate (SDS) and/or N-lauroylsarcosine or N-lauroylsarcosine sodium salt. In some embodiments, a biological sample can be permeabilized by exposing the sample (e.g., for about 5 minutes to about 1 hour, about 5 minutes to about 40 minutes, about 5 minutes to about 30 minutes, about 5 minutes to about 20 minutes, or about 5 minutes to about 10 minutes) to about 1.0 w/v % to about 14.0 w/v % (e.g., about 2.0 w/v % to about 14.0 w/v %, about 2.0 w/v % to about 12.0 w/v %, about 2.0 w/v % to about 10.0 w/v %, about 4.0 w/v % to about 14.0 w/v %, about 4.0 w/v % to about 12.0 w/v %, about 4.0 w/v % to about 10.0 w/v %, about 6.0 w/v % to about 14.0 w/v %, about 6.0 w/v % to about 12.0 w/v %, about 6.0 w/v % to about 10.0 w/v %, about 8.0 w/v % to about 14.0 w/v %, about 8.0 w/v % to about 12.0 w/v %, about 8.0 w/v % to about 10.0 w/v %, about 10.0% w/v % to about 14.0 w/v %, about 10.0 w/v % to about 12.0 w/v %, or about 12.0 w/v % to about 14.0 w/v %) SDS and/or N-lauroylsarcosine salt solution and/or proteinase K (e.g., at a temperature of about 4% to about 35° C., about 4° C. to about 25° C., about 4° C. to about 20° C., about 4° C. to about 10° C., about 10° C. to about 25° C., about 10° C. to about 20° C., about 10° C. to about 15° C., about 35° C. to about 50° C., about 35° C. to about 45° C., about 35° C. to about 40° C., about 40° C. to about 50° C., about 40° C. to about 45° C., or about 45° C. to about 50° C.).

In some embodiments, the biological sample can be incubated with a permeabilizing agent to facilitate permeabilization of the sample. Additional methods for sample permeabilization are described, for example, in Jamur et al., *Method Mol. Biol.* 588:63-66, 2010, the entire contents of which are incorporated herein by reference.

Lysis Reagents

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Proteases

In some embodiments, a medium, solution, or permeabilization solution may contain one or more proteases. In some embodiments, a biological sample treated with a protease capable of degrading histone proteins can result in the generation of fragmented genomic DNA. The fragmented genomic DNA can be captured using the same capture domain (e.g., capture domain having a poly(T) sequence) used to capture mRNA. In some embodiments, a biological sample is treated with a protease capable of degrading histone proteins and an RNA protectant prior to spatial profiling in order to facilitate the capture of both genomic DNA and mRNA.

Proteases are disclosed in WO 2020/047010 A2; WO 2020/047004 A2; WO 2020/047007 A2; WO 2020-047005 A2; WO 2020/047002 A1; PCT/US2019/065077, PCT/US2019/065048, PCT/US2019/064987, PCT/US2019/065013, PCT/US2019/065100, PCT/US2019/065072, PCT/US2019/065081, PCT/US2019/065096, and PCT/US2019/065041; each of which is herein incorporated by reference in its entirety.

Other Reagents

In some embodiments, a permeabilization solution can contain additional reagents or a biological sample may be treated with additional reagents in order to optimize biological sample permeabilization. In some embodiments, an additional reagent is an RNA protectant, which is described in WO 2020/047010 A2; WO 2020/047004 A2; WO 2020/047007 A2; WO 2020-047005 A2; WO 2020/047002 A1; PCT/US2019/065077, PCT/US2019/065048, PCT/US2019/064987, PCT/US2019/065013, PCT/US2019/065100, PCT/US2019/065072, PCT/US2019/065081, PCT/US2019/065096, and PCT/US2019/065041; each of which is herein incorporated by reference in its entirety.

In some embodiments, identifying the location of the captured analyte in the biological sample includes a nucleic acid extension reaction. In some embodiments where a capture probe captures a fragmented genomic DNA molecule, a nucleic acid extension reaction includes DNA polymerase. For example, a nucleic acid extension reaction includes using a DNA polymerase to extend the capture probe that is hybridized to the captured analyte (e.g., fragmented genomic DNA) using the captured analyte (e.g., fragmented genomic DNA) as a template. The product of the extension reaction includes a spatially-barcoded analyte (e.g., spatially-barcoded fragmented genomic DNA). The spatially-barcoded analyte (e.g., spatially-barcoded fragmented genomic DNA) can be used to identify the spatial location of the analyte in the biological sample. Any DNA polymerase that is capable of extending the capture probe using the captured analyte as a template can be used for the methods described herein. Non-limiting examples of DNA polymerases include T7 DNA polymerase; Bsu DNA polymerase; and *E. coli* DNA Polymerase pol I.

Diffusion-Resistant Media

In some embodiments, a diffusion-resistant medium, typically used to limit diffusion of analytes, can include at least one permeabilization reagent. For example, the diffusion-resistant medium (e.g., a hydrogel) can include wells (e.g., micro-, nano-, or picowells or pores) containing a permeabilization buffer or reagents. In some embodiments, the diffusion-resistant medium (e.g., a hydrogel) is soaked in permeabilization buffer prior to contacting the hydrogel with a sample. In some embodiments, the hydrogel or other diffusion-resistant medium can contain dried reagents or monomers to deliver permeabilization reagents when the diffusion-resistant medium is applied to a biological sample. In some embodiments, the diffusion-resistant medium, (e.g., hydrogel) is covalently attached to a solid substrate (e.g., an acrylated glass slide).

In some embodiments, the hydrogel can be modified to both deliver permeabilization reagents and contain capture probes. For example, a hydrogel film can be modified to include spatially-barcoded capture probes. The spatially-barcoded hydrogel film is then soaked in permeabilization buffer before contacting the spatially-barcoded hydrogel film to the sample. In another example, a hydrogel can be modified to include spatially-barcoded capture probes and designed to serve as a porous membrane (e.g., a permeable hydrogel) when exposed to permeabilization buffer or any other biological sample preparation reagent. The permeabilization reagent diffuses through the spatially-barcoded permeable hydrogel and permeabilizes the biological sample on the other side of the hydrogel. The analytes then diffuse into the spatially-barcoded hydrogel after exposure to permeabilization reagents. In such cases, the spatially-barcoded hydrogel (e.g., porous membrane) is facilitating the diffusion of the biological analytes in the biological sample into the hydrogel. In some embodiments, biological analytes diffuse into the hydrogel before exposure to permeabilization reagents (e.g., when secreted analytes are present outside of the biological sample or in instances where a biological sample is lysed or permeabilized by other means prior to addition of permeabilization reagents). In some embodiments, the permeabilization reagent is flowed over the hydrogel at a variable flow rate (e.g., any flow rate that facilitates diffusion of the permeabilization reagent across the spatially-barcoded hydrogel). In some embodiments, the permeabilization reagents are flowed through a microfluidic chamber or channel over the spatially-barcoded hydrogel. In some embodiments, after using flow to introduce permeabilization reagents to the biological sample, biological sample preparation reagents can be flowed over the hydrogel to further facilitate diffusion of the biological analytes into the spatially-barcoded hydrogel. The spatially-barcoded hydrogel film thus delivers permeabilization reagents to a sample surface in contact with the spatially-barcoded hydrogel, enhancing analyte migration and capture. In some embodiments, the spatially-barcoded hydrogel is applied to a sample and placed in a permeabilization bulk solution. In some embodiments, the hydrogel film soaked in permeabilization reagents is sandwiched between a sample and a spatially-barcoded array. In some embodiments, target analytes are able to diffuse through the permeabilizing reagent soaked hydrogel and hybridize or bind the capture probes on the other side of the hydrogel. In some embodiments, the thickness of the hydrogel is proportional to the resolution loss. In some embodiments, wells (e.g., micro-, nano-, or picowells) can contain spatially-barcoded capture probes and permeabilization reagents and/or buffer. In some embodiments, spatially-barcoded capture probes and permeabilization reagents are held between spacers. In some embodiments, the sample is punch, cut, or transferred into the well, wherein a target analyte diffuses through the permeabilization reagent/buffer and to the spatially-barcoded capture probes. In some embodiments, resolution loss may be proportional to gap thickness (e.g., the amount of permeabilization buffer between the sample and the capture probes). In some embodiments, the diffusion-resistant medium (e.g., hydrogel) is between approximately 50-500 micrometers thick including 500, 450, 400, 350, 300, 250, 200, 150, 100, or 50 micrometers thick, or any thickness within 50 and 500 micrometers.

In some embodiments, a biological sample is exposed to a porous membrane (e.g., a permeable hydrogel) to aid in permeabilization and limit diffusive analyte losses, while allowing permeabilization reagents to reach a sample. Membrane chemistry and pore volume can be manipulated to minimize analyte loss. In some embodiments, the porous membrane may be made of glass, silicon, paper, hydrogel, polymer monoliths, or other material. In some embodiments, the material may be naturally porous. In some embodiments, the material may have pores or wells etched into solid material. In some embodiments, the permeabilization reagents are flowed through a microfluidic chamber or channel over the porous membrane. In some embodiments, the flow controls the sample's access to the permeabilization reagents. In some embodiments, the porous membrane is a permeable hydrogel. For example, a hydrogel is permeable when permeabilization reagents and/or biological sample preparation reagents can pass through the hydrogel using diffusion. Any suitable permeabilization reagents and/or biological sample preparation reagents described herein can be used under conditions sufficient to release analytes (e.g., nucleic acid, protein, metabolites, lipids, etc.) from the biological sample. In some embodiments, a hydrogel is exposed to the biological sample on one side and permeabilization reagent on the other side. The permeabilization reagent diffuses through the permeable hydrogel and permeabilizes the biological sample on the other side of the hydrogel. In some embodiments, permeabilization reagents are flowed over the hydrogel at a variable flow rate (e.g., any flow rate that facilitates diffusion of the permeabilization reagent across the hydrogel). In some embodiments, the permeabilization reagents are flowed through a microfluidic chamber or channel over the hydrogel. Flowing permeabilization reagents across the hydrogel enables control of the concentration of reagents. In some embodiments, hydrogel chemistry and pore volume can be tuned to enhance permeabilization and limit diffusive analyte losses.

In some embodiments, a porous membrane is sandwiched between a spatially-barcoded array and the sample, wherein permeabilization solution is applied over the porous membrane. The permeabilization reagents diffuse through the pores of the membrane and into the biological sample. In some embodiments, the biological sample can be placed on a substrate (e.g., a glass slide). Biological analytes then diffuse through the porous membrane and into to the space containing the capture probes. In some embodiments, the porous membrane is modified to include capture probes. For example, the capture probes can be attached to a surface of the porous membrane using any of the methods described herein. In another example, the capture probes can be embedded in the porous membrane at any depth that allows interaction with a biological analyte. In some embodiments, the porous membrane is placed onto a biological sample in a configuration that allows interaction between the capture probes on the porous membrane and the biological analytes from the biological sample. For example, the capture probes are located on the side of the porous membrane that is proximal to the biological sample. In such cases, permeabilization reagents on the other side of the porous membrane diffuse through the porous membrane into the location containing the biological sample and the capture probes in order to facilitate permeabilization of the biological sample (e.g., also facilitating capture of the biological analytes by the capture probes). In some embodiments, the porous membrane is located between the sample and the capture probes. In some embodiments, the permeabilization reagents are flowed through a microfluidic chamber or channel over the porous membrane.

Selective Permeabilization/Selective Lysis

In some embodiments, biological samples can be processed to selectively release an analyte from a subcellular region of a cell according to established methods. In some embodiments, a method provided herein can include detecting at least one biological analyte present in a subcellular region of a cell in a biological sample. As used herein, a "subcellular region" can refer to any subcellular region. For example, a subcellular region can refer to cytosol, a mitochondria, a nucleus, a nucleolus, an endoplasmic reticulum, a lysosome, a vesicle, a Golgi apparatus, a plastid, a vacuole, a ribosome, cytoskeleton, or combinations thereof. In some embodiments, the subcellular region comprises at least one of cytosol, a nucleus, a mitochondria, and a microsome. In some embodiments, the subcellular region is cytosol. In some embodiments, the subcellular region is a nucleus. In some embodiments, the subcellular region is a mitochondria. In some embodiments, the subcellular region is a microsome.

For example, a biological analyte can be selectively released from a subcellular region of a cell by selective permeabilization or selective lysing. In some embodiments, "selective permeabilization" can refer to a permeabilization method that can permeabilize a membrane of a subcellular region while leaving a different subcellular region substantially intact (e.g., biological analytes are not released from subcellular region due to the applied permeabilization method). Non-limiting examples of selective permeabilization methods include using electrophoresis and/or applying a permeabilization reagent. In some embodiments, "selective lysing" can refer to a lysis method that can lyse a membrane of a subcellular region while leaving a different subcellular region substantially intact (e.g., biological analytes are not released from subcellular region due to the applied lysis method). Several methods for selective permeabilization or lysis are known to one of skill in the art including the methods described in Lu et al. *Lab Chip*. 2005 January; 5(1):23-9; Niklas et al. *Anal Biochem*. 2011 Sep. 15; 416(2):218-27; Cox and Emili. *Nat Protoc*. 2006; 1(4): 1872-8; Chiang et al. *J Biochem. Biophys. Methods*. 2000 Nov. 20; 46(1-2):53-68; and Yamauchi and Herr et al. *Microsyst. Nanoeng*. 2017; 3. pii: 16079; each of which is incorporated herein by reference in its entirety.

In some embodiments, "selective permeabilization" or "selective lysis" refer to the selective permeabilization or selective lysis of a specific cell type. For example, "selective permeabilization" or "selective lysis" can refer to lysing one cell type while leaving a different cell type substantially intact (e.g., biological analytes are not released from the cell due to the applied permeabilization or lysis method). A cell that is a "different cell type" than another cell can refer to a cell from a different taxonomic kingdom, a prokaryotic cell versus a eukaryotic cell, a cell from a different tissue type, etc. Many methods are known to one of skill in the art for selectively permeabilizing or lysing different cell types. Non-limiting examples include applying a permeabilization reagent, electroporation, and/or sonication. See, e.g., International Application No. WO 2012/168003; Han et al. *Microsyst Nanoeng*. 2019 Jun. 17; 5:30; Gould et al. *Oncotarget*. 2018 Mar. 20; 9(21): 15606-15615; Oren and Shai. *Biochemistry*. 1997 Feb. 18; 36(7):1826-35; Algayer et al. *Molecules*. 2019 May 31; 24(11). pii: E2079; Hipp et al. *Leukemia*. 2017 October; 31(10):2278; International Application No. WO 2012/168003; and U.S. Pat. No. 7,785,869; all of which are incorporated by reference herein in their entireties.

In some embodiments, applying a selective permeabilization or lysis reagent comprises contacting the biological sample with a hydrogel comprising the permeabilization or lysis reagent.

In some embodiments, the biological sample is contacted with two or more arrays (e.g., flexible arrays, as described herein). For example, after a subcellular region is permeabilized and a biological analyte from the subcellular region is captured on a first array, the first array can be removed, and a biological analyte from a different subcellular region can be captured on a second array.

(2) Selective Enrichment of RNA Species

In some embodiments, where RNA is the analyte, one or more RNA analyte species of interest can be selectively enriched (e.g., Adiconis, et. al., Comparative analysis of RNA sequencing methods for degraded and low-input samples, *Nature*, vol. 10, July 2013, 623-632, herein incorporated by reference in its entirety). For example, one or more species of RNA can be selected by addition of one or more oligonucleotides to the sample. In some embodiments, the additional oligonucleotide is a sequence used for priming a reaction by a polymerase. For example, one or more primer sequences with sequence complementarity to one or more RNAs of interest can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. For example, biotinylated oligonucleotides with sequence complementary to one or more cDNAs of interest binds to the cDNA and can be selected using biotinylation-streptavidin affinity using any of a variety of methods known to the field (e.g., streptavidin beads).

Alternatively, one or more species of RNA (e.g., ribosomal and/or mitochondrial RNA) can be down-selected (e.g., removed, depleted) using any of a variety of methods. Non-limiting examples of a hybridization and capture method of ribosomal RNA depletion include RiboMinus™, RiboCop™, and Ribo-Zero™. Another non-limiting RNA depletion method involves hybridization of complementary DNA oligonucleotides to unwanted RNA followed by degradation of the RNA/DNA hybrids using RNase H. Non-limiting examples of a hybridization and degradation method include NEBNext® rRNA depletion, NuGEN Any-Deplete, or RiboZero Plus. Another non-limiting ribosomal RNA depletion method includes ZapR™ digestion, for example SMARTer. In the SMARTer method, random nucleic acid adapters are hybridized to RNA for first-strand synthesis and tailing by reverse transcriptase, followed by template switching and extension by reverse transcriptase. Additionally, first round PCR amplification adds full-length Illumina sequencing adapters (e.g., Illumina indexes). Ribosomal RNA is cleaved by ZapR v2 and R probes v2. A second round of PCR is performed, amplifying non-rRNA molecules (e.g., cDNA). Parts or steps of these ribosomal depletion protocols/kits can be further combined with the methods described herein to optimize protocols for a specific biological sample.

In depletion protocols, probes can be administered to a sample that selectively hybridize to ribosomal RNA (rRNA), thereby reducing the pool and concentration of rRNA in the sample. Probes can be administered to a biological sample that selectively hybridize to mitochondria RNA (mtRNA), thereby reducing the pool and concentration of mtRNA in the sample. In some embodiments, probes complementary to mitochondrial RNA can be added during cDNA synthesis, or probes complementary to both ribosomal and mitochondrial RNA can be added during cDNA synthesis. Subsequent application of capture probes to the sample can result in improved capture of other types of RNA due to a reduction in non-specific RNA (e.g., down-selected RNA) present in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which are incorporated herein by reference). Furthermore, hydroxy-apatite chromatography can remove abundant species (e.g., rRNA) (see, e.g., Vandernoot, V.A., cDNA normalization by hydroxyapatite chromatography to enrich transcriptome diversity in RNA-seq applications, *Biotechniques,* 53(6) 373-80, (2012), the entire contents of which are incorporated herein by reference).

(3) Other Reagents

Additional reagents can be added to a biological sample to perform various functions prior to analysis of the biological sample. Exemplary additional reagents can be found at least in WO 2020/047010 A2; WO 2020/047004 A2; WO 2020/047007 A2; WO 2020-047005 A2; WO 2020/047002 A1; PCT/US2019/065077, PCT/US2019/065048, PCT/US2019/064987, PCT/US2019/065013, PCT/US2019/065100, PCT/US2019/065072, PCT/US2019/065081, PCT/US2019/065096, and PCT/US2019/065041; each of which is herein incorporated by reference in its entirety.

II. General Spatial Array-Based Analytical Methodology

Provided herein are methods, apparatus, systems, and compositions for spatial array-based analysis of biological samples.

(a) Spatial Analysis Methods

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of each analyte within the biological sample. The spatial location of each analyte within the biological sample is determined based on the feature to which each analyte is bound on the array, and the feature's relative spatial location within the array.

There are at least two general methods to associate a spatial barcode with one or more neighboring cells, such that the spatial barcode identifies the one or more cells, and/or contents of the one or more cells, as associated with a particular spatial location. One general method is to promote analytes out of a cell and towards the spatially-barcoded array. FIG. 1 depicts an exemplary embodiment of this general method. In FIG. 1, the spatially-barcoded array populated with capture probes (as described further herein) is contacted with a biological sample 101, and biological sample is permeabilized, allowing the analyte to migrate away from the sample and toward the array. The analyte interacts with a capture probe on the spatially-barcoded array 102. Once the analyte hybridizes/is bound to the capture probe, the sample is optionally removed from the array and the capture probes are analyzed in order to obtain spatially-resolved analyte information 103.

Figure 2:
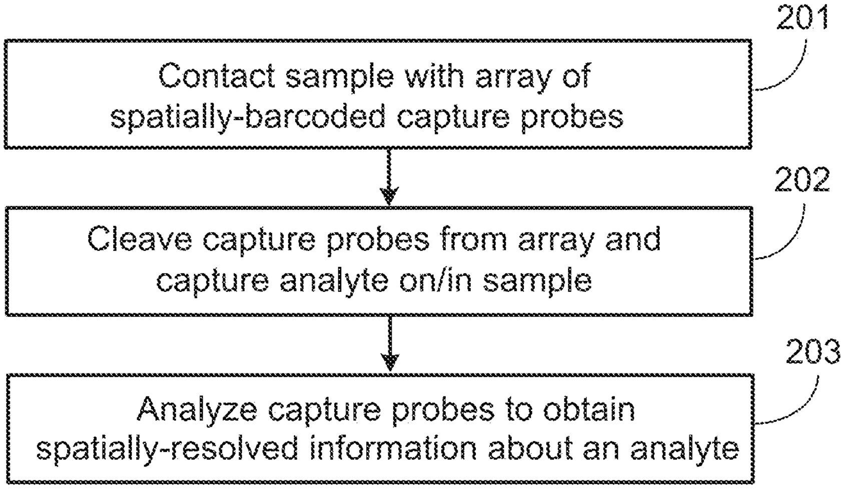
FIG. 2 shows an exemplary spatial analysis workflow.

Another general method is to cleave the spatially-barcoded capture probes from an array, and promote the spatially-barcoded capture probes towards and/or into or onto the biological sample. FIG. 2 depicts an exemplary embodiment of this general method, the spatially-barcoded array populated with capture probes (as described further herein) can be contacted with a sample 201. The spatially-barcoded capture probes are cleaved and then interact with cells within the provided biological sample 202. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed to obtain spatially-resolved information about the tagged cell 203.

Figure 3:
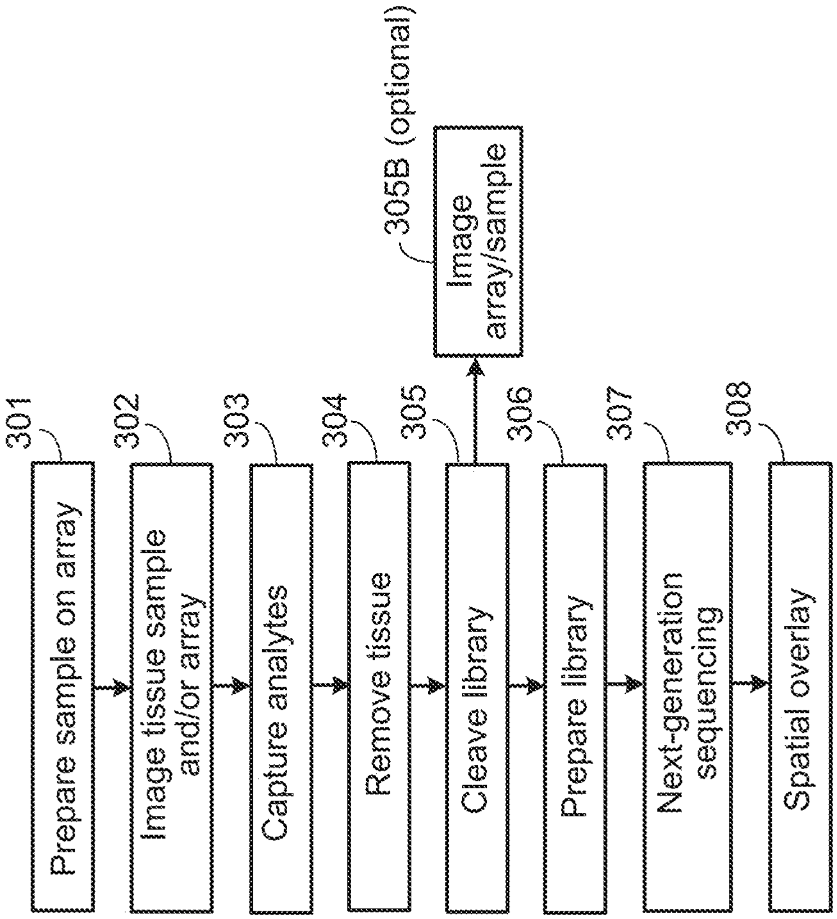
FIG. 3 shows an exemplary spatial analysis workflow.

FIG. 3 shows an exemplary workflow that includes preparing a biological sample on a spatially-barcoded array 301. Sample preparation may include placing the sample on a slide, fixing the sample, and/or staining the biological sample for imaging. The stained sample can be then imaged on the array 302 using both brightfield (to image the sample hematoxylin and eosin stain) and/or fluorescence (to image features) modalities. Optionally, the sample can be destained prior to permeabilization. In some embodiments, analytes are then released from the sample and capture probes forming the spatially-barcoded array hybridize or bind the released analytes 303. The sample is then removed from the array 304 and the capture probes cleaved from the array 305. The biological sample and array are then optionally imaged a second time in one or both modalities 305B while the analytes are reverse transcribed into cDNA, and an amplicon library is prepared 306 and sequenced 307. Images are then spatially-overlaid in order to correlate spatially-identified biological sample information 308. When the sample and array are not imaged a second time, 305B, a spot coordinate file is supplied instead. The spot coordinate file replaces the second imaging step 305B. Further, amplicon library preparation 306 can be performed with a unique PCR adapter and sequenced 307.

Figure 4:
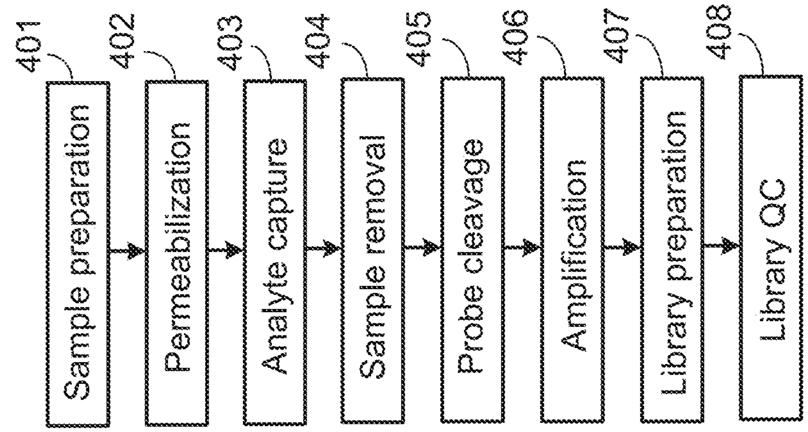
FIG. 4 shows an exemplary spatial analysis workflow.

FIG. 4 shows another exemplary workflow that utilizes a spatially-barcoded array on a substrate, where spatially-barcoded capture probes are clustered at areas called features. The spatially-barcoded capture probes can include a cleavage domain, one or more functional domains, a spatial barcode, a unique molecular identifier, and a capture domain. The spatially-barcoded capture probes can also include a 5' end modification for reversible attachment to the substrate. The spatially-barcoded array is contacted with a biological sample 401, and the sample is permeabilized through application of permeabilization reagents 402. Permeabilization reagents may be administered by placing the array/sample assembly within a bulk solution. Alternatively, permeabilization reagents may be administered to the sample via a diffusion-resistant medium and/or a physical barrier such as a lid, wherein the sample is sandwiched between the diffusion-resistant medium and/or barrier and the array-containing substrate. The analytes are migrated toward the spatially-barcoded capture array using any number of techniques disclosed herein. For example, analyte migration can occur using a diffusion-resistant medium lid and passive migration. As another example, analyte migration can be active migration, using an electrophoretic transfer system, for example. Once the analytes are in close proximity to the spatially-barcoded capture probes, the capture probes can hybridize or otherwise bind a target analyte 403. The biological sample can be optionally removed from the array 404.

The capture probes can be optionally cleaved from the array 405, and the captured analytes can be spatially-barcoded by performing a reverse transcriptase first strand cDNA reaction. A first strand cDNA reaction can be optionally performed using template switching oligonucleotides. For example, a template switching oligonucleotide can hybridize to a poly(C) tail added to a 3'end of the cDNA by a reverse transcriptase enzyme in a template independent manner. The original mRNA template and template switching oligonucleotide can then be denatured from the cDNA and the spatially-barcoded capture probe can then hybridize with the cDNA and a complement of the cDNA can be generated. The first strand cDNA can then be purified and collected for downstream amplification steps. The first strand cDNA can be amplified using PCR 406, where the forward and reverse primers flank the spatial barcode and analyte regions of interest, generating a library associated with a particular spatial barcode 407. In some embodiments, the library preparation can be quantitated and/or quality controlled to verify the success of the library preparation steps 408. In some embodiments, the cDNA comprises a sequencing by synthesis (SBS) primer sequence. The library amplicons are sequenced and analyzed to decode spatial information 407.

Using the methods, compositions, systems, kits, and devices described herein, RNA transcripts present in biological samples (e.g., tissue samples) can be used for spatial transcriptome analysis. In particular, in some cases, the barcoded oligonucleotides may be configured to prime, replicate, and consequently yield barcoded extension products from an RNA template, or derivatives thereof. For example, in some cases, the barcoded oligonucleotides may include mRNA specific priming sequences, e.g., poly-T primer segments that allow priming and replication of mRNA in a reverse transcription reaction or other targeted priming sequences. Alternatively or additionally, random RNA priming may be carried out using random N-mer primer segments of the barcoded oligonucleotides. Reverse transcriptases (RTs) can use an RNA template and a primer complementary to the 3' end of the RNA template to direct the synthesis of the first strand complementary DNA (cDNA). Many RTs can be used in this reverse transcription reactions, including, for example, avian myeloblastosis virus (AMV) reverse transcriptase, moloney murine leukemia virus (M-MuLV or MMLV), and other variants thereof. Some recombinant M-MuLV reverse transcriptase, such as, for example, PROTOSCRIPT® II reverse transcriptase, can have reduced RNase H activity and increased thermostability when compared to its wild type counterpart, and provide higher specificity, higher yield of cDNA and more full-length cDNA products with up to 12 kilobase (kb) in length. In some embodiments, the reverse transcriptase enzyme is a mutant reverse transcriptase enzyme such as, but not limited to, mutant MMLV reverse transcriptase. In another embodiment, the reverse transcriptase is a mutant MMLV reverse transcriptase such as, but not limited to, one or more variants described in US Patent Publication No. 20180312822 and U.S. Provisional Patent Application No. 62/946,885 filed on Dec. 11, 2019, both of which are incorporated herein by reference in their entireties.

Figure 5:
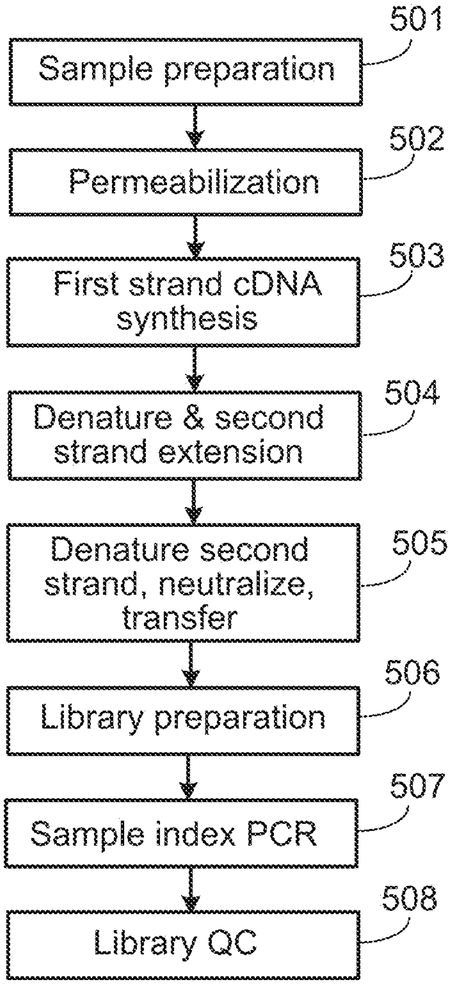
FIG. 5 shows an exemplary spatial analysis workflow.

FIG. 5 depicts an exemplary workflow where the biological sample is removed from the spatially-barcoded array and the spatially-barcoded capture probes are removed from the array for barcoded analyte amplification and library preparation. Another embodiment includes performing first strand synthesis using template switching oligonucleotides on the spatially-barcoded array without cleaving the capture probes. In this embodiment, sample preparation 501 and permeabilization 502 are performed as described elsewhere herein. Once the capture probes capture the analyte(s), first strand cDNA created by template switching and reverse transcriptase 503 is then denatured and the second strand is then extended 504. The second strand cDNA is then denatured from the first strand cDNA, neutralized, and transferred to a tube 505. cDNA quantification and amplification can be performed using standard techniques discussed herein. The cDNA can then be subjected to library preparation 506 and indexing 507, including fragmentation, end-repair, and a-tailing, and indexing PCR steps. The library preparation can optionally be quality controlled to verify the success of the library preparation methods 508.

In a non-limiting example of the workflows described above, a biological sample (e.g., tissue section), can be fixed with methanol, stained with hematoxylin and eosin, and imaged. Optionally, the sample can be destained prior to permeabilization. The images can be used to map spatial gene expression patterns back to the biological sample. A permeabilization enzyme can be used to permeabilize the biological sample directly on the slide. Analytes (e.g., polyadenylated mRNA) released from the overlying cells of the biological sample can be captured by capture probes within a capture area on a substrate. Reverse transcription (RT) reagents can be added to permeabilized biological samples. Incubation with the RT reagents can produce spatially-barcoded full-length cDNA from the captured analytes (e.g., polyadenylated mRNA). Second strand reagents (e.g., second strand primers, enzymes) can be added to the biological sample on the slide to initiate second strand synthesis. The resulting cDNA can be denatured from the capture probe template and transferred (e.g., to a clean tube) for amplification, and/or library construction. The spatially-barcoded, full-length cDNA can be amplified via PCR prior to library construction. The amplicons can then be enzymatically fragmented and/or size-selected in order to provide for desired amplicon size. In some embodiments, when utilizing an Illumina® library preparation methodology, P5 and P7 sequences can be added to the amplifcons thereby allowing for capture of the library preparation on a sequencing flowcell (e.g., on Illumina sequencing instruments). Additionally, i7 and i5 can index sequences be added as sample indexes if multiple libraries are to be pooled and sequenced together. Further, Read 1 and Read 2 sequences can be added to the library preparation for sequencing purposes. The aforementioned sequences can be added to a library preparation sample, fore example, via End Repair, A-tailing, Adaptor Ligation, and/or PCR. The cDNA fragments can then be sequenced using, for example, paired-end sequencing using TruSeq Read 1 and TruSeq Read 2 as sequencing primer sites.

In some embodiments, performing correlative analysis of data produced by this workflow, and other workflows described herein, can yield over 95% correlation of genes expressed across two capture areas (e.g., 95% or greater, 96% or greater, 97% or greater, 98% or greater, or 99% or greater). When performing the described workflows using single cell RNA sequencing of nuclei, in some embodiments, correlative analysis of the data can yield over 90% (e.g., over 90%, 91%, 92%, 93%, 94%, 95%, 96%, 97%, 98%, or 99%) correlation of genes expressed across two capture areas.

In some embodiments, after cDNA is generated (e.g., by reverse transcription) the cDNA can be amplified directly on the substrate surface. Generating multiple copies of the cDNA (e.g., cDNA synthesized from captured analytes) via amplification directly on the substrate surface can improve final sequencing library complexity. Thus, in some embodiments, cDNA can be amplified directly on the substrate surface by isothermal nucleic acid amplification. In some embodiments, isothermal nucleic acid amplification can amplify RNA or DNA.

In some embodiments, isothermal amplification can be faster than a standard PCR reaction. In some embodiments, isothermal amplification can be linear amplification (e.g., asymmetrical with a single primer), or exponential amplification (e.g., with two primers). In some embodiments, isothermal nucleic acid amplification can be performed by a template-switching oligonucleotide primer. In some embodiments, the template switching oligonucleotide adds a common sequence onto the 5' end of the RNA being reverse transcribed. For example, after a capture probe interacts with an analyte (e.g., mRNA) and reverse transcription is performed such that additional nucleotides are added to the end of the cDNA creating a 3' overhang as described herein. In some embodiments, a template switching oligonucleotide hybridizes to untemplated poly(C) nucleotides added by a reverse transcriptase to continue replication to the 5' end of the template switching oligonucleotide, thereby generating full-length cDNA ready for further amplification. In some embodiments, the template switching oligonucleotide adds a common 5' sequence to full-length cDNA that is used for cDNA amplification (e.g., a reverse complement of the template switching oligonucleotide).

In some embodiments, once a full-length cDNA molecule is generated, the template switching oligonucleotide can serve as a primer in a cDNA amplification reaction (e.g., with a DNA polymerase). In some embodiments, double stranded cDNA (e.g., first strand cDNA and second strand reverse complement cDNA) can be amplified via isothermal amplification with either a helicase or recombinase, followed by a strand displacing DNA polymerase. The strand displacing DNA polymerase can generate a displaced second strand resulting in an amplified product.

In any of isothermal amplification methods described herein, barcode exchange (e.g., spatial barcode) can occur after the first amplification cycle where there are unused capture probes on the substrate surface. In some embodiments, the free 3'OH end of the unused capture probes can be blocked by any suitable 3'OH blocking method. In some embodiments, the 3'OH can be blocked by hairpin ligation.

Isothermal nucleic acid amplification can be used in addition to, or as an alternative to standard PCR reactions (e.g., a PCR reaction that requires heating to about 95° C. to denature double stranded DNA). Isothermal nucleic acid amplification generally does not require the use of a thermocycler, however in some embodiments, isothermal amplification can be performed in a thermocycler. In some embodiments, isothermal amplification can be performed from about 35° C. to about 75° C. In some embodiments, isothermal amplification can be performed from about 40° C., about 45° C., about 50° C., about 55° C., about 60° C., about 65° C., or about 70° C. or anywhere in between depending on the polymerase and auxiliary enzymes used.

Isothermal nucleic acid amplification techniques are known in the art, and can be used alone or in combination with any of the spatial methods described herein. For example, non-limiting examples of suitable isothermal nucleic acid amplification techniques include transcription mediated amplification, nucleic acid sequence-based amplification, signal mediated amplification of RNA technology, strand displacement amplification, rolling circle amplification, loop-mediated isothermal amplification of DNA (LAMP), isothermal multiple displacement amplification, recombinase polymerase amplification, helicase-dependent amplification, single primer isothermal amplification, and circular helicase-dependent amplification (See, e.g., Gill and Ghaemi, Nucleic acid isothermal amplification technologies: a review, *Nucleosides, Nucleotides, & Nucleic Acids,* 27(3), 224-43, doi: 10.1080/15257770701845204 (2008), which is incorporated herein by reference in its entirety).

In some embodiments, the isothermal nucleic acid amplification is helicase-dependent nucleic acid amplification. Helicase-dependent isothermal nucleic acid amplification is described in Vincent, et. al., Helicase-dependent isothermal DNA amplification, *EMBO Rep.,* 795-800 (2004) and U.S. Pat. No. 7,282,328, which are both incorporated herein by reference in their entireties. Further, helicase-dependent nucleic acid amplification on a substrate (e.g., on-chip) is described in Andresen, et. al., Helicase-dependent amplification: use in OnChip amplification and potential for point-of-care diagnostics, *Expert Rev Mol Diagn.,* 9, 645-650, doi: 10.1586/erm.09.46 (2009), which is incorporated herein by reference in its entirety. In some embodiments, the isothermal nucleic acid amplification is recombinase polymerase nucleic acid amplification. Recombinase polymerase nucleic acid amplification is described in Piepenburg, et al., DNA Detection Using Recombinant Proteins, *PLoS Biol.,* 4, 7 e204 (2006) and Li, et. al., Review: a comprehensive summary of a decade development of the recombinase polymerase amplification, *Analyst,* 144, 31-67, doi: 10.1039/C8AN01621F (2019), both of which are incorporated herein by reference in their entireties.

Generally, isothermal amplification techniques use standard PCR reagents (e.g., buffer, dNTPs etc.) known in the art. Some isothermal amplification techniques can require additional reagents. For example, helicase dependent nucleic acid amplification uses a single-strand binding protein and an accessory protein. In another example, recombinase polymerase nucleic acid amplification uses recombinase (e.g., T4 UvsX), recombinase loading factor (e.g., TF UvsY), single-strand binding protein (e.g., T4 gp32), crowding agent (e.g., PEG-35K), and ATP.

After isothermal nucleic acid amplification of the full-length cDNA described by any of the methods herein, the isothermally amplified cDNAs (e.g., single-stranded or double-stranded) can be recovered from the substrate, and optionally followed by amplification with typical cDNA PCR in microcentrifuge tubes. The sample can then be used with any of the spatial methods described herein.

(i) Immunohistochemistry and Immunofluorescence

In some embodiments, immunofluorescence or immunohistochemistry protocols (direct and indirect staining techniques) can be performed as a part of, or in addition to, the exemplary spatial workflows presented herein. For example, tissue sections can be fixed according to methods described herein. The biological sample can be transferred to an array (e.g., capture probe array), wherein analytes (e.g., proteins) are probed using immunofluorescence protocols. For example, the sample can be rehydrated, blocked, and permeabilized (3×SSC, 2% BSA, 0.1% Triton X, 1 U/μl RNAse inhibitor for 10 min at 4° C.) before being stained with fluorescent primary antibodies (1:100 in 3×SSC, 2% BSA, 0.1% Triton X, 1 U/μl RNAse inhibitor for 30 min at 4° C.). The biological sample can be washed, coverslipped (in glycerol+1 U/μl RNAse inhibitor), imaged (e.g., using a confocal microscope or other apparatus capable of fluorescent detection), washed, and processed according to analyte capture or spatial workflows described herein.

As used herein, an "antigen retrieval buffer" can improve antibody capture in IF/IHC protocols. An exemplary protocol for antigen retrieval can be preheating the antigen retrieval buffer (e.g., to 95° C.), immersing the biological sample in the heated antigen retrieval buffer for a predetermined time, and then removing the biological sample from the antigen retrieval buffer and washing the biological sample.

In some embodiments, optimizing permeabilization can be useful for identifying intracellular analytes. Permeabilization optimization can include selection of permeabilization agents, concentration of permeabilization agents, and permeabilization duration. Tissue permeabilization is discussed elsewhere herein.

In some embodiments, blocking an array and/or a biological sample in preparation of labeling the biological sample decreases unspecific binding of the antibodies to the array and/or biological sample (decreases background). Some embodiments provide for blocking buffers/blocking solutions that can be applied before and/or during application of the label, wherein the blocking buffer can include a blocking agent, and optionally a surfactant and/or a salt solution. In some embodiments, a blocking agent can be bovine serum albumin (BSA), serum, gelatin (e.g., fish gelatin), milk (e.g., non-fat dry milk), casein, polyethylene glycol (PEG), polyvinyl alcohol (PVA), or polyvinylpyrrolidone (PVP), biotin blocking reagent, a peroxidase blocking reagent, levamisole, Carnoy's solution, glycine, lysine, sodium borohydride, pontamine sky blue, Sudan Black, trypan blue, FITC blocking agent, and/or acetic acid. The blocking buffer/blocking solution can be applied to the array and/or biological sample prior to and/or during labeling (e.g., application of fluorophore-conjugated antibodies) to the biological sample.

In some embodiments, additional steps or optimizations can be included in performing IF/IHC protocols in conjunction with spatial arrays. Additional steps or optimizations can be included in performing spatially-tagged analyte capture agent workflows discussed herein.

In some embodiments, provided herein are methods for spatially detecting an analyte (e.g., detecting the location of an analyte, e.g., a biological analyte) from a biological sample (e.g., an analyte present in a biological sample, such as a tissue section) that include: (a) providing a biological sample on a substrate; (b) staining the biological sample on the substrate, imaging the stained biological sample, and selecting the biological sample or subsection of the biological sample (e.g., region of interest) to subject to analysis; (c) providing an array comprising one or more pluralities of capture probes on a substrate; (d) contacting the biological sample with the array, thereby allowing a capture probe of the one or more pluralities of capture probes to capture the analyte of interest; and (e) analyzing the captured analyte, thereby spatially detecting the analyte of interest. Any variety of staining and imaging techniques as described herein or known in the art can be used in accordance with methods described herein. In some embodiments, the staining includes optical labels as described herein, including, but not limited to, fluorescent, radioactive, chemiluminescent, calorimetric, or colorimetric detectable labels. In some embodiments, the staining includes a fluorescent antibody directed to a target analyte (e.g., cell surface or intracellular proteins) in the biological sample. In some embodiments, the staining includes an immunohistochemistry stain directed to a target analyte (e.g., cell surface or intracellular proteins) in the biological sample. In some embodiments, the staining includes a chemical stain such as hematoxylin and eosin (H&E) or periodic acid-schiff (PAS). In some embodiments, significant time (e.g., days, months, or years) can elapse between staining and/or imaging the biological sample and performing analysis. In some embodiments, reagents for performing analysis are added to the biological sample before, contemporaneously with, or after the array is contacted to the biological sample. In some embodiments, step (d) includes placing the array onto the biological sample. In some embodiments, the array is a flexible array where the plurality of spatially-barcoded features (e.g., a substrate with capture probes, a bead with capture probes) are attached to a flexible substrate. In some embodiments, measures are taken to slow down a reaction (e.g., cooling the temperature of the biological sample or using enzymes that preferentially perform their primary function at lower or higher temperature as compared to their optimal functional temperature) before the array is contacted with the biological sample. In some embodiments, step (e) is performed without bringing the biological sample out of contact with the array. In some embodiments, step (e) is performed after the biological sample is no longer in contact with the array. In some embodiments, the biological sample is tagged with an analyte capture agent before, contemporaneously with, or after staining and/or imaging of the biological sample. In such cases, significant time (e.g., days, months, or years) can elapse between staining and/or imaging and performing analysis. In some embodiments, the array is adapted to facilitate biological analyte migration from the stained and/or imaged biological sample onto the array (e.g., using any of the materials or methods described herein). In some embodiments, a biological sample is permeabilized before being contacted with an array. In some embodiments, the rate of permeabilization is slowed prior to contacting a biological sample with an array (e.g., to limit diffusion of analytes away from their original locations in the biological sample). In some embodiments, modulating the rate of permeabilization (e.g., modulating the activity of a permeabilization reagent) can occur by modulating a condition that the biological sample is exposed to (e.g., modulating temperature, pH, and/or light). In some embodiments, modulating the rate of permeabilization includes use of external stimuli (e.g., small molecules, enzymes, and/or activating reagents) to modulate the rate of permeabilization. For example, a permeabilization reagent can be provided to a biological sample prior to contact with an array, which permeabilization reagent is inactive until a condition (e.g., temperature, pH, and/or light) is changed or an external stimulus (e.g., a small molecule, an enzyme, and/or an activating reagent) is provided.

In some embodiments, provided herein are methods for spatially detecting an analyte (e.g., detecting the location of an analyte, e.g., a biological analyte) from a biological sample (e.g., present in a biological sample such as a tissue section) that include: (a) providing a biological sample on a substrate; (b) staining the biological sample on the substrate, imaging the stained biological sample, and selecting the biological sample or subsection of the biological sample (e.g., a region of interest) to subject to spatial transcriptomic analysis; (c) providing an array comprising one or more pluralities of capture probes on a substrate; (d) contacting the biological sample with the array, thereby allowing a capture probe of the one or more pluralities of capture probes to capture the biological analyte of interest; and (e)

analyzing the captured biological analyte, thereby spatially detecting the biological analyte of interest.

(b) Capture Probes

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

Figure 6:
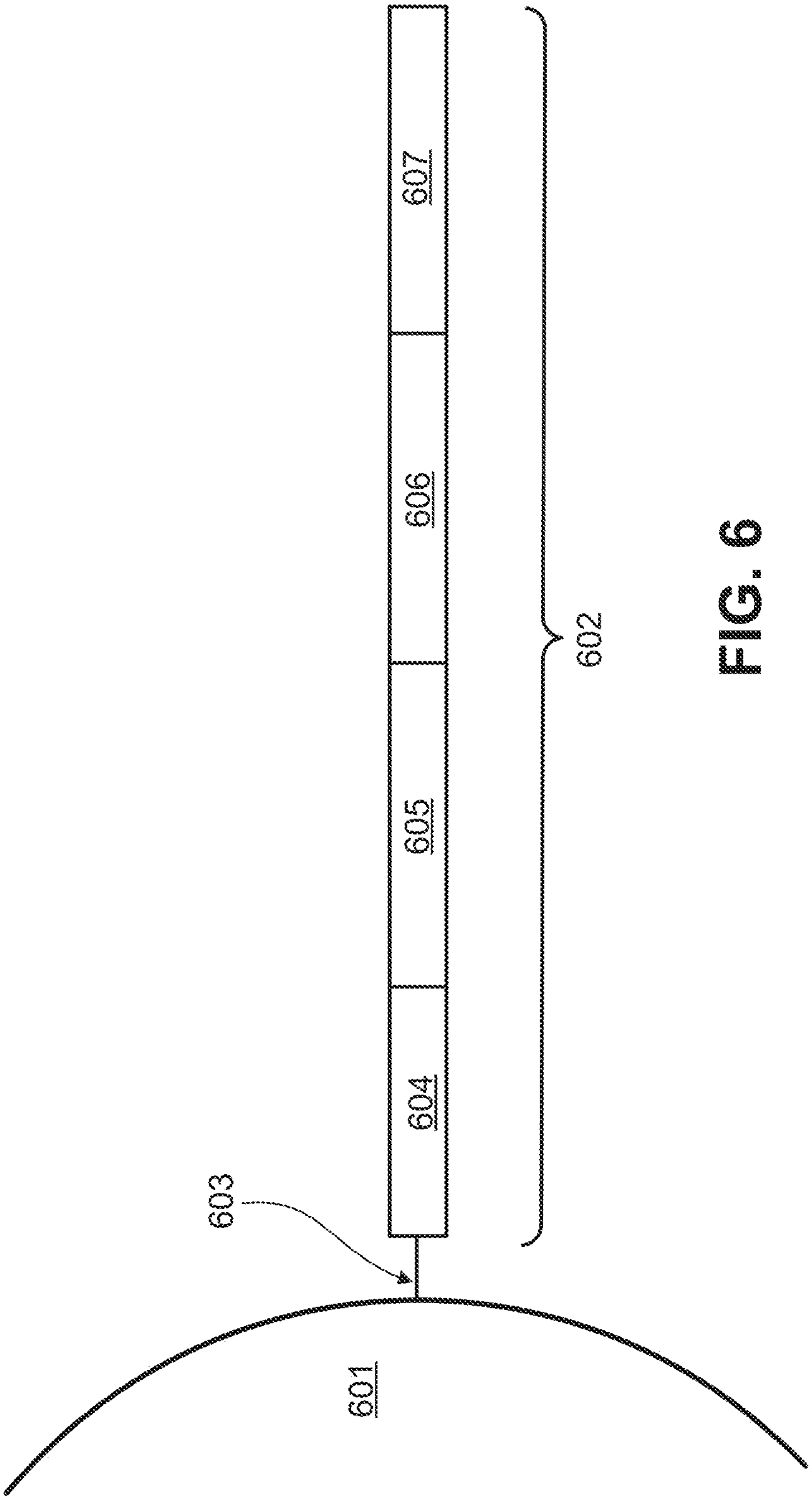
FIG. 6 is a schematic diagram showing an example of a barcoded capture probe, as described herein.

FIG. 6 is a schematic diagram showing an example of a capture probe, as described herein. As shown, the capture probe 602 is optionally coupled to a feature 601 by a cleavage domain 603, such as a disulfide linker. The capture probe can include functional sequences that are useful for subsequent processing, such as functional sequence 604, which can include a sequencer specific flow cell attachment sequence, e.g., a P5 or P7 sequence, as well as functional sequence 606, which can include sequencing primer sequences, e.g., a R1 primer binding site, a R2 primer binding site. In some embodiments, sequence 604 is a P7 sequence and sequence 606 is a R2 primer binding site. A spatial barcode 605 can be included within the capture probe for use in barcoding the target analyte. The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 605, functional sequences 604 (e.g., flow cell attachment sequence) and 606 (e.g., sequencing primer sequences) can be common to all of the probes attached to a given feature. The spatial barcode can also include a capture domain 607 to facilitate capture of a target analyte.

(i) Capture Domain

As discussed above, each capture probe includes at least one capture domain. The "capture domain" can be an oligonucleotide, a polypeptide, a small molecule, or any combination thereof, that binds specifically to a desired analyte. In some embodiments, a capture domain can be used to capture or detect a desired analyte.

In some embodiments, the capture domain is a functional nucleic acid sequence configured to interact with one or more analytes, such as one or more different types of nucleic acids (e.g., RNA molecules and DNA molecules). In some embodiments, the functional nucleic acid sequence can include an N-mer sequence (e.g., a random N-mer sequence), which N-mer sequences are configured to interact with a plurality of DNA molecules. In some embodiments, the functional sequence can include a poly(T) sequence, which poly(T) sequences are configured to interact with messenger RNA (mRNA) molecules via the poly (A) tail of an mRNA transcript. In some embodiments, the functional nucleic acid sequence is the binding target of a protein (e.g., a transcription factor, a DNA binding protein, or a RNA binding protein), where the analyte of interest is a protein.

Capture probes can include ribonucleotides and/or deoxyribonucleotides as well as synthetic nucleotide residues that are capable of participating in Watson-Crick type or analogous base pair interactions. In some embodiments, the capture domain is capable of priming a reverse transcription reaction to generate cDNA that is complementary to the captured RNA molecules. In some embodiments, the capture domain of the capture probe can prime a DNA extension (polymerase) reaction to generate DNA that is complementary to the captured DNA molecules. In some embodiments, the capture domain can template a ligation reaction between the captured DNA molecules and a surface probe that is directly or indirectly immobilized on the substrate. In some embodiments, the capture domain can be ligated to one strand of the captured DNA molecules. For example, SplintR ligase along with RNA or DNA sequences (e.g., degenerate RNA) can be used to ligate a single-stranded DNA or RNA to the capture domain. In some embodiments, ligases with RNA-templated ligase activity, e.g., SplintR ligase, T4 RNA ligase 2 or KOD ligase, can be used to ligate a single-stranded DNA or RNA to the capture domain. In some embodiments, a capture domain includes a splint oligonucleotide. In some embodiments, a capture domain captures a splint oligonucleotide.

In some embodiments, the capture domain is located at the 3' end of the capture probe and includes a free 3' end that can be extended, e.g., by template dependent polymerization, to form an extended capture probe as described herein. In some embodiments, the capture domain includes a nucleotide sequence that is capable of hybridizing to nucleic acid, e.g., RNA or other analyte, present in the cells of the biological sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, e.g., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly(U) oligonucleotide or an oligonucleotide included of deoxythymidine analogues. In some embodiments, the capture domain includes at least 10, 11, 12, 13, 14, 15, 16, 17, 18, 19, or 20 nucleotides. In some embodiments, the capture domain includes at least 25, 30, or 35 nucleotides.

In some embodiments, a capture probe includes a capture domain having a sequence that is capable of binding to mRNA and/or genomic DNA. For example, the capture probe can include a capture domain that includes a nucleic acid sequence (e.g., a poly(T) sequence) capable of binding to a poly(A) tail of an mRNA and/or to a poly(A) homopolymeric sequence present in genomic DNA. In some embodiments, a homopolymeric sequence is added to an mRNA molecule or a genomic DNA molecule using a terminal transferase enzyme in order to produce an analyte that has a poly(A) or poly(T) sequence. For example, a poly(A) sequence can be added to an analyte (e.g., a fragment of genomic DNA) thereby making the analyte capable of capture by a poly(T) capture domain.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located 5' or 3' of the poly(T) sequence, e.g., at the 3' end of the capture domain. The poly(T)-random sequence probe can facilitate the capture of the mRNA poly(A) tail. In some embodiments, the capture domain can be an entirely random sequence. In some embodiments, degenerate capture domains can be used.

In some embodiments, a pool of two or more capture probes form a mixture, where the capture domain of one or more capture probes includes a poly(T) sequence and the capture domain of one or more capture probes includes random sequences. In some embodiments, a pool of two or more capture probes form a mixture where the capture domain of one or more capture probes includes poly(T)-like sequence and the capture domain of one or more capture probes includes random sequences. In some embodiments, a pool of two or more capture probes form a mixture where the capture domain of one or more capture probes includes a poly(T)-random sequences and the capture domain of one or more capture probes includes random sequences. In some embodiments, probes with degenerate capture domains can be added to any of the preceding combinations listed herein. In some embodiments, probes with degenerate capture domains can be substituted for one of the probes in each of the pairs described herein.

The capture domain can be based on a particular gene sequence or particular motif sequence or common/conserved sequence, that it is designed to capture (i.e., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, RNase MRP, TERC, SL RNA, aRNA, cis-NAT, crRNA, lncRNA, miRNA, piRNA, siRNA, shRNA, tasiRNA, rasiRNA, 7SK, eRNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended analyte. In some embodiments, an anchor sequence includes a sequence of nucleotides, including a 1-mer, 2-mer, 3-mer or longer sequence. In some embodiments, the short sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains of capture probes are blocked prior to contacting the biological sample with the array, and blocking probes are used when the nucleic acid in the biological sample is modified prior to its capture on the array. In some embodiments, the blocking probe is used to block or modify the free 3' end of the capture domain. In some embodiments, blocking probes can be hybridized to the capture probes to mask the free 3' end of the capture domain, e.g., hairpin probes, partially double stranded probes, or complementary sequences. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the biological sample with the array, prevents modification of the capture probes, e.g., prevents the addition of a poly(A) tail to the free 3' end of the capture probes.

Non-limiting examples of 3' modifications include dideoxy C-3' (3'-ddC), 3' inverted dT, 3' C3 spacer, 3'Amino, and 3' phosphorylation. In some embodiments, the nucleic acid in the biological sample can be modified such that it can be captured by the capture domain. For example, an adaptor sequence (including a binding domain capable of binding to the capture domain of the capture probe) can be added to the end of the nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the biological sample, e.g., ligation or extension.

In some embodiments, the capture domain of the capture probe is modified to allow the removal of any modifications of the capture probe that occur during modification of the nucleic acid molecules of the biological sample. In some embodiments, the capture probes can include an additional sequence downstream of the capture domain, e.g., 3' to the capture domain, namely a blocking domain.

In some embodiments, the capture domain of the capture probe can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

(ii) Cleavage Domain

Each capture probe can optionally include at least one cleavage domain. The cleavage domain represents the portion of the probe that is used to reversibly attach the probe to an array feature, as will be described further herein. Further, one or more segments or regions of the capture probe can optionally be released from the array feature by cleavage of the cleavage domain. As an example, spatial barcodes and/or universal molecular identifiers (UMIs) can be released by cleavage of the cleavage domain.

Figure 7:
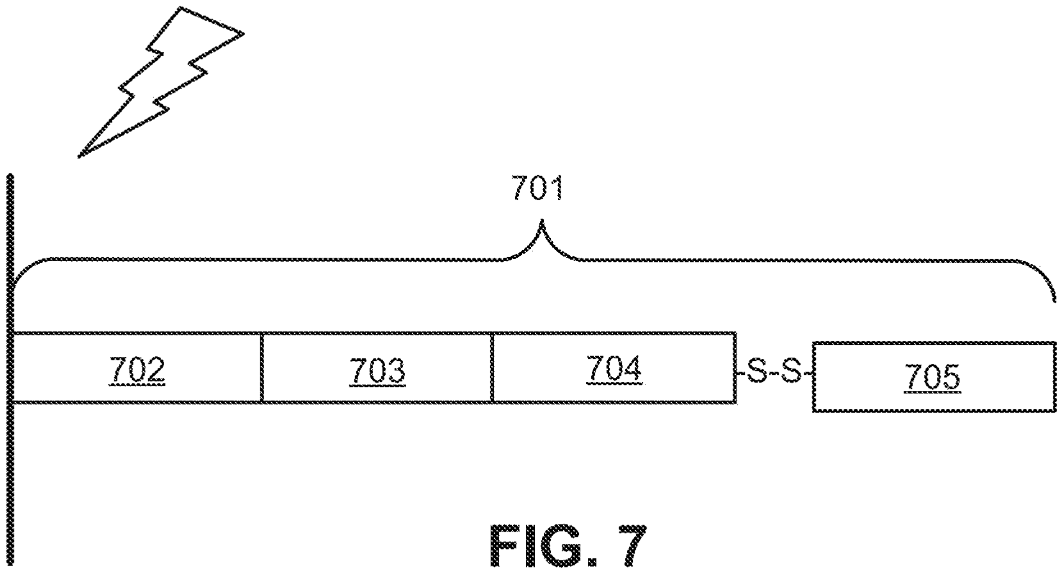
FIG. 7 is a schematic illustrating a cleavable capture probe, wherein the cleaved capture probe can enter into a non-permeabilized cell and bind to target analytes within the sample.

FIG. 7 is a schematic illustrating a cleavable capture probe, wherein the cleaved capture probe can enter into a non-permeabilized cell and bind to analytes within the sample. The capture probe 701 contains a cleavage domain 702, a cell penetrating peptide 703, a reporter molecule 704, and a disulfide bond (—S—S—). 705 represents all other parts of a capture probe, for example a spatial barcode and a capture domain.

In some embodiments, the cleavage domain linking the capture probe to a feature is a bond capable of cleavage by an enzyme. An enzyme can be added to cleave the cleavage domain, resulting in release of the capture probe from the feature. As another example, heating can also result in degradation of the cleavage domain and release of the attached capture probe from the array feature. In some embodiments, laser radiation is used to heat and degrade cleavage domains of capture probes at specific locations. In some embodiments, the cleavage domain is a photo-sensitive chemical bond (e.g., a chemical bond that dissociates when exposed to light such as ultraviolet light). In some embodiments, the cleavage domain can be an ultrasonic cleavage domain. For example, ultrasonic cleavage can depend on nucleotide sequence, length, pH, ionic strength, temperature, and the ultrasonic frequency (e.g., 22 kHz, 44 kHz) (Grokhovsky, S. L., Specificity of DNA cleavage by ultrasound, *Molecular Biology,* 40(2), 276-283 (2006)).

Oligonucleotides with photo-sensitive chemical bonds (e.g., photo-cleavable linkers) have various advantages. They can be cleaved efficiently and rapidly (e.g., in nanoseconds and milliseconds). In some cases, photo-masks can be used such that only specific regions of the array are exposed to cleavable stimuli (e.g., exposure to UV light, exposure to light, exposure to heat induced by laser). When a photo-cleavable linker is used, the cleavable reaction is triggered by light, and can be highly selective to the linker and consequently biorthogonal. Typically, wavelength absorption for the photocleavable linker is located in the near-UV range of the spectrum. In some embodiments, $\lambda_{max}$ of the photocleavable linker is from about 300 nm to about 400 nm, or from about 310 nm to about 365 nm. In some embodiments, λmax of the photocleavable linker is about 300 nm, about 312 nm, about 325 nm, about 330 nm, about 340 nm, about 345 nm, about 355 nm, about 365 nm, or about 400 nm.

Non-limiting examples of a photo-sensitive chemical bond that can be used in a cleavage domain include those described in Leriche et al. *Bioorg Med Chem.* 2012 Jan. 15; 20(2):571-82, U.S. Publication No. 2017/0275669, WO 2020/047010 A2; WO 2020/047004 A2; WO 2020/047007 A2; WO 2020-047005 A2; WO 2020/047002 A1; PCT/US2019/065077, PCT/US2019/065048, PCT/US2019/064987, PCT/US2019/065013, PCT/US2019/065100, PCT/US2019/065072, PCT/US2019/065081, PCT/US2019/065096, and PCT/US2019/065041; each of which is herein incorporated by reference in its entirety.

Other examples of cleavage domains include labile chemical bonds such as, but not limited to, ester linkages (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), an abasic or apurinic/apyrimidinic (AP) site (e.g., cleavable with an alkali or an AP endonuclease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, e.g., enzymes with a long recognition site (at least 8 base pairs in length), is used to reduce the possibility of cleaving elsewhere in the capture probe.

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. Releasable capture probes can be available for reaction once released. Thus, for example, an activatable capture probe can be activated by releasing the capture probes from a feature.

In some embodiments, where the capture probe is attached indirectly to a substrate, e.g., via a surface probe, the cleavage domain includes one or more mismatch nucleotides, so that the complementary parts of the surface probe and the capture probe are not 100% complementary (for example, the number of mismatched base pairs can be one, two, or three base pairs). Such a mismatch is recognized, e.g., by the MutY and T7 endonuclease I enzymes, which results in cleavage of the nucleic acid molecule at the position of the mismatch. As described herein a "surface probe" can be any moiety present on the surface of the substrate capable of attaching to an agent (e.g., a capture probe). In some embodiments, the surface probe is an oligonucleotide. In some embodiments, the surface probe is part of the capture probe.

In some embodiments, where the capture probe is attached (e.g., immobilized) to a feature indirectly, e.g., via a surface probe, the cleavage domain includes a nickase recognition site or sequence. Nickases are endonucleases which cleave only a single strand of a DNA duplex. Thus, the cleavage domain can include a nickase recognition site close to the 5' end of the surface probe (and/or the 5' end of the capture probe) such that cleavage of the surface probe or capture probe destabilizes the duplex between the surface probe and capture probe thereby releasing the capture probe) from the feature.

Nickase enzymes can also be used in some embodiments where the capture probe is attached (e.g., immobilized) to the feature directly. For example, the substrate can be contacted with a nucleic acid molecule that hybridizes to the cleavage domain of the capture probe to provide or reconstitute a nickase recognition site, e.g., a cleavage helper probe. Thus, contact with a nickase enzyme will result in cleavage of the cleavage domain thereby releasing the capture probe from the feature. Such cleavage helper probes can also be used to provide or reconstitute cleavage recognition sites for other cleavage enzymes, e.g., restriction enzymes.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is incorporated herein by reference in its entirety. In general, any suitable nickase can be used to bind to a complementary nickase recognition site of a cleavage domain. Following use, the nickase enzyme can be removed from the assay or inactivated following release of the capture probes to prevent unwanted cleavage of the capture probes.

Examples of suitable capture domains that are not exclusively nucleic-acid based include, but are not limited to, proteins, peptides, aptamers, antigens, antibodies, and molecular analogs that mimic the functionality of any of the capture domains described herein.

In some embodiments, a cleavage domain is absent from the capture probe. Examples of substrates with attached capture probes lacking a cleavage domain are described for example in Macosko et al., (2015) Cell 161, 1202-1214, the entire contents of which are incorporated herein by reference.

In some embodiments, the region of the capture probe corresponding to the cleavage domain can be used for some other function. For example, an additional region for nucleic acid extension or amplification can be included where the cleavage domain would normally be positioned. In such embodiments, the region can supplement the functional domain or even exist as an additional functional domain. In some embodiments, the cleavage domain is present but its use is optional.

(iii) Functional Domain

Each capture probe can optionally include at least one functional domain. Each functional domain typically includes a functional nucleotide sequence for a downstream analytical step in the overall analysis procedure.

In some embodiments, the capture probe can include a functional domain for attachment to a sequencing flow cell, such as, for example, a P5 sequence for Illumina® sequencing. In some embodiments, the capture probe or derivative thereof can include another functional domain, such as, for example, a P7 sequence for attachment to a sequencing flow cell for Illumina® sequencing. The functional domains can be selected for compatibility with a variety of different sequencing systems, e.g., 454 Sequencing, Ion Torrent Proton or PGM, Illumina X10, etc., and the requirements thereof.

In some embodiments, the functional domain includes a primer. The primer can include an R1 primer sequence for Illumina® sequencing, and in some embodiments, an R2 primer sequence for Illumina® sequencing. Examples of such capture probes and uses thereof are described in U.S. Patent Publication Nos. 2014/0378345 and 2015/0376609, the entire contents of each of which are incorporated herein by reference.

(iv) Spatial Barcode

As discussed above, the capture probe can include one or more spatial barcodes (e.g., two or more, three or more, four or more, five or more) spatial barcodes. A "spatial barcode" is a contiguous nucleic acid segment or two or more non-contiguous nucleic acid segments that function as a label or identifier that conveys or is capable of conveying spatial information. In some embodiments, a capture probe includes a spatial barcode that possesses a spatial aspect, where the barcode is associated with a particular location within an array or a particular location on a substrate.

A spatial barcode can be part of an analyte, or independent from an analyte (e.g., part of the capture probe). A spatial barcode can be a tag attached to an analyte (e.g., a nucleic acid molecule) or a combination of a tag in addition to an endogenous characteristic of the analyte (e.g., size of the analyte or end sequence(s)). A spatial barcode can be unique. In some embodiments where the spatial barcode is unique, the spatial barcode functions both as a spatial barcode and as a unique molecular identifier (UMI), associated with one particular capture probe.

Spatial barcodes can have a variety of different formats. For example, spatial barcodes can include polynucleotide spatial barcodes; random nucleic acid and/or amino acid sequences; and synthetic nucleic acid and/or amino acid sequences. In some embodiments, a spatial barcode is attached to an analyte in a reversible or irreversible manner. In some embodiments, a spatial barcode is added to, for example, a fragment of a DNA or RNA sample before, during, and/or after sequencing of the sample. In some embodiments, a spatial barcode allows for identification and/or quantification of individual sequencing-reads. In some embodiments, a spatial barcode is a used as a fluorescent barcode for which fluorescently labeled oligonucleotide probes hybridize to the spatial barcode.

In some embodiments, the spatial barcode is a nucleic acid sequence that does not substantially hybridize to analyte nucleic acid molecules in a biological sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The spatial barcode sequences can include from about 6 to about 20 or more nucleotides within the sequence of the capture probes. In some embodiments, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer. In some embodiments, the length of a spatial barcode sequence is at most about 6, 7, 8, 9, 10, 11, 12, 13, 14, 15, 16, 17, 18, 19, 20 nucleotides or shorter.

These nucleotides can be completely contiguous, e.g., in a single stretch of adjacent nucleotides, or they can be separated into two or more separate subsequences that are separated by 1 or more nucleotides. Separated spatial barcode subsequences can be from about 4 to about 16 nucleotides in length. In some embodiments, the spatial barcode subsequence can be about 4, 5, 6, 7, 8, 9, 10, 11, 12, 13, 14, 15, 16 nucleotides or longer. In some embodiments, the spatial barcode subsequence can be at least about 4, 5, 6, 7, 8, 9, 10, 11, 12, 13, 14, 15, 16 nucleotides or longer. In some embodiments, the spatial barcode subsequence can be at most about 4, 5, 6, 7, 8, 9, 10, 11, 12, 13, 14, 15, 16 nucleotides or shorter.

For multiple capture probes that are attached to a common array feature, the one or more spatial barcode sequences of the multiple capture probes can include sequences that are the same for all capture probes coupled to the feature, and/or sequences that are different across all capture probes coupled to the feature.

Figure 8:
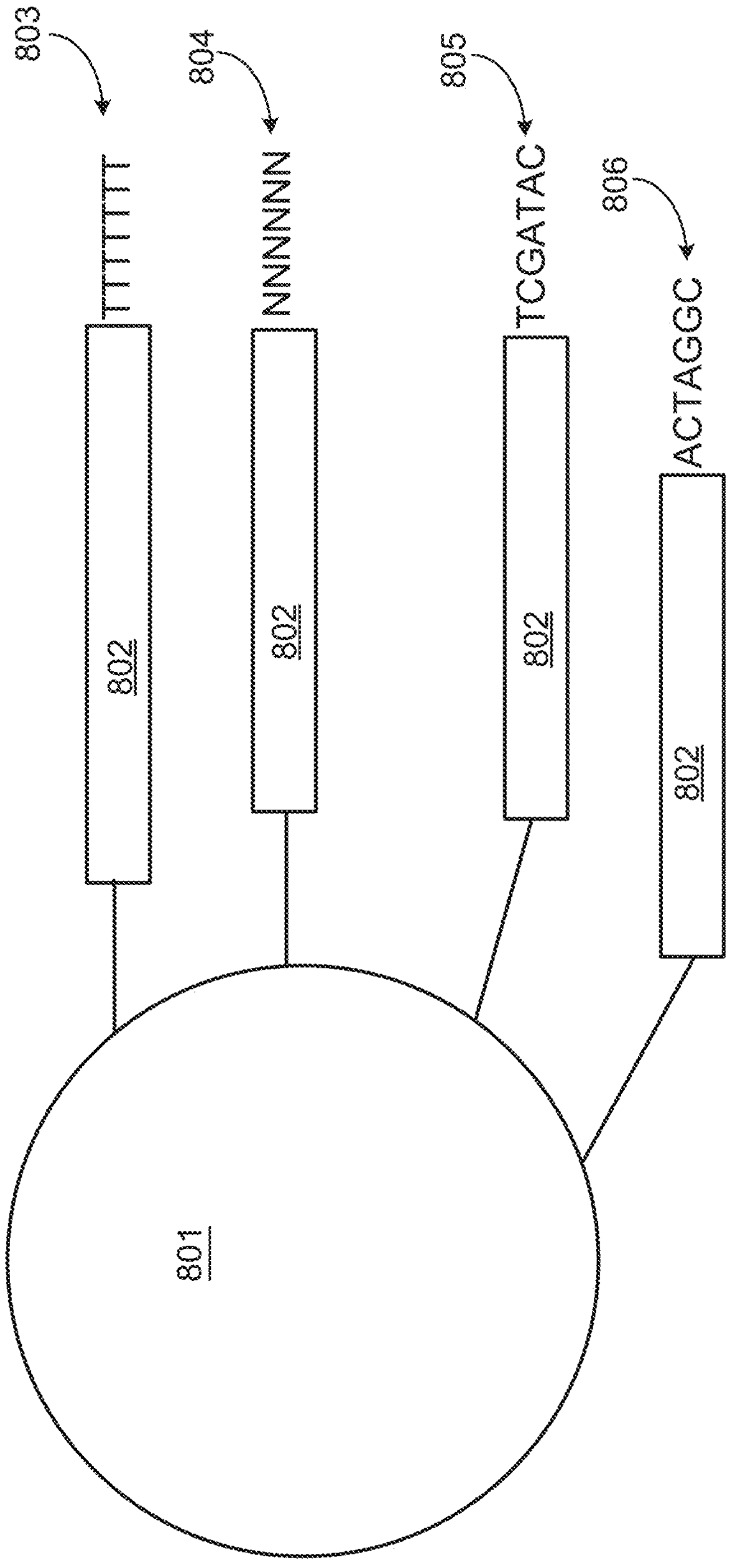
FIG. 8 is a schematic diagram of an exemplary multiplexed spatially-barcoded feature.

FIG. 8 is a schematic diagram of an exemplary multiplexed spatially-barcoded feature. In FIG. 8, the feature 801 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 802. One type of capture probe associated with the feature includes the spatial barcode 802 in combination with a poly(T) capture domain 803, designed to capture mRNA target analytes. A second type of capture probe associated with the feature includes the spatial barcode 802 in combination with a random N-mer capture domain 804 for gDNA analysis. A third type of capture probe associated with the feature includes the spatial barcode 802 in combination with a capture domain complementary to the analyte capture agent of interest 805. A fourth type of capture probe associated with the feature includes the spatial barcode 802 in combination with a capture probe that can specifically bind a nucleic acid molecule 806 that can function in a CRISPR assay (e.g., CRISPR/Cas9). While only four different capture probe-barcoded constructs are shown in FIG. 8, capture-probe barcoded constructs can be tailored for analyses of any given analyte associated with a nucleic acid and capable of binding with such a construct. For example, the schemes shown in FIG. 8 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor). In some embodiments, a perturbation agent can be a small molecule, an antibody, a drug, an aptamer, a miRNA, a physical environmental (e.g., temperature change), or any other known perturbation agents.

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

(v) Unique Molecular Identifier

The capture probe can include one or more (e.g., two or more, three or more, four or more, five or more) Unique Molecular Identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain).

A UMI can be unique. A UMI can include one or more specific polynucleotides sequences, one or more random nucleic acid and/or amino acid sequences, and/or one or more synthetic nucleic acid and/or amino acid sequences, or combinations thereof.

In some embodiments, the UMI is a nucleic acid sequence that does not substantially hybridize to analyte nucleic acid molecules in a biological sample. In some embodiments, the UMI has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The UMI can include from about 6 to about 20 or more nucleotides within the sequence of the capture probes. In some embodiments, the length of a UMI sequence can be about 6, 7, 8, 9, 10, 11, 12, 13, 14, 15, 16, 17, 18, 19, 20 nucleotides or longer. In some embodiments, the length of a UMI sequence can be at least about 6, 7, 8, 9, 10, 11, 12, 13, 14, 15, 16, 17, 18, 19, 20 nucleotides or longer. In some embodiments, the length of a UMI sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated UMI subsequences can be from about 4 to about 16 nucleotides in length. In some embodiments, the UMI subsequence can be about 4, 5, 6, 7, 8, 9, 10, 11, 12, 13, 14, 15, 16 nucleotides or longer. In some embodiments, the UMI subsequence can be at least about 4, 5, 6, 7, 8, 9, 10, 11, 12, 13, 14, 15, 16 nucleotides or longer. In some embodiments, the UMI subsequence can be at most about 4, 5, 6, 7, 8, 9, 10, 11, 12, 13, 14, 15, 16 nucleotides or shorter.

In some embodiments, a UMI is attached to an analyte in a reversible or irreversible manner. In some embodiments, a UMI is added to, for example, a fragment of a DNA or RNA sample before, during, and/or after sequencing of the analyte. In some embodiments, a UMI allows for identification and/or quantification of individual sequencing-reads. In some embodiments, a UMI is a used as a fluorescent barcode for which fluorescently labeled oligonucleotide probes hybridize to the UMI.

(vi) Other Aspects of Capture Probes

For capture probes that are attached to an array feature, an individual array feature can include one or more capture probes. In some embodiments, an individual array feature includes hundreds or thousands of capture probes. In some embodiments, the capture probes are associated with a particular individual feature, where the individual feature contains a capture probe including a spatial barcode unique to a defined region or location on the array.

In some embodiments, a particular feature can contain capture probes including more than one spatial barcode (e.g., one capture probe at a particular feature can include a spatial barcode that is different than the spatial barcode included in another capture probe at the same particular feature, while both capture probes include a second, common spatial barcode), where each spatial barcode corresponds to a particular defined region or location on the array. For example, multiple spatial barcode sequences associated with one particular feature on an array can provide a stronger address or attribution to a given location by providing duplicate or independent confirmation of the location. In some embodiments, the multiple spatial barcodes represent increasing specificity of the location of the particular array point. In a non-limiting example, a particular array point can be coded with two different spatial barcodes, where each spatial barcode identifies a particular defined region within the array, and an array point possessing both spatial barcodes identifies the sub-region where two defined regions overlap, e.g., such as the overlapping portion of a Venn diagram.

In another non-limiting example, a particular array point can be coded with three different spatial barcodes, where the first spatial barcode identifies a first region within the array, the second spatial barcode identifies a second region, where the second region is a subregion entirely within the first region, and the third spatial barcode identifies a third region, where the third region is a subregion entirely within the first and second subregions.

In some embodiments, capture probes attached to array features are released from the array features for sequencing. Alternatively, in some embodiments, capture probes remain attached to the array features, and the probes are sequenced while remaining attached to the array features (e.g., via in situ sequencing). Further aspects of the sequencing of capture probes are described in subsequent sections of this disclosure.

In some embodiments, an array feature can include different types of capture probes attached to the feature. For example, the array feature can include a first type of capture probe with a capture domain designed to bind to one type of analyte, and a second type of capture probe with a capture domain designed to bind to a second type of analyte. In general, array features can include one or more (e.g., two or more, three or more, four or more, five or more, six or more, eight or more, ten or more, 12 or more, 15 or more, 20 or more, 30 or more, 50 or more) different types of capture probes attached to a single array feature.

In some embodiments, the capture probe is nucleic acid. In some embodiments, the capture probe is attached to the array feature via its 5' end. In some embodiments, the capture probe includes from the 5' to 3' end: one or more barcodes (e.g., a spatial barcode and/or a UMI) and one or more capture domains. In some embodiments, the capture probe includes from the 5' to 3' end: one barcode (e.g., a spatial barcode or a UMI) and one capture domain. In some embodiments, the capture probe includes from the 5' to 3' end: a cleavage domain, a functional domain, one or more barcodes (e.g., a spatial barcode and/or a UMI), and a capture domain. In some embodiments, the capture probe includes from the 5' to 3' end: a cleavage domain, a functional domain, one or more barcodes (e.g., a spatial barcode and/or a UMI), a second functional domain, and a capture domain. In some embodiments, the capture probe includes from the 5' to 3' end: a cleavage domain, a functional domain, a spatial barcode, a UMI, and a capture domain. In some embodiments, the capture probe does not include a spatial barcode. In some embodiments, the capture probe does not include a UMI. In some embodiments, the capture probe includes a sequence for initiating a sequencing reaction.

In some embodiments, the capture probe is immobilized on a feature via its 3' end. In some embodiments, the capture probe includes from the 3' to 5' end: one or more barcodes (e.g., a spatial barcode and/or a UMI) and one or more capture domains. In some embodiments, the capture probe includes from the 3' to 5' end: one barcode (e.g., a spatial barcode or a UMI) and one capture domain. In some embodiments, the capture probe includes from the 3' to 5' end: a cleavage domain, a functional domain, one or more barcodes (e.g., a spatial barcode and/or a UMI), and a capture domain. In some embodiments, the capture probe includes from the 3' to 5' end: a cleavage domain, a functional domain, a spatial barcode, a UMI, and a capture domain.

In some embodiments, a capture probe includes an in situ synthesized oligonucleotide. The in situ synthesized oligonucleotide can be attached to a substrate, or to a feature on a substrate. In some embodiments, the in situ synthesized oligonucleotide includes one or more constant sequences, one or more of which serves as a priming sequence (e.g., a primer for amplifying target nucleic acids). The in situ synthesized oligonucleotide can, for example, include a constant sequence at the 3'end that is attached to a substrate, or attached to a feature on a substrate. Additionally or alternatively, the in situ synthesized oligonucleotide can include a constant sequence at the free 5' end. In some embodiments, the one or more constant sequences can be a cleavable sequence. In some embodiments, the in situ synthesized oligonucleotide includes a barcode sequence, e.g., a variable barcode sequence. The barcode can be any of the barcodes described herein. The length of the barcode can be approximately 8 to 16 nucleotides (e.g., 8, 9, 10, 11, 12, 13, 14, 15, or 16 nucleotides). The length of the in situ synthesized oligonucleotide can be less than 100 nucleotides (e.g., less than 90, 80, 75, 70, 60, 50, 45, 40, 35, 30, 25 or 20 nucleotides). In some instances, the length of the in situ synthesized oligonucleotide is about 20 to about 40 nucleotides. Exemplary in situ synthesized oligonucleotides are produced by Affymetrix. In some embodiments, the in situ synthesized oligonucleotide is attached to a feature of an array.

Additional oligonucleotides can be ligated to an in situ synthesized oligonucleotide to generate a capture probe. For example, a primer complementary to a portion of the in situ synthesized oligonucleotide (e.g., a constant sequence in the oligonucleotide) can be used to hybridize an additional oligonucleotide and extend (using the in situ synthesized oligonucleotide as a template e.g., a primer extension reaction) to form a double stranded oligonucleotide and to further create a 3' overhang. In some embodiments, the 3' overhang can be created by template-independent ligases (e.g., terminal deoxynucleotidyl transferase (TdT) or poly (A) polymerase). An additional oligonucleotide comprising one or more capture domains can be ligated to the 3' overhang using a suitable enzyme (e.g., a ligase) and a splint oligonucleotide, to generate a capture probe. Thus, in some embodiments, a capture probe is a product of two or more oligonucleotide sequences, (e.g., the in situ synthesized oligonucleotide and the additional oligonucleotide) that are ligated together. In some embodiments, one of the oligonucleotide sequences is an in situ synthesized oligonucleotide.

In some embodiments, the capture probe can be prepared using a splint oligonucleotide (e.g., any of the splint oligonucleotides described herein). Two or more oligonucleotides can be ligated together using a splint oligonucleotide and any variety of ligases known in the art or described herein (e.g., SplintR ligase).

One of the oligonucleotides can include, for example, a constant sequence (e.g., a sequence complementary to a portion of a splint oligonucleotide), a degenerate sequence, and/or a capture domain (e.g., as described herein). One of the oligonucleotides can also include a sequence compatible for ligating or hybridizing to an analyte of interest in the biological sample. An analyte of interest (e.g., an mRNA) can also be used as a splint oligonucleotide to ligate further oligonucleotides onto the capture probe. In some embodiments, the capture probe is generated by having an enzyme add polynucleotides at the end of an oligonucleotide sequence. The capture probe can include a degenerate sequence, which can function as a unique molecular identifier.

A degenerate sequence, which is a sequence in which some positions of a nucleotide sequence contain a number of possible bases. A degenerate sequence can be a degenerate nucleotide sequence including about or at least 5, 6, 7, 8, 9, 10, 11, 12, 13, 14, 15, 16, 17, 18, 19, 20, 25, 30, 35, 40, 45, or 50 nucleotides. In some embodiments, a nucleotide sequence contains 1, 2, 3, 4, 5, 6, 7, 8, 9, 10, 15, 20, 25, or more degenerate positions within the nucleotide sequence. In some embodiments, the degenerate sequence is used as a UMI.

In some embodiments, a capture probe includes a restriction endonuclease recognition sequence or a sequence of nucleotides cleavable by specific enzyme activities. For example, uracil sequences can be enzymatically cleaved from a nucleotide sequence using uracil DNA glycosylase (UDG) or Uracil Specific Excision Reagent (USER). As another example, other modified bases (e.g., modified by methylation) can be recognized and cleaved by specific endonucleases. The capture probes can be subjected to an enzymatic cleavage, which removes the blocking domain and any of the additional nucleotides that are added to the 3' end of the capture probe during the modification process. Removal of the blocking domain reveals and/or restores the free 3' end of the capture domain of the capture probe. In some embodiments, additional nucleotides can be removed to reveal and/or restore the 3' end of the capture domain of the capture probe.

In some embodiments, a blocking domain can be incorporated into the capture probe when it is synthesized, or after its synthesis. The terminal nucleotide of the capture domain is a reversible terminator nucleotide (e.g., 3'-O-blocked reversible terminator and 3'-unblocked reversible terminator), and can be included in the capture probe during or after probe synthesis.

(vii) Extended Capture Probes

An "extended capture probe" is a capture probe with an enlarged nucleic acid sequence. For example, where the capture probe includes nucleic acid, an "extended 3' end" indicates that further nucleotides were added to the most 3' nucleotide of the capture probe to extend the length of the capture probe, for example, by standard polymerization reactions utilized to extend nucleic acid molecules including templated polymerization catalyzed by a polymerase (e.g., a DNA polymerase or reverse transcriptase).

In some embodiments, extending the capture probe includes generating cDNA from the captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending the capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, the capture domain of the capture probe includes a primer for producing the complementary strand of the nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA, e.g., cDNA, molecule is generated. In some embodiments, a "full-length" DNA molecule refers to the whole of the captured nucleic acid molecule. However, if the nucleic acid, e.g., RNA, was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9°N) DNA ligase (9°N™ DNA ligase, New England Biolabs), Ampligase™ (available from Lucigen, Middleton, WI), and SplintR (available from New England Biolabs, Ipswich, MA). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to an array feature specific for the affinity group. In some embodiments, the substrate can include an antibody or antibody fragment. In some embodiments, the array feature includes avidin or streptavidin and the affinity group includes biotin. In some embodiments, the array feature includes maltose and the affinity group includes maltose-binding protein. In some embodiments, the array feature includes maltose-binding protein and the affinity group includes maltose. In some embodiments, amplifying the extended capture probes can function to release the extended probes from the array feature, insofar as copies of the extended probes are not attached to the array feature.

In some embodiments, the extended capture probe or complement or amplicon thereof is released from an array feature. The step of releasing the extended capture probe or complement or amplicon thereof from an array feature can be achieved in a number of ways. In some embodiments, an extended capture probe or a complement thereof is released from the feature by nucleic acid cleavage and/or by denaturation (e.g., by heating to denature a double-stranded molecule).

In some embodiments, the extended capture probe or complement or amplicon thereof is released from the array feature by physical means. For example, methods for inducing physical release include denaturing double stranded nucleic acid molecules. Another method for releasing the extended capture probes is to use a solution that interferes with the hydrogen bonds of the double stranded molecules. In some embodiments, the extended capture probe is released by applying heated water such as water or buffer of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the array feature. In some embodiments, a formamide solution can be used to destabilize the interaction between nucleic acid molecules to release the extended capture probe from the array feature.

(viii) Amplification of Capture Probes

In some embodiments, methods are provided herein for amplifying a capture probe affixed to a spatial array, where amplification of the capture probe increases the number of capture domains and spatial barcodes on the spatial array. In some embodiments where a capture probe is amplified, the amplification is performed by rolling circle amplification. In some embodiments, the capture probe to be amplified includes sequences (e.g., docking sequences, functional sequences, and/or primer sequences) that enable rolling circle amplification. In one example, the capture probe can include a functional sequence that is capable of binding to a primer used for amplification. In another example, the capture probe can include one or more docking sequences (e.g., a first docking sequence and a second docking sequence) that can hybridize to one or more oligonucleotides (e.g., a padlock probe(s)) used for rolling circle amplification. In some embodiments, additional probes are affixed to the substrate, where the additional probes include sequences (e.g., a docking sequence(s), a functional sequence(s), and/or a primer sequence(s)) that enable rolling circle amplification. In some embodiments, the spatial array is contacted with an oligonucleotide (e.g., a padlock probe). As used herein, a "padlock probe" refers to an oligonucleotide that has, at its 5' and 3' ends, sequences that are complementary to adjacent or nearby target sequences (e.g., docking sequences) on a capture probe. Upon hybridization to the target sequences (e.g., docking sequences), the two ends of the padlock probe are either brought into contact or an end is extended until the two ends are brought into contact, allowing circularization of the padlock probe by ligation (e.g., ligation using any of the methods described herein). In some embodiments, after circularization of the oligonucleotide, rolling circle amplification can be used to amplify the ligation product, which includes at least a capture domain and a spatial barcode from the capture probe. In some embodiments, amplification of the capture probe using a padlock oligonucleotide and rolling circle amplification increases the number of capture domains and the number of spatial barcodes on the spatial array.

In some embodiments, a method of increasing capture efficiency of a spatial array includes amplifying all or part of a capture probe affixed to a substrate. For example, amplification of all or part of the capture probes affixed to the substrate can increase the capture efficiency of the spatial array by increasing the number of capture domains and spatial barcodes. In some embodiments, a method of determining a location of an analyte in a biological sample includes using a spatial array having increased capture efficiency (e.g., a spatial array where a capture probe has been amplified as described herein). For example, the capture efficiency of a spatial array can be increased by amplification of all or part of the capture probe prior to contact with a biological sample. The amplification results in an increased number of capture domains that enable capture of more analytes as compared to a spatial array where the capture probe was not amplified prior to contacting the biological sample. In some embodiments, a method of producing a spatial array that has increased capture efficiency includes amplifying all or part of a capture probe. In some embodiments where a spatial array having increased capture efficiency is produced by amplifying all or part of a capture probe, the amplification increases the number of capture domains and the number of spatial barcodes on the spatial array. In some embodiments, a method of determining the location of a capture probe (i.e., a capture probe on a feature) on a spatial array includes amplifying all or part of a capture probe. For example, amplification of the capture probe affixed to the substrate can increase the number of spatial barcodes used for direct decoding (e.g., direct decoding using any of the methods described herein including, without limitation, in situ sequencing) of the location of the capture probe.

(ix) Analyte Capture Agents

This disclosure also provides methods and materials for using analyte capture agents for spatial profiling of biological analytes (e.g., mRNA, genomic DNA, accessible chromatin, and cell surface or intracellular proteins and/or metabolites). As used herein, an "analyte capture agent" (also referred to previously at times as a "cell labelling" agent") refers to an agent that interacts with an analyte (e.g., an analyte in a sample) and with a capture probe (e.g., a capture probe attached to a substrate) to identify the analyte. In some embodiments, the analyte capture agent includes an analyte binding moiety and a capture agent barcode domain.

Figure 9:
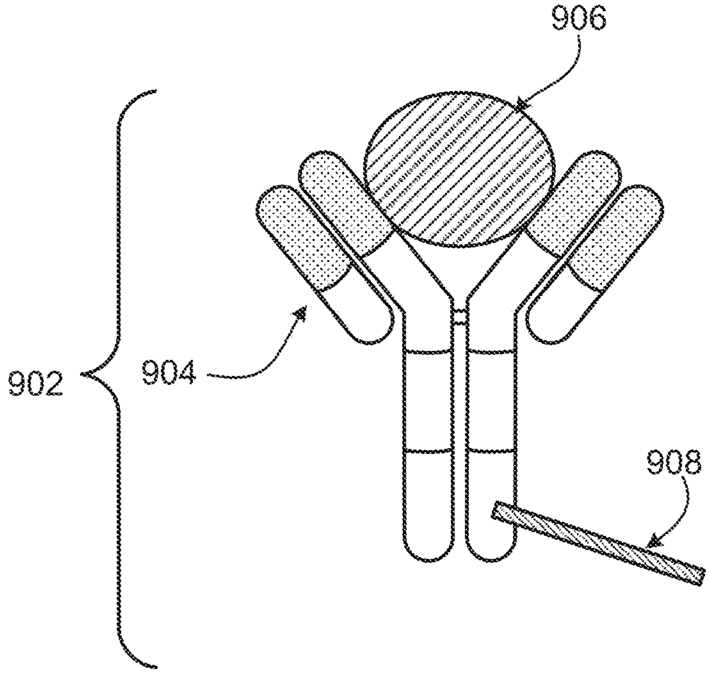
FIG. 9 is a schematic diagram of an exemplary analyte capture agent.

FIG. 9 is a schematic diagram of an exemplary analyte capture agent 902 comprised of an analyte binding moiety 904 and a capture agent barcode domain 908. An analyte binding moiety 904 is a molecule capable of binding to an analyte 906 and interacting with a spatially-barcoded capture probe. The analyte binding moiety can bind to the analyte 906 with high affinity and/or with high specificity. The analyte capture agent can include a capture agent barcode domain 908, a nucleotide sequence (e.g., an oligonucleotide), which can hybridize to at least a portion or an entirety of a capture domain of a capture probe. The analyte binding moiety 904 can include a polypeptide and/or an aptamer (e.g., an oligonucleotide or peptide molecule that binds to a specific target analyte). The analyte binding moiety 904 can include an antibody or antibody fragment (e.g., an antigen-binding fragment).

As used herein, the term "analyte binding moiety" refers to a molecule or moiety capable of binding to a macromolecular constituent (e.g., an analyte, e.g., a biological analyte). In some embodiments of any of the spatial profiling methods described herein, the analyte binding moiety of the analyte capture agent that binds to a biological analyte can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can bind to the macromolecular constituent (e.g., analyte) with high affinity and/or with high specificity. The analyte binding moiety can include a nucleotide sequence (e.g., an oligonucleotide), which can correspond to at least a portion or an entirety of the analyte binding moiety. The analyte binding moiety can include a polypeptide and/or an aptamer (e.g., a polypeptide and/or an aptamer that binds to a specific target molecule, e.g., an analyte). The analyte binding moiety can include an antibody or antibody fragment (e.g., an antigen-binding fragment) that binds to a specific analyte (e.g., a polypeptide).

In some embodiments, an analyte binding moiety of an analyte capture agent includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte capture agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte capture agents are the same. In some embodiments in which the plurality of analytes includes a single species of analyte, the analyte binding moieties of the plurality of analyte capture agents are the different (e.g., members of the plurality of analyte capture agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

An analyte capture agent can include an analyte binding moiety. The analyte binding moiety can be an antibody. Exemplary, non-limiting antibodies that can be used as analyte binding moieties in an analyte capture agent or that can be used in the IHC/IF applications disclosed herein include any of the following including variations thereof: A-ACT, A-AT, ACTH, Actin-Muscle-specific, Actin-Smooth Muscle (SMA), AE1, AE1/AE3, AE3, AFP, AKT Phosphate, ALK-1, Amyloid A, Androgen Receptor, Annexin A1, B72.3, BCA-225, BCL-1 (Cyclin D1), BCL-1/CD20, BCL-2, BCL-2/BCL-6, BCL-6, Ber-EP4, Beta-amyloid, Beta-catenin, BG8 (Lewis Y), BOB-1, CA 19.9, CA 125, CAIX, Calcitonin, Caldesmon, Calponin, Calretinin, CAM 5.2, CAM 5.2/AE1, CD1a, CD2, CD3 (M), CD3 (P), CD3/CD20, CD4, CD5, CD7, CD8, CD10, CD14, CD15, CD20, CD21, CD22, CD 23, CD25, CD30, CD31, CD33, CD34, CD35, CD43, CD45 (LCA), CD45RA, CD56, CD57, CD61, CD68, CD71, CD74, CD79a, CD99, CD117 (c-KIT), CD123, CD138, CD163, CDX-2, CDX-2/CK-7, CEA (M), CEA (P), Chromogranin A, Chymotrypsin, CK-5, CK-5/6, CK-7, CK-7/TTF-1, CK-14, CK-17, CK-18, CK-19, CK-20, CK-HMW, CK-LMW, CMV-IH, COLL-IV, COX-2, D2-40, DBA44, Desmin, DOG1, EBER-ISH, EBV (LMP1), E-Cadherin, EGFR, EMA, ER, ERCC1, Factor VIII (vWF), Factor XIIIa, Fascin, FLI-1, FHS, Galectin-3, Gastrin, GCDFP-15, GFAP, Glucagon, Glycophorin A, Glypican-3, Granzyme B, Growth Hormone (GH), GST, HAM 56, HMBE-1, HBP, HCAg, HCG, Hemoglobin A, HEP B CORE (HBcAg), HEP B SURF, (HBsAg), HepPar1, HER2, Herpes I, Herpes II, HHV-8, HLA-DR, HMB 45, HPL, HPV-IHC, HPV (6/11)-ISH, HPV (16/18)-ISH, HPV (31/33)-ISH, HPV WSS-ISH, HPV High-ISH, HPV Low-ISH, HPV High & Low-ISH, IgA, IgD, IgG, IgG4, IgM, Inhibin, Insulin, JC Virus-ISH, Kappa-ISH, KER PAN, Ki-67, Lambda-IHC, Lambda-ISH, LH, Lipase, Lysozyme (MURA), Mammaglobin, MART-1, MBP, M-Cell Tryptase, MEL-5, Melan-A, Melan-A/Ki-67, Mesothelin, MiTF, MLH-1, MOC-31, MPO, MSH-2, MSH-6, MUC1, MUC2, MUC4, MUC5AC, MUM-1, MYO D1, Myogenin, Myoglobin, Myoin Heavy Chain, Napsin A, NB84a, NEW-N, NF, NK1-C3, NPM, NSE, OCT-2, OCT-3/4, OSCAR, p16, p21, p27/Kip1, p53, p57, p63, p120, P504S, Pan Melanoma, PANC.POLY, Parvovirus B19, PAX-2, PAX-5, PAX-5/CD43, PAX=5/CD5, PAX-8, PC, PD1, Perforin, PGP 9.5, PLAP, PMS-2, PR, Prolactin, PSA, PSAP, PSMA, PTEN, PTH, PTS, RB, RCC, S6, S100, Serotonin, Somatostatin, Surfactant (SP-A), Synaptophysin, Synuclein, TAU, TCL-1, TCR beta, TdT, Thrombomodulin, Thyroglobulin, TIA-1, TOXO, TRAP, TriView™ breast, TriView™ prostate, Trypsin, TS, TSH, TTF-1, Tyrosinase, Ubiqutin, Uroplakin, VEGF, Villin, Vimentin (VIM), VIP, VZV, WT1 (M)N-Terminus, WT1 (P)C-Terminus, ZAP-70.

Further, exemplary, non-limiting antibodies that can be used as analyte binding moieties in an analyte capture agent or that can be used in the IHC/IF applications disclosed herein include any of the following antibodies (and variations thereof) to: cell surface proteins, intracellular proteins, kinases (e.g., AGC kinase family (e.g., AKT1, AKT2, PDK1, Protein Kinase C, ROCK1, ROCK2, SGK3), CAMK kinase family (e.g., AMPK1, AMPK2, CAMK, Chk1, Chk2, Zip), CK1 kinase family, TK kinase family (e.g., Abl2, AXL, CD167, CD246/ALK, c-Met, CSK, c-Src, EGFR, ErbB2 (HER2/neu), ErbB3, ErbB4, FAK, Fyn, LCK, Lyn, PKT7, Syk, Zap70), STE kinase family (e.g., ASK1, MAPK, MEK1, MEK2, MEK3 MEK4, MEK5, PAK1, PAK2, PAK4, PAK6), CMGC kinase family (e.g., Cdk2, Cdk4, Cdk5, Cdk6, Cdk7, Cdk9, Erk1, GSK3, Jnk/MAPK8, Jnk2/MAPK9, JNK3/MAPK10, p38/MAPK), and TKL kinase family (e.g., ALK1, ILK1, IRAK1, IRAK2, IRAK3, IRAK4, LIMK1, LIMK2, M3K11, RAF1, RIP1, RIP3, VEGFR1, VEGFR2, VEGFR3), Aurora A kinase, Aurora B kinase, IKK, Nemo-like kinase, PINK, PLK3, ULK2, WEE1, transcription factors (e.g., FOXP3, ATF3, BACH1, EGR, ELF3, FOXA1, FOXA2, FOXO1, GATA), growth factor receptors, tumor suppressors (e.g., anti-p53, anti-BLM, anti-Cdk2, anti-Chk2, anti-BRCA-1, anti-NBS1, anti-BRCA-2, anti-WRN, anti-PTEN, anti-WT1, anti-p38).

In some embodiments, analyte capture agents are capable of binding to analytes present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some embodiments, the analyte capture agent includes a capture agent barcode domain that is conjugated or otherwise attached to the analyte binding moiety. In some embodiments, the capture agent barcode domain is covalently-linked to the analyte binding moiety. In some embodiments, a capture agent barcode domain is a nucleic acid sequence. In some embodiments, a capture agent barcode domain includes an analyte binding moiety barcode and an analyte capture sequence.

As used herein, the term "analyte binding moiety barcode" refers to a barcode that is associated with or otherwise identifies the analyte binding moiety. In some embodiments, by identifying an analyte binding moiety and its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein. For example, an analyte capture agent that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety to which the capture agent barcode domain is coupled. The selection of the capture agent barcode domain can allow significant diversity in terms of sequence, while also being readily attachable to most analyte binding moieties (e.g., antibodies or aptamers) as well as being readily detected, (e.g., using sequencing or array technologies).

In some embodiments, the capture agent barcode domain of an analyte capture agent includes an analyte capture sequence. As used herein, the term "analyte capture sequence" refers to a region or moiety configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

In some embodiments of any of the spatial analysis methods described herein that employ an analyte capture agent, the capture agent barcode domain can be directly coupled to the analyte binding moiety, or they can be attached to a bead, molecular lattice, e.g., a linear, globular, cross-slinked, or other polymer, or other framework that is attached or otherwise associated with the analyte binding moiety, which allows attachment of multiple capture agent barcode domains to a single analyte binding moiety. Attachment (coupling) of the capture agent barcode domains to the analyte binding moieties can be achieved through any of a variety of direct or indirect, covalent or non-covalent associations or attachments. For example, in the case of a capture agent barcode domain coupled to an analyte binding moiety that includes an antibody or antigen-binding fragment, such capture agent barcode domains can be covalently attached to a portion of the antibody or antigen-binding fragment using chemical conjugation techniques (e.g., Lightning-Link® antibody labelling kits available from Innova Biosciences). In some embodiments, a capture agent barcode domain can be coupled to an antibody or antigen-binding fragment using non-covalent attachment mechanisms (e.g., using biotinylated antibodies and oligonucleotides or beads that include one or more biotinylated linker(s), coupled to oligonucleotides with an avidin or streptavidin linker.) Antibody and oligonucleotide biotinylation techniques can be used, and are described for example in Fang et al., *Nucleic Acids Res.* (2003), 31(2): 708-715, the entire contents of which are incorporated by reference herein. Likewise, protein and peptide biotinylation techniques have been developed and can be used, and are described for example in U.S. Pat. No. 6,265,552, the entire contents of which are incorporated by reference herein. Furthermore, click reaction chemistry such as a methyltetrazine-PEG5-NHS ester reaction, a TCO-PEG4-NHS ester reaction, or the like, can be used to couple capture agent barcode domains to analyte binding moieties. The reactive moiety on the analyte binding moiety can also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., NH2). The reactive moiety on the analyte binding moiety can be a chemical compound or group that binds to the reactive moiety on the analyte binding moiety. Exemplary strategies to conjugate the analyte binding moiety to the capture agent barcode domain include the use of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the analyte binding moiety is an antibody, the antibody can be modified prior to or contemporaneously with conjugation of the oligonucleotide. For example, the antibody can be glycosylated with a chemical substrate-permissive mutant of β-1,4-galactosyltransferase, GalT (Y289L) and azide-bearing uridine diphosphate-N-acetylgalactosamine analog uridine diphosphate -GalNAz. The modified antibody can be conjugated to an oligonucleotide with a dibenzocyclooctyne-PEG4-NHS group. In some embodiments, certain steps (e.g., COOH activation (e.g., EDC) and homobifunctional cross linkers) can be avoided to prevent the analyte binding moieties from conjugating to themselves. In some embodiments of any of the spatial profiling methods described herein, the analyte capture agent (e.g., analyte binding moiety coupled to an oligonucleotide) can be delivered into the cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-Dioleoyl-sn-glycero-3-phosphocholine (DOPC)), or by transporter proteins. An analyte capture agent can be delivered into a cell using exosomes. For example, a first cell can be generated that releases exosomes comprising an analyte capture agent. An analyte capture agent can be attached to an exosome membrane. An analyte capture agent can be contained within the cytosol of an exosome. Released exosomes can be harvested and provided to a second cell, thereby delivering the analyte capture agent into the second cell. An analyte capture agent can be releasable from an exosome membrane before, during, or after delivery into a cell. In some embodiments, the cell is permeabilized to allow the analyte capture agent to couple with intracellular constituents (such as, without limitation, intracellular proteins, metabolites, and nuclear membrane proteins). Following intracellular delivery, analyte capture agents can be used to analyze intracellular constituents as described herein.

In some embodiments of any of the spatial profiling methods described herein, the capture agent barcode domain coupled to an analyte capture agent can include modifications that render it non-extendable by a polymerase. In some embodiments, when binding to a capture domain of a capture probe or nucleic acid in a sample for a primer extension reaction, the capture agent barcode domain can serve as a template, not a primer. When the capture agent barcode domain also includes a barcode (e.g., an analyte binding moiety barcode), such a design can increase the efficiency of molecular barcoding by increasing the affinity between the capture agent barcode domain and unbarcoded sample nucleic acids, and eliminate the potential formation of adaptor artifacts. In some embodiments, the capture agent barcode domain can include a random N-mer sequence that is capped with modifications that render it non-extendable by a polymerase. In some cases, the composition of the random N-mer sequence can be designed to maximize the binding efficiency to free, unbarcoded ssDNA molecules. The design can include a random sequence composition with a higher GC content, a partial random sequence with fixed G or C at specific positions, the use of guanosines, the use of locked nucleic acids, or any combination thereof.

A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1', 2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, di-deoxynucleotide triphosphate, ethylene glycol, amine, or phosphate.

In some embodiments of any of the spatial profiling methods described herein, the capture agent barcode domain coupled to the analyte binding moiety includes a cleavable domain. For example, after the analyte capture agent binds to an analyte (e.g., a cell surface analyte), the capture agent barcode domain can be cleaved and collected for downstream analysis according to the methods as described herein. In some embodiments, the cleavable domain of the capture agent barcode domain includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment can be included in downstream processing to eliminate the phosphate group, e.g., prior to ligation of additional sequencing handle elements, e.g., Illumina full P5 sequence, partial P5 sequence, full R1 sequence, and/or partial R1 sequence.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte capture agent comprising an analyte binding moiety that binds to the cell surface protein and an analyte binding moiety barcode that identifies that analyte binding moiety, and the cell can be subjected to spatial analysis (e.g., any of the variety of spatial analysis methods described herein). For example, the analyte capture agent bound to the cell surface protein can be bound to a capture probe (e.g., a capture probe on an array), which capture probe includes a capture domain that interacts with an analyte capture sequence present on the capture agent barcode domain of the analyte capture agent. All or part of the capture agent barcode domain (including the analyte binding moiety barcode) can be copied with a polymerase using a 3' end of the capture domain as a priming site, generating an extended capture probe that includes the all or part of complementary sequence that corresponds to the capture probe (including a spatial barcode present on the capture probe) and a copy of the analyte binding moiety barcode. In some embodiments, an analyte capture agent with an extended capture agent barcode domain that includes a sequence complementary to a spatial barcode of a capture probe is called a "spatially-tagged analyte capture agent."

In some embodiments, the spatial array with spatially-tagged analyte capture agents can be contacted with a sample, where the analyte capture agent(s) associated with the spatial array capture the target analyte(s). The analyte capture agent(s) containing the extended capture probe(s), which includes a sequence complementary to the spatial barcode(s) of the capture probe(s) and the analyte binding moiety barcode(s), can then be denatured from the capture probe(s) of the spatial array. This allows the spatial array to be reused. The sample can be dissociated into non-aggregated cells (e.g., single cells) and analyzed by the single cell/droplet methods described herein. The spatially-tagged analyte capture agent can be sequenced to obtain the nucleic acid sequence of the spatial barcode of the capture probe and the analyte binding moiety barcode of the analyte capture agent. The nucleic acid sequence of the extended capture probe can thus be associated with an analyte (e.g., cell surface protein), and in turn, with the one or more physical properties of the cell (e.g., a shape or cell type). In some embodiments, the nucleic acid sequence of the extended capture probe can be associated with an intracellular analyte of a nearby cell, where the intracellular analyte was released using any of the cell permeabilization or analyte migration techniques described herein.

In some embodiments of any of the spatial profiling methods described herein, the capture agent barcode domains released from the analyte capture agents can then be subjected to sequence analysis to identify which analyte capture agents were bound to analytes. Based upon the capture agent barcode domains that are associated with a feature (e.g., a feature at a particular location) on a spatial array and the presence of the analyte binding moiety barcode sequence, an analyte profile can be created for a biological sample. Profiles of individual cells or populations of cells can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

Figure 10:
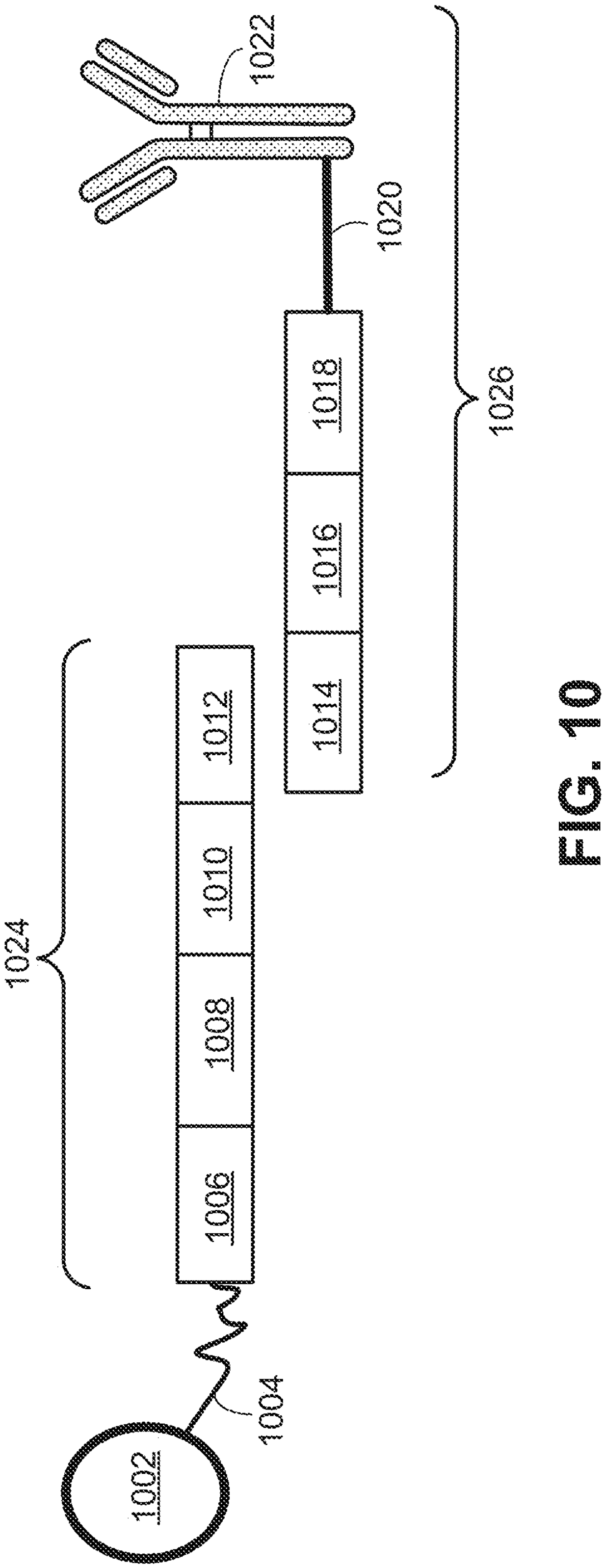
FIG. 10 is a schematic diagram depicting an exemplary interaction between a feature-immobilized capture probe 1024 and an analyte capture agent 1026.

FIG. 10 is a schematic diagram depicting an exemplary interaction between a feature-immobilized capture probe 1024 and an analyte capture agent 1026. The feature-immobilized capture probe 1024 can include a spatial barcode 1008 as well as one or more functional sequences 1006 and 1010, as described elsewhere herein. The capture probe can also include a capture domain 1012 that is capable of binding to an analyte capture agent 1026. The analyte capture agent 1026 can include a functional sequence 1018, capture agent barcode domain 1016, and an analyte capture sequence 1014 that is capable of binding to the capture domain 1012 of the capture probe 1024. The analyte capture agent can also include a linker 1020 that allows the capture agent barcode domain 1016 to couple to the analyte binding moiety 1022.

In some embodiments of any of the spatial profiling methods described herein, the methods are used to identify immune cell profiles. Immune cells express various adaptive immunological receptors relating to immune function, such as T cell receptors (TCRs) and B cell receptors (BCRs). T cell receptors and B cell receptors play a part in the immune response by specifically recognizing and binding to antigens and aiding in their destruction.

The T cell receptor, or TCR, is a molecule found on the surface of T cells that is generally responsible for recognizing fragments of antigen as peptides bound to major histocompatibility complex (MHC) molecules. The TCR is generally a heterodimer of two chains, each of which is a member of the immunoglobulin superfamily, possessing an N-terminal variable (V) domain, and a C terminal constant domain. In humans, in 95% of T cells, the TCR consists of an alpha ($\alpha$) and beta ($\beta$) chain, whereas in 5% of T cells, the TCR consists of gamma and delta ($\gamma/\delta$) chains. This ratio can change during ontogeny and in diseased states as well as in different species. When the TCR engages with antigenic peptide and MHC (peptide/MHC or pMHC), the T lymphocyte is activated through signal transduction.

Each of the two chains of a TCR contains multiple copies of gene segments—a variable 'V' gene segment, a diversity 'D' gene segment, and a joining 'J' gene segment. The TCR alpha chain (TCRa) is generated by recombination of V and J segments, while the beta chain (TCRb) is generated by recombination of V, D, and J segments. Similarly, generation of the TCR gamma chain involves recombination of V and J gene segments, while generation of the TCR delta chain occurs by recombination of V, D, and J gene segments. The intersection of these specific regions (V and J for the alpha or gamma chain, or V, D and J for the beta or delta chain) corresponds to the CDR3 region that is important for antigen-MHC recognition. Complementarity determining regions (e.g., CDR1, CDR2, and CDR3), or hypervariable regions, are sequences in the variable domains of antigen receptors (e.g., T cell receptor and immunoglobulin) that can complement an antigen. Most of the diversity of CDRs is found in CDR3, with the diversity being generated by somatic recombination events during the development of T lymphocytes. A unique nucleotide sequence that arises during the gene arrangement process can be referred to as a clonotype.

The B cell receptor, or BCR, is a molecule found on the surface of B cells. The antigen binding portion of a BCR is composed of a membrane-bound antibody that, like most antibodies (e.g., immunoglobulins), has a unique and randomly determined antigen-binding site. The antigen binding portion of a BCR includes membrane-bound immunoglobulin molecule of one isotype (e.g., IgD, IgM, IgA, IgG, or IgE). When a B cell is activated by its first encounter with a cognate antigen, the cell proliferates and differentiates to generate a population of antibody-secreting plasma B cells and memory B cells. The various immunoglobulin isotypes differ in their biological features, structure, target specificity, and distribution. A variety of molecular mechanisms exist to generate initial diversity, including genetic recombination at multiple sites.

The BCR is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining 'J' gene segment. Each light chain gene contains multiple copies of two different gene segments for the variable region of the protein—a variable 'V' gene segment and a joining 'J' gene segment.

The recombination can generate a molecule with one of each of the V, D, and J segments. Furthermore, several bases can be deleted and others added (called N and P nucleotides) at each of the two junctions, thereby generating further diversity. After B cell activation, a process of affinity maturation through somatic hypermutation occurs. In this process, progeny cells of the activated B cells accumulate distinct somatic mutations throughout the gene with higher mutation concentration in the CDR regions leading to the generation of antibodies with higher affinity to the antigens.

In addition to somatic hypermutation, activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA, and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype.

Certain methods described herein are utilized to analyze the various sequences of TCRs and BCRs from immune cells, for example, various clonotypes. In some embodiments, the methods are used to analyze the sequence of a TCR alpha chain, a TCR beta chain, a TCR delta chain, a TCR gamma chain, or any fragment thereof (e.g., variable regions including V(D)J or VJ regions, constant regions, transmembrane regions, fragments thereof, combinations thereof, and combinations of fragments thereof). In some embodiments, the methods described herein can be used to analyze the sequence of a B cell receptor heavy chain, B cell receptor light chain, or any fragment thereof (e.g., variable regions including V(D)J or VJ regions, constant regions, transmembrane regions, fragments thereof, combinations thereof, and combinations of fragments thereof).

Where immune cells are to be analyzed, primer sequences useful in any of the various operations for attaching barcode sequences and/or amplification reactions can include gene specific sequences which target genes or regions of genes of immune cell proteins, for example immune receptors. Such gene sequences include, but are not limited to, sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), and T cell receptor delta constant genes (TRDC genes).

In some embodiments, the analyte binding moiety is based on the Major Histocompatibility Complex (MHC) class I or class II. In some embodiments, the analyte binding moiety is an MHC multimer including, without limitation, MHC dextramers, MHC tetramers, and MHC pentamers (see, for example, U.S. Patent Application Publication Nos. US 2018/0180601 and US 2017/0343545, the entire contents of each of which are incorporated herein by reference. MHCs (e.g., a soluble MHC monomer molecule), including full or partial MHC-peptides, can be used as analyte binding moieties of analyte capture agents that are coupled to capture agent barcode domains that include an analyte binding moiety barcode that identifies its associated MHC (and, thus, for example, the MHC's TCR binding partner). In some embodiments, MHCs are used to analyze one or more cell-surface features of a T-cell, such as a TCR. In some cases, multiple MHCs are associated together in a larger complex (MHC multi-mer) to improve binding affinity of MHCs to TCRs via multiple ligand binding synergies.

Figure 11A:
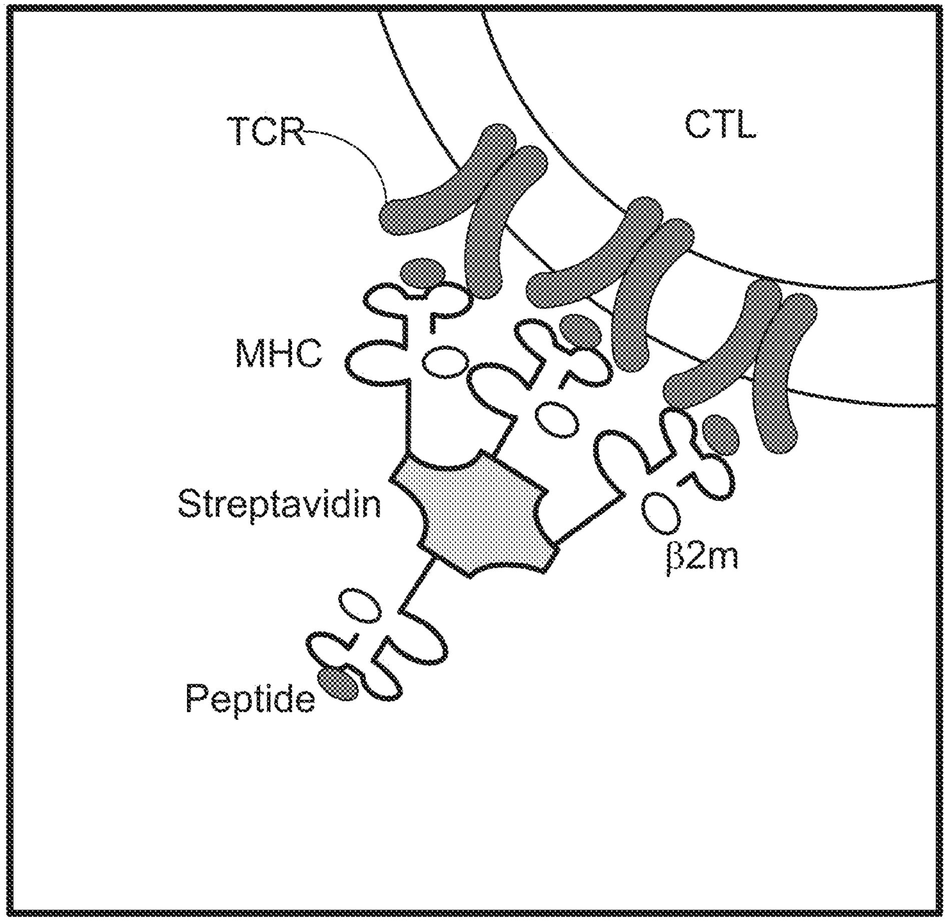
FIGS. 11A, 11B, and 11C are schematics illustrating how streptavidin cell tags can be utilized in an array-based system to produce a spatially-barcoded cells or cellular contents.
Figure 11B:
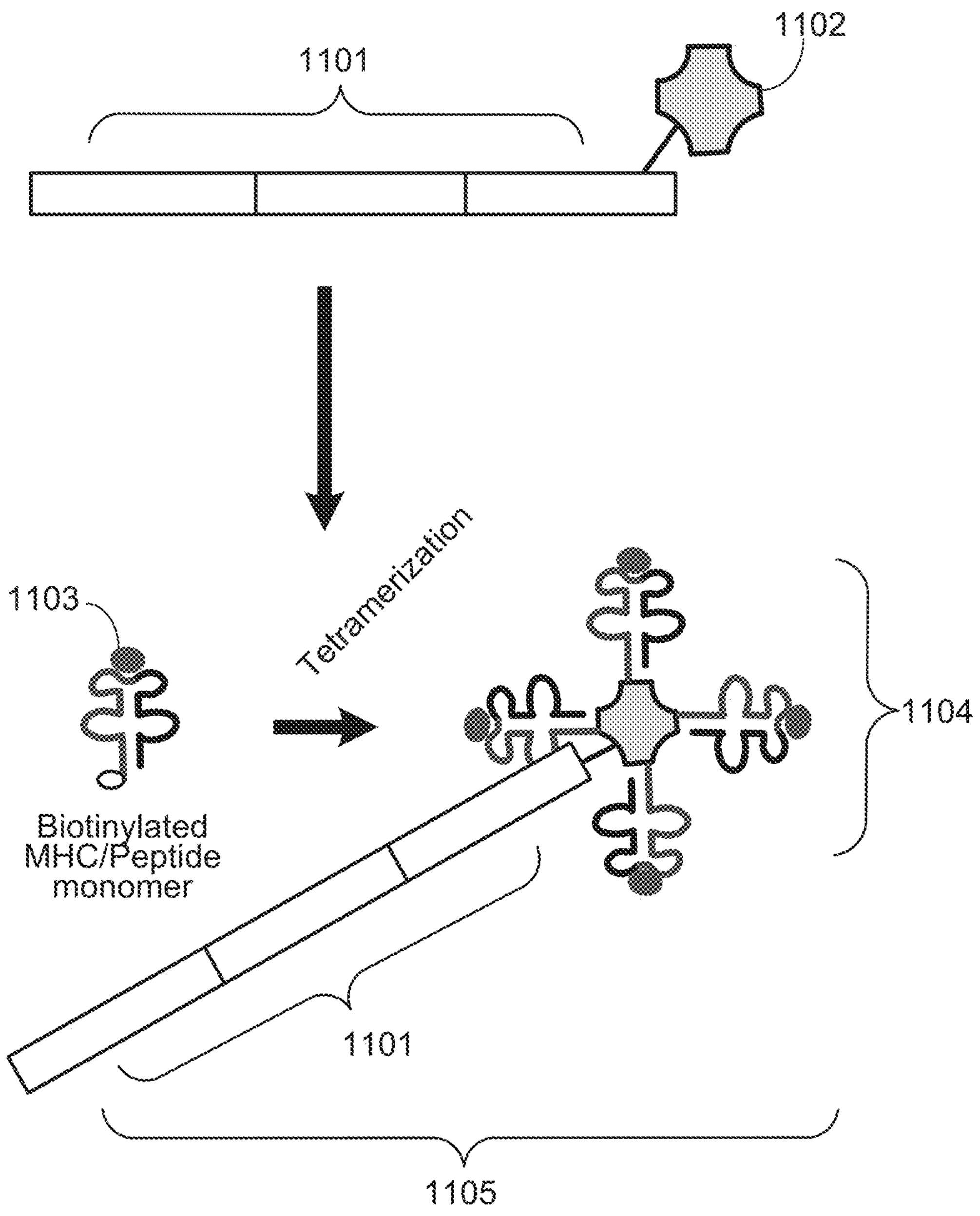
Figure 11C:
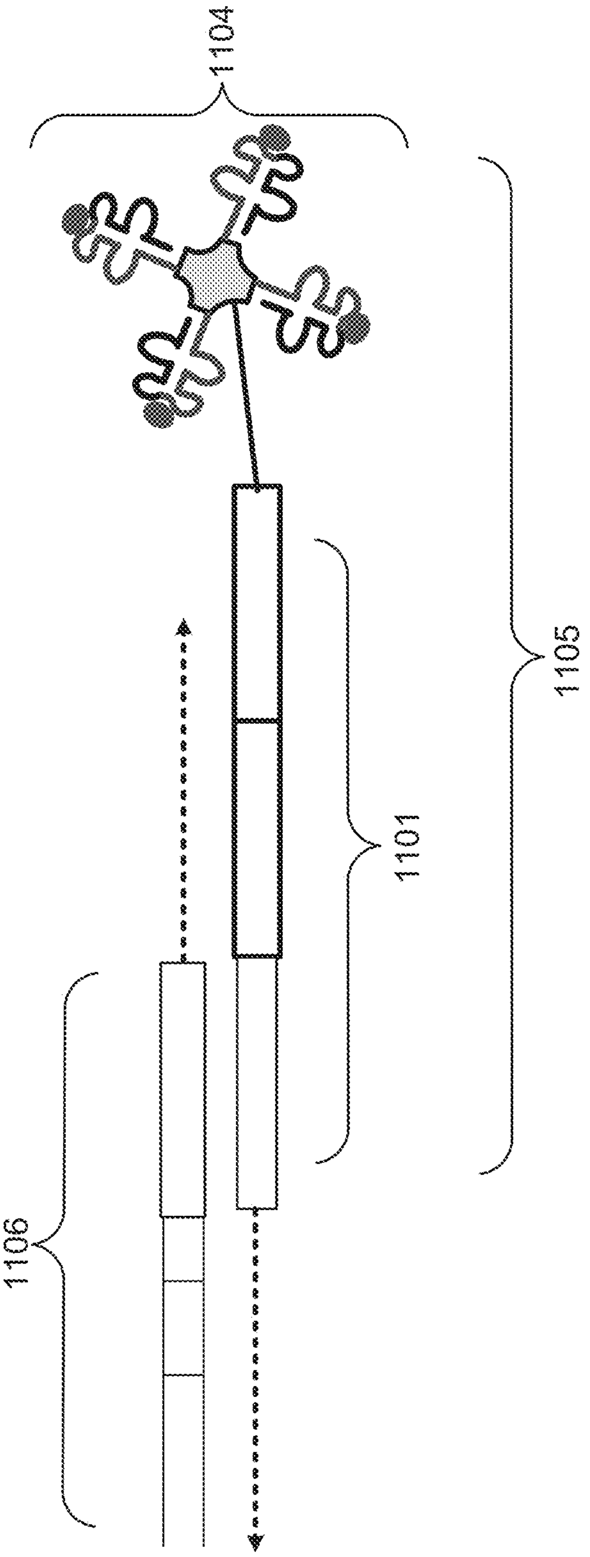

FIGS. 11A, 11B, and 11C are schematics illustrating how streptavidin cell tags can be utilized in an array-based system to produce a spatially-barcoded cell or cellular contents. For example, as shown in FIG. 11A, peptide-bound major histocompatibility complex (MHC) can be individually associated with biotin (β2m) and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 11B, a capture agent barcode domain 1101 can be modified with streptavidin 1102 and contacted with multiple molecules of biotinylated MHC 1103 such that the biotinylated MHC 1103 molecules are coupled with the streptavidin conjugated capture agent barcode domain 1101. The result is a barcoded MHC multimer complex 1105. As shown in FIG. 11B, the capture agent barcode domain sequence 1101 can identify the MHC as its associated label and also includes optional functional sequences such as sequences for hybridization with other oligonucleotides. As shown in FIG. 11C, one example oligonucleotide is capture probe 1106 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1"), R2), a flow cell attachment sequence (e.g., P5 or P7 or partial sequences thereof)), etc. In some cases, capture probe 1106 may at first be associated with a feature (e.g., a gel bead) and released from the feature. In other embodiments, capture probe 1106 can hybridize with a capture agent barcode domain 1101 of the MHC-oligonucleotide complex 1105. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 1106 or capture agent barcode domain 1101. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 1106 spatial barcode sequence may be used to identify a feature and the sequence derived from spatial barcode sequence on the capture agent barcode domain 1101 may be used to identify the particular peptide MHC complex 1104 bound on the surface of the cell (e.g., when using MHC-peptide libraries for screening immune cells or immune cell populations).

(c) Substrates

For the spatial array-based analytical methods described herein, a substrate functions as a support for direct or indirect attachment of capture probes to features of the array. In addition, in some embodiments, a substrate (e.g., the same substrate or a different substrate) can be used to provide support to a biological sample, particularly, for example, a thin tissue section. Accordingly, a "substrate" is a support that is insoluble in aqueous liquid and which allows for positioning of biological samples, analytes, features, and/or capture probes on the substrate.

Further, a "substrate" as used herein, and when not preceded by the modifier "chemical", refers to a member with at least one surface that generally functions to provide physical support for biological samples, analytes, and/or any of the other chemical and/or physical moieties, agents, and structures described herein. Substrates can be formed from a variety of solid materials, gel-based materials, colloidal materials, semi-solid materials (e.g., materials that are at least partially cross-linked), materials that are fully or partially cured, and materials that undergo a phase change or transition to provide physical support. Examples of substrates that can be used in the methods and systems described herein include, but are not limited to, slides (e.g., slides formed from various glasses, slides formed from various polymers), hydrogels, layers and/or films, membranes (e.g., porous membranes), flow cells, cuvettes, wafers, plates, or combinations thereof. In some embodiments, substrates can optionally include functional elements such as recesses, protruding structures, microfluidic elements (e.g., channels, reservoirs, electrodes, valves, seals), and various markings, as will be discussed in further detail below.

(i) Substrate Attributes

A substrate can generally have any suitable form or format. For example, a substrate can be flat, curved, e.g., convexly or concavely curved towards the area where the interaction between a biological sample, e.g., tissue sample, and a substrate takes place. In some embodiments, a substrate is flat, e.g., planar, chip, or slide. A substrate can contain one or more patterned surfaces within the substrate (e.g., channels, wells, projections, ridges, divots, etc.).

A substrate can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or cross-table). In some embodiments, where a substrate structure is flat, the substrate structure can be any appropriate type of support having a flat surface (e.g., a chip or a slide such as a microscope slide).

Substrates can optionally include various structures such as, but not limited to, projections, ridges, and channels. A substrate can be micropatterned to limit lateral diffusion (e.g., to prevent overlap of spatial barcodes). A substrate modified with such structures can be modified to allow association of analytes, features (e.g., beads), or probes at individual sites. For example, the sites where a substrate is modified with various structures can be contiguous or non-contiguous with other sites.

In some embodiments, the surface of a substrate can be modified so that discrete sites are formed that can only have or accommodate a single feature. In some embodiments, the surface of a substrate can be modified so that features adhere to random sites.

In some embodiments, the surface of a substrate is modified to contain one or more wells, using techniques such as (but not limited to) stamping, microetching, or molding techniques. In some embodiments in which a substrate includes one or more wells, the substrate can be a concavity slide or cavity slide. For example, wells can be formed by one or more shallow depressions on the surface of the substrate. In some embodiments, where a substrate includes one or more wells, the wells can be formed by attaching a cassette (e.g., a cassette containing one or more chambers) to a surface of the substrate structure.

In some embodiments, the structures of a substrate (e.g., wells or features) can each bear a different capture probe. Different capture probes attached to each structure can be identified according to the locations of the structures in or on the surface of the substrate. Exemplary substrates include arrays in which separate structures are located on the substrate including, for example, those having wells that accommodate features.

In some embodiments where the substrate is modified to contain one or more structures, including but not limited to, wells, projections, ridges, features, or markings, the structures can include physically altered sites. For example, a substrate modified with various structures can include physical properties, including, but not limited to, physical configurations, magnetic or compressive forces, chemically functionalized sites, chemically altered sites, and/or electrostatically altered sites. In some embodiments where the substrate is modified to contain various structures, including but not limited to wells, projections, ridges, features, or markings, the structures are applied in a pattern. Alternatively, the structures can be randomly distributed.

The substrate (e.g., or a bead or a feature on an array) can include tens to hundreds of thousands or millions of individual oligonucleotide molecules (e.g., at least about 10,000, 50,000, 100,000, 500,000, 1,000,000, 10,000,000, 100,000, 000, 1,000,000,000, or 10,000,000,000 oligonucleotide molecules).

In some embodiments, a substrate includes one or more markings on a surface of a substrate, e.g., to provide guidance for correlating spatial information with the characterization of the analyte of interest. For example, a substrate can be marked with a grid of lines (e.g., to allow the size of objects seen under magnification to be easily estimated and/or to provide reference areas for counting objects). In some embodiments, fiducial markers can be included on a substrate. Such markings can be made using techniques including, but not limited to, printing, sand-blasting, and depositing on the surface.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, and colorimetric labels. The use of fiducial markers to stabilize and orient biological samples is described, for example, in Carter et al., *Applied Optics* 46:421-427, 2007), the entire contents of which are incorporated herein by reference. In some embodiments, a fiducial marker can be a physical particle (e.g., a nanoparticle, a microsphere, a nanosphere, a bead, a post, or any of the other exemplary physical particles described herein or known in the art).

In some embodiments, a fiducial marker can be present on a substrate to provide orientation of the biological sample. In some embodiments, a microsphere can be coupled to a substrate to aid in orientation of the biological sample. In some examples, a microsphere coupled to a substrate can produce an optical signal (e.g., fluorescence). In another example, a microsphere can be attached to a portion (e.g., corner) of an array in a specific pattern or design (e.g., hexagonal design) to aid in orientation of a biological sample on an array of features on the substrate. In some embodiments, a quantum dot can be coupled to the substrate to aid in the orientation of the biological sample. In some examples, a quantum dot coupled to a substrate can produce an optical signal.

In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Such a marker nucleic acid molecule can be contacted with an array before, contemporaneously with, or after the tissue sample is stained to visualize or image the tissue section. Although not required, it can be advantageous to use a marker that can be detected using the same conditions (e.g., imaging conditions) used to detect a labelled cDNA.

In some embodiments, fiducial markers are included to facilitate the orientation of a tissue sample or an image thereof in relation to an immobilized capture probes on a substrate. Any number of methods for marking an array can be used such that a marker is detectable only when a tissue section is imaged. For instance, a molecule, e.g., a fluorescent molecule that generates a signal, can be immobilized directly or indirectly on the surface of a substrate. Markers can be provided on a substrate in a pattern (e.g., an edge, one or more rows, one or more lines, etc.).

In some embodiments, a fiducial marker can be randomly placed in the field of view. For example, an oligonucleotide containing a fluorophore can be randomly printed, stamped, synthesized, or attached to a substrate (e.g., a glass slide) at a random position on the substrate. A tissue section can be contacted with the substrate such that the oligonucleotide containing the fluorophore contacts, or is in proximity to, a cell from the tissue section or a component of the cell (e.g., an mRNA or DNA molecule). An image of the substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a substrate). In this instance, a fiducial marker can be stamped, attached, or synthesized on the substrate and contacted with a biological sample. Typically, an image of the sample and the fiducial marker is taken, and the position of the fiducial marker on the substrate can be confirmed by viewing the image.

In some embodiments, a fiducial marker can be an immobilized molecule (e.g., a physical particle) attached to the substrate. For example, a fiducial marker can be a nanoparticle, e.g., a nanorod, a nanowire, a nanocube, a nanopyramid, or a spherical nanoparticle. In some examples, the nanoparticle can be made of a heavy metal (e.g., gold). In some embodiments, the nanoparticle can be made from diamond. In some embodiments, the fiducial marker can be visible by eye.

As noted herein, any of the fiducial markers described herein (e.g., microspheres, beads, or any of the other physical particles described herein) can be located at a portion (e.g., corner) of an array in a specific pattern or design (e.g., hexagonal design) to aid in orientation of a biological sample on an array of features on the substrate. In some embodiments, the fiducial markers located at a portion (e.g., corner) of an array (e.g., an array on a substrate) can be patterned or designed in at least 1, at least 2, at least 3, or at least 4 unique patterns. In some examples, the fiducial markers located at the corners of the array (e.g., an array on a substrate) can have four unique patterns of fiducial markers.

In some examples, fiducial markers can surround the array. In some embodiments the fiducial markers allow for detection of, e.g., mirroring. In some embodiments, the fiducial markers may completely surround the array. In some embodiments, the fiducial markers may not completely surround the array. In some embodiments, the fiducial markers identify the corners of the array. In some embodiments, one or more fiducial markers identify the center of the array. In some embodiments, the fiducial markers comprise patterned spots, wherein the diameter of one or more patterned spot fiducial markers is approximately 100 micrometers. The diameter of the fiducial markers can be any useful diameter including, but not limited to, 50 micrometers to 500 micrometers in diameter. The fiducial markers may be arranged in such a way that the center of one fiducial marker is between 100 micrometers and 200 micrometers from the center of one or more other fiducial markers surrounding the array. In some embodiments, the array with the surrounding fiducial markers is approximately 8 mm by 8 mm. In some embodiments, the array without the surrounding fiducial markers is smaller than 8 mm by 50 mm.

In some embodiments, an array can be enclosed within a frame. Put another way, the perimeter of an array can have fiducial markers such that the array is enclosed, or substantially enclosed. In some embodiments, the perimeter of an array can be fiducial markers (e.g., any fiducial marker described herein). In some embodiments, the perimeter of an array can be uniform. For example, the fiducial markings can connect, or substantially connect, consecutive corners of an array in such a fashion that the non-corner portion of the array perimeter is the same on all sides (e.g., four sides) of the array. In some embodiments, the fiducial markers attached to the non-corner portions of the perimeter can be pattered or designed to aid in the orientation of the biological sample on the array. In some embodiments, the particles attached to the non-corner portions of the perimeter can be patterned or designed in at least 1, at least 2, at least 3, or at least 4 patterns. In some embodiments, the patterns can have at least 2, at least 3, or at least 4 unique patterns of fiducial markings on the non-corner portion of the array perimeter.

In some embodiments, an array can include at least two fiducial markers (e.g., at least 3, at least 4, at least 5, at least 6, at least 7, at least 8, at least 9, at least 10, at least 12, at least 15, at least 20, at least 30, at least 40, at least 50, at least 60, at least 70, at least 80, at least 90, at least 100 fiducial markers or more (e.g., several hundred, several thousand, or tens of thousands of fiducial markers)) in distinct positions on the surface of a substrate. Fiducial markers can be provided on a substrate in a pattern (e.g., an edge, one or more rows, one or more lines, etc.).

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™ cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene polycarbonate, or combinations thereof.

Among the examples of substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In another example, a substrate can be a flow cell. Flow cells can be formed of any of the foregoing materials, and can include channels that permit reagents, solvents, features, and analytes to pass through the flow cell. In some embodiments, a hydrogel embedded biological sample is assembled in a flow cell (e.g., the flow cell is utilized to introduce the hydrogel to the biological sample). In some embodiments, a hydrogel embedded biological sample is not assembled in a flow cell. In some embodiments, the hydrogel embedded biological sample can then be prepared and/or isometrically expanded as described herein.

(d) Arrays

In many of the methods described herein, features (as described further below) are collectively positioned on a substrate. An "array" is a specific arrangement of a plurality of features that is either irregular or forms a regular pattern. Individual features in the array differ from one another based on their relative spatial locations. In general, at least two of the plurality of features in the array include a distinct capture probe (e.g., any of the examples of capture probes described herein).

Arrays can be used to measure large numbers of analytes simultaneously. In some embodiments, oligonucleotides are used, at least in part, to create an array. For example, one or more copies of a single species of oligonucleotide (e.g., capture probe) can correspond to or be directly or indirectly attached to a given feature in the array. In some embodiments, a given feature in the array includes two or more species of oligonucleotides (e.g., capture probes). In some embodiments, the two or more species of oligonucleotides (e.g., capture probes) attached directly or indirectly to a given feature on the array include a common (e.g., identical) spatial barcode.

In some instances, arrays include bead array, flexible array, arrays with shrinking hydrogel features, microcapillary arrays, hydrogel arrays, well arrays, and bead tethering arrays. Further disclosure of exemplary arrays is provided in WO 2020/047010 A2; WO 2020/047004 A2; WO 2020/047007 A2; WO 2020/047005 A2; WO 2020/047002 A1; PCT/US2019/065077; PCT/US2019/065048; PCT/US2019/064987; PCT/US2019/065013; PCT/US2019/065100; PCT/US2019/065072; PCT/US2019/065081; PCT/US2019/065096; and PCT/US2019/065041; each of which is incorporated by reference in its entirety.

In some instances of bead arrays, a set of barcoded beads includes a two-part barcode, where the first part is correlated with the location to which the set of beads are bound, and the second part is correlated with the location of a bead relative to the beads in the set. For example, the location of a bead within a set of beads bound to the substrate can be identified based on the sequence information of the first and second part barcodes. The first part of the barcode can be identical across beads within the same set, and can be attached to the beads before or after the beads are bound to the substrate. The second part of the barcode can be different between two beads within the set, and can be attached to the beads (e.g., ligated onto the first part barcode) before or after the beads are bound to the substrate. In some instances, the second part of the barcode is attached to the beads after they are bound to the substrate.

In some instances of a shrinking hydrogel array, the array includes one or more pluralities of first oligonucleotides and the first hydrogel includes one or more pluralities of second oligonucleotides. Upon contacting the hydrogel with the array, members of the one or more pluralities of the first oligonucleotides can be attached to members of the one or more pluralities of second oligonucleotides. The array can include more species of first oligonucleotides than the number of species of the second oligonucleotides in the hydrogel such that first oligonucleotides comprising the same sequence can be coupled to second oligonucleotides comprising different sequences. The diversity of the oligonucleotides (e.g., spatial barcodes) in the first hydrogel can thereby be increased.

In some embodiments of a microcapillary array, features are introduced to the microcapillary array by flowing the features through microcapillary channels. In some embodiments, the microcapillar channel can reduce the cross-sectional area of a feature. In some embodiments, a portion of a biological sample contained in a microcapillary channel is one cell. In some embodiments, the microcapillary array is incubated in a humidified chamber. In some embodiments, the microcapillary array is incubated for an amount of time and at a temperature conducive to allowing amplification of a nucleic acid to occur. In some embodiments, the sequencing information from the pooled reaction solution is spatial information for one or more biological analytes.

(i) Arrays for Analyte Capture

In some embodiments, an array can include a capture probe attached directly or indirectly to the substrate. The capture probe can include a capture domain (e.g., a nucleotide sequence) that can specifically bind (e.g., hybridize) to a target analyte (e.g., mRNA, DNA, or protein) within a sample. In some embodiments, the binding of the capture probe to the target (e.g., hybridization) can be detected and quantified by detection of a visual signal, e.g., a fluorophore, a heavy metal (e.g., silver ion), or chemiluminescent label, which has been incorporated into the target. In some embodiments, the intensity of the visual signal correlates with the relative abundance of each analyte in the biological sample. Since an array can contain thousands or millions of capture probes (or more), an array can interrogate many analytes in parallel.

In some embodiments, a substrate includes one or more capture probes that are designed to capture analytes from one or more organisms. In a non-limiting example, a substrate can contain one or more capture probes designed to capture mRNA from one organism (e.g., a human) and one or more capture probes designed to capture DNA from a second organism (e.g., a bacterium).

The capture probes can be attached to a substrate or feature using a variety of techniques. In some embodiments, the capture probe is directly attached to a feature that is fixed on an array. In some embodiments, the capture probes are immobilized to a substrate by chemical immobilization. For example, a chemical immobilization can take place between functional groups on the substrate and corresponding functional elements on the capture probes. Exemplary corresponding functional elements in the capture probes can either be an inherent chemical group of the capture probe, e.g., a hydroxyl group, or a functional element can be introduced on to the capture probe. An example of a functional group on the substrate is an amine group. In some embodiments, the capture probe to be immobilized includes a functional amine group or is chemically modified in order to include a functional amine group. Means and methods for such a chemical modification are well known in the art.

In some embodiments, the capture probe is a nucleic acid. In some embodiments, the capture probe is immobilized on a substrate or feature via its 5' end. In some embodiments, the capture probe is immobilized on a substrate or feature via its 5' end and includes from the 5' to 3' end: one or more barcodes (e.g., a spatial barcode and/or a UMI) and one or more capture domains. In some embodiments, the capture probe is immobilized on a substrate or feature via its 5' end and includes from the 5' to 3' end: one barcode (e.g., a spatial barcode or a UMI) and one capture domain. In some embodiments, the capture probe is immobilized on a substrate or feature via its 5' end and includes from the 5' to 3' end: a cleavage domain, a functional domain, one or more barcodes (e.g., a spatial barcode and/or a UMI), and a capture domain.

In some embodiments, the capture probe is immobilized on a substrate or feature via its 5' end and includes from the 5' to 3' end: a cleavage domain, a functional domain, one or more barcodes (e.g., a spatial barcode and/or a UMI), a second functional domain, and a capture domain. In some embodiments, the capture probe is immobilized on a substrate or feature via its 5' end and includes from the 5' to 3' end: a cleavage domain, a functional domain, a spatial barcode, a UMI, and a capture domain. In some embodiments, the capture probe is immobilized on a substrate or feature via its 5' end and does not include a spatial barcode. In some embodiments, the capture probe is immobilized on a substrate or feature via its 5' end and does not include a UMI. In some embodiments, the capture probe includes a sequence for initiating a sequencing reaction.

In some embodiments, the capture probe is immobilized on a substrate or feature via its 3' end. In some embodiments, the capture probe is immobilized on a substrate or feature via its 3' end and includes from the 3' to 5' end: one or more barcodes (e.g., a spatial barcode and/or a UMI) and one or more capture domains. In some embodiments, the capture probe is immobilized on a substrate or feature via its 3' end and includes from the 3' to 5' end: one barcode (e.g., a spatial barcode or a UMI) and one capture domain. In some embodiments, the capture probe is immobilized on a substrate or feature via its 3' end and includes from the 3' to 5' end: a cleavage domain, a functional domain, one or more barcodes (e.g., a spatial barcode and/or a UMI), and a capture domain. In some embodiments, the capture probe is immobilized on a substrate or feature via its 3' end and includes from the 3' to 5' end: a cleavage domain, a functional domain, a spatial barcode, a UMI, and a capture domain.

The localization of the functional group within the capture probe to be immobilized can be used to control and shape the binding behavior and/or orientation of the capture probe, e.g., the functional group can be placed at the 5' or 3' end of the capture probe or within the sequence of the capture probe. In some embodiments, a capture probe can further include a substrate. A typical substrate for a capture probe to be immobilized includes moieties which are capable of binding to such capture probes, e.g., to amine-functionalized nucleic acids. Examples of such substrates are carboxy, aldehyde, or epoxy substrates.

In some embodiments, the substrates on which capture probes can be immobilized can be chemically activated, e.g., by the activation of functional groups available on the substrate. The term "activated substrate" relates to a material in which interacting or reactive chemical functional groups are established or enabled by chemical modification procedures. For example, a substrate including carboxyl groups can be activated before use. Furthermore, certain substrates contain functional groups that can react with specific moieties already present in the capture probes.

In some embodiments, a covalent linkage is used to directly couple a capture probe to a substrate. In some embodiments a capture probe is indirectly coupled to a substrate through a linker separating the "first" nucleotide of the capture probe from the substrate, e.g., a chemical linker. In some embodiments, a capture probe does not bind directly to the substrate, but interacts indirectly, for example by binding to a molecule which itself binds directly or indirectly to the substrate. In some embodiments, the capture probe is indirectly attached to a substrate (e.g., attached to a substrate via a solution including a polymer).

In some embodiments where the capture probe is immobilized on a feature of the array indirectly, e.g., via hybridization to a surface probe capable of binding the capture probe, the capture probe can further include an upstream sequence (5' to the sequence that hybridizes to the nucleic acid, e.g., RNA of the tissue sample) that is capable of hybridizing to 5' end of a surface probe. Alone, the capture domain of the capture probe can be seen as a capture domain oligonucleotide, which can be used in the synthesis of the capture probe in embodiments where the capture probe is immobilized on the array indirectly.

In some embodiments, a substrate is comprised of an inert material or matrix (e.g., glass slides) that has been functionalized by, for example, treating the substrate with a material comprising reactive groups which enable immobilization of capture probes. See, for example, WO 2017/019456, the entire contents of which is herein incorporated by reference. Non-limiting examples include polyacrylamide hydrogels supported on an inert substrate (e.g., glass slide; see WO 2005/065814 and U.S. Patent Application No. 2008/0280773, the entire contents of which is incorporated herein by reference).

In some embodiments, functionalized biomolecules (e.g., capture probes) are immobilized on a functionalized substrate using covalent methods. Methods for covalent attachment include, for example, condensation of amines and activated carboxylic esters (e.g., N-hydroxysuccinimide esters); condensation of amine and aldehydes under reductive amination conditions; and cycloaddition reactions such as the Diels-Alder [4+2] reaction, 1,3-dipolar cycloaddition reactions, and [2+2] cycloaddition reactions. Methods for covalent attachment also include, for example, click chemistry reactions, including [3+2] cycloaddition reactions (e.g., Huisgen 1,3-dipolar cycloaddition reaction and copper(I)-catalyzed azide-alkyne cycloaddition (CuAAC)); thiol-ene reactions; the Diels-Alder reaction and inverse electron demand Diels-Alder reaction; [4+1]cycloaddition of isonitriles and tetrazines; and nucleophilic ring-opening of small carbocycles (e.g., epoxide opening with amino oligonucleotides). Methods for covalent attachment also include, for example, maleimides and thiols; and para-nitrophenyl ester-functionalized oligonucleotides and polylysine-functionalized substrate. Methods for covalent attachment also include, for example, disulfide reactions; radical reactions (see, e.g., U.S. Pat. No. 5,919,626, the entire contents of which are herein incorporated by reference); and hydrazide-functionalized substrate (e.g., wherein the hydrazide functional group is directly or indirectly attached to the substrate) and aldehyde-functionalized oligonucleotides (see, e.g., Yershov et al. (1996) *Proc. Natl. Acad. Sci. USA* 93, 4913-4918, the entire contents of which are herein incorporated by reference).

In some embodiments, functionalized biomolecules (e.g., capture probes) are immobilized on a functionalized substrate using photochemical covalent methods. Methods for photochemical covalent attachment include, for example, immobilization of antraquinone-conjugated oligonucleotides (see, e.g., Koch et al. (2000) *Bioconjugate Chem.* 11, 474-483, the entire contents of which is herein incorporated by reference).

In some embodiments, functionalized biomolecules (e.g., capture probes) are immobilized on a functionalized substrate using non-covalent methods. Methods for non-covalent attachment include, for example, biotin-functionalized oligonucleotides and streptavidin-treated substrates (see, e.g., Holmstrom et al. (1993) *Analytical Biochemistry* 209, 278-283 and Gilles et al. (1999) *Nature Biotechnology* 17, 365-370, the entire contents of which are herein incorporated by reference).

In some embodiments, an oligonucleotide (e.g., a capture probe) can be attached to a substrate or feature according to the methods set forth in U.S. Pat. Nos. 6,737,236, 7,259,258, 7,375,234, 7,427,678, 5,610,287, 5,807,522, 5,837,860, and 5,472,881; U.S. Patent Application Publication Nos. 2008/0280773 and 2011/0059865; Shalon et al. (1996) *Genome Research,* 639-645; Rogers et al. (1999) *Analytical Biochemistry* 266, 23-30; Stimpson et al. (1995) *Proc. Natl. Acad. Sci. USA* 92, 6379-6383; Beattie et al. (1995) *Clin. Chem.* 45, 700-706; Lamture et al. (1994) *Nucleic Acids Research* 22, 2121-2125; Beier et al. (1999) *Nucleic Acids Research* 27, 1970-1977; Joos et al. (1997) *Analytical Biochemistry* 247, 96-101; Nikiforov et al. (1995) *Analytical Biochemistry* 227, 201-209; Timofeev et al. (1996) *Nucleic Acids Research* 24, 3142-3148; Chrisey et al. (1996) *Nucleic Acids Research* 24, 3031-3039; Guo et al. (1994) *Nucleic Acids Research* 22, 5456-5465; Running and Urdea (1990) *BioTechniques* 8, 276-279; Fahy et al. (1993) *Nucleic Acids Research* 21, 1819-1826; Zhang et al. (1991) 19, 3929-3933; and Rogers et al. (1997) *Gene Therapy* 4, 1387-1392. The entire contents of each of the foregoing documents is incorporated herein by reference.

(ii) Generation of Capture Probes in an Array Format

Arrays can be prepared by a variety of methods. In some embodiments, arrays are prepared through the synthesis (e.g., in situ synthesis) of oligonucleotides on the array, or by jet printing or lithography. For example, light-directed synthesis of high-density DNA oligonucleotides can be achieved by photolithography or solid-phase DNA synthesis. To implement photolithographic synthesis, synthetic linkers modified with photochemical protecting groups can be attached to a substrate and the photochemical protecting groups can be modified using a photolithographic mask (applied to specific areas of the substrate) and light, thereby producing an array having localized photo-deprotection. Many of these methods are known in the art, and are described e.g., in Miller et al., "Basic concepts of microarrays and potential applications in clinical microbiology." *Clinical Microbiology Reviews* 22.4 (2009): 611-633; US201314111482A; U.S. Pat. No. 9,593,365B2; US2019203275; and WO2018091676, which are each incorporated herein by reference in its entirety.

Generation of capture probes in an array format can be performed using spotting or printing, in situ synthesis, using electric fields, through ligation, using polymerases. Further existing capture probes can be modified. Exemplary methods of generating capture probes in an array format are disclosed in WO 2020/047010 A2; WO 2020/047004 A2; WO 2020/047007 A2; WO 2020/047005 A2; WO 2020/047002 A1; PCT/US2019/065077; PCT/US2019/065048; PCT/US2019/064987; PCT/US2019/065013; PCT/US2019/065100; PCT/US2019/065072; PCT/US2019/065081; PCT/US2019/065096; and PCT/US2019/065041; each of which is incorporated by reference in its entirety.

(iii) Features

A "feature" is an entity that acts as a support or repository for various molecular entities used in sample analysis. In some embodiments, some or all of the features in an array are functionalized for analyte capture. In some embodiments, functionalized features include one or more capture probe(s). Examples of features include, but are not limited to, a bead, a spot of any two- or three-dimensional geometry (e.g., an ink jet spot, a masked spot, a square on a grid), a well, and a hydrogel pad. In some embodiments, features are directly or indirectly attached or fixed to a substrate. In some embodiments, the features are not directly or indirectly attached or fixed to a substrate, but instead, for example, are disposed within an enclosed or partially enclosed three dimensional space (e.g., wells or divots).

In addition to those above, a wide variety of other features can be used to form the arrays described herein. For example, in some embodiments, features that are formed from polymers and/or biopolymers that are jet printed, screen printed, or electrostatically deposited on a substrate can be used to form arrays. Jet printing of biopolymers is described, for example, in PCT Patent Application Publication No. WO 2014/085725. Jet printing of polymers is described, for example, in de Gans et al., *Adv Mater.* 16(3): 203-213 (2004). Methods for electrostatic deposition of polymers and biopolymers are described, for example, in Hoyer et al., *Anal. Chem.* 68(21): 3840-3844 (1996). The entire contents of each of the foregoing references are incorporated herein by reference.

As another example, in some embodiments, features are formed by metallic micro- or nanoparticles. Suitable methods for depositing such particles to form arrays are described, for example, in Lee et al., *Beilstein J. Nanotechnol.* 8: 1049-1055 (2017), the entire contents of which are incorporated herein by reference.

As a further example, in some embodiments, features are formed by magnetic particles that are assembled on a substrate. Examples of such particles and methods for assembling arrays are described in Ye et al., *Scientific Reports* 6: 23145 (2016), the entire contents of which are incorporated herein by reference.

As another example, in some embodiments, features correspond to regions of a substrate in which one or more optical labels have been incorporated, and/or which have been altered by a process such as permanent photobleaching. Suitable substrates to implement features in this manner include a wide variety of polymers, for example. Methods for forming such features are described, for example, in Moshrefzadeh et al., *Appl. Phys. Lett.* 62: 16 (1993), the entire contents of which are incorporated herein by reference.

As yet another example, in some embodiments, features can correspond to colloidal particles assembled (e.g., via self-assembly) to form an array. Suitable colloidal particles are described for example in Sharma, *Resonance* 23(3): 263-275 (2018), the entire contents of which are incorporated herein by reference.

As a further example, in some embodiments, features can be formed via spot-array photopolymerization of a monomer solution on a substrate. In particular, two-photon and three-photon polymerization can be used to fabricate features of relatively small (e.g., sub-micron) dimensions. Suitable methods for preparing features on a substrate in this manner are described for example in Nguyen et al., *Materials Today* 20(6): 314-322 (2017), the entire contents of which are incorporated herein by reference.

In some embodiments, features are directly or indirectly attached or fixed to a substrate that is liquid permeable. In some embodiments, features are directly or indirectly attached or fixed to a substrate that is biocompatible. In some embodiments, features are directly or indirectly attached or fixed to a substrate that is a hydrogel.

Figure 12:
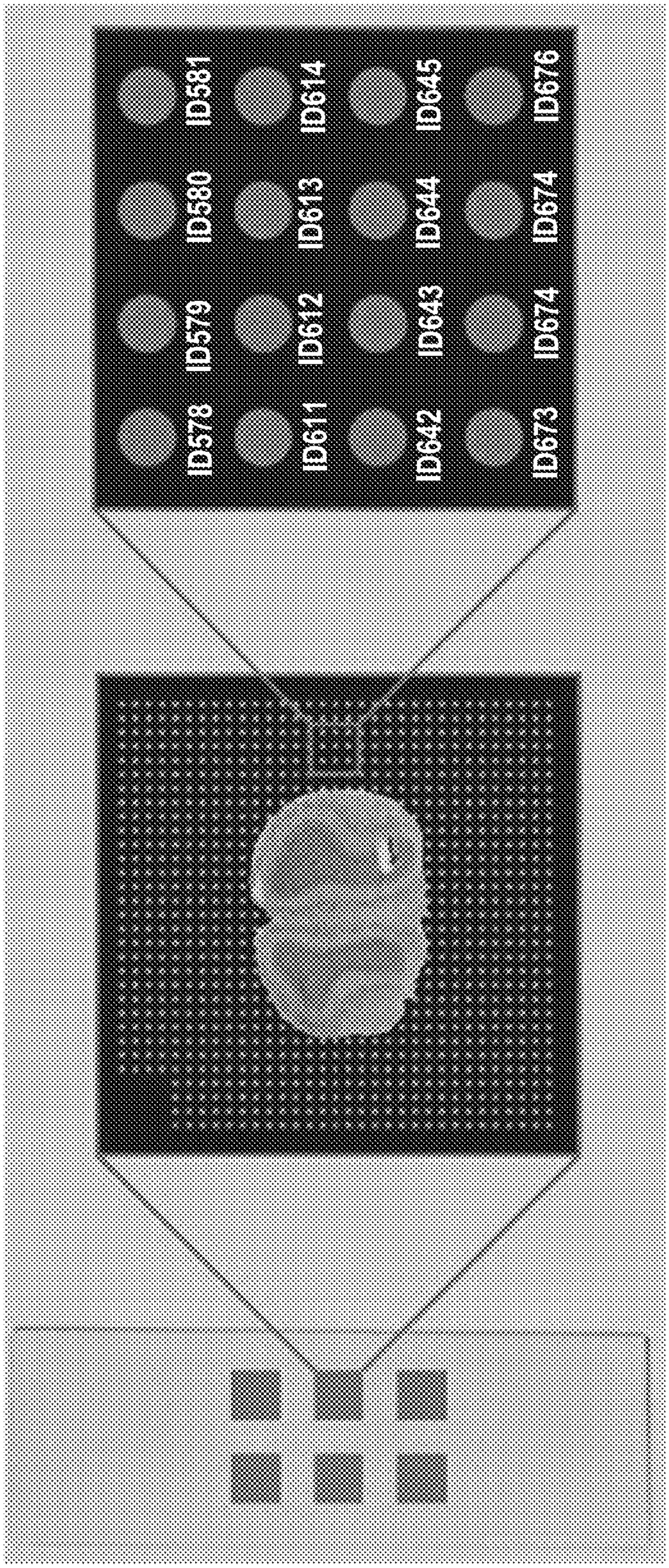
FIG. 12 is a schematic showing the arrangement of barcoded features within an array.

FIG. 12 depicts an exemplary arrangement of barcoded features within an array. From left to right, FIG. 12 shows (L) a slide including six spatially-barcoded arrays, (C) an enlarged schematic of one of the six spatially-barcoded arrays, showing a grid of barcoded features in relation to a biological sample, and (R) an enlarged schematic of one section of an array, showing the specific identification of multiple features within the array (labelled as ID578, ID579, ID560, etc.).

(1) Beads

A "bead" can be a particle. A bead can be porous, non-porous, solid, semi-solid, and/or a combination thereof. In some embodiments, a bead can be dissolvable, disruptable, and/or degradable, whereas in certain embodiments, a bead is not degradable. A semi-solid bead can be a liposomal bead. Solid beads can include metals including, without limitation, iron oxide, gold, and silver. In some embodiments, the bead can be a silica bead. In some embodiments, the bead can be rigid. In some embodiments, the bead can be flexible and/or compressible.

Exemplary beads are further disclosed in WO 2020/047010 A2; WO 2020/047004 A2; WO 2020/047007 A2; WO 2020/047005 A2; WO 2020/047002 A1; PCT/US2019/065077; PCT/US2019/065048; PCT/US2019/064987; PCT/US2019/065013; PCT/US2019/065100; PCT/US2019/065072; PCT/US2019/065081; PCT/US2019/065096; and PCT/US2019/065041; each of which is incorporated by reference in its entirety.

(iv) Array Geometric Attributes

In some embodiments, an array includes a plurality of features. For example, an array includes between 4,000 and 50,000 features, or any range within 4,000 to 40,000 features. For example, an array includes between 4,000 to 35,000 features, 4,000 to 30,000 features, 4,000 to 25,000 features, 4,000 to 20,000 features, 4,000 to 15,000 features, 4,000 to 10,000 features, 4,000 to 6,000 features, or 4,400 to 6,000 features. In some embodiments, the array includes between 4,100 and 5,900 features, between 4,200 and 5,800 features, between 4,300 and 5,700 features, between 4,400 and 5,600 features, between 4,500 and 5,500 features, between 4,600 and 5,400 features, between 4,700 and 5,300 features, between 4,800 and 5,200 features, between 4,900 and 5,100 features, or any range within the disclosed sub-ranges. For example, the array can include about 4,000 features, about 4,200 features, about 4,400 features, about 4,800 features, about 5,000 features, about 5,200 features, about 5,400 features, about 5,600 features, or about 6,000 features, about 10,000 features, about 20,000 features, about 30,000 features, about 40,000 features, or about 50,000 features. In some embodiments, the array comprises at least 4,000 features. In some embodiments, the array includes approximately 5,000 features.

In some embodiments, features within an array have an irregular arrangement or relationship to one another, such that no discernable pattern or regularity is evident in the geometrical spacing relationships among the features. For example, features within an array may be positioned randomly with respect to one another. Alternatively, features within an array may be positioned irregularly, but the spacings may be selected deterministically to ensure that the resulting arrangement of features is irregular.

In some embodiments, features within an array are positioned regularly with respect to one another to form a pattern. A wide variety of different patterns of features can be implemented in arrays. Examples of such patterns include, but are not limited to, square arrays of features, rectangular arrays of features, hexagonal arrays of features (including hexagonal close-packed arrays), radial arrays of features, spiral arrays of features, triangular arrays of features, and more generally, any array in which adjacent features in the array are reached from one another by regular increments in linear and/or angular coordinate dimensions.

In some embodiments, features within an array are positioned with a degree of regularity with respect to one another such that the array of features is neither perfectly regular nor perfectly irregular (i.e., the array is "partially regular"). For example, in some embodiments, adjacent features in an array can be separated by a displacement in one or more linear and/or angular coordinate dimensions that is 10% or more (e.g., 20% or more, 30% or more, 40% or more, 50% or more, 60% or more, 70% or more, 80% or more, 90% or more, 100% or more, 110% or more, 120% or more, 130% or more, 140% or more, 150% or more, 160% or more, 170% or more, 180% or more, 190% or more, 200% or more) of an average displacement or a nominal displacement between adjacent features in the array. In certain embodiments, the distribution of displacements (linear and/or angular) between adjacent features in an array has a full-width at half-maximum of between 0% and 200% (e.g., between 0% and 100%, between 0% and 75%, between 0% and 50%, between 0% and 25%, between 0% and 15%, between 0% and 10%) of an average displacement or nominal displacement between adjacent features in the array.

In some embodiments, arrays of features can have a variable geometry. For example, a first subset of features in an array can be arranged according to a first geometrical pattern, and a second subset of features in the array can be arranged according to a second geometrical pattern that is different from the first pattern. Any of the patterns described above can correspond to the first and/or second geometrical patterns, for example.

In general, arrays of different feature densities can be prepared by adjusting the spacing between adjacent features in the array. In some embodiments, the geometric center-to-center (e.g., pitch) spacing between adjacent features in an array is between 100 nm to 10 μm, 500 nm to 2 μm, 1 m to 5 μm, and 20 μm to 200 μm. For example, the center-to-center spacing can be between 100 nm to 10 μm, 500 nm to 2 μm, 1 μm, to 5 μm, 20 m to 40 μm, 20 μm to 60 μm, 20 m to 80 μm, 80 μm to 100 μm, 100 m to 120 am, 120 μm to 140 μm, 140 μm to 160 μm, 160 μm to 180 μm, 180 μm to 200 μm, 60 μm to 100 μm, or 40 μm to 100 μm, 50 μm to 150 μm, 80 m to 120 μm, or 90 m to 110 μm. In some embodiments, the pitch between adjacent array features is between 30 m and 100 μm, 40 m and 90 μm, 50 m and 80 μm, 60 μm and 70 μm, 80 m and 120 μm, or any range within the disclosed sub-ranges. In some embodiments, the pitch between adjacent array features of an array is approximately 65 μm, approximately 60 μm, approximately 55 μm, approximately 50 μm, approximately 45 μm, approximately 40 μm, approximately 35 μm, approximately 30 μm, approximately 25 μm, approximately 20 μm, approximately 15 μm, approximately 10 μm, approximately 5 μm, approximately 4 μm, approximately 3 μm, approximately 2 μm, or approximately 1 μm. In some embodiments, the pitch between adjacent array features of an array is less than 100 μm.

An array of features can have any appropriate resolution. In some embodiments, an array of features can have a spatially constant (e.g., within a margin of error) resolution. In general, an array with a spatially consistent resolution is an array in which the pitch between adjacent features in the array is constant (e.g., within a margin of error). Such arrays can be useful in a variety of applications. In some embodiments, an array of features can have a spatially varying resolution. In general, an array with a spatially varying resolution is an array in which the center-to-center spacing (e.g., pitch) (along linear, angular, or both linear and angular coordinate dimensions) between adjacent features in the array varies. Such arrays can be useful in a variety of applications. For example, in some embodiments, depending upon the spatial resolution at which the sample is to be investigated, the sample can be selectively associated with the portion of the array that corresponds approximately to the desired spatial resolution of the measurement.

In some embodiments, it may be useful to describe the resolution of an array of features by functional aspects, for example, the number of reads that can be carried out per feature (which can be a proxy for sequencing saturation), the number of transcripts that can be detected per feature, or the number of genes that can be detected per feature. For example, in some embodiments, the number of reads that can be performed per feature is between 50,000 and 1,000,000. For example, the number of reads that can be performed per feature can be between 50,000 and 100,000, 50,000 and 150,000, 50,000 and 200,000, 50,000 and 250,000, 50,000 and 300,000, 50,000 and 350,000, 50,000 and 400,000, 50,000 and 500,000, 50,000 and 550,000, 50,000 and 600,000, 50,000 and 650,000, 50,000 and 700,000, 50,000 and 750,000, 50,000 and 800,000, 50,000 and 850,000, 50,000 and 900,000, 50,000 and 950,000, 50,000 and 1,000,000, 100,000 to 500,000, 150,000 to 500,000, 200,000 to 500,000, 250,000 to 500,000, 300,000 and 500,000, 350,000 and 500,000, 400,000 and 500,000, 450,000 and 500,000, 150,000 to 250,000, or 300,000 to 400,000. In some embodiments, the number of reads that can be performed per feature is about 70,000. In some embodiments, the number of reads that can be performed per feature is about 170,000. In some embodiments, the number reads that can be performed per feature is about 330,000. In some embodiments, the number reads that can be performed per feature is about 500,000. In some embodiments, the number reads that can be performed per feature is about 800,000.

In some embodiments, the number of transcripts that can be detected per feature is between 20,000 and 200,000. For example, in some embodiments, the number of transcripts that can be detected per feature can be between 20,000 and 30,000, 20,000 and 40,000, 20,000 and 50,000, 30,000 and 60,000, 40,000 and 60,000, 50,000 and 60,000, 20,000 and 100,000, 30,000 and 100,000, 40,000 and 200,000, 50,000 and 200,000, or 30,000 and 200,000. In some embodiments, the number of transcripts that can be detected per feature is about 40,000. In some embodiments, the number of transcripts that can be detected per feature is about 60,000. In some embodiments, the number of transcripts that can be detected per feature is about 80,000. In some embodiments, the number of transcripts that can be detected per feature is about 100,000.

In some embodiments, the number of genes that can be detected per feature is between 1,000 and 5,000. For example, the number of genes that can be detected per feature can be between 1,000 and 1,500, 1,000 and 2,000, 1,000 and 2,500, 1,000 and 3,000, 1,000 and 3,500, 1,000 and 4,000, 1,000 and 4,500, 1,500 and 5,000, 2,000 and 5,000, 2,500 and 5,000, 3,000 and 5,000, 3,500 and 5,000, 4,000 and 5,000, 4,500 and 5,000, 1,500 and 2,500, 2,500 and 3,500, or 3,500 and 4,000. In some embodiments, the number of genes that can be detected per feature is about 2,000. In some embodiments, the number of genes that can be detected per feature is about 3,000. In some embodiments, the number of genes that can be detected per feature is about 4,000.

In some embodiments, it may be useful to describe the resolution of an array of features by functional aspects, for example, the number of UMI counts per feature. For example, in some embodiments, the number of UMI counts that can be performed per feature is between 1,000 and 50,000. In some embodiments, the number of UMI counts can be averaged to obtain a mean UMI per feature. In some embodiments, the number of UMI counts can be averaged to obtain a median UMI count per feature. For example, the median UMI count per feature can be between 1,000 and 50,000, 1,000 and 40,000, 1,000 and 30,000, 1,000 and 20,000, 1,000 and 10,000, 1,000 and 5,000. In some embodiments, the median UMI count per feature is about 5,000. In some embodiments, the median UMI count per feature is about 10,000.

These components can be used to determine the sequencing saturation of the array. The sequencing saturation can be a measure of the library complexity and sequencing depth. For example, different cell types will have different amounts of RNA, thus different number of transcripts, influencing library complexity. Additionally, sequencing depth is related to the number of sequencing reads. In some embodiments, the inverse of sequencing saturation is the number of additional reads it would take to detect a new transcript. One way of measuring the sequencing saturation of an array is to determine the number of reads to detect a new UMI. For example, if a new UMI is detected every 2 reads of the feature, the sequencing saturation would be 50%. As another example, if a new UMI is detected every 10 reads of a feature, the sequencing saturation would be 90%.

Arrays of spatially varying resolution can be implemented in a variety of ways. In some embodiments, for example, the pitch between adjacent features in the array varies continuously along one or more linear and/or angular coordinate directions. Thus, for a rectangular array, the spacing between successive rows of features, between successive columns of features, or between both successive rows and successive columns of features, can vary continuously.

In certain embodiments, arrays of spatially varying resolution can include discrete domains with populations of features. Within each domain, adjacent features can have a regular pitch. Thus, for example, an array can include a first domain within which adjacent features are spaced from one another along linear and/or angular coordinate dimensions by a first set of uniform coordinate displacements, and a second domain within which adjacent features are spaced from one another along linear and/or angular coordinate dimensions by a second set of uniform coordinate displacements. The first and second sets of displacements differ in at least one coordinate displacement, such that adjacent features in the two domains are spaced differently, and the resolution of the array in the first domain is therefore different from the resolution of the array in the second domain.

In some embodiments, the pitch of array features can be sufficiently small such that array features are effectively positioned continuously or nearly continuously along one or more array dimensions, with little or no displacement between array features along those dimensions. For example, in a feature array where the features correspond to regions of a substrate (i.e., oligonucleotides are directly bound to the substrate), the displacement between adjacent oligonucleotides can be very small—effectively, the molecular width of a single oligonucleotide. In such embodiments, each oligonucleotide can include a distinct spatial barcode such that the spatial location of each oligonucleotide in the array can be determined during sample analysis. Arrays of this type can have very high spatial resolution, but may only include a single oligonucleotide corresponding to each distinct spatial location in a sample.

In general, the size of the array (which corresponds to the maximum dimension of the smallest boundary that encloses all features in the array along one coordinate direction) can be selected as desired, based on criteria such as the size of the sample, the feature diameter, and the density of capture probes within each feature. For example, in some embodiments, the array can be a rectangular or square array for which the maximum array dimension along each coordinate direction is 10 mm or less (e.g., 9 mm or less, 8 mm or less, 7 mm or less, 6 mm or less, 5 mm or less, 4 mm or less, 3 mm or less). Thus, for example, a square array of features can have dimensions of 8 mm by 8 mm, 7 mm by 7 mm, 5 mm by 5 mm, or be smaller than 5 mm by 5 mm.

(v) Building Arrays with Linkers

In some embodiments, an array includes a linker that is branched or dendrimeric. In some embodiments, the linker includes dendrimeric polyamines. Non-limiting examples of dendrimeric polyamines include symmetrical and unsymmetrical dendrimers, nucleic acid dendrimers, polyamidoamine dendrimers, and lysine-based dendrimers. In some embodiments, a linker is a nucleic acid dendrimer. In some embodiments, a nucleic acid dendrimer includes individual molecules of nucleic acids that share a region of at least partial complementarity located in a position of each nucleic acid molecule where upon binding at least 2 (e.g., 2, 3, 4, or more) single-strand overhangs are generated. In some embodiments, the four single-stranded overhangs are designed to interact with additional nucleic acid dendrimers or specific complementary sequence (e.g., sequences on capture probes). In some embodiments, the dendrimeric linkers (e.g., nucleic acid dendrimers) are affixed to a substrate (e.g., affixed using any of the methods described herein (e.g., covalent bonding or physical absorption)). For example, a nucleic acid dendrimer is affixed to a substrate and also interacts with capture probes via the single-stranded overhangs. In another example, a nucleic acid dendrimer is affixed to a substrate and also interacts with additional nucleic acid dendrimers. The additional nucleic acid dendrimers can also interact with capture probes via the single-strand overhangs not already interacting with other nucleic acid dendrimers. In such cases, with each additional layer of nucleic acid dendrimer, there is the potential to increase the number of sites to which capture probes can interact, thereby increasing the number of capture domains (e.g., any of the exemplary capture domains described herein) on the array.

(vi) Array/Feature Preservation

In some embodiments, the biological sample can be preserved after completion of an assay with a feature or arrangement of features for additional rounds of spatial detection of analytes. In some embodiments, the biological sample, features, array, or any combination thereof can be preserved after the spatial profiling. In some embodiments, the biological sample, features, array, or combinations thereof can be protected from dehydration (e.g., drying, desiccation). In some embodiments, the biological sample, features, array, or combinations thereof, can be protected from evaporation. Methods of preserving and/or protecting biological samples, features, or arrays are known in the art. For example, in a non-limiting way, the biological sample, features, array, or combinations thereof can be covered by a reversible sealing agent. Any suitable reversible sealing agent can be used. Methods of reversible sealing are known in the art (See, e.g., WO 2019/104337, which is incorporated herein by reference). In a non-limiting way, suitable reversible sealing agents can include non-porous materials, membranes, lids, or oils (e.g., silicone oil, mineral oil). In further non-limiting examples, the biological sample, features, array, or combinations thereof can be preserved in an environmental chamber (e.g., hermetically sealed) and removed for additional rounds of spatial analysis at a later time.

(e) Analyte Capture

In this section, general aspects of methods and systems for capturing analytes are described. Individual method steps and system features can be present in combination in many different embodiments; the specific combinations described herein do not in any way limit other combinations of steps or features.

(i) Conditions for Capture

Generally, analytes can be captured when contacting a biological sample with a substrate including capture probes (e.g., substrate with capture probes embedded, spotted, printed on the substrate or a substrate with features (e.g., beads, wells) comprising capture probes).

As used herein, "contact," "contacted," and/or "contacting," a biological sample with a substrate refers to any contact (e.g., direct or indirect) such that capture probes can interact (e.g., capture) with analytes from the biological sample. For example, a substrate may be near or adjacent to the biological sample without direct physical contact, yet capable of capturing analytes from the biological sample. In some embodiments a biological sample is in direct physical contact with a substrate. In some embodiments, a biological sample is in indirect physical contact with a substrate. For example, a liquid layer may be between the biological sample and the substrate. In some embodiments, analytes diffuse through a liquid layer. In some embodiments capture probes diffuse through a liquid layer. In some embodiments reagents may be delivered via a liquid layer between a biological sample and a substrate. In some embodiments, indirect physical contact may include a second substrate (e.g., a hydrogel, a film, a porous membrane) between the biological sample and the first substrate comprising capture probes. In some embodiments, reagents may be delivered by a second substrate to a biological sample.

In some embodiments, a cell immobilization agent can be used to contact a biological sample with a substrate (e.g., by immobilizing non-aggregated or disaggregated sample on a spatially-barcoded array prior to analyte capture). A "cell immobilization agent" as used herein can refer to an agent (e.g., an antibody), attached to a substrate, which can bind to a cell surface marker. Non-limiting examples of a cell surface marker include CD45, CD3, CD4, CD8, CD56, CD19, CD20, CD11c, CD14, CD33, CD66b, CD34, CD41, CD61, CD235a, CD146, and epithelial cellular adhesion molecule (EpCAM). A cell immobilization agent can include any probe or component that can bind to (e.g., immobilize) a cell or tissue when on a substrate. A cell immobilization agent attached to the surface of a substrate can be used to bind a cell that has a cell surface maker. The cell surface marker can be a ubiquitous cell surface marker, wherein the purpose of the cell immobilization agent is to capture a high percentage of cells within the sample. The cell surface marker can be a specific, or more rarely expressed, cell surface marker, wherein the purpose of the cell immobilization agent is to capture a specific cell population expressing the target cell surface marker. Accordingly, a cell immobilization agent can be used to selectively capture a cell expressing the target cell surface marker from a population of cells that do not have the same cell surface marker.

Capture probes on a substrate (or on a feature on the substrate) may interact with released analytes through a capture domain, described elsewhere, to capture analytes. In some embodiments, certain steps are performed to enhance the transfer or capture of analytes to the capture probes of the array. Examples of such modifications include, but are not limited to, adjusting conditions for contacting the substrate with a biological sample (e.g., time, temperature, orientation, pH levels, pre-treating of biological samples, etc.), using force to transport analytes (e.g., electrophoretic, centrifugal, mechanical, etc.), performing amplification reactions to increase the amount of biological analytes (e.g., PCR amplification, in situ amplification, clonal amplification), and/or using labeled probes for detecting of amplicons and barcodes.

In some embodiments, an array is adapted in order to facilitate biological analyte migration. Non-limiting examples of adapting an array to facilitate biological analyte migration include arrays with substrates containing nanopores, nanowells, and/or microfluidic channels; arrays with porous membranes; and arrays with substrates that are made of hydrogel. In some cases, the array substrate is liquid permeable. In some cases, the array is a coverslip or slide that includes nanowells or patterning, (e.g., via fabrication). In some cases where the substrate includes nanopores, nanowells, and/or microfluidic channels, these structures can facilitate exposure of the biological sample to reagents (e.g., reagents for permeabilization, biological analyte capture, and/or a nucleic acid extension reaction), thereby increasing analyte capture efficiency as compared to a substrate lacking such characteristics.

In some embodiments, analyte capture is facilitated by treating a biological sample with permeabilization reagents. If a biological sample is not permeabilized sufficiently, the amount of analyte captured on a substrate can be too low to enable adequate analysis. Conversely, if a biological sample is too permeable, an analyte can diffuse away from its origin in the biological sample, such that the relative spatial relationship of the analytes within the biological sample is lost. Hence, a balance between permeabilizing the biological sample enough to obtain good signal intensity while still maintaining the spatial resolution of the analyte distribution in the biological sample is desired. Methods of preparing biological samples to facilitate analyte capture are known in the art and can be modified depending on the biological sample and how the biological sample is prepared (e.g., fresh frozen, FFPE, etc.).

(ii) Diffusion-Resistant Media/Lids

Figure 13:
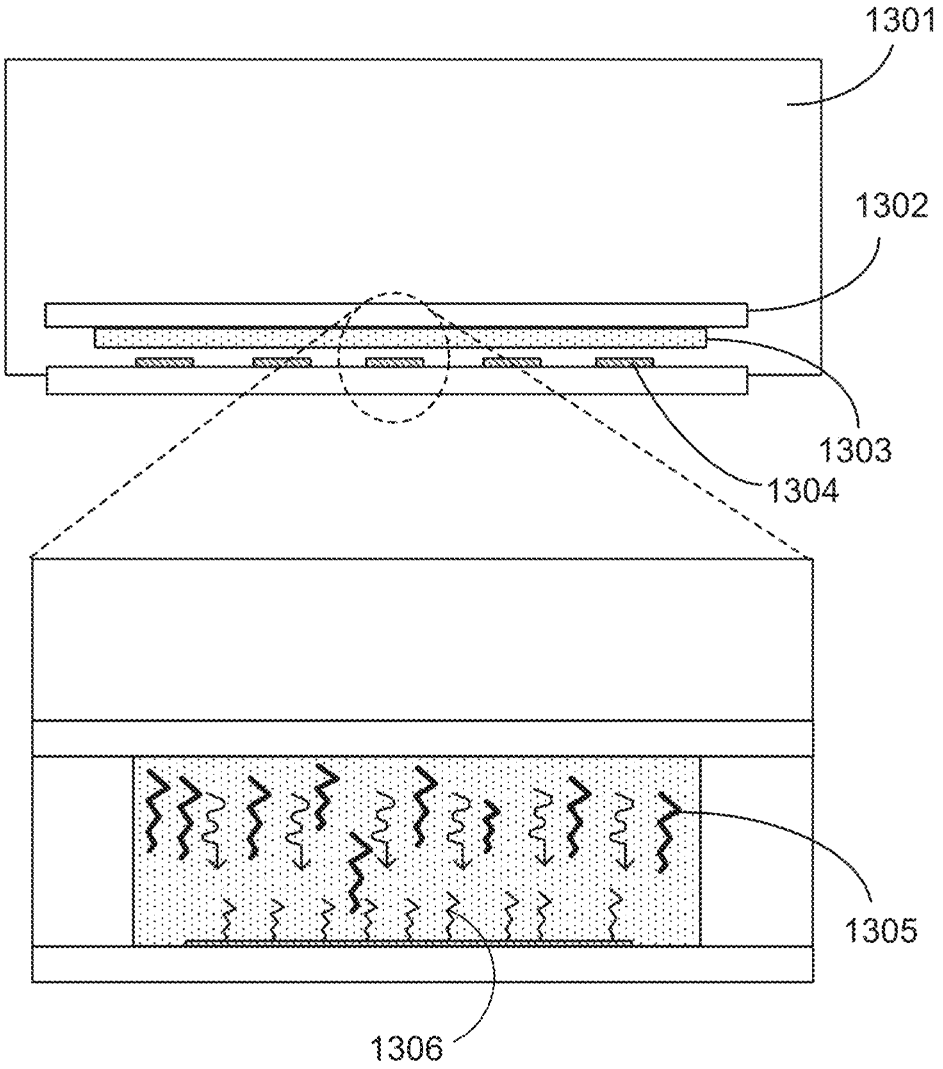
FIG. 13 is a schematic illustrating a side view of a diffusion-resistant medium, e.g., a lid.

FIG. 13 is an illustration of an exemplary use of a diffusion-resistant medium. A diffusion-resistant medium/lid 1302 can be contacted with a sample 1303. In FIG. 13, a glass slide 1304 is populated with spatially-barcoded capture probes 1306, and the sample 1303, 1305 is contacted with the array 1304, 1306. A diffusion-resistant medium/lid 1302 can be applied to the sample 1303, wherein the sample 1303 is sandwiched between a diffusion-resistant medium 1302 and a capture probe coated slide 1304. When a permeabilization solution 1301 is applied to the sample, using the diffusion-resistant medium/lid 1302 directs migration of the analytes 1305 toward the capture probes 1306 by reducing diffusion of the analytes out into the medium. Alternatively, the diffusion resistant medium/lid may contain permeabilization reagents.

(iii) Active Capture Methods

In some of the methods described herein, an analyte in a biological sample (e.g., in a cell or tissue section) can be transported (e.g., passively or actively) to a capture probe (e.g., a capture probe affixed to a substrate (e.g., a substrate or bead)).

For example, analytes can be transported to a capture probe (e.g., an immobilized capture probe) using an electric field (e.g., using electrophoresis), pressure, fluid flow, gravity, temperature, and/or a magnetic field. For example, analytes can be transported through, e.g., a gel (e.g., hydrogel), a fluid, or a permeabilized cell, to a capture probe (e.g., an immobilized capture probe) using a pressure gradient, a chemical concentration gradient, a temperature gradient, and/or a pH gradient. For example, analytes can be transported through a gel (e.g., hydrogel), a fluid, or a permeabilized cell, to a capture probe (e.g., an immobilized capture probe).

In some examples, an electrophoretic field can be applied to analytes to facilitate migration of analytes towards a capture probe. In some examples, a sample containing analytes contacts a substrate having capture probes fixed on the substrate (e.g., a slide, cover slip, or bead), and an electric current is applied to promote the directional migration of charged analytes towards capture probes on a substrate. An electrophoresis assembly (e.g., an electrophoretic chamber), where a biological sample is in contact with a cathode and capture probes (e.g., capture probes fixed on a substrate), and where the capture probes are in contact with the biological sample and an anode, can be used to apply the current.

In some embodiments, methods utilizing an active capture method can employ a conductive substrate (e.g., any of the conductive substrates described herein). In some embodiments, a conductive substrate includes paper, a hydrogel film, or a glass slide having a conductive coating. In some embodiments, a conductive substrate (e.g., any of the conductive substrates described herein) includes one or more capture probes.

Figure 24A:
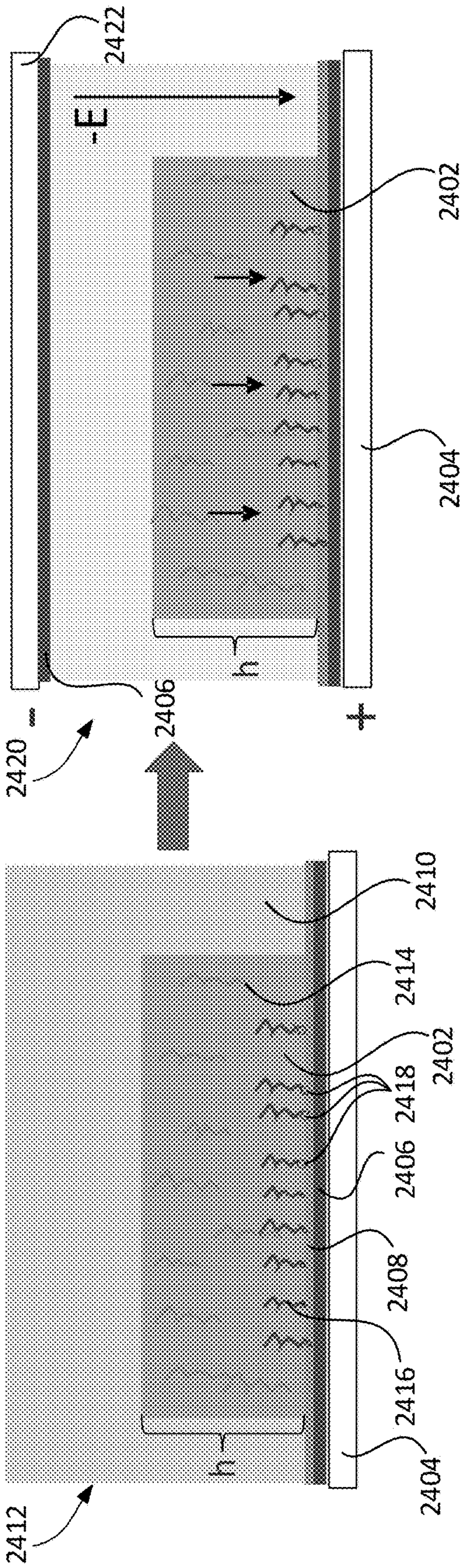
FIG. 24A shows a schematic of an example analytical workflow in which electrophoretic migration of analytes is performed after permeabilization.
Figure 24B:
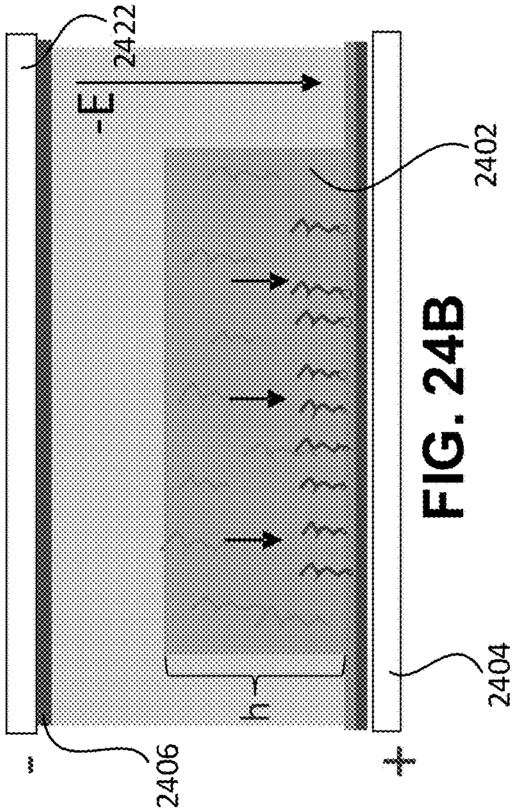
FIG. 24B shows a schematic of an example analytical workflow in which electrophoretic migration of analytes and permeabilization are performed simultaneously.

FIGS. 24A and 24B show different example analytical workflows of active capture methods using an electric field (e.g., using electrophoresis). In some examples, a biological sample 2402 (e.g., a tissue sample) can be in contact with a first substrate 2404. In some embodiments, first substrate 2404 can have one or more coatings (e.g., any of the conductive substrates described herein) on its surface. Non-limiting examples of coatings include, nucleic acids (e.g., RNA) and conductive oxides (e.g., indium tin oxide). In some embodiments, first substrate 2404 can have a functionalization chemistry on its surface. In the examples shown in FIGS. 24A and 24B, first substrate 2404 is overlaid with a first coating 2406, and first coating 2406 (e.g., a conductive coating) is further overlaid with a second coating 2408. In some embodiments, first coating 2406 is an indium tin oxide (ITO) coating. In some embodiments, second coating 2408 is a lawn of capture probes (e.g., any of the capture probes described herein). In some embodiments, a substrate can include an ITO coating. In some embodiments, a substrate can include capture probes or capture probes attached to features on the substrate.

Biological sample 2402 and second coating 2408 (e.g., a lawn of capture probes) can be in contact with a permeabilization solution 2410. Non-limiting examples of permeabilization solutions include, enzymes (e.g., proteinase K, pepsin, and collagenase), detergents (e.g., sodium dodecyl sulfate (SDS), polyethylene glycol tert-octylphenyl ether, polysorbate 80, and polysorbate 20), ribonuclease inhibitors, buffers optimized for electrophoresis, buffers optimized for permeabilization, buffers optimized for hybridization, or combinations thereof. Permeabilization reagents can also include but are not limited to a dried permeabilization reagent, a permeabilization buffer, a buffer without a permeabilization reagent, a permeabilization gel, and a permeabilization solution. In some examples, biological samples (e.g., tissue samples) can be permeabilized first and then be subjected to electrophoresis.

FIG. 24A shows an example analytical workflow including a first step 2412 in which biological sample 2402 can be permeabilized prior to subjecting the sample 2402 to electrophoresis. Any of the permeabilization methods disclosed herein can be used during first step 2412. Biological sample 2402 includes an analyte 2414. In some embodiments, the analyte 2414 is a negatively charged analyte. First substrate 2404 can include a capture probe 2416 that is fixed or attached to the first substrate 2404 or attached to features (e.g., beads) 2418 on the substrate. In some embodiments, capture probe 2416 can include any of the capture probes disclosed herein. In some embodiments, first substrate 2402 does not include features and instead, capture probes 2416 are directly attached to the substrate surface. In some embodiments, the capture probe 2416 is positively charged.

In step 2420, after permeabilization of biological sample 2402 concludes, the sample 2402 can be subjected to electrophoresis. During electrophoresis, the biological sample 2402 is subjected to an electric field that can be generated by sandwiching biological sample 2402 between the first substrate 2404 and a second substrate 2422, connecting each substrate to a cathode and an anode, respectively, and running an electric current through the substrates. The application of the electric field "-E" causes the analyte 2404 (e.g., a negatively charged analyte) to migrate towards the substrate 2404 and capture probe 2416 (e.g., a positively charged capture probe) in the direction of the arrows shown in FIG. 24A. In some embodiments, the analyte 2414 migrates towards the capture probe 2416 for a distance "h." In some embodiments, the analyte 2414 migrates towards a capture probe 2416 through one or more permeabilized cells within the permeabilized biological sample (e.g., from an original location in a permeabilized cell to a final location in or close to the capture probe 2416). Second substrate 2422 can include the first coating 2406 (e.g., a conductive coating), thereby allowing electric field "-E" to be generated.

In some embodiments, the analyte 2414 is a protein or a nucleic acid. In some embodiments, the analyte 2414 is a negatively charged protein or a nucleic acid. In some embodiments, the analyte 2414 is a positively charged protein or a nucleic acid. In some embodiments, the capture probe 2416 is a protein or a nucleic acid. In some embodiments, the capture probe 2416 is a positively charged protein or a nucleic acid. In some embodiments, the capture probe 2416 is a negatively charged protein or a nucleic acid. In some embodiments, the analyte 2414 is a negatively charged transcript. In some embodiments, the analyte 2414 is a poly(A) transcript. In some embodiments, the capture probe 2416 is attached to a feature in a feature array. In some embodiments, permeabilization reagent 2410 can be in contact with sample 2402, first substrate 2404 second substrate 2422, or any combination thereof.

FIG. 24B shows an example analytical workflow in which biological sample 2402 can be permeabilized and subjected to electrophoresis simultaneously. In some embodiments, simultaneous permeabilization and electrophoresis of biological sample 2402 can decrease the total duration of the analytical workflow translating into a more efficient workflow.

In some embodiments, the permeabilization reaction is conducted at a chilled temperature (e.g., about 4° C.). In some embodiments, conducting the permeabilization reaction at a chilled temperature controls the enzyme activity of the permeabilization reaction. In some embodiments, the permeabilization reaction is conducted at a chilled temperature in order to prevent drift and/or diffusion of the analyte 2414 from an original location (e.g., a location in a cell of the biological sample 2402) until a user is ready to initiate the permeabilization reaction. In some embodiments, the permeabilization reaction is conducted at a warm temperature (e.g., a temperature ranging from about 15° C. to about 37° C. or more) in order to initiate and/or increase the rate of the permeabilization reaction. In some embodiments, once electrophoresis is applied and/or the permeabilization reaction is heated, the permeabilization reaction allows for analyte migration from an original location (e.g., a location in a cell of the biological sample 2402) to the capture probe 2416 anchored to the first substrate 2404.

Figure 25A:
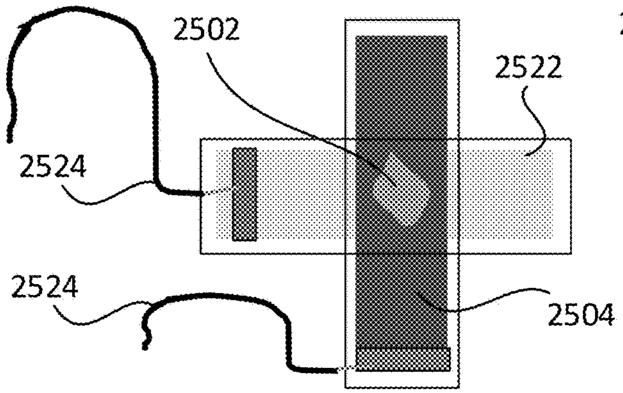
FIG. 25A shows an example perpendicular, single slide configuration for use during electrophoresis.
Figure 25B:
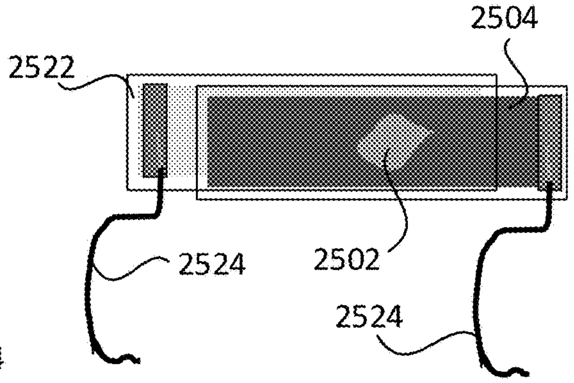
FIG. 25B shows an example parallel, single slide configuration for use during electrophoresis
Figure 25C:
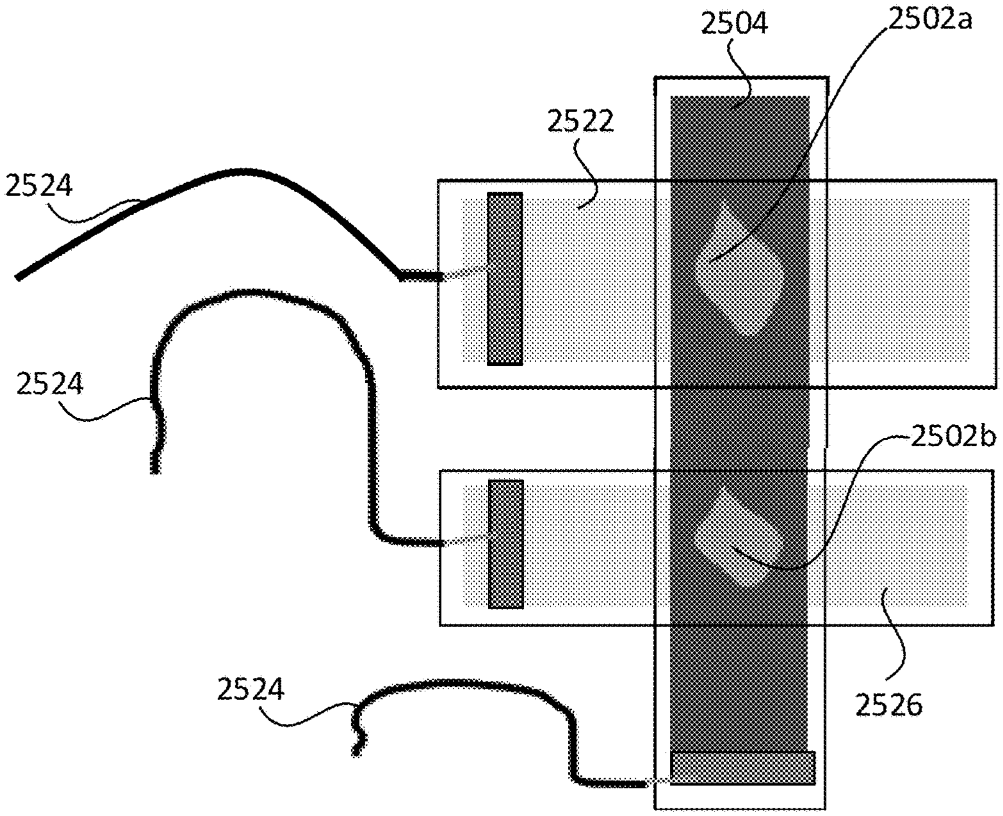
FIG. 25C shows an example multi-slide configuration for use during electrophoresis.

Referring generally to FIGS. 25A-C, example substrate configurations for use in the active migration of analytes from a first location to a second location via electrophoresis are shown. FIG. 25A shows an example substrate configuration for use in electrophoresis in which the first substrate 2502 and the second substrate 2522 are aligned at about 90 degrees with respect to each other. In this example, the first substrate 2502 including biological sample 2504 is placed beneath second substrate 2522. Both the first substrate 2502 and the second substrate 2522 can be connected to electrical wires 2524 that direct an electric current from a power supply to the substrates, thereby generating an electric field between the substrates. FIG. 25B shows an additional example substrate configuration for use during electrophoresis in which the first substrate 2502 and the second substrate 2522 are parallel with respect to each other. In this example, the first substrate 2502 including biological sample 2504 is also placed beneath second substrate 2522.

FIG. 25C shows yet an additional example substrate configuration for use in electrophoresis in which the second substrate 2522 and a third substrate 2526 are aligned at about 90 degrees with respect to the first substrate 2502. Thus, in this example, a first biological sample 2502*a* and a second biological sample 2502*b* can be subjected to electrophoresis simultaneously. In some embodiments, 3, 4, 5, 6, 7, 8, 9, 10, or more biological samples can be placed on a same substrate and be subjected to electrophoresis simultaneously. In some embodiments, 2, 3, 4, 5, 6, 7, 8, 9, 10, or more top substrates can be placed above a same bottom substrate containing one or more samples in order to simultaneously subject the one or more samples to electrophoresis. In some embodiments, 2, 3, 4, 5, 6, 7, 8, 9, 10, or more top substrates can be perpendicularly placed (e.g., at about 90 degrees) above a same bottom substrate containing one or more samples in order to simultaneously subject the one or more samples to electrophoresis. In some embodiments, 2, 3, 4, 5, 6, 7, 8, 9, 10, or more top substrates can be placed in a parallel orientation above a same bottom substrate containing one or more biological samples in order to simultaneously subject the one or more samples to electrophoresis. In some embodiments, a configuration of top substrates can be arranged above a same bottom substrate containing one or more biological samples in order to simultaneously subject the one or more samples to electrophoresis. In some embodiments, a first configuration of top substrates can be arranged above a second array of bottom substrates containing one or more biological samples in order to simultaneously subject the one or more biological samples to electrophoresis. In some embodiments, simultaneously subjecting two or more biological samples on a same substrate to electrophoresis can provide the advantage of a more effective workflow. In some embodiments, one or more of the top substrates can contain the biological sample.

In some embodiments, methods utilizing an active capture method can include one or more solutions between the biological sample and the substrate (e.g., a substrate including capture probes). In some embodiments, the one or more solutions between the biological sample and the substrate including capture probes can include a permeabilization buffer (e.g., any of the permeabilization buffers described herein). In some embodiments, the one or more solutions between the biological sample and the substrate including capture probes can include an electrophoresis buffer.

In some embodiments, actively capturing analytes can include one or more porous materials between the biological sample and the substrate including capture probes. In some embodiments, the one or more porous materials between the biological sample and substrate including capture probes can include a paper or a blotting membrane. In some embodiments, the one or more porous materials between the biological sample and the substrate including capture probes can include a gel containing one or more solutions. For example, in a non-limiting way, the gel can be a SDS-PAGE gel. In some embodiments, the one or more porous materials between the biological sample and the substrate including capture probes can contain a permeabilization buffer. In some embodiments, the one or more porous materials between the biological sample and the substrate including capture probes can contain an electrophoresis buffer. In some embodiments, actively capturing analytes can include one or more solutions and one or more porous materials between the biological sample and the substrate including capture probes.

In some embodiments, the one or more porous materials between the biological sample and the substrate including capture probes (e.g., an array) can act as a filter to separate analytes (e.g., analytes of interest) from other molecules or analytes present in the biological sample. In some embodiments, the analytes (e.g., analytes of interest) are RNA transcripts. In some embodiments, the one or more porous materials between the biological sample and the substrate including capture probes can act as a filter to separate RNA transcripts from other molecules (e.g., analytes) such as proteins, lipids and/or other nucleic acids. In some embodiments, the one or more porous materials between the biological sample and the substrate including capture probes can act as a filter to separate the analytes and other molecules based on physicochemical properties. For example, in a non-limiting way, analytes can be separated on properties such as charge, size (e.g., length, radius of gyration, effective diameters, etc.), hydrophobicity, hydrophilicity, molecular binding (e.g., immunoaffinity), and combinations thereof. In some embodiments, the one or more porous materials between the biological sample and the substrate including capture probes can separate the analytes from other molecules to reduce non-specific binding near the capture probes and therefore improve binding between the analytes and the capture probes, thus improving subsequent assay performance.

In some embodiments, the one or more porous materials between the biological sample and the substrate including capture probes can act as molecular sieving matrices for electrophoretic analyte separation. For example, in a non-limiting way, separation of analytes can occur based on physicochemical properties such as charge, size (e.g., length, radius of gyration, and effective diameters, etc.), electrophoretic mobility, zeta potential, isoelectric point, hydrophobicity, hydrophilicity, molecular binding (e.g., immunoaffinity), and combinations thereof. In some embodiments, the one or more porous materials between the biological sample and the substrate including capture probes can be of a uniform pore size. In some embodiments, the one or more porous materials between the biological sample and the substrate including capture probes can have discontinuities in pore sizes, as generally used in different gel electrophoresis schemes. In some embodiments, the one or more porous materials between the biological sample and the substrate including capture probes can have gradients in pore sizes. For example, the one or more porous materials (e.g., a hydrogel) can have a gradient of pore sizes such that the gradient separates the analytes as the analytes migrate to the substrate including capture probes (e.g., an array).

In some embodiments, the one or more porous materials between the biological sample and the substrate including capture probes can separate the analytes based on length. For example, shorter analytes will have a higher electrophoretic mobility, and therefore migrate faster towards the capture probes relative to longer analytes in an electrophoretic setup. In some embodiments, the one or more porous materials between the biological sample and the substrate including capture probes separate the analytes based on length, such that only shorter analytes can migrate through the one or more porous materials to reach the capture probes, while longer analytes cannot reach the capture probes.

In some embodiments, specific subsets of analytes (e.g., a subset of transcripts) can be captured by applying an electrophoretic field for a certain amount of time. In some embodiments, specific subsets of analytes (e.g., a subset of transcripts) can be captured by selecting different porous materials (e.g., porous materials with different compositions) between the biological sample and the substrate including capture probes. In some embodiments, specific subsets of analytes (e.g., a subset of transcripts) can be captured by applying an electrophoretic field for a certain amount of time and selecting different porous materials between the biological sample and the substrate including capture probes (e.g., an array).

In some embodiments, the one or more porous materials between the biological sample and the substrate including capture probes can have discontinuities in pore sizes that can cause an increase in the concentration of the migrating analytes (e.g., "stacking"). For example, the one or more porous materials (e.g., a hydrogel) between the biological sample and the substrate including capture probes can have discontinuities in pore sizes that can cause an increase in the concentration of the analytes near the capture probes resulting in favorable binding kinetics and increased sensitivity. In some embodiments, the one or more porous materials between the biological sample and the substrate including capture probes can have discontinuities in pore sizes that enhance the separation between migrating analytes of different sizes and/or lengths. In some embodiments, the one or more porous materials between the biological sample and the substrate including capture probes can include a first porous material and a second porous material, with the first porous material having a larger pore size than the second porous material. In some embodiments, the first porous material is located on the surface, or near the surface, of the biological sample. In some embodiments, the second porous material (e.g., second porous material with a smaller pore size than the first porous material) can be placed on the surface, or near the surface, of the first porous material. In some embodiments, as analytes migrate (e.g., migrate via electrophoresis) from the biological sample through the first porous material and the second porous material sequentially, the migrating analytes can collect (e.g., "stack") at the interface between the first porous material and the second porous material.

In some embodiments, the one or more porous materials between the biological sample and the substrate including capture probes can include a gradient in pore sizes for continuous stacking as analytes migrate through decreasing pore sizes (e.g., decreasing pore diameter). In some embodiments, the one or more porous materials between the biological sample and the substrate including capture probes can include a gradient in pore sizes such that the pores decrease in diameter as the analytes migrate from the biological sample to the substrate including capture probes. In some embodiments, the pore size gradient can increase the resolution among analytes of different sizes. In some embodiments, the pore size gradient can increase the concentration of the analytes near the capture probes. In some embodiments, the pore size gradient can continuously reduce the speed at which the analytes migrate and collect (e.g., "stack") as the analytes migrate through the gradient of decreasing pore sizes (e.g., decreasing pore diameter).

In some embodiments, the one or more porous materials between the biological sample and the substrate including capture probes can include a gradient gel for continuous stacking as analytes migrate through decreasing pore sizes (e.g., decreasing pore diameter) of the gradient gel. In some embodiments, the gradient gel can have pores with a decreasing diameter as the analytes migrate toward the capture probes. In some embodiments, the gradient gel can increase the separation resolution among analytes of different sizes. In some embodiments, the gradient gel can increase the concentration of analytes near the capture probes. In some embodiments, the gradient gel can continuously reduce the speed at which analytes migrate and collect (e.g., "stack") as the analytes migrate through the gradient gel of decreasing pore sizes (e.g., decreasing in diameter).

In some embodiments, a biological sample can be placed in a first substrate holder (e.g., a substrate holder described herein). In some embodiments, a spatially-barcoded capture probe array (e.g., capture probes, barcoded array) can be placed on a second substrate holder (e.g., a substrate holder described herein). In some embodiments, a biological sample can be placed in a first substrate holder that also contains capture probes. In some embodiments, the first substrate holder, the second substrate holder, or both can be conductive (e.g. any of the conductive substrates described herein). In some embodiments, the first substrate holder including the biological sample, the second substrate holder including capture probes, or both, can be contacted with permeabilization reagents (e.g., a permeabilization buffer) and analytes can be migrated from the biological sample toward the barcoded array using an electric field.

In some embodiments, electrophoresis can be applied to a biological sample on a barcoded array while in contact with a permeabilization buffer. In some embodiments, electrophoresis can be applied to a biological sample on a barcoded array while in contact with an electrophoresis buffer (e.g. a buffer that lacks permeabilization reagents). In some embodiments, the permeabilization buffer can be replaced with an electrophoresis buffer after a desired amount of time. In some embodiments, electrophoresis can be applied simultaneously with the permeabilization buffer or electrophoresis buffer. In some embodiments, electrophoresis can be applied after a desired amount of time of contact between the biological sample and the permeabilization buffer or electrophoresis buffer.

In some embodiments, the biological sample can be placed on a substrate (e.g., a porous membrane, a hydrogel, paper, etc.). In some embodiments, the biological sample placed on the substrate can have a gap (e.g., a space) between the substrate and the substrate holder (e.g., conductive substrate holder). In some embodiments, the barcoded array can be placed on a substrate (e.g., a porous membrane, a hydrogel, paper, etc.). In some embodiments, the barcoded array can have a gap between the substrate and substrate holder (e.g., conductive substrate holder). In some embodiments, the barcoded array can be placed in direct proximity to the biological sample or at a desired distance from the biological sample. In some embodiments, a buffer reservoir can be used between the substrate holder (e.g., conductive substrate holder) and the barcoded array, the biological sample, or both. This setup allows the analytes to be migrated to a barcoded array while not in proximity with the electrodes (e.g. conductive substrate holder), thus resulting in more stable electrophoresis.

In some embodiments, a combination of at least two buffers with different ionic compositions can be used to differentially migrate analytes based on their ionic mobility (e.g., isotachophoresis (ITP)). For example, using two or more buffers with different ionic compositions can increase the concentration of analytes prior to contact with a barcoded array. Isotachophoresis includes at least two buffers that contain a common counter-ion (e.g., ions that have different charge sign than the analytes) and different co-ions (e.g., ions that have the same charge sign as the analytes) (Smejkal P., et al., Microfluidic isotachophoresis: A review, Electrophoresis, 34.11 1493-1509, (2013) which is incorporated herein by reference in its entirety). In some embodiments, one buffer can contain a co-ion with a higher ionic mobility (e.g. speed at which they travel through solution in an electric field) than the analytes (e.g., the "leading" buffer). In some embodiments, a second buffer can contain a co-ion with a lower ionic mobility than the analytes (e.g., the "trailing" buffer). In some embodiments, a third buffer can contain a co-ion with an ionic mobility that is between the electric mobility of the analytes. In some embodiments, a biological sample can be placed on a first substrate holder (e.g., a conductive substrate holder) and the barcoded array can be placed on a second substrate holder (e.g., a second conductive substrate holder) and contacted with a permeabilization buffer and the analytes can be migrated away from the biological sample and toward the barcoded array using an electric field. As the electric field is applied to the biological sample the analytes can be concentrated in the buffer as they are migrated toward the capture probes. In some embodiments, isotachophoresis can be used with gel-based separations (e.g., any of the gel-based separations described herein).

In some embodiments, a permeabilization buffer can be applied to a region of interest (e.g., region of interest as described herein) in a biological sample. In some embodiments, permeabilization reagents (e.g. a hydrogel containing permeabilization reagents) can be applied to a region of interest in a biological sample. For example, a region of interest can be a region that is smaller in area relative to the overall area of the biological sample. In some embodiments, the permeabilization buffer or permeabilization reagents can be contacted with the biological sample and a substrate including capture probes (e.g., an array). In some embodiments, the biological sample can have more than one region of interest (e.g. two, three). In some embodiments, the biological sample, the substrate including capture probes, or both, can be placed in a conductive substrate holder. In some embodiments, analytes can be released from the region(s) of interest and migrated from the biological sample toward the capture probes with an electric field.

In some embodiments, electrophoretic transfer of analytes can be performed while retaining the relative spatial locations of analytes in a biological sample while minimizing passive diffusion of an analyte away from its location in a biological sample. In some embodiments, an analyte captured by a capture probe (e.g., capture probes on a substrate) retains the spatial location of the analyte present in the biological sample from which it was obtained (e.g., the spatial location of the analyte that is captured by a capture probe on a substrate when the analyte is actively migrated to the capture probe by electrophoretic transfer can be more precise or representative of the spatial location of the analyte in the biological sample than when the analyte is not actively migrated to the capture probe). In some embodiments, electrophoretic transport and binding process is described by the Damköhler number (Da), which is a ratio of reaction and mass transport rates. The fraction of analytes bound and the shape of the biological sample will depend on the parameters in the Da. There parameters include electromigration velocity $U_e$ (depending on analyte electrophoretic mobility $\mu_e$ and electric field strength E), density of capture probes (e.g., barcoded oligonucleotides) $p_0$, the binding rate between probes (e.g., barcoded oligonucleotides) and analytes $k_{on}$, and capture area thickness L.

$$Da \sim \frac{k_{on} p_0 L}{\mu_e E}$$

Fast migration (e.g., electromigration) can reduce assay time and can minimize molecular diffusion of analytes.

In some embodiments, electrophoretic transfer of analytes can be performed while retaining the relative spatial alignment of the analytes in the sample. As such, an analyte captured by the capture probes (e.g., capture probes on a substrate) retains the spatial information of the cell or the biological sample from which it was obtained. Applying an electrophoretic field to analytes can also result in an increase in temperature (e.g., heat). In some embodiments, the increased temperature (e.g., heat) can facilitate the migration of the analytes towards a capture probe.

In some examples, a spatially-addressable microelectrode array is used for spatially-constrained capture of at least one charged analyte of interest by a capture probe. For example, a spatially-addressable microelectrode array can allow for discrete (e.g., localized) application of an electric field rather than a uniform electric field. The spatially-addressable microelectrode array can be independently addressable. In some embodiments, the electric field can be applied to one or more regions of interest in a biological sample. The electrodes may be adjacent to each other or distant from each other. The microelectrode array can be configured to include a high density of discrete sites having a small area for applying an electric field to promote the migration of charged analyte(s) of interest. For example, electrophoretic capture can be performed on a region of interest using a spatially-addressable microelectrode array.

A high density of discrete sites on a microelectrode array can be used. The surface can include any suitable density of discrete sites (e.g., a density suitable for processing the sample on the conductive substrate in a given amount of time). In one embodiment, the surface has a density of discrete sites greater than or equal to about 500 sites per 1 $mm^2$. In some embodiments, the surface has a density of discrete sites of about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 20,000, about 40,000, about 60,000, about 80,000, about 100,000, or about 500,000 sites per 1 $mm^2$. In some embodiments, the surface has a density of discrete sites of at least about 200, at least about 300, at least about 400, at least about 500, at least about 600, at least about 700, at least about 800, at least about 900, at least about 1,000, at least about 2,000, at least about 3,000, at least about 4,000, at least about 5,000, at least about 6,000, at least about 7,000, at least about 8,000, at least about 9,000, at least about 10,000, at least about 20,000, at least about 40,000, at least about 60,000, at least about 80,000, at least about 100,000, or at least about 500,000 sites per 1 $mm^2$.

Figure 14A:
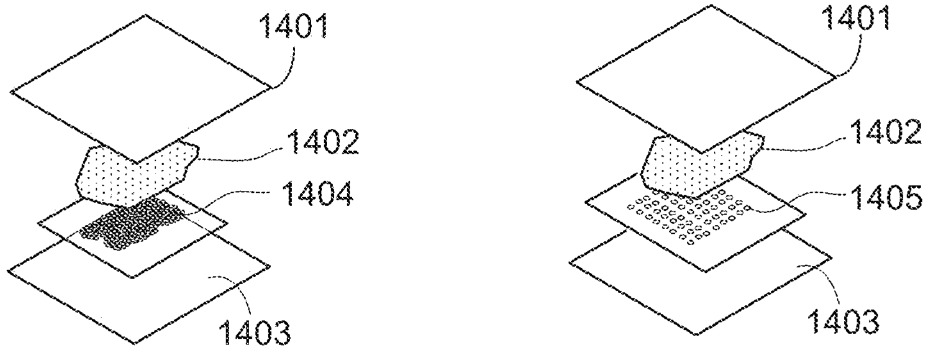
FIGS. 14A and 14B are schematics illustrating expanded FIG. 14A and side views FIG. 14B of an electrophoretic transfer system configured to direct transcript analytes toward a spatially-barcoded capture probe array.
Figure 14B:
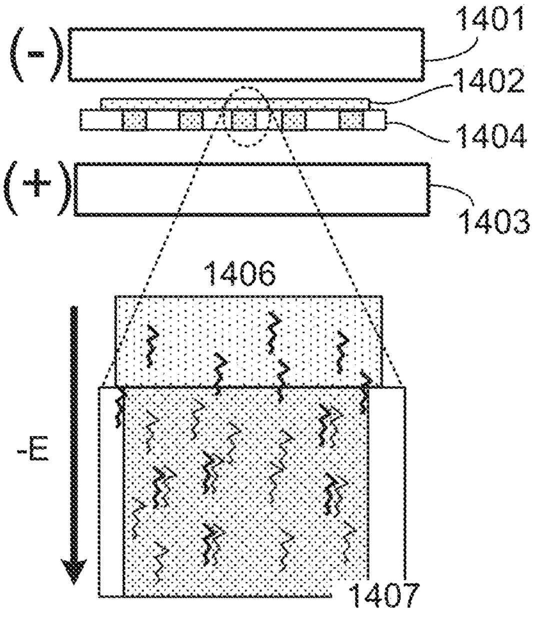

Schematics illustrating an electrophoretic transfer system configured to direct nucleic acid analytes (e.g., mRNA transcripts) toward a spatially-barcoded capture probe array are shown in FIG. 14A and FIG. 14B. In this exemplary configuration of an electrophoretic system, a sample 1402 is sandwiched between the cathode 1401 and the spatially-barcoded capture probe array 1404, 1405, and the spatially-barcoded capture probe array 1404, 1405 is sandwiched between the sample 1402 and the anode 1403, such that the sample 1402, 1406 is in contact with the spatially-barcoded capture probes 1407. When an electric field is applied to the electrophoretic transfer system, negatively charged nucleic acid analytes 1406 will be pulled toward the positively charged anode 1403 and into the spatially-barcoded array 1404, 1405 containing the spatially-barcoded capture probes 1407. The spatially-barcoded capture probes 1407 interact with the nucleic acid analytes (e.g., mRNA transcripts hybridize to spatially-barcoded nucleic acid capture probes forming DNA/RNA hybrids) 1406, making the analyte capture more efficient. The electrophoretic system set-up may change depending on the target analyte. For example, proteins may be positive, negative, neutral, or polar depending on the protein as well as other factors (e.g., isoelectric point, solubility, etc.). The skilled practitioner has the knowledge and experience to arrange the electrophoretic transfer system to facilitate capture of a particular target analyte.

Figure 15:
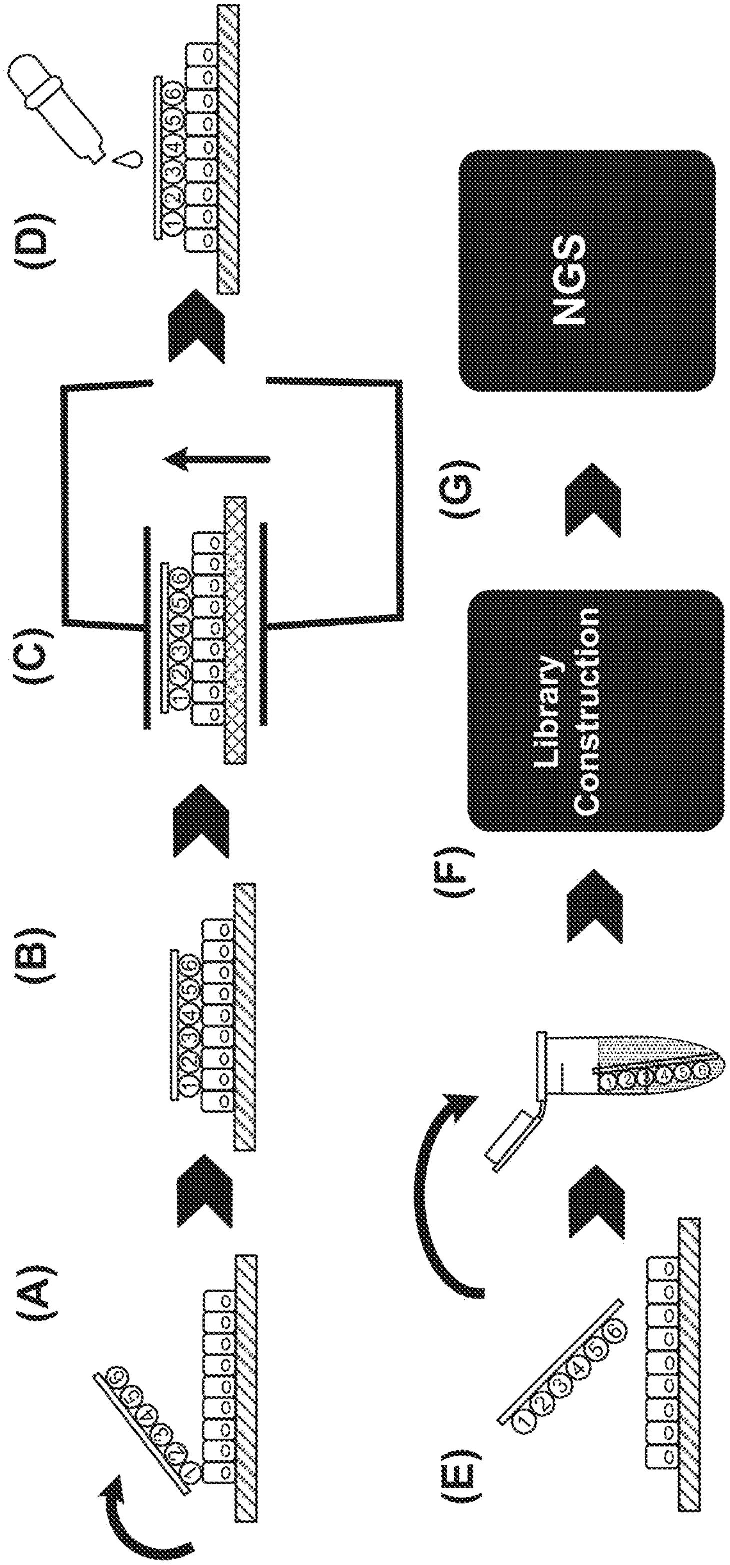
FIG. 15 is a schematic illustrating an exemplary workflow protocol utilizing an electrophoretic transfer system.

FIG. 15 is an illustration showing an exemplary workflow protocol utilizing an electrophoretic transfer system. In the example, Panel A depicts a flexible spatially-barcoded feature array being contacted with a sample. The sample can be a flexible array, wherein the array is immobilized on a hydrogel, membrane, or other flexible substrate. Panel B depicts contact of the array with the sample and imaging of the array-sample assembly. The image of the sample/array assembly can be used to verify sample placement, choose a region of interest, or any other reason for imaging a sample on an array as described herein. Panel C depicts application of an electric field using an electrophoretic transfer system to aid in efficient capture of a target analyte. Here, negatively charged mRNA target analytes migrate toward the positively charged anode. Panel D depicts application of reverse transcription reagents and first strand cDNA synthesis of the captured target analytes. Panel E depicts array removal and preparation for library construction (Panel F) and next-generation sequencing (Panel G).

(iv) Targeted Analysis

In some aspects, arrays (e.g., glass slides) include a plurality of capture probes that bind to one or more specific biological targets in a sample. The capture probes can be directly or indirectly attached to a substrate. The capture probe can be or include, for example, DNA or RNA. In some aspects, the capture probes on an array can be immobilized, e.g., attached or bound, to the array via their 5' or 3' ends, depending on the chemical matrix of the array. In some aspects, the probes are attached via a 3' linkage, thereby leaving a free 5' end. In some aspects, the probes are attached via a 5' linkage, thereby leaving a free 3' end. In some aspects, the probes are immobilized indirectly. For example, a probe can be attached to a bead, which bead can be deposited on a substrate. A capture probe as disclosed in this section can include any of the various components of a capture probe as provided throughout this disclosure (e.g., spatial barcodes, UMIs, functional domains, cleavage domains, etc.).

In some aspects, a capture probe or plurality of capture probes interact with an analyte specific for a particular species or organism (e.g., host or pathogen). In some aspects, the probe or plurality of probes can be used to detect a viral, bacterial, or plant protein or nucleic acid. In some aspects, the capture probe or plurality of capture probes can be used to detect the presence of a pathogen (e.g., bacteria or virus) in the biological sample. In some aspects, the capture probe or plurality of capture probes can be used to detect the expression of a particular nucleic acid associated with a pathogen (e.g., presence of 16S ribosomal RNA or Human Immunodeficiency Virus (HIV) RNA in a human sample).

In some aspects, the capture domain in the capture probe can interact with one or more specific analytes (e.g., an analyte or a subset of analytes out of the pool of total analytes). The specific analyte(s) to be detected can be any of a variety of biological molecules including but not limited to proteins, nucleic acids, lipids, carbohydrates, ions, small molecules, subcellular targets, or multicomponent complexes containing any of the above. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes.

In some aspects, analytes from a biological sample interact with one or more capture probes (e.g., one or more capture probes immobilized directly or indirectly on a substrate), and the capture probes interact with specific analytes in the biological sample. In some aspects, the capture probes are allowed to interact with (e.g., hybridize to) specific analytes, e.g., under appropriate conditions where oligonucleotide capture probes can hybridize to the target nucleic acids. In some aspects, analytes that did not hybridize to capture probes are removed (e.g., analytes that do not interact with capture domains of the capture probes). In some embodiments, removal of analytes that did not interact with a capture probe can be accomplished by, e.g., washing the sample to remove such analytes.

In some aspects, a capture probe or plurality of capture probes includes a capture domain that interacts with an analyte or analytes present in a biological sample. In some aspects, the capture probe or plurality of capture probes includes a capture domain that detects the presence or level amount (e.g., expression level) of a particular analyte or analytes of interest. The capture domain of a capture probe (immobilized directly or indirectly on a substrate) can be capable of binding selectively to a desired subtype or subset of nucleic acid. In some aspects, for example, the capture domain binds to a subset of nucleic acids in a genome or a subset of nucleic acids in a transcriptome. In some aspects, the analyte(s) can include one or more nucleic acids. In some aspects, the capture probe or plurality of capture probes can be used to detect the expression of a particular transcript (e.g., a particular mRNA). In some aspects, a capture probe or plurality of capture probes can be specific for (e.g., binds to) an individual change in a nucleic acid or protein (e.g., a mutation or single nucleotide polymorphism (SNP)).

In some aspects, the biological sample includes an analyte that is or includes a nucleic acid. The nucleic acid can be RNA or DNA. In some aspects, the capture probe or plurality of capture probes detects DNA copy number of a particular set of nucleic acid analyte or analytes. For example, capture probe or plurality of capture probes provided herein can be used to detect DNA copy number of nucleic acids that share homology to each other.

In some aspects, the capture probe or plurality of capture probes includes a capture domain that detects the presence or level amount (e.g., expression level) of one or more RNA transcripts (e.g., specific RNA transcripts). In some aspects, the capture probe or plurality of capture probes includes a capture domain that detects the presence or amount (e.g., expression level) of one or more non-coding RNAs (e.g., microRNA, transfer RNA (tRNA), ribosomal RNA (rRNA), small interfering RNA (siRNA) and small nucleolar RNA (snoRNA). In some aspects, the probe or plurality of probes includes a capture domain that detects the presence or level amount (e.g., expression level) of one or more proteins (e.g., proteins expressed of a nucleic acid of interest).

In some aspects, the capture probe or plurality of capture probes can be specific for a particular protein. In some aspects, the capture probe or plurality of capture probes can be used to detect the presence of a particular protein of interest. In some aspects, the capture probe or plurality of capture probes can be used to detect translation of a particular protein. In some aspects, the capture probe or plurality of capture probes can specifically interact with an active region of an enzyme, a binding domain of an immunoglobulin, defined domains of proteins, whole proteins, synthetic peptides, peptides with introduced mutations, aptamer, or any combination thereof. In some aspects, the analyte(s) can include one or more proteins. In some aspects, the analyte(s) can include one or more nucleic acids and one or more proteins.

In some aspects, the capture probe or plurality of capture probes can be used to detect particular post-translational modifications of a particular protein. In such embodiments, analyte capture agents can be specific for cell surface analytes having a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some aspects, the capture probe or plurality of capture probes can be specific for a particular set of nucleic acids (e.g., nucleic acids that are associated with a specific cellular pathway or pathways). In some aspects, the set of nucleic acids is DNA. In some aspects, the set of nucleic acids is RNA. In some aspects, the set of nucleic acids has similar and/or homologous sequences. In some aspects, the set of nucleic acids encodes for analytes that function in a similar cellular pathway. In some aspects, the set of nucleic acids encodes for analytes that are expressed in a certain pathological state (e.g., cancer, Alzheimer's, or Parkinson's disease). In some aspects, the set of nucleic acids encodes for analytes that are over-expressed in a certain pathological state. In some aspects, the set of nucleic acids encodes for analytes that are under-expressed in a certain pathological state.

In some aspects, the capture probe or plurality of capture probes can be specific for a particular nucleic acid, or detection or expression of a particular set of proteins (e.g., in a similar cellular pathway). In some aspects, the set of proteins has similar functional domains. In some aspects, the set of proteins functions in a similar cellular pathway. In some aspects, the set of proteins is expressed in a certain pathological state (e.g., cancer, Alzheimer's or Parkinson's disease). In some aspects, the set of proteins is over-expressed in a certain pathological state. In some aspects, the set of proteins is under-expressed in a certain pathological state.

In some embodiments, a capture probe includes a capture domain that is capable of binding to more than one analyte. In some embodiments, a capture domain can bind to one or more analytes that are about 80% identical, about 85% identical, about 90% identical, about 95% identical, about 96% identical, about 97% identical, about 98% identical, about 99% identical, 100% identical to the target analyte. In some aspects, the capture probe can bind to an analyte that is about 80% identical, about 85% identical, about 90% identical, about 95% identical, about 96% identical, about 97% identical, about 98% identical, or about 99% identical to each other. In some embodiments, a capture domain can bind to a conserved region of one or more analytes, in which the conserved regions are about 80% identical, about 85% identical, about 90% identical, about 95% identical, about 96% identical, about 97% identical, about 98% identical, about 99% identical, 100% identical to the target analyte.

In some aspects, a capture probe or plurality of capture probes interacts with two or more analytes (e.g., nucleic acids or proteins) that are not similar in sequence and/or do not share a conserved domain. In some embodiments, a capture probe includes two or more capture domains, each of which interacts with a different analyte. In such embodiments, members of the two or more capture domains can be adjacent to each other in the capture probe and/or members of the two or more capture domains can be separated from each other in the capture probe by one or more domains (e.g., nucleic acid domains). For example, in some aspects, the sets of analytes that are detected include mutational changes in the targeted nucleic acids or proteins. In some aspects, the capture probe or plurality of capture probes detects sets of nucleic acids or proteins (e.g., non-homologous nucleic acids or proteins) that are individually mutated during a pathogenic state. In some aspects, the pathogenic state is cancer.

In some aspects, a capture probe or plurality of capture probes include capture domains that can be used to detect analytes that are typically detected using diagnostic panels. In some aspects, the capture probe or plurality of capture probes are used to detect changes in one or more analytes. In some aspects, the analyte changes include one or more of increased analyte expression, decreased analyte expression, mutated nucleic acid sequences, or any combination thereof. In some aspects, the changes in the analytes are associated with and/or lead to manifestation of a pathogenic state in a subject. In some aspects, the detected changes are compared to a reference analyte or analytes.

(v) Polypeptide Capture

Provided herein are methods and materials for identifying the location of a polypeptide in a biological sample. In some embodiments, an analyte (e.g., a polypeptide analyte) can be directly captured on a substrate. For example, polypeptide analytes can be captured by amine groups on a functionalized substrate. In other examples, an analyte (e.g., a polypeptide analyte) can be captured via an analyte binding moiety directly attached to a substrate. In some embodiments, the substrate may be populated with analyte minding moieties directly attached to the substrate as well as spatially-barcoded capture probes directly attached to the substrate. In other embodiments, an analyte (e.g., a polypeptide analyte) can be captured via an analyte binding moiety indirectly attached to a substrate. In an example, the substrate may be populated with capture probes that are bound to an analyte capture agent, wherein the analyte capture domain of the analyte capture agent binds to the capture domain of the capture probe and the analyte binding moiety binds the polypeptide analyte.

In some embodiments, an analyte (e.g., a polypeptide analyte) can be directly captured or immobilized on a substrate. Direct immobilization may be achieved by covalently coupling the polypeptide analyte to the substrate via amide bonds between the carboxylic acid of the C-terminal amino acid residue and a functionalized substrate surface. For example, a substrate (e.g., a glass coverslip or slide) can be functionalized through amino-silanization with amino-propyltriethoxysilane. The substrate surfaces are further passivated by overnight incubation with polyethylene glycol (PEG)-NHS solution, and functionalized slides can be stored in a vacuum desiccator until use. The t-butyloxycarbonyl protecting groups can be removed by incubating the substrate with 90% TFA (v/v in water) for 5 hours before use, thus exposing free amine groups for peptide immobilization. The resulting functionalized substrate is stable to multiple cycles of Edman degradation and washing steps.

In some embodiments, methods for capturing polypeptides in a biological sample include providing a substrate where an analyte binding moiety is directly immobilized on the substrate. In some embodiments, direct immobilization is achieved through chemical modification of the substrate and/or chemical modification of the analyte binding moiety. For example, a substrate can be prepared with free amines on the surface. When exposed to an analyte binding moiety with a free carboxylic acid on the C-terminal residue, the free amines can form amide bonds with the carboxylic acid thereby covalently coupling the analyte binding moiety to the substrate. Substrates and/or analyte binding moieties can be modified in any manner that facilitates covalent bonding of the analyte binding moiety to the substrate. Non-limiting examples of chemical modification that can be used to covalently bind the analyte binding moiety to the substrate include are described herein.

In some embodiments, methods for capturing analyte polypeptides include providing a substrate (e.g., an array) where the analyte binding moiety is indirectly attached to the substrate. For example, an analyte binding moiety can be indirectly attached to a substrate via an oligonucleotide (e.g., a capture agent barcode domain or capture agent barcode domain hybridized to a capture probe) or other domain capable of binding to both the substrate and the analyte binding domain. The capture agent barcode domain is described elsewhere herein. The capture agent barcode domain can be modified to include a cleavage domain, which can attach to a substrate using any of the chemistries described herein. In some embodiments, the capture agent barcode domain can include an analyte capture sequence as described herein, wherein the analyte capture sequence can hybridize to the capture domain of a capture probe. In some embodiments, a substrate (e.g., an array) containing capture probes can be modified to capture polypeptide analytes by hybridizing the analyte capture sequence of the analyte capture agent to the capture domain of a capture probe.

In some embodiments, methods for capturing analyte polypeptides include providing a substrate (e.g., an array) and providing an analyte capture agent to the biological sample. For example, after drying and fixing sectioned tissue samples, the tissue samples can be positioned on a substrate (e.g., a spatial array), rehydrated, blocked, and permeabilized (e.g., 3×SSC, 2% BSA, 0.1% Triton X, 1 U/μl RNAse inhibitor for 10 min at 4° C.) before being stained with fluorescent primary antibodies (1:100) and a pool of analyte capture agents (in 3×SSC, 2% BSA, 0.1% Triton X, 1 U/μl RNAse inhibitor for 30 min at 4° C.). The biological sample can be washed, coverslipped (in glycerol+1 U/μl RNAse inhibitor), imaged for detected analytes (e.g., using a confocal microscope or other apparatus capable of fluorescent detection), and washed again. The analyte-bound analyte capture agents can be released from the biological sample (e.g., the biological sample can be treated with proteinase, e.g., proteinase K) and migrated to the spatial array. An analyte capture sequence of the analyte-bound analyte capture agent can be captured by a capture probe capture domain, and the capture agent barcode domain can be extended to produce a spatially-tagged analyte capture agent. The spatially-tagged analyte capture agents can be processed according to spatial workflows described herein.

In some embodiments, methods for capturing analyte polypeptides include providing blocking probes to analyte capture agents before introducing the analyte capture agents to a biological sample. In some embodiments, the blocking probes can be alternatively or additionally provided in any of the rehydrating or blocking buffers provided herein. In some embodiments, the analyte capture agent analyte capture sequence can be blocked prior to binding to the capture probe capture domain using a blocking probe sequence complementary to the analyte capture sequence. Blocking the capture agent barcode domain, particularly the free 3' end of the capture agent barcode domain (e.g., analyte capture sequence), prior to contacting the analyte capture agents with the biological sample and/or substrate, can prevent binding of the analyte capture sequence of the capture agent barcode domains, e.g., prevents the binding of a poly(A) tail to the capture probe capture domain. In some embodiments, blocking the analyte capture agent analyte capture domain reduces non-specific background staining. In some embodiments, the blocking probes are reversible, such that the blocking probes can be removed from the analyte capture sequence during or after the time that analyte capture agents are in contact with the biological sample. In some embodiments, the blocking probe can be removing with RNAse treatment (e.g., RNAse H treatment).

In some embodiments, methods for capturing polypeptides in a biological sample include active transfer (e.g., electrophoresis). For example, the biological sample is placed on a conductive substrate and contacted with a spatial array including one or more analyte binding moieties. An electric filed can be applied to the conductive substrate to promote migration of the polypeptides towards the analyte binding moieties, as described herein.

In some embodiments, methods for identifying the spatial location of a polypeptide in a biological sample include determining the sequence of a captured polypeptide. In some embodiments, the sequence of the captured polypeptide is determined through detection of amino acid residues labeled with a detectable label (e.g., radiolabel of a fluorophore). Non-limiting examples of detectable labels that can be used for labelling the captured polypeptide include fluorophores and radiolabels. In some embodiments, the polypeptides are labeled at specific amino acid residues only (e.g., not all amino acid residues are labeled). In some embodiments, the polypeptide is labeled prior to contacting the biological sample with the substrate. In some embodiments, a captured polypeptide is labeled with fluorophores using standard coupling schemes (see Hernandez et al., *New J. Chem.* 41:462-469 (2017)). For example, polypeptides may be labeled by reaction with Atto647N-NHS, Atto647- Niodoacetamide, TMR-NHS, or JF549-NHS, as appropriate, to label lysines (via NHS) or cysteines (via iodoacetamide). In addition, serine or threonine phosphorylation sites may be selectively labeled via beta elimination followed by conjugate addition via thiols to substitute thiol-linked fluorophores in place of phosphates (see Stevens et al., *Rapid Commun. Mass Specrtom.,* 15: 2157-2162 (2005)). The number of fluorophores incorporated into a polypeptide is any number that may be spectrally resolved. In some instances, four or more fluorophores are utilized.

In some embodiments, a captured polypeptide is radiolabeled. In some embodiments, specific amino acids can be labeled with an isotope. Non-limiting examples of isotopes used to label amino acids include $^{3}H$, $^{14}C$, $^{15}N$, $^{32}P$, and $^{125}I$. In some embodiments, the isotope is incorporated into the selected amino acid prior to incorporation into a polypeptide. In some embodiments, the radiolabeled amino acid can be incorporated into the polypeptide after polypeptide formation.

In some embodiments, the sequence of the captured polypeptide is determined using Edman degradation (and in some embodiments successive rounds of Edman degradation). In such cases, a polypeptide is captured, and the polypeptide sequence can be resolved by imaging the substrate following repeated rounds of Edman degradation. For example, the substrate is imaged following each Edman reaction in order to capture the detectable labels that are produced due to the removal of amino acids that are a byproduct of the reaction. The information obtained by the Edman degradation can be complied to identify a polypeptide. In some embodiments, the biological sample is visualized or imaged using light or fluorescence microscopy.

(vi) Enrichment of Captured Analytes after Capture

In some aspects, spatial analysis of targeted analytes includes an enrichment step or steps post-capture to enrich the captured analytes for the targeted analyte. For example, the capture domain can be selected or designed for the selective capture of more analytes than the practitioner desires to analyze. In some embodiments, capture probes that include random sequences (e.g., random hexamers or similar sequences) that form all or part of the capture domain can be used to capture nucleic acids from a biological sample in an unbiased way. For example, capture probes having capture domains that include random sequences can be used to generically capture DNA, RNA, or both from a biological sample. Alternatively, capture probes can include capture domains can that capture mRNA generally. As is well known in the art, this can be on the basis of hybridization to the poly-A tail of mRNAs. In some embodiments, the capture domain includes a sequence that interacts with (e.g., hybridizes to) the poly-A tail of mRNAs. Non-limiting examples of such sequences include poly-T DNA sequences and poly-U RNA sequences. In some embodiments, random sequences can be used in conjunction with poly-T (or poly-T analogue etc.) sequences. Thus, where a capture domain includes a poly-T (or a “poly-T-like”) oligonucleotide, it can also include a random oligonucleotide sequence.

In some aspects, after capture of more analytes than the practitioner desires to analyze, methods disclosed herein include enrichment of particular captured analytes. In some aspects, methods include enrichment of analytes that include mutations (e.g., SNPs,) of interest, nucleic acid(s) of interest, and/or proteins(s) of interest.

In some embodiments, methods of spatial analysis provided herein include selectively enriching one or more analytes of interest (e.g., target analytes) after analyte capture. For example, one or more analytes of interest can be enriched by addition of one or more oligonucleotides to the pool of captured analytes. In some embodiments, one or more analytes of interest can be enriched by addition of one or more oligonucleotides to the pool of captured analytes on the array. In some embodiments, one or more analytes of interest can be enriched by addition of one or more oligonucleotides to the pool of captured analytes where the pool of captured analytes have been released (e.g., removed) from the array. In some embodiments, when captured analytes have been released from the array the one or more nucleotides can be complementary to a portion of a TSO and R1 sequence, or portion thereof. In some embodiments, the additional oligonucleotide(s) include a sequence used for priming a reaction by a polymerase. For example, one or more primer sequences with sequence complementarity to one or more analytes of interest can be used to amplify the one or more analyte(s) of interest, thereby selectively enriching these analytes. In some embodiments, one or more primer sequences can be complementary to other domains on the capture probe (e.g., R1 sequence, or portion thereof, as above), and not complementary to the analyte. In some embodiments, enrichment by amplification (e.g., PCR) occurs by using a first primer complementary to an analyte or analytes of interest (or another domain in the capture probe and the TSO), or complement thereof, and a second primer complementary to a region of the capture probe, or complement thereof. In some embodiments, the region of the capture probe, or complement thereof, is distal to a spatial barcode from the capture domain, such that enrichment by amplification amplifies both the captured analyte or analytes and its or their associated spatial barcodes, thus permitting spatial analysis of the enriched analyte or analytes.

In some embodiments, two or more capture probes capture two or more distinct analytes, which analytes are enriched (e.g., simultaneously or sequentially) from the pool of captured analytes. In some embodiments, enrichment by PCR amplification includes multiple rounds of amplification. For example, enrichment by PCR amplification can include nested PCR reactions using different primers that are specific for the analyte or analytes of interest. In some embodiments, enrichment by amplification can be performed using an amplification method that is not PCR. A non-limiting example of a non-PCR amplification method is rolling circle amplification. Other non-PCR amplification methods are known in the art.

In some embodiments, an oligonucleotide with sequence complementarity to a captured analyte or analytes of interest, or complement thereof, can be used to enrich the captured analyte or analytes of interest from the pool of captured analytes. In some embodiments, an oligonucleotide with sequence complementarity to a captured analyte or analytes of interest (or another domain the capture probe), or complement thereof, can include one or more functional moieties that are useful in the enrichment process. For example, biotinylated oligonucleotides with sequence complementary to one or more analytes interest, or complements thereof, can bind to the analyte(s) of interest and can be selected using biotinylation-strepavidin affinity using any of a variety of methods known in the art (e.g., streptavidin beads). In some embodiments, oligonucleotides with sequence complementary to one or more analytes interest, or complements thereof, include a magnetic moiety (e.g., a magnetic bead) that can be used in the enrichment process.

Additionally or alternatively, one or more species of analyte (e.g., mitochondrial DNA or RNA) can be down-selected (e.g., removed) using any of a variety of methods. In some embodiments, such down-selection of analytes that are not of interest can result in improved capture of other types of analytes that are of interest. For example, probes can be administered to a sample that selectively hybridize to ribosomal RNA (rRNA), thereby reducing the pool and concentration of rRNA in the sample. In some embodiments, such down-selection can result in improved capture of other types of RNA due to the reduction in non-specific RNA present in the sample. Additionally or alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which is incorporated herein by reference). In some embodiments, hydroxyapatite chromatography can be used to remove abundant species (e.g., rRNA).

(vii) Region of Interest

A biological sample can have regions that show morphological feature(s) that may indicate the presence of disease or the development of a disease phenotype. For example, morphological features at a specific site within a tumor biopsy sample can indicate the aggressiveness, therapeutic resistance, metastatic potential, migration, stage, diagnosis, and/or prognosis of cancer in a subject. A change in the morphological features at a specific site within a tumor biopsy sample often correlate with a change in the level or expression of an analyte in a cell within the specific site, which can, in turn, be used to provide information regarding the aggressiveness, therapeutic resistance, metastatic potential, migration, stage, diagnosis, and/or prognosis of cancer in a subject. A region or area within a biological sample that is selected for specific analysis (e.g., a region in a biological sample that has morphological features of interest) is often described as "a region of interest."

A region of interest in a biological sample can be used to analyze a specific area of interest within a biological sample, and thereby, focus experimentation and data gathering to a specific region of a biological sample (rather than an entire biological sample). This results in increased time efficiency of the analysis of a biological sample.

A region of interest can be identified in a biological sample using a variety of different techniques, e.g., expansion microscopy, bright field microscopy, dark field microscopy, phase contrast microscopy, electron microscopy, fluorescence microscopy, reflection microscopy, interference microscopy, confocal microscopy, and visual identification (e.g., by eye), and combinations thereof. For example, the staining and imaging of a biological sample can be performed to identify a region of interest. In some examples, the region of interest can correspond to a specific structure of cytoarchitecture. In some embodiments, a biological sample can be stained prior to visualization to provide contrast between the different regions of the biological sample. The type of stain can be chosen depending on the type of biological sample and the region of the cells to be stained. In some embodiments, more than one stain can be used to visualize different aspects of the biological sample, e.g., different regions of the sample, specific cell structures (e.g., organelles), or different cell types. In other embodiments, the biological sample can be visualized or imaged without staining the biological sample.

In some embodiments, staining and imaging a biological sample prior to contacting the biological sample with a spatial array is performed to select samples for spatial analysis. In some embodiments, the staining includes applying a fiducial marker as described herein, including fluorescent, radioactive, chemiluminescent, or colorimetric detectable markers. In some embodiments, the staining and imaging of biological samples allows the user to identify the specific sample (or region of interest) the user wishes to assess.

In some examples, an array (e.g., any of the exemplary arrays described herein) can be contacted with only a portion of a biological sample (e.g., a cell, a tissue section, or a region of interest). In some examples, a biological sample is contacted with only a portion of an array (e.g., any of the exemplary arrays described herein). In some embodiments, capture probes on an array corresponding to regions of interest of a biological sample (e.g., proximal to the region of interest) can be selectively cleaved and analyzed. For example, capture probes on an array may be deactivated or eliminated outside of areas corresponding to regions of interest of a biological sample. In some embodiments, capture probes including a photocleavable bond and on the array in areas corresponding to regions of interest of a biological sample can be selectively cleaved by using light. A mirror, mirror array, a lens, a moving stage, and/or a photomask can be used to direct the light to regions of the array that correspond to areas outside one or more regions of interest in the biological sample. Some embodiments include deactivating or eliminating capture probes, e.g., capture probes comprising a photocleavable bond as described herein, using light. In some embodiments, a laser, e.g., a scanning laser, can be used to deactivate or eliminate capture probes. In some embodiments, the eliminated member of the plurality of capture probes can be washed away. In some embodiments, regions of interest can be labeled with different heavy metals, and a laser can sequentially ablate these regions of interest before mass spectrometry identification. A laser can, for example, deactivate or eliminate capture probes through UV light destruction of DNA, heat, inducing a chemical reaction that prevents the capture probes from moving to the next step, inducing photocleavage of a photocleavable bond, or a combination thereof. In some examples, a portion of the array can be deactivated such that it does not interact with the analytes in the biological sample (e.g., optical deactivation, chemical deactivation, heat deactivation, or blocking of the capture probes in the array (e.g., using blocking probes)). In some embodiments, the capture probes can be blocked (e.g., masked or modified) prior to contacting the biological sample with the array. For example, the free 3' end of the capture probe can be blocked or modified prior to contacting the biological sample with the array to avoid modification of the capture probes (e.g., to avoid the removal or modification or the free 3' OH group on the end of the capture probes). In some embodiments, the capture probes can be blocked prior to contacting the biological sample to the array. In some embodiments, the blocking probe is used to block or modify the free 3' end of the capture domain of the capture probe. In some embodiments, the blocking probes can be hybridized to the capture probe. In some embodiments, the free 3' end of the capture domain can be blocked by chemical modification.

In some examples, a region of interest can be removed from a biological sample and then the region of interest can be contacted to the array (e.g., any of the arrays described herein). A region of interest can be removed from a biological sample using microsurgery, laser capture microdissection, chunking, a microtome, dicing, trypsinization, labelling, and/or fluorescence-assisted cell sorting, and the like. In some embodiments, the biological sample is dissected using laser capture microdissection, retaining one or more portions of biological sample for analysis and/or discarding one or more portions of biological sample. In some embodiments, the biological sample is dissected on the array. In some embodiments, one or more regions of interest are selected using spatially addressable microelectrode arrays.

In some examples, a region of interest can be permeabilized or lysed while areas outside the region of interest are not permeabilized or lysed (e.g., Kashyap et al. *Sci Rep.* 2016; 6: 29579, herein incorporated by reference in its entirety). For example, in some embodiments, a region of interest can be contacted with a hydrogel comprising a permeabilization or lysing reagent. In some embodiments, the area(s) outside the region of interest are not contacted with the hydrogel comprising the permeabilization or lysing reagent. In some embodiments, the eliminated members of the plurality of capture probes are washed away after the permeabilization of the biological sample.

(f) Partitioning

As discussed above, in some embodiments, the sample can optionally be separated into single cells, cell groups, or other fragments/pieces that are smaller than the original, unfragmented sample. Each of these smaller portions of the sample can be analyzed to obtain spatially-resolved analyte information for the sample.

For samples that have been separated into smaller fragments—and particularly, for samples that have been disaggregated, dissociated, or otherwise separated into individual cells—one method for analyzing the fragments involves separating the fragments into individual partitions (e.g., fluid droplets), and then analyzing the contents of the partitions. In general, each partition maintains separation of its own contents from the contents of other partitions. The partition can be a droplet in an emulsion, for example.

The partitions can be flowable within fluid streams. The partitions can include, for example, micro-vesicles that have an outer barrier surrounding an inner fluid center or core. In some cases, the partitions can include a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions can be provided in a water-in-oil emulsion or oil-in-water emulsion. A variety of different vessels are described in, for example, U.S. Patent Application Publication No. 2014/0155295, the entire contents of which are incorporated herein by reference. Emulsion systems for creating stable droplets in non-aqueous or oil continuous phases are described, for example, in U.S. Patent Application Publication No. 2010/0105112, the entire contents of which are incorporated herein by reference.

For droplets in an emulsion, allocating individual particles to discrete partitions can be accomplished, for example, by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle volume, particle concentration, etc.), microfluidic architectures (e.g., channel geometry, etc.), and other parameters can be adjusted to control the occupancy of the resulting partitions (e.g., number of analytes per partition, number of beads per partition, etc.). For example, partition occupancy can be controlled by providing the aqueous stream at a certain concentration and/or flow rate of analytes.

To generate single analyte partitions, the relative flow rates of the immiscible fluids can be selected such that, on average, the partitions can contain less than one analyte per partition to ensure that those partitions that are occupied are primarily singly occupied. In some cases, partitions among a plurality of partitions can contain at most one analyte. In some embodiments, the various parameters (e.g., fluid properties, particle properties, microfluidic architectures, etc.) can be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The channel segments described herein can be coupled to any of a variety of different fluid sources or receiving components, including reservoirs, tubing, manifolds, or fluidic components of other systems. As will be appreciated, the microfluidic channel structure can have a variety of geometries. For example, a microfluidic channel structure can have one or more than one channel junction. As another example, a microfluidic channel structure can have 2, 3, 4, or 5 channel segments each carrying particles that meet at a channel junction. Fluid can be directed to flow along one or more channels or reservoirs via one or more fluid flow units. A fluid flow unit can include compressors (e.g., providing positive pressure), pumps (e.g., providing negative pressure), actuators, and the like to control flow of the fluid. Fluid can also or otherwise be controlled via applied pressure differentials, centrifugal force, electrokinetic pumping, vacuum, capillary, and/or gravity flow.

In addition to cells and/or analytes, a partition can include additional components, and in particular, one or more beads. A partition can include a single gel bead, a single cell bead, or both a single cell bead and single gel bead. A variety of different beads can be incorporated into partitions. In some embodiments, for example, non-barcoded beads can be incorporated into the partitions. For example, where the biological particle (e.g., a cell) that is incorporated into the partitions carries one or more barcodes (e.g., spatial barcode(s), UMI(s), and combinations thereof), the bead can be a non-barcoded bead.

In some embodiments, a barcode carrying bead can be incorporated into partitions. In general, an individual bead can be coupled to any number of individual nucleic acid molecules, for example, from one to tens to hundreds of thousands or even millions of individual nucleic acid molecules. The respective barcodes for the individual nucleic acid molecules can include both common sequence segments or relatively common sequence segments and variable or unique sequence segments between different individual nucleic acid molecules coupled to the same bead. For example, a nucleic acid molecule (e.g., an oligonucleotide), can be coupled to a bead by a releasable linkage (e.g., a disulfide linker), wherein the nucleic acid molecule can be or include a barcode. For example, barcodes can be injected into droplets previous to, subsequent to, or concurrently with droplet generation. The delivery of the barcodes to a particular partition allows for the later attribution of the characteristics of the individual biological particle to the particular partition. Barcodes can be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can include a bead. The same bead can be coupled (e.g., via releasable linkage) to one or more other nucleic acid molecules.

In some embodiments, a microcapillary array with spatially barcoded beads can be generated. A plurality of spatially barcoded beads can be flowed into channels on a microcapillary array such that each microcapillary channel can be loaded with one spatially barcoded bead. In some embodiments, the spatially barcoded bead microcapillary array can be contacted to a biological sample for subsequent spatial analysis of biological analytes within the biological sample. In some embodiments, a microcapillary array channel can mechanically compress the biological sample and form fluidically isolated reaction chambers. In some embodiments, reagents (e.g., enzymes, nucleic acids) are introduced into the reaction chambers. The reagents can be sealed (e.g., by silicone oil, mineral oil) within the reaction chambers and incubated, allowing for a cellular and/or nuclear permeabilization reaction to occur. In some embodiments, biological analytes (e.g., DNA, RNA, proteins, metabolites, small molecules, and lipids) are released and captured onto the spatially barcoded microcapillary array, preserving their spatial information. In some embodiments, spatial analysis using a spatially barcoded feature microcapillary array can be used to obtain spatial information of the biological sample analytes at single-cell resolution.

The nucleic acid molecule can include a functional domain that can be used in subsequent processing. For example, the functional domain can include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule can include a barcode sequence for use in barcoding the sample (e.g., DNA, RNA, protein, etc.). In some cases, the barcode sequence can be bead-specific such that the barcode sequence is common to all nucleic acid molecules coupled to the same bead. Alternatively or in addition, the barcode sequence can be partition-specific such that the barcode sequence is common to all nucleic acid molecules coupled to one or more beads that are partitioned into the same partition. The nucleic acid molecule can include a specific priming sequence, such as an mRNA specific priming sequence (e.g., poly(T) sequence), a targeted priming sequence, and/or a random priming sequence. The nucleic acid molecule can include an anchoring sequence to ensure that the specific priming sequence hybridizes at the sequence end (e.g., of the mRNA). For example, the anchoring sequence can include a random short sequence of nucleotides, such as a 1-mer, 2-mer, 3-mer or longer sequence, which can ensure that a poly(T) segment is more likely to hybridize at the sequence end of the poly(A) tail of the mRNA.

The nucleic acid molecule can include a unique molecular identifying sequence (e.g., unique molecular identifier (UMI)). In some embodiments, the unique molecular identifying sequence can include from about 5 to about 8 nucleotides. Alternatively, the unique molecular identifying sequence can include less than about 5 or more than about 8 nucleotides. The unique molecular identifying sequence can be a unique sequence that varies across individual nucleic acid molecules coupled to a single bead. In some embodiments, the unique molecular identifying sequence can be a random sequence (e.g., such as a random N-mer sequence). For example, the UMI can provide a unique identifier of the starting mRNA molecule that was captured, in order to allow quantitation of the number of original expressed RNA.

A partition can also include one or more reagents. Unique identifiers, such as barcodes, can be injected into the droplets previous to, subsequent to, or concurrently with droplet generation, such as via a microcapsule (e.g., bead). Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids.

In some embodiments, barcoded nucleic acid molecules can be initially associated with a microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus can disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some embodiments, one more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well. As described above, FIG. 16 shows an example of a microfluidical channel structure for partitioning individual analytes (e.g., cells) into discrete partitions.

Figure 16:
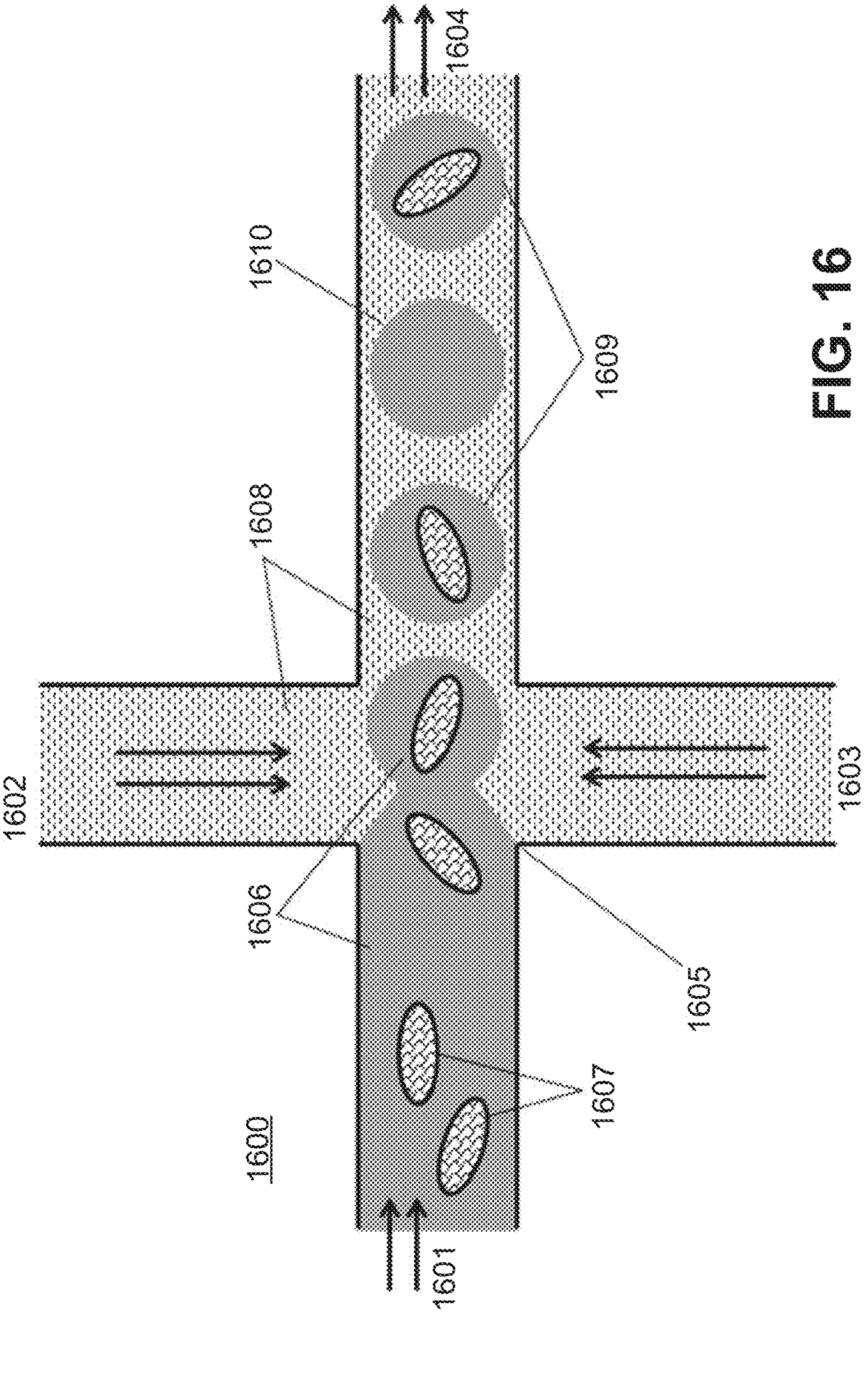
FIG. 16 shows an example of a microfluidic channel structure 1600 for partitioning dissociated sample (e.g., biological particles or individual cells from a sample).

FIG. 16 shows an example of a microfluidic channel structure for partitioning individual analytes (e.g., cells) into discrete partitions. The channel structure can include channel segments 1601, 1602, 1603, and 1604 communicating at a channel junction 1605. In operation, a first aqueous fluid 1606 that includes suspended biological particles (or cells) 1607 may be transported along channel segment 1601 into junction 1605, while a second fluid 1608 that is immiscible with the aqueous fluid 1606 is delivered to the junction 1605 from each of channel segments 1602 and 1603 to create discrete droplets 1609, 1610 of the first aqueous fluid 1606 flowing into channel segment 1604, and flowing away from junction 1605. The channel segment 1604 may be fluidically coupled to an outlet reservoir where the discrete droplets can be stored and/or harvested. A discrete droplet generated may include an individual biological particle 1607 (such as droplets 1609). A discrete droplet generated may include more than one individual biological particle 1607. A discrete droplet may contain no biological particle 1607 (such as droplet 1610). Each discrete partition may maintain separation of its own contents (e.g., individual biological particle 1607) from the contents of other partitions.

Figure 17A:
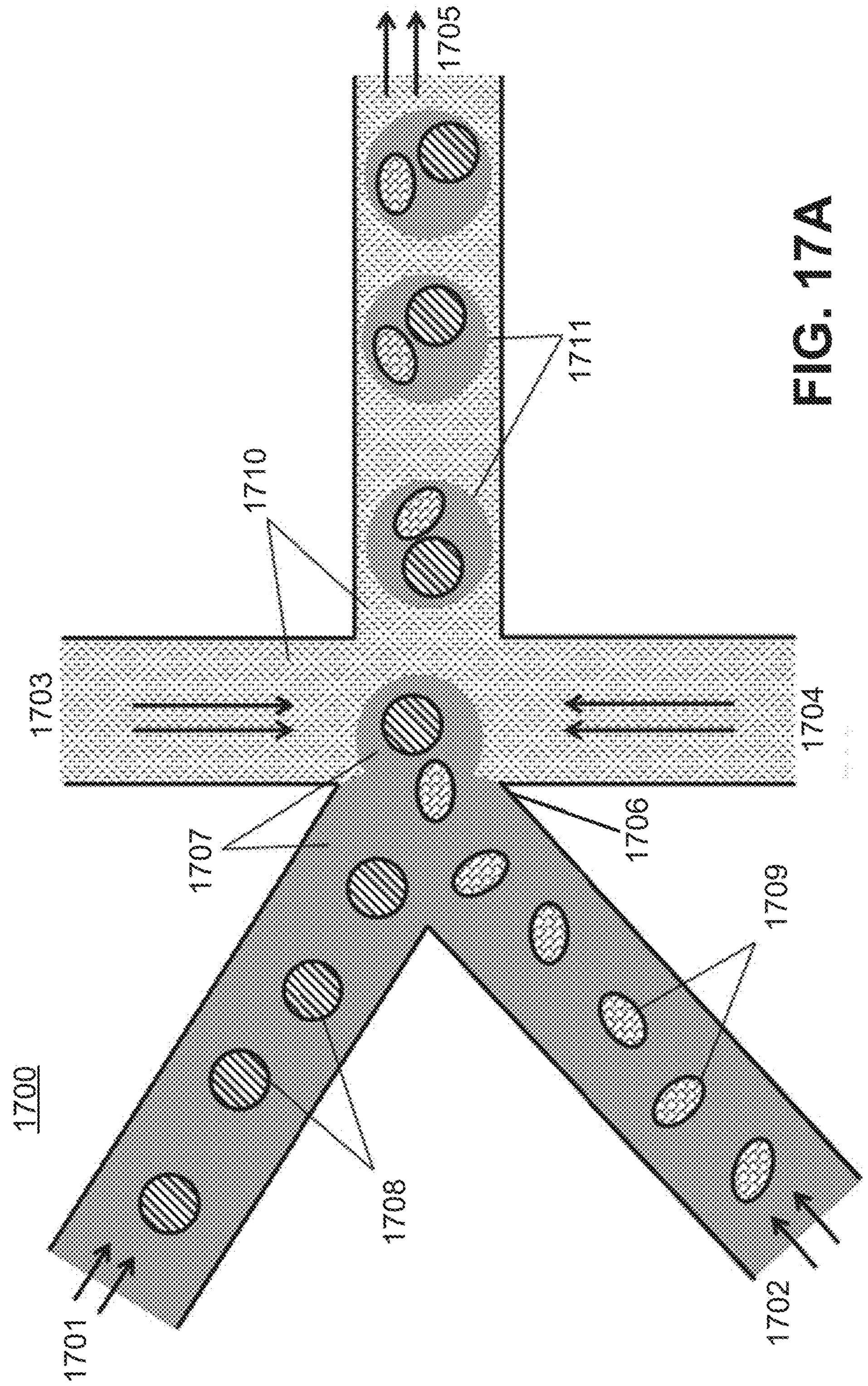
FIG. 17A shows an example of a microfluidic channel structure 1700 for delivering spatial barcode carrying beads to droplets.

FIG. 17A shows another example of a microfluidic channel structure 1700 for delivering beads to droplets. The channel structure includes channel segments 1701, 1702, 1703, 1704 and 1705 communicating at a channel junction 1706. During operation, the channel segment 1701 can transport an aqueous fluid 1707 that includes a plurality of beads 1708 along the channel segment 1701 into junction 1706. The plurality of beads 1708 can be sourced from a suspension of beads. For example, the channel segment 1701 can be connected to a reservoir that includes an aqueous suspension of beads 1708. The channel segment 1702 can transport the aqueous fluid 1707 that includes a plurality of particles 1709 (e.g., cells) along the channel segment 1702 into junction 1706. In some embodiments, the aqueous fluid 1707 in either the first channel segment 1701 or the second channel segment 1702, or in both segments, can include one or more reagents, as further described below.

A second fluid 1710 that is immiscible with the aqueous fluid 1707 (e.g., oil) can be delivered to the junction 1706 from each of channel segments 1703 and 1704. Upon meeting of the aqueous fluid 1707 from each of channel segments 1701 and 1702 and the second fluid 1710 from each of channel segments 1703 and 1704 at the channel junction 1706, the aqueous fluid 1707 can be partitioned as discrete droplets 1711 in the second fluid 1710 and flow away from the junction 1706 along channel segment 1705. The channel segment 1705 can deliver the discrete droplets to an outlet reservoir fluidly coupled to the channel segment 1705, where they can be harvested.

As an alternative, the channel segments 1701 and 1702 can meet at another junction upstream of the junction 1706. At such junction, beads and biological particles can form a mixture that is directed along another channel to the junction 1706 to yield droplets 1711. The mixture can provide the beads and biological particles in an alternating fashion, such that, for example, a droplet includes a single bead and a single biological particle.

The second fluid 1710 can include an oil, such as a fluorinated oil, that includes a fluorosurfactant for stabilizing the resulting droplets, for example, inhibiting subsequent coalescence of the resulting droplets 1711.

The partitions described herein can include small volumes, for example, less than about 10 microliters (TL), 5 TL, 1 TL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less.

In the foregoing discussion, droplets with beads were formed at the junction of different fluid streams. In some embodiments, droplets can be formed by gravity-based partitioning methods.

Figure 17B:
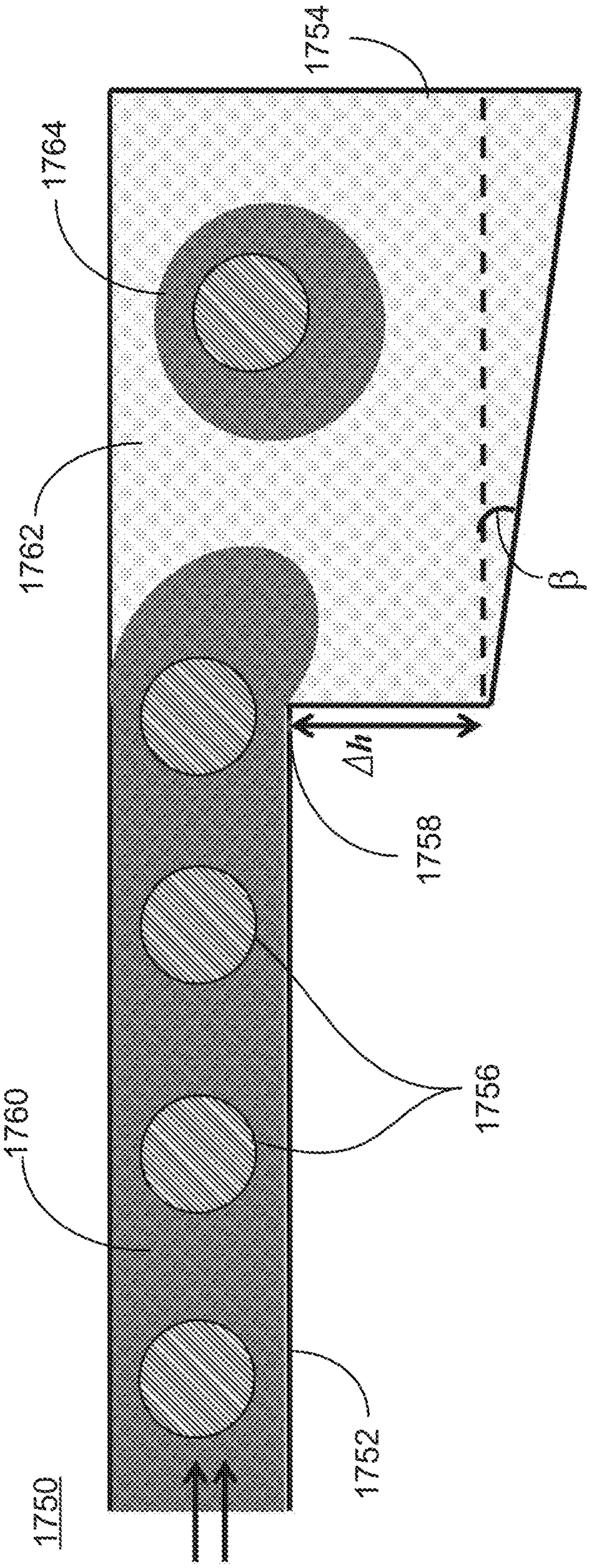
FIG. 17B shows a cross-section view of another example of a microfluidic channel structure 1750 with a geometric feature for controlled partitioning.

FIG. 17B shows a cross-section view of another example of a microfluidic channel structure 1750 with a geometric feature for controlled partitioning. A channel structure 1750 can include a channel segment 1752 communicating at a channel junction 1758 (or intersection) with a reservoir 1754. In some instances, the channel structure 1750 and one or more of its components can correspond to the channel structure 1700 and one or more of its components.

An aqueous fluid 1760 comprising a plurality of particles 1756 may be transported along the channel segment 1752 into the junction 1758 to meet a second fluid 1762 (e.g., oil, etc.) that is immiscible with the aqueous fluid 1760 in the reservoir 1754 to create droplets 1764 of the aqueous fluid 1760 flowing into the reservoir 1754. At the junction 1758 where the aqueous fluid 1760 and the second fluid 1762 meet, droplets can form based on factors such as the hydrodynamic forces at the junction 1758, relative flow rates of the two fluids 1760, 1762, fluid properties, and certain geometric parameters (e.g., Δh, etc.) of the channel structure 1750. A plurality of droplets can be collected in the reservoir 1754 by continuously injecting the aqueous fluid 1760 from the channel segment 1752 at the junction 1758.

A discrete droplet generated may comprise one or more particles of the plurality of particles 1756. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 1760 can have a substantially uniform concentration or frequency of particles 1756. As described elsewhere herein, the particles 1756 (e.g., beads) can be introduced into the channel segment 1752 from a separate channel (not shown in FIG. 17). The frequency of particles 1756 in the channel segment 1752 may be controlled by controlling the frequency in which the particles 1756 are introduced into the channel segment 1752 and/or the relative flow rates of the fluids in the channel segment 1752 and the separate channel. In some instances, the particles 1756 can be introduced into the channel segment 1752 from a plurality of different channels, and the frequency controlled accordingly. In some instances, different particles may be introduced via separate channels. For example, a first separate channel can introduce beads and a second separate channel can introduce biological particles into the channel segment 1752. The first separate channel introducing the beads may be upstream or downstream of the second separate channel introducing the biological particles.

In some instances, the second fluid 1762 may not be subjected to and/or directed to any flow in or out of the reservoir 1754. For example, the second fluid 1762 may be substantially stationary in the reservoir 1754. In some instances, the second fluid 1762 may be subjected to flow within the reservoir 1754, but not in or out of the reservoir 1754, such as via application of pressure to the reservoir 1754 and/or as affected by the incoming flow of the aqueous fluid 1760 at the junction 1758. Alternatively, the second fluid 1762 may be subjected and/or directed to flow in or out of the reservoir 1754. For example, the reservoir 1754 can be a channel directing the second fluid 1762 from upstream to downstream, transporting the generated droplets.

The channel structure 1750 at or near the junction 1758 may have certain geometric features that at least partly determine the volumes and/or shapes of the droplets formed by the channel structure 1750. The channel segment 1752 can have a first cross-section height, h1, and the reservoir 1754 can have a second cross-section height, h2. The first cross-section height, h1, and the second cross-section height, h2, may be different, such that at the junction 1758, there is a height difference of Δh. The second cross-section height, h2, may be greater than the first cross-section height, h1. In some instances, the reservoir may thereafter gradually increase in cross-section height, for example, the more distant it is from the junction 1758. In some instances, the cross-section height of the reservoir may increase in accordance with expansion angle, β, at or near the junction 1758. The height difference, Δh, and/or expansion angle, β, can allow the tongue (portion of the aqueous fluid 1760 leaving channel segment 1752 at junction 1758 and entering the reservoir 1754 before droplet formation) to increase in depth and facilitate decrease in curvature of the intermediately formed droplet. For example, droplet volume may decrease with increasing height difference and/or increasing expansion angle.

The height difference, Δh, can be at least about 1 μm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 μm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 μm or less. In some instances, the expansion angle, J, may be between a range of from about 0.50 to about 4°, from about 0.10 to about 10°, or from about 0° to about 90°. For example, the expansion angle can be at least about 0.010, 0.10, 0.2°, 0.3°, 0.4°, 0.5°, 0.6°, 0.7°, 0.8°, 0.9°, 10, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1, 0.1°, 0.01°, or less.

In some instances, the flow rate of the aqueous fluid 1760 entering the junction 1758 can be between about 0.04 microliters (μL)/minute (min) and about 40 μL/min. In some instances, the flow rate of the aqueous fluid 1760 entering the junction 1758 can be between about 0.01 microliters (μL)/minute (min) and about 100 μL/min. Alternatively, the flow rate of the aqueous fluid 1760 entering the junction 1758 can be less than about 0.01 μL/min. alternatively, the flow rate of the aqueous fluid 1760 entering the junction 1758 can be greater than about 40 μL/min, such as 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, 110 μL/min, 120 μL/min, 130 μL/min, 140 μL/min, 150 μL/min, or greater. At lower flow rates, such as flow rates of about less than or equal to 10 microliters/minute, the droplet radius may not be dependent on the flow rate of the aqueous fluid 1760 entering the junction 1758. The second fluid 1762 may be stationary, or substantially stationary, in the reservoir 1754. Alternatively, the second fluid 1762 may be flowing, such as at the above flow rates described for the aqueous fluid 1760.

While FIG. 17B illustrates the height difference, Δh, being abrupt at the junction 1758 (e.g., a step increase), the height difference may increase gradually (e.g., from about 0 μm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 1758, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIG. 17B illustrates the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

Figure 17C:
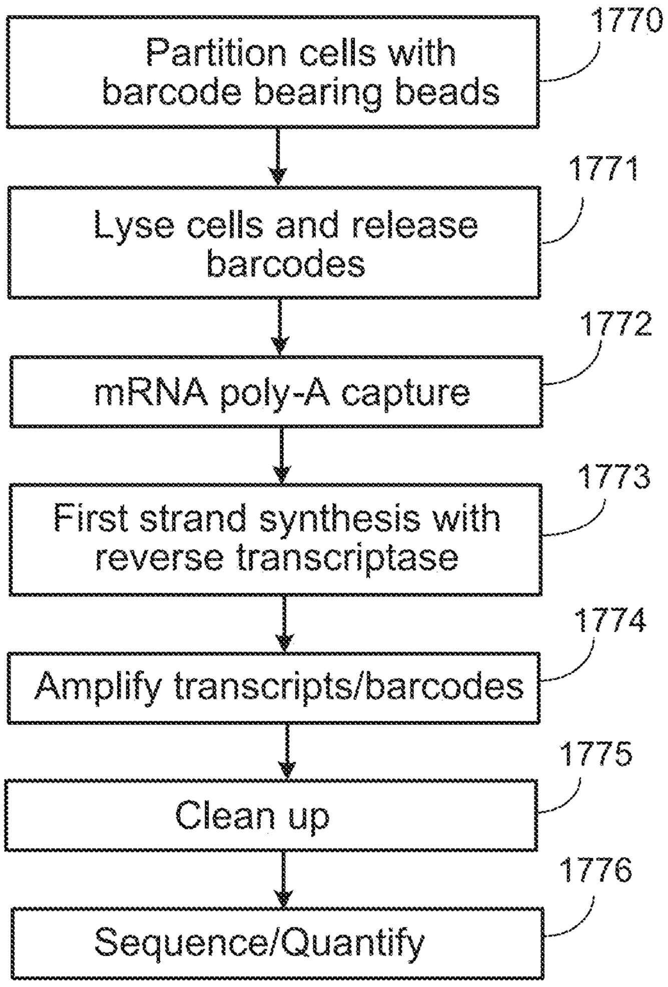
FIG. 17C shows an example of a workflow schematic.

FIG. 17C depicts a workflow wherein cells are partitioned into droplets along with barcode-bearing beads 1770. See FIG. 17A. The droplet forms an isolated reaction chamber wherein the cells can be lysed 1771 and target analytes within the cells can then be captured 1772 and amplified 1773, 1774 according to previously described methods. After sequence library preparation clean-up 1775, the material is sequenced and/or quantified 1776 according to methods described herein. For example, the workflow shown in FIG. 17C can be used with a biological sample on an array, where the features of the array have been delivered to the substrate via a droplet manipulation system. In some embodiments, capture probes on the features can specifically bind analytes present in the biological sample. In some embodiments, the features can be removed from the substrate (e.g., removed by any method described herein) and partitioned into droplets with barcode-bearing beads for further analysis according to methods described herein.

It should be noted that while the example workflow in FIG. 17C includes steps specifically for the analysis of mRNA, analogous workflows can be implemented for a wide variety of other analytes, including any of the analytes described previously.

By way of example, in the context of analyzing sample RNA as shown in FIG. 17C, the poly(T) segment of one of the released nucleic acid molecules (e.g., from the bead) can hybridize to the poly(A) tail of a mRNA molecule. Reverse transcription can result in a cDNA transcript of the mRNA, which transcript includes each of the sequence segments of the nucleic acid molecule. If the nucleic acid molecule includes an anchoring sequence, it will more likely hybridize to and prime reverse transcription at the sequence end of the poly(A) tail of the mRNA.

Within any given partition, all of the cDNA transcripts of the individual mRNA molecules can include a common barcode sequence segment. However, the transcripts made from the different mRNA molecules within a given partition can vary at the unique molecular identifying sequence segment (e.g., UMI segment). Beneficially, even following any subsequent amplification of the contents of a given partition, the number of different UMIs can be indicative of the quantity of mRNA originating from a given partition. As noted above, the transcripts can be amplified, cleaned up and sequenced to identify the sequence of the cDNA transcript of the mRNA, as well as to sequence the barcode segment and the UMI segment. While a poly(T) primer sequence is described, other targeted or random priming sequences can also be used in priming the reverse transcription reaction. Likewise, although described as releasing the barcoded oligonucleotides into the partition, in some cases, the nucleic acid molecules bound to the bead can be used to hybridize and capture the mRNA on the solid phase of the bead, for example, in order to facilitate the separation of the RNA from other cell contents.

In some embodiments, partitions include precursors that include a functional group that is reactive or capable of being activated such that it becomes reactive can be polymerized with other precursors to generate gel beads that include the activated or activatable functional group. The functional group can then be used to attach additional species (e.g., disulfide linkers, primers, other oligonucleotides, etc.) to the gel beads. For example, some precursors featuring a carboxylic acid (COOH) group can co-polymerize with other precursors to form a bead that also includes a COOH functional group. In some cases, acrylic acid (a species comprising free COOH groups), acrylamide, and bis(acryloyl)cystamine can be co-polymerized together to generate a bead with free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

In some embodiments, a bead can be formed from materials that include degradable chemical cross-linkers, such as BAC or cystamine. Degradation of such degradable cross-linkers can be accomplished through a number of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof. A reducing agent can degrade the disulfide bonds formed between gel precursors forming the bead, and thus, degrade the bead.

A degradable bead can include one or more species with a labile bond such that, when the bead/species is exposed to the appropriate stimulus, the bond is broken and the bead degrades within the partition. The labile bond can be a chemical bond (e.g., covalent bond, ionic bond) or can be another type of physical interaction (e.g., van der Waals interactions, dipole-dipole interactions, etc.). In some embodiments, a cross-linker used to generate a bead can include a labile bond. Upon exposure to the appropriate conditions, the labile bond can be broken and the bead degraded. For example, a polyacrylamide bead featuring cystamine and linked, via a disulfide bond, to a barcode sequence, can be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet with a bead-bound barcode sequence in basic solution can also result in bead degradation and release of the attached barcode sequence into the aqueous, inner environment of the droplet. The free species (e.g., oligonucleotides, nucleic acid molecules) can interact with other reagents contained in the partition.

A degradable bead can be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a barcode sequence can be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

Any suitable number of species (e.g., primer, barcoded oligonucleotide) can be associated with a bead such that, upon release from the bead, the species (e.g., primer, e.g., barcoded oligonucleotide) are present in the partition at a pre-defined concentration. Such pre-defined concentration can be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

As will be appreciated from the above description, while referred to as degradation of a bead, in many embodiments, degradation can refer to the disassociation of a bound or entrained species from a bead, both with and without structurally degrading the physical bead itself. For example, entrained species can be released from beads through osmotic pressure differences due to, for example, changing chemical environments. By way of example, alteration of bead pore volumes due to osmotic pressure differences can generally occur without structural degradation of the bead itself. In some cases, an increase in pore volume due to osmotic swelling of a bead can permit the release of entrained species within the bead. In some embodiments, osmotic shrinking of a bead can cause a bead to better retain an entrained species due to pore volume contraction.

Numerous chemical triggers can be used to trigger the degradation of beads within partitions. Examples of these chemical changes can include, but are not limited to pH-mediated changes to the integrity of a component within the bead, degradation of a component of a bead via cleavage of cross-linked bonds, and depolymerization of a component of a bead.

In certain embodiments, a change in pH of a solution, such as an increase in pH, can trigger degradation of a bead. In other embodiments, exposure to an aqueous solution, such as water, can trigger hydrolytic degradation, and thus degradation of the bead. In some cases, any combination of stimuli can trigger degradation of a bead. For example, a change in pH can enable a chemical agent (e.g., DTT) to become an effective reducing agent.

Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In other cases, heat can increase the internal pressure of the bead components such that the bead ruptures or explodes. Heat can also act upon heat-sensitive polymers used as materials to construct beads.

In addition to beads and analytes, partitions that are formed can include a variety of different reagents and species. For example, when lysis reagents are present within the partitions, the lysis reagents can facilitate the release of analytes within the partition. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St. Louis, MO), as well as other commercially available lysis enzymes. Other lysis agents can additionally or alternatively be co-partitioned to cause the release analytes into the partitions. For example, in some cases, surfactant-based lysis solutions can be used to lyse cells, although these can be less desirable for emulsion based systems where the surfactants can interfere with stable emulsions. In some embodiments, lysis solutions can include non-ionic surfactants such as, for example, TritonX-100 and Tween 20. In some embodiments, lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of analytes that can be in addition to or in place of droplet partitioning, where any pore size of the encapsulate is sufficiently small to retain nucleic acid fragments of a given volume, following cellular disruption.

Examples of other species that can be co-partitioned with analytes in the partitions include, but are not limited to, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. Additional reagents can also be co-partitioned, including endonucleases to fragment DNA, DNA polymerase enzymes and dNTPs used to amplify nucleic acid fragments and to attach the barcode molecular tags to the amplified fragments.

Additional reagents can also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some embodiments, template switching can be used to increase the length of a cDNA. Template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., poly(C), to the cDNA in a template independent manner. Switch oligos can include sequences complementary to the additional nucleotides, e.g., poly(G). The additional nucleotides (e.g., poly(C)) on the cDNA can hybridize to the additional nucleotides (e.g., poly(G)) on the switch oligo, whereby the switch oligo can be used by the reverse transcriptase as template to further extend the cDNA. Template switching oligonucleotides can include a hybridization region and a template region. The hybridization region can include any sequence capable of hybridizing to the target. In some cases, the hybridization region includes a series of G bases to complement the overhanging C bases at the 3' end of a cDNA molecule. The series of G bases can include 1 G base, 2 G bases, 3 G bases, 4 G bases, 5 G bases or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos can include deoxyribonucleic acids; ribonucleic acids; bridged nucleic acids, modified nucleic acids including 2-Aminopurine, 2,6-Diaminopurine (2-Amino-dA), inverted dT, 5-Methyl dC, 2'-deoxylnosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), and combinations of the foregoing.

In some embodiments, beads that are partitioned with the analyte can include different types of oligonucleotides bound to the bead, where the different types of oligonucleotides bind to different types of analytes. For example, a bead can include one or more first oligonucleotides (which can be capture probes, for example) that can bind or hybridize to a first type of analyte, such as mRNA for example, and one or more second oligonucleotides (which can be capture probes, for example) that can bind or hybridize to a second type of analyte, such as gDNA for example. Partitions can also include lysis agents that aid in releasing nucleic acids from the co-partitioned cell, and can also include an agent (e.g., a reducing agent) that can degrade the bead and/or break covalent linkages between the oligonucleotides and the bead, releasing the oligonucleotides into the partition. The released barcoded oligonucleotides (which can also be barcoded) can hybridize with mRNA released from the cell and also with gDNA released from the cell.

Barcoded constructs thus formed from hybridization can include a first type of construct that includes a sequence corresponding to an original barcode sequence from the bead and a sequence corresponding to a transcript from the cell, and a second type of construct that includes a sequence corresponding to the original barcode sequence from the bead and a sequence corresponding to genomic DNA from the cell. The barcoded constructs can then be released/removed from the partition and, in some embodiments, further processed to add any additional sequences. The resulting constructs can then be sequenced, the sequencing data processed, and the results used to spatially characterize the mRNA and the gDNA from the cell.

In another example, a partition includes a bead that includes a first type of oligonucleotide (e.g., a first capture probe) with a first barcode sequence, a poly(T) priming sequence that can hybridize with the poly(A) tail of an mRNA transcript, and a UMI barcode sequence that can uniquely identify a given transcript. The bead also includes a second type of oligonucleotide (e.g., a second capture probe) with a second barcode sequence, a targeted priming sequence that is capable of specifically hybridizing with a third barcoded oligonucleotide (e.g., an analyte capture agent) coupled to an antibody that is bound to the surface of the partitioned cell. The third barcoded oligonucleotide includes a UMI barcode sequence that uniquely identifies the antibody (and thus, the particular cell surface feature to which it is bound).

In this example, the first and second barcoded oligonucleotides include the same spatial barcode sequence (e.g., the first and second barcode sequences are the same), which permits downstream association of barcoded nucleic acids with the partition. In some embodiments, however, the first and second barcode sequences are different.

The partition also includes lysis agents that aid in releasing nucleic acids from the cell and can also include an agent (e.g., a reducing agent) that can degrade the bead and/or break a covalent linkage between the barcoded oligonucleotides and the bead, releasing them into the partition. The first type of released barcoded oligonucleotide can hybridize with mRNA released from the cell and the second type of released barcoded oligonucleotide can hybridize with the third type of barcoded oligonucleotide, forming barcoded constructs.

The first type of barcoded construct includes a spatial barcode sequence corresponding to the first barcode sequence from the bead and a sequence corresponding to the UMI barcode sequence from the first type of oligonucleotide, which identifies cell transcripts. The second type of barcoded construct includes a spatial barcode sequence corresponding to the second barcode sequence from the second type of oligonucleotide, and a UMI barcode sequence corresponding to the third type of oligonucleotide (e.g., the analyte capture agent) and used to identify the cell surface feature. The barcoded constructs can then be released/removed from the partition and, in some embodiments, further processed to add any additional sequences. The resulting constructs are then sequenced, sequencing data processed, and the results used to characterize the mRNA and cell surface feature of the cell.

The foregoing discussion involves two specific examples of beads with oligonucleotides for analyzing two different analytes within a partition. More generally, beads that are partitioned can have any of the structures described previously, and can include any of the described combinations of oligonucleotides for analysis of two or more (e.g., three or more, four or more, five or more, six or more, eight or more, ten or more, 12 or more, 15 or more, 20 or more, 25 or more, 30 or more, 40 or more, 50 or more) different types of analytes within a partition. Examples of beads with combinations of different types of oligonucleotides (e.g., capture probes) for concurrently analyzing different combinations of analytes within partitions include, but are not limited to: (a) genomic DNA and cell surface features (e.g., using the analyte capture agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites; (f) a barcoded analyte capture agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein). In some embodiments, a perturbation agent can be a small molecule, an antibody, a drug, an aptamer, a miRNA, a physical environmental (e.g., temperature change), or any other known perturbation agents.

Additionally, in some embodiments, the unaggregated cell or disaggregated cells introduced and processed within partitions or droplets as described herein, can be removed from the partition, contacted with a spatial array, and spatially-barcoded according to methods described herein. For example, single cells of an unaggregated cell sample can be partitioned into partitions or droplets as described herein. The partitions or droplets can include reagents to permeabilize a cell, barcode targeted cellular analyte(s) with a cellular barcode, and amplify the barcoded analytes. The partitions or droplets can be contacted with any of the spatial arrays described herein. In some embodiments, the partition can be dissolved, such that the contents of the partition are placed in contact with the capture probes of the spatial array. The capture probes of the spatial array can then capture target analytes from the ruptured partitions or the droplets, and processed by the spatial workflows described herein.

(g) Analysis of Captured Analytes (i) Sample Removal from an Array

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, the biological sample remains on the substrate during removal (e.g., via denaturation) of a copy of the capture probe (e.g., complement). In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture prove bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes selecting a region of interest in the biological sample to subject to spatial transcriptomic analysis. In some embodiments, one or more of the one or more capture probes include a capture domain. In some embodiments, one or more of the one or more capture probe pluralities comprise a unique molecular identifier (UMI). In some embodiments, one or more of the one or more capture probe pluralities comprise a cleavage domain. In some embodiments, the cleavage domain comprises a sequence recognized and cleaved by a uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array.

(ii) Extended Capture Probes

In some embodiments, a capture probe can be extended (an "extended capture probe," e.g., as described herein (e.g., Section II(b)(vii))). For example, extending a capture probe can include generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA (e.g., cDNA) molecule is generated. In some embodiments, a "full-length" DNA molecule refers to the whole of the captured nucleic acid molecule. However, if a nucleic acid (e.g., RNA) was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Lucigen, Middleton, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9°N) DNA ligase (9°N™ DNA ligase, New England Biolabs), Ampligase™ (available from Lucigen, Middleton, WI), and SplintR (available from New England Biolabs, Ipswich, MA). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g., sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g., by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g., via hybridization to a surface probe, it can be sufficient to disrupt the interaction between the extended capture probe and the surface probe. Methods for disrupting the interaction between nucleic acid molecules include denaturing double stranded nucleic acid molecules are known in the art. A straightforward method for releasing the DNA molecules (i.e., of stripping the array of extended probes) is to use a solution that interferes with the hydrogen bonds of the double stranded molecules. In some embodiments, the extended capture probe is released by a applying heated solution, such as water or buffer, of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

In some embodiments, probes complementary to the extended capture probe can be contacted with the substrate. In some embodiments, the biological sample can be in contact with the substrate when the probes are contacted with the substrate. In some embodiments, the biological sample can be removed from the substrate prior to contacting the substrate with probes. In some embodiments, the probes can be labeled with a detectable label (e.g., any of the detectable labels described herein). In some embodiments, probes that do not specially bind (e.g., hybridize) to an extended capture probe can be washed away. In some embodiments, probes complementary to the extended capture probe can be detected on the substrate (e.g., imaging, any of the detection methods described herein).

In some embodiments, probes complementary to an extended capture probe can be about 4 nucleotides to about 100 nucleotides long. In some embodiments, probes (e.g., detectable probes) complementary to an extended capture probe can be about 10 nucleotides to about 90 nucleotides long. In some embodiments, probes (e.g., detectable probes) complementary to an extended capture probe can be about 20 nucleotides to about 80 nucleotides long. In some embodiments, probes (e.g., detectable probes) complementary to an extended capture probe can be about 30 nucleotides to about 60 nucleotides long. In some embodiments, probes (e.g., detectable probes) complementary to an extended capture probe can be about 40 nucleotides to about 50 nucleotides long. In some embodiments, probes (e.g., detectable probes) complementary to an extended capture probe can be about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 nucleotides long.

In some embodiments, about 1 to about 100 probes can be contacted to the substrate and specifically bind (e.g., hybridize) to an extended capture probe. In some embodiments, about 1 to about 10 probes can be contacted to the substrate and specifically bind (e.g., hybridize) to an extended capture probe. In some embodiments, about 10 to about 100 probes can be contacted to the substrate and specifically bind (e.g., hybridize) to an extended capture probe. In some embodiments, about 20 to about 90 probes can be contacted to the substrate and specifically bind (e.g., hybridize) to an extended capture probe. In some embodiments, about 30 to about 80 probes (e.g., detectable probes) can be contacted to the substrate and specifically bind (e.g., hybridize) to an extended capture probe. In some embodiments, about 40 to about 70 probes can be contacted to the substrate and specifically bind (e.g., hybridize) to an extended capture probe. In some embodiments, about 50 to about 60 probes can be contacted to the substrate and specifically bind (e.g., hybridize) to an extended capture probe. In some embodiments, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, and about 99 probes can be contacted to the substrate and specifically bind (e.g., hybridize) to an extended capture probe.

In some embodiments, the probes can be complementary to a single analyte (e.g., a single gene). In some embodiments, the probes can be complementary to one or more analytes (e.g., analytes in a family of genes). In some embodiments, the probes (e.g., detectable probes) can be for a panel of genes associated with a disease (e.g., cancer, Alzheimer's disease, Parkinson's disease).

(iii) Cleavage Domain

Capture probes can optionally include a "cleavage domain," where one or more segments or regions of the capture probe (e.g., spatial barcodes and/or UMIs) can be releasably, cleavably, or reversibly attached to a feature, or some other substrate, so that spatial barcodes and/or UMIs can be released or be releasable through cleavage of a linkage between the capture probe and the feature, or released through degradation of the underlying substrate or chemical substrate, allowing the spatial barcode(s) and/or UMI(s) of the cleaved capture probe to be accessed or be accessible by other reagents, or both. Non-limiting aspects of cleavage domains are described herein (e.g., in Section II(b)(ii)).

In some embodiments, the capture probe is linked, (e.g., via a disulfide bond), to a feature. In some embodiments, the capture probe is linked to a feature via a propylene group (e.g., Spacer C3). A reducing agent can be added to break the various disulfide bonds, resulting in release of the capture probe including the spatial barcode sequence. In another example, heating can also result in degradation and release of the attached capture probe. In some embodiments, the heating is done by laser (e.g., laser ablation) and features at specific locations can be degraded. In addition to thermally cleavable bonds, disulfide bonds, photo-sensitive bonds, and UV sensitive bonds, other non-limiting examples of labile bonds that can be coupled to a capture probe (e.g., spatial barcode) include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. In some embodiments, the cleavage domain can be a single U. In some embodiments, the cleavage domain can be an abasic site that can be cleaved with an abasic site-specific endonuclease (e.g., Endonuclease IV or Endonuclease VIII).

In some embodiments, the cleavage domain of the capture probe is a nucleotide sequence within the capture probe that is cleaved specifically, e.g., physically by light or heat, chemically or enzymatically. The location of the cleavage domain within the capture probe will depend on whether or not the capture probe is immobilized on the substrate such that it has a free 3' end capable of functioning as an extension primer (e.g., by its 5' or 3' end). For example, if the capture probe is immobilized by its 5' end, the cleavage domain will be located 5' to the spatial barcode and/or UMI, and cleavage of said domain results in the release of part of the capture probe including the spatial barcode and/or UMI and the sequence 3' to the spatial barcode, and optionally part of the cleavage domain, from a feature. Alternatively, if the capture probe is immobilized by its 3' end, the cleavage domain will be located 3' to the capture domain (and spatial barcode) and cleavage of said domain results in the release of part of the capture probe including the spatial barcode and the sequence 3' to the spatial barcode from a feature. In some embodiments, cleavage results in partial removal of the cleavage domain. In some embodiments, cleavage results in complete removal of the cleavage domain, particularly when the capture probes are immobilized via their 3' end as the presence of a part of the cleavage domain can interfere with the hybridization of the capture domain and the target nucleic acid and/or its subsequent extension.

(iv) Sequencing

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g., sequencing), i.e., can directly take part in the sequence analysis reaction or process (e.g., the sequencing reaction or sequencing process, or be the molecule which is sequenced or otherwise identified). Alternatively, the barcoded nucleic acid molecule can be subjected to a step of second strand synthesis or amplification before sequence analysis (e.g., sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g., barcoded nucleic acid molecules) can be analyzed (e.g., sequenced). To perform single molecule sequencing, the nucleic acid strand can be modified at the 3' end.

Massively parallel pyrosequencing techniques can be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., *Anal. Biochem.* 242(1), 84-9 (1996); Ronaghi, *Genome Res.* 11(1), 3-11 (2001); Ronaghi et al. *Science* 281 (5375), 363 (1998); and U.S. Pat. Nos. 6,210,891, 6,258,568, and 6,274,320, the entire contents of each of which are incorporated herein by reference.

In some embodiments, a massively parallel sequencing technique can be based on reversible dye-terminators. As an example, DNA molecules are first attached to primers on, e.g., a glass or silicon substrate, and amplified so that local clonal colonies are formed (bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, sequencing can be performed in situ. In situ sequencing methods are particularly useful, for example, when the biological sample remains intact after analytes on the sample surface (e.g., cell surface analytes) or within the sample (e.g., intracellular analytes) have been barcoded. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343(6177), 1360-1363, the entire contents of each of which are incorporated herein by reference.

In addition, examples of methods and systems for performing in situ sequencing are described in PCT Patent Application Publication Nos. WO2014/163886, WO2018/045181, WO2018/045186, and in U.S. Pat. Nos. 10,138,509 and 10,179,932, the entire contents of each of which are incorporated herein by reference. Exemplary techniques for in situ sequencing include, but are not limited to, STARmap (described for example in Wang et al., (2018) *Science,* 361(6499) 5691), MERFISH (described for example in Moffitt, (2016) *Methods in Enzymology,* 572, 1-49), and FISSEQ (described for example in U.S. Patent Application Publication No. 2019/0032121). The entire contents of each of the foregoing references are incorporated herein by reference.

For analytes that have been barcoded via partitioning, barcoded nucleic acid molecules or derivatives thereof (e.g., barcoded nucleic acid molecules to which one or more functional sequences have been added, or from which one or more features have been removed) can be pooled and processed together for subsequent analysis such as sequencing on high throughput sequencers. Processing with pooling can be implemented using barcode sequences. For example, barcoded nucleic acid molecules of a given partition can have the same barcode, which is different from barcodes of other spatial partitions. Alternatively, barcoded nucleic acid molecules of different partitions can be processed separately for subsequent analysis (e.g., sequencing).

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte (e.g., reverse transcription and polymerase amplification of RNA). In some embodiments, analyte analysis uses direct sequencing of one or more captured analytes, such as direct sequencing of hybridized RNA. In some embodiments, direct sequencing is performed after reverse transcription of hybridized RNA. In some embodiments direct sequencing is performed after amplification of reverse transcription of hybridized RNA.

In some embodiments, direct sequencing of captured RNA is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid features are present in a double stranded form these can be processed to provide single stranded nucleic acid templates using methods well known in the art, for example by denaturation, cleavage, etc. The sequencing primers which are hybridized to the nucleic acid template and used for primer extension are preferably short oligonucleotides, for example, 15 to 25 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010,251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., *Trends Biotechnol.* 18, 14 7-151 (2000); Deamer et al., *Acc. Chem. Res.* 35:817-825 (2002); Li et al., *Nat. Mater.* 2:611-615 (2003); Soni et al., *Clin. Chem.* 53, 1996-2001 (2007); Healy et al., *Nanomed.* 2, 459-481 (2007); Cockroft et al., *J. Am. Chem. Soc.* 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina© sequencing (e.g., flow cell-based sequencing by synthesis techniques), using modified nucleotides (such as commercialized in HiSeq™ and additional sequencing technology instruments by Illumina, Inc., San Diego, CA), HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA), and sequencing of DNA nanoballs (Complete Genomics, Inc., Mountain View, CA).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes.

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181. The entire contents of each of the foregoing references are incorporated herein by reference herein.

(v) Temporal Analysis

In some embodiments, the methods described herein can be used to assess analyte levels and/or expression in a cell or a biological sample over time (e.g., before or after treatment with an agent or different stages of differentiation). In some examples, the methods described herein can be performed on multiple similar biological samples or cells obtained from the subject at a different time points (e.g., before or after treatment with an agent, different stages of differentiation, different stages of disease progression, different ages of the subject, before or after physical perturbation, before or after treatment with a perturbation agent as described herein, or before or after development of resistance to an agent). As described herein, a “perturbation agent” or “perturbation reagent” can be a small molecule, an antibody, a drug, an aptamer, a nucleic acid (e.g., miRNA), a CRISPR crRNA/sgRNA, TALEN, zinc finger nuclease, antisense oligonucleotide a physical environmental (e.g., temperature change), and/or any other known perturbation agents where the agent alters equilibrium or homeostasis.

In some embodiments, the methods described herein can be performed on multiple similar biological samples or cells obtained from the subject at 2, 3, 4, 5, 6, 7, 8, 9, 10, or more times. For example, the multiple similar biological samples can be repetitive samples from the same subject, the same tissue, the same organoid, the same cell suspension, or any other biological sample described herein. In some embodiments, the methods described herein can be performed on the same biological sample or cells obtained from the subject at a different time points (e.g., before or after treatment with a perturbation agent, different stages of differentiation, different stages of disease progression, different ages of the subject, or before or after development of resistance to an agent). In some embodiments, a perturbation agent can be small-molecules, antibodies, nucleic acids, peptides, and/or other external stimuli (e.g., temperature change). In some embodiments, the biological sample is contacted with a different array at each time point.

In some embodiments, a sample can be placed in a controlled environment permissive for cellular growth and/or maintenance, and/or to prevent hypoxia. In some embodiments, a controlled environment allows a sample to be analyzed at different time points. Barcoded arrays can be placed proximal to (e.g., on top of) the sample and imaged using a microscope or other suitable instrument to register the relative position of the biological sample to the barcoded array, optionally using optically encoded fiducial markers. An electric field can be applied for a period of time, such that biological analytes (e.g., DNA, RNA, proteins, metabolites, small molecules, lipids, and the like) are released from the sample and captured by capture probes on the spatially-barcoded array, preserving spatial information of the sample. The barcoded array can be removed, and the spatial and molecular information therein is determined (e.g., by performing library construction for next generation sequencing or in situ sequencing). Sequencing can be followed by computational analysis to correlate the molecular information (e.g., gene expression values with the spatial barcode). These steps can be repeated one or more times to capture the spatial information of analytes at different time-points.

In some embodiments, methods as described herein can be combined with a cell migration assay. A cell migration assay can comprise one or more microprinted lines, or suspended 3D nanofibers, on which the cells migrate. Migration using these assays can be measured by imaging cell migration and/or contacting migrated cells with a spatially-barcoded array. An array used in a cell migration assay can comprise one or more channels on the substrate of the array, e.g., to confine cell migration to one dimension along the substrate. Additionally, the channels can direct the migration of a cell such that it does not contact another cell on the array (e.g., the channels do not overlap with each other), and in some embodiments, the channels are about the same width as or wider than a cell (e.g., for a mammalian cell, a channel can have a width of about 2 μm to about 10 μm). Cellular location on the spatially-barcoded array can be identified using any method described herein.

In some embodiments, cells can be disposed on an array as described herein and allowed to migrate. Cell migration in cell migration assays can be used to measure target phenotypes (e.g., phenotype for invasiveness). In some embodiments, the cell migration distance can be measured and correlated to a biological analyte. Reagents can be added to the array to facilitate cell migration. For example, the array can be coated with one or more extracellular matrix (ECM) components (e.g., basement membrane extract (BME), laminin I, collagen I, collagen IV, fibronectin, vitronectin, elastin), a cell culture medium, a chemoattractant, a chemorepellant, or a combination thereof. In some embodiments, a reagent such as a chemoattractant or chemorepellant can be disposed on only a portion of the array, present as a gradient along the one or more axis or channels of the array, or a combination thereof.

(vi) Spatially Resolving Analyte Information

In some embodiments, a lookup table (LUT) can be used to associate one property with another property of a feature. These properties include, e.g., locations, barcodes (e.g., nucleic acid barcode molecules), spatial barcodes, optical labels, molecular tags, and other properties.

In some embodiments, a lookup table can associate a nucleic acid barcode molecule with a feature. In some embodiments, an optical label of a feature can permit associating the feature with a biological particle (e.g., cell or nuclei). The association of a feature with a biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a feature, thus associating the location of the feature with the barcode sequence of the feature. Subsequent analysis (e.g., sequencing) can associate the barcode sequence and the analyte from the sample. Accordingly, based on the relationship between the location and the barcode sequence, the location of the biological analyte can be determined (e.g., in a specific type of cell or in a cell at a specific location of the biological sample).

In some embodiments, a feature can have a plurality of nucleic acid barcode molecules attached thereto. The plurality of nucleic acid barcode molecules can include barcode sequences. The plurality of nucleic acid molecules attached to a given feature can have the same barcode sequences, or two or more different barcode sequences. Different barcode sequences can be used to provide improved spatial location accuracy.

As discussed above, analytes obtained from a sample, such as RNA, DNA, peptides, lipids, and proteins, can be further processed. In particular, the contents of individual cells from the sample can be provided with unique spatial barcode sequences such that, upon characterization of the analytes, the analytes can be attributed as having been derived from the same cell. More generally, spatial barcodes can be used to attribute analytes to corresponding spatial locations in the sample. For example, hierarchical spatial positioning of multiple pluralities of spatial barcodes can be used to identify and characterize analytes over a particular spatial region of the sample. In some embodiments, the spatial region corresponds to a particular spatial region of interest previously identified, e.g., a particular structure of cytoarchitecture previously identified. In some embodiments, the spatial region corresponds to a small structure or group of cells that cannot be seen with the naked eye. In some embodiments, a unique molecular identifier can be used to identify and characterize analytes at a single cell level.

The analyte can include a nucleic acid molecule, which can be barcoded with a barcode sequence of a nucleic acid barcode molecule. In some embodiments, the barcoded analyte can be sequenced to obtain a nucleic acid sequence. In some embodiments, the nucleic acid sequence can include genetic information associated with the sample. The nucleic acid sequence can include the barcode sequence, or a complement thereof. The barcode sequence, or a complement thereof, of the nucleic acid sequence can be electronically associated with the property (e.g., color and/or intensity) of the analyte using the LUT to identify the associated feature in an array.

(vii) Proximity Capture

In some embodiments, two- or three-dimensional spatial profiling of one or more analytes present in a biological sample can be performed using a proximity capture reaction, which is a reaction that detects two analytes that are spatially close to each other and/or interacting with each other. For example, a proximity capture reaction can be used to detect sequences of DNA that are close in space to each other, e.g., the DNA sequences can be within the same chromosome, but separated by about 700 bp or less. As another example, a proximity capture reaction can be used to detect protein associations, e.g., two proteins that interact with each other. A proximity capture reaction can be performed in situ to detect two analytes that are spatially close to each other and/or interacting with each other inside a cell. Non-limiting examples of proximity capture reactions include DNA nanoscopy, DNA microscopy, and chromosome conformation capture methods. Chromosome conformation capture (3C) and derivative experimental procedures can be used to estimate the spatial proximity between different genomic elements. Non-limiting examples of chromatin capture methods include chromosome conformation capture (3-C), conformation capture-on-chip (4-C), 5-C, ChIA-PET, Hi-C, targeted chromatin capture (T2C). Examples of such methods are described, for example, in Miele et al., *Methods Mol Biol.* (2009), 464, Simonis et al., *Nat. Genet.* (2006), 38(11): 1348-54, Raab et al., *Embo. J.* (2012), 31(2): 330-350, and Eagen et al., *Trends Biochem. Sci.* (2018) 43(6): 469-478, the entire contents of each of which is incorporated herein by reference.

In some embodiments, the proximity capture reaction includes proximity ligation. In some embodiments, proximity ligation can include using antibodies with attached DNA strands that can participate in ligation, replication, and sequence decoding reactions. For example, a proximity ligation reaction can include oligonucleotides attached to pairs of antibodies that can be joined by ligation if the antibodies have been brought in proximity to each oligonucleotide, e.g., by binding the same target protein (complex), and the DNA ligation products that form are then used to template PCR amplification, as described for example in Soderberg et al., *Methods.* (2008), 45(3): 227-32, the entire contents of which are incorporated herein by reference. In some embodiments, proximity ligation can include chromosome conformation capture methods.

In some embodiments, the proximity capture reaction is performed on analytes within about 400 nm distance (e.g., about 300 nm, about 200 nm, about 150 nm, about 100 nm, about 50 nm, about 25 nm, about 10 nm, or about 5 nm) from each other. In general, proximity capture reactions can be reversible or irreversible.

(viii) Feature Removal from an Array

A spatially-barcoded array can be contacted with a biological sample to spatially detect analytes present in the biological sample. In some embodiments, the features (e.g., gel pads, beads) can be removed from the substrate surface for additional analysis (e.g., imaging, sequencing, or quantification). For example, features on a substrate delivered by a droplet manipulation system as described herein can be removed from the substrate surface. In some embodiments, the features (e.g., gel pads, beads) can be removed mechanically (e.g., scraping), by an enzymatic reaction, or by a chemical reaction. In some embodiments, the features (e.g., gel pads, beads) can be aspirated. In some embodiments, after the features are removed (by any method), the features can be combined with a uniquely barcoded bead. In some embodiments, the oligonucleotides within a feature can be ligated or hybridized to the barcode sequence on the barcoded bead. For example, the spatial barcode oligonucleotide within a feature can be ligated to the barcode sequence on the barcoded bead. Additionally, the capture probes can be ligated to the barcode sequence on the barcoded bead. In some embodiments, the features and the bead can be partitioned. In some embodiments, the features (e.g., gels pads, beads) and the uniquely barcoded bead can be partitioned into a vesicle. In some embodiments, the vesicle can have a lipid bilayer. In some embodiments, the features and the bead can be encapsulated. In some embodiments, the features and the bead can be encapsulated in an oil emulsion. In some embodiments, the features and the bead can be encapsulated in a water-in-oil emulsion. Once partitioned, the features (e.g., gel pads, beads) can be processed for further analysis (e.g., quantitation, amplification, or sequencing) according to any method described herein.

(ix) Other Applications

The spatial analysis methods described herein can be used to detect and characterize the spatial distribution of one or more haplotypes in a biological sample. As used in the present disclosure, a haplotype is used to describe one or more mutations, DNA variations, polymorphisms in a given segment of the genome, which can be used to classify the genetic segment, or a collection of alleles or genetic segments containing single nucleotide polymorphisms (SNPs). Haplotype association studies are used to inform a greater understanding of biological conditions. For example, identifying and characterizing haplotype variants at or associated with putative disease loci in humans can provide a foundation for mapping genetic causes underlying disease susceptibility. The term "locus" (plural "loci"), as used in the art, can be a fixed location on a chromosome, including the location of a gene or a genetic marker, which can contain a plurality of haplotypes, including alleles and SNPs.

Variant haplotype detection is a technique used to identify heterozygous cells in single cell studies. In combination with spatial analysis, variant haplotype detection can further provide novel information on the distribution of heterozygous cells in biological samples (e.g., tissues) affected by or exhibiting a variety of biological conditions. These data may reveal causal relationships between variant haplotypes and disease outcomes, to aid in identification of disease-associated variants, or to reveal heterogeneity within a biological sample.

In some embodiments, variant haplotype detection is a technique that can be used in combination with, in addition to, or as a part of, the spatial analysis methods described herein. Briefly, variant haplotype detection can include providing inputs for executing an algorithm on a computer system, and performing an analysis to identify and determine the spatial distribution of haplotypes. One input can be a plurality of sequence reads obtained from a two-dimensional spatial array in contact with a biological sample and subsequently aligned to a genome. The sequence reads can also contain spatial barcodes with positional information, such that the sequence reads can be mapped to a location on the biological sample. Other inputs can include electronic data files of gene sequence variations, or haplotypes, and a reference genome. For each locus, the corresponding sequence reads and variant haplotypes are aligned to determine the haplotype identity of each sequence read. The haplotype identity and the spatial barcode of the sequence reads are then categorized to determine the spatial distribution of haplotypes within the biological sample. As described above, this spatial distribution can be used to characterize a biological condition of the sample. In some embodiments, sequence reads are obtained by in situ sequencing of the two-dimensional array of positions on the substrate, while in some embodiments, sequence reads are obtained by high-throughput sequencing. In some embodiments, other methods for generating sequence reads described herein are used, such as paired end sequencings.

In some embodiments, a respective loci in the plurality of loci is bi-allelic and the corresponding set of haplotypes for the respective loci consists of a first allele and a second allele. In some such embodiments, the respective loci includes a heterozygous single nucleotide polymorphism (SNP), a heterozygous insert, or a heterozygous deletion.

In some embodiments, analytes captured by any of the spatial analysis methods described herein can be analyzed (e.g., sequenced) via in situ sequencing methods. For example, a substrate including a plurality of capture probes (e.g., an array), attached either directly or indirectly (e.g., via a feature), that include a spatial barcode and a capture domain. In some embodiments, the capture domain can be configured to interact (e.g., hybridize) with an analyte (e.g., mRNA). In some embodiments, a biological sample can be contacted to the array such that the capture domain of the capture probe interacts with (e.g., hybridizes) the analyte. In some embodiments, the capture probe can function as a template for a hybridization or ligation reaction with the captured analyte. For example, a reverse transcription reaction can be performed to extend the 3' end of a capture probe hybridized to the analyte using any of the exemplary reverse transcriptases described herein, thereby generating an extended capture probe (e.g., an extended capture probe including the spatial barcode and a sequence that is complementary to a sequence in the analyte). After the extended capture probe is synthesized, a second strand that is complementary to the extended capture probe can be synthesized. In some embodiments, second strand synthesis can be performed using any of the methods described herein. In some embodiments, amine-modified nucleotides can be used when generating the extended capture probe or the second strand, or both. For example, the amine-modified nucleotides can be aminoallyl (aa)-dUTP, aa-dCTP, aa-dGTP, and/or aa-dATP.

In some embodiments, after generation of the extended capture probe, the second strand, or both the extended capture probe and/or the second strand can be released from the surface of the substrate. For example, the extended capture probe and/or the second strand can be released by any of the methods described herein (e.g., heat or cleavage via a cleavage domain). In some embodiments, the amine-modified nucleotides incorporated into the extended capture probe can be cross-linked to the surface of a substrate or cross-linked to the biological sample using its amine-modified nucleotides. In some embodiments, the surface of the substrate can be coated in a hydrogel. In some embodiments, the surface of the substrate can be coated in a protein matrix. In some embodiments, the cross-linking can be irreversible. In some embodiments, the cross-linked extended capture probe and/or second strand can be circularized. For example, circular template ligation can be performed by a DNA ligase (e.g., T4 DNA ligase) or circular template-free ligation can be performed by a template independent ligase (e.g., CircLigase). In some embodiments, the extended capture probe is circularized with CircLigase. In some embodiments, the circularized extended capture probe can be amplified. For example, rolling circle amplification can be performed with a suitable DNA polymerase (e.g., phi29). In some embodiments, the capture probe includes a functional domain (e.g., sequencing adapter). In some embodiments, rolling circle amplification can be performed with a primer complementary to the functional domain (e.g., sequencing adapter). In some embodiments, the rolling circle amplification can be performed to generate two or more amplicons (e.g., one or more amplicons including any of the amine-modified nucleotides described herein). In some embodiments, the two or more amplicons produced by the rolling circle amplification can be cross-linked to the surface of the substrate and/or cross-linked to the biological sample. In some embodiments, the two or more amplicons can be sequenced in situ. The in situ sequencing can be performed by any method described herein (See, Lee, J. H., Fluorescent in situ sequencing (FISSEQ) of RNA for gene expression profiling, *Nat Protoc.,* 10(3): 442-458, doi:10.1038/nprot.2014.191 (2015), which is incorporated herein by reference). In some embodiments, the two or more amplicons can be imaged.

In some embodiments, spatial analysis by any of the methods described herein can be performed on ribosomal RNA (rRNA), including, endogenous ribosomal RNA (e.g., native to the biological sample), and/or exogenous RNA (e.g., microbial ribosomal RNA and/or viral RNA also present in the biological sample). As used herein, "metagenomics," can refer to the study of exogenous nucleic acids (e.g., DNA, RNA, or other nucleic acids described herein) present in a biological sample. As used herein, "spatial metagenomics," can refer to the study of the spatial location of exogenous nucleic acid present in a biological sample. Spatial metagenomics can also refer to the identification of one or more species (e.g., viral or microbial) present in the biological sample and/or the study of identifying patterns of proximity (e.g., co-localization) amongst species.

In some embodiments, microbial rRNA can be spatially detected, quantified, and/or amplified from a biological sample. In some embodiments, rRNA (e.g., 16S ribosomal RNA) can be associated with a particular microbial species. For example, microbial ribosomal RNA (e.g., 16S ribosomal RNA) can be used to identify one or more species of microbe present in the biological sample (See e.g., Kolbert, C. P., and Persing, D. H., Ribosomal DNA sequencing as a tool for identification of bacterial pathogens, *Current Opinion in Microbiology.* 2 (3): 299-305. doi:10.1016/S1369-5274(99)80052-6. PMID 10383862 (1999), which is incorporated herein by reference). In some embodiments, identification of microbial species in proximity to one or more other microbial species can be identified.

In some embodiments, a biological sample be covered (e.g., coated) or embedded in with a photo-crosslinkable coating (e.g., conditionally dissolvable polymer, e.g., DTT sensitive hydrogel). A biological sample can be contacted with the photo-crosslinkable coated substrate. In some embodiments, the biological sample and photo-crosslinkable substrate are assembled into a flow-cell and the photo-crosslinkable polymer can be incubated with the biological sample. The biological sample can be cross-linked into hydrogel-voxels of defined dimensions using a light source and a photomask. In some embodiments, the flow-cell can be dismantled and washed to remove unpolymerized hydrogel. The photo-crosslinkable coating can be treated with DTT to yield single-cell portions or approximately single-cell portions.

In some embodiments, the single-cell or approximately single-cell portions can be encapsulated in a vesicle. The vesicle can contain a barcoded feature (e.g., a bead), and the barcoded feature can contain a capture domain. In some embodiments, the capture domain can bind specifically to microbial rRNA (e.g., microbial 16S rRNA). In some embodiments, the captured microbial rRNA can be amplified and analyzed (e.g., sequenced) by any of the methods described herein. In some embodiments, the amplified and sequenced microbial rRNA can identify microbial species and/or patterns of proximity (e.g., co-localization) of one or more species.

Alternatively, spatial analysis can be performed on exogenous rRNA (e.g., microbial or viral) with a plurality of capture probes on a substrate (e.g., an array), wherein the capture probes include a spatial barcode and a capture domain. In some embodiments, the capture domain can be configured to interact (e.g., hybridize) with microbial rRNA present in the biological sample. The capture probe can be configured to interact with any microbial rRNA. In some embodiments, the capture probe is configured to interact with microbial 16S rRNA. The biological sample can be treated (e.g., permeabilized) such that the capture domain and the analyte (e.g., microbial rRNA) interact (e.g., hybridize). In some embodiments, the captured analyte (e.g., microbial rRNA) can be reverse transcribed generating an extended capture probe, followed generation of a second strand that is complementary to the extended capture probe as described herein. The extended capture probe and/or the second strand can include a portion or all of a capture probe sequence, or a complement thereof. The capture probe sequence, or complement thereof, can include the spatial barcode, or complement thereof. In some embodiments, the first strand cDNA, and optionally, the second strand cDNA can be amplified by any method described herein. The amplified capture probes and analytes can be analyzed (e.g., sequenced) by any method described herein. The spatial information of the spatially-barcoded features can be used to determine the spatial location of the captured analytes (e.g., microbial rRNA) in the biological sample, or a portion thereof. In some embodiments, the captured analyte can identify the microbial species present in the biological sample, or a portion thereof. In some embodiments, the spatial information and identity of microbial species present in the biological sample can be correlated with one another, thus revealing whether certain microbial species may be found in proximity (e.g., co-localize) with one another in the biological sample.

In exemplary embodiments, provided herein are methods for detecting a nucleic acid within a portion of biological sample that include: (a) immobilizing the biological sample in a gel matrix to produce an embedded biological sample; (b) breaking up the embedded biological sample into portions; (c) lysing cell(s) present in the portions; (d) encapsulating a portion from step (c) together with a bead having an attached capture probe comprising a spatial barcode and a capture domain that binds specifically to the nucleic acid in the portion; and (e) determining (i) all or a part of the sequence of the spatial barcode, or a complement thereof, and (ii) all or part of the sequence of the nucleic acid, or a complement thereof, and using the determined sequences of (i) and (ii) to detect the nucleic acid within the portion of the biological sample. In some embodiments of these methods, the nucleic acid comprises microbial ribosomal RNA (rRNA). In some embodiments of these methods, the microbial rRNA comprises 16S rRNA. In some embodiments of these methods, the method comprises detecting 16S rRNA from at least two different microbacteria within the portion of the biological sample. In some embodiments of these methods, the nucleic acid is an mRNA.

Provided herein are methods for spatially profiling analytes within a biological sample. Profiles of biological samples (e.g., individual cells, populations of cells, tissue sections, etc.) can be compared to profiles of other cells, e.g., "normal," or "healthy," biological samples. In some embodiments of any the methods for spatially profiling analytes described herein, the method can provide for diagnosis of a disease (e.g., cancer, Alzheimer's disease, Parkinson's disease). In some embodiments of any the methods for spatially profiling analytes described herein, the methods can be used in drug screening. In some embodiments of any the methods for spatially profiling analytes described herein, the methods can be used to perform drug screening with an organoid. In some embodiments of any the methods for spatially profiling analytes described herein, the methods can be used to detect changes in (e.g., altered) cellular signaling. In some embodiments of any the methods for spatially profiling analytes described herein, the methods can include the introduction of a pathogen to the biological sample and evaluation of the response of the biological sample to the pathogen. In some embodiments of any the methods for spatially profiling analytes described herein, the methods include exposing the biological sample to a perturbation agent (e.g., any of the perturbation agents described herein) and evaluating the response of the biological sample to the perturbation agent. In some embodiments of any the methods for spatially profiling analytes described herein, the methods include monitoring cell differentiation in a biological sample (e.g., an organoid). In some embodiments of any the methods for spatially profiling analytes described herein, the methods include analyzing tissue morphogenesis. In some embodiments of any the methods for spatially profiling analytes described herein, the methods include identifying spatial heterogeneity in a biological sample (e.g., identifying different cell types or populations in a biological sample). In some embodiments of any the methods for spatially profiling analytes described herein, the methods include analyzing the spatiotemporal order (e.g., timing) of molecular events. For example, the methods for spatially profiling analytes can include monitoring expression levels over the course of a disease.

The methods provided herein can also be used to determine a relative level of inflammation in a subject (e.g., determine an inflammatory score) or a subject's response to treatment or the development of resistance to treatment. The methods described herein can also be used to identify candidate targets for potential therapeutic intervention and/or to identify biomarkers associated with different disease states in a subject.

(h) Quality Control (i) Control Sample

As used herein, the term "control sample" typically refers to a substrate that is insoluble in aqueous liquid and that allows for an accurate and traceable positioning of test analytes on the substrate. The term "control sample" and "test substrate" are used interchangeably herein. The control sample can be any suitable substrate known to the person skilled in the art. Exemplary control samples comprise a semi-porous material. Non-limiting examples of a semi-porous material include a nitrocellulose membrane, a hydrogel, and a nylon filter.

A control sample or test substrate can be of any appropriate dimension or volume (e.g., size or shape). In some embodiments, a control sample is a regular shape (e.g., a square, circle, or a rectangle). In some embodiments, a surface of a control sample has any appropriate form or format. For example, the surface of a control sample can be flat or curved (e.g., convexly or concavely curved towards the area where the interaction between the substrate and the control sample takes place). In some embodiments, a control sample has rounded corners (e.g., for increased safety or robustness). In some embodiments, a control sample has one or more cut-off corners (e.g., for use with a slide clamp or cross-table).

A control sample can comprise a plurality of test analytes. In some embodiments, the members of the plurality of test analytes are disposed on the substrate in a known amount and in a known location. For example, a plurality of test analytes are disposed at a known amount on the control sample at one or more locations. In some embodiments, the plurality of test analytes are disposed on the substrate in a defined pattern (e.g., an x-y grid pattern). In some embodiments, the defined pattern includes one or more locations or spots.

In some embodiments, each location comprises a plurality of the same species of test analyte. In some embodiments, each location comprises a plurality of one or more different species of test analytes. In some embodiments, each location on the control sample represents a different region of a biological sample, e.g., a tissue sample. In some embodiments, an area on the control sample that does not comprise a plurality of test analytes represents an area where no biological sample is present.

In some embodiments, the plurality of test analytes comprises one or more test analytes, e.g., a first test analyte, a second test analyte, a third test analyte, a fourth test analyte, etc. In some embodiments, the plurality of test analytes comprises nucleic acids. In some embodiments, each location or feature comprises a population of nucleic acid sequences. In some embodiments, the nucleic acid sequence of a first test analyte differs from the nucleic acid sequence of a second test analyte by a single nucleic acid residue. In some embodiments, each location or feature comprises a population of RNA transcripts and one or more specific surface marker proteins or one or more CRISPR guide RNAs. In some embodiments, the plurality of test analytes comprises a bacterial artificial chromosomes (BAC). In some embodiments, each location on the control sample comprises a unique blend of BACs. In some embodiments, proteins are cross-linked to the BACs, for example, to mimic histone binding on DNA.

In some embodiments, the concentration of a first test analyte differs from the concentration of a second test analyte at a different location or feature on the control sample. In some embodiments, the first test analyte and the second test analyte comprise an identical nucleotide sequence.

A control sample can be used to determine process bias. Barcoded arrays can be placed on top of a control sample comprising a plurality of test analytes, where members of the plurality of test analytes can be disposed on a substrate in a known amount and in a known location. The array can then be removed, and the molecular information therein can be determined by performing library construction for next generation sequencing, followed by computational analysis to correlate the expression values of the test analytes with the barcodes (e.g., spatial barcodes) on the array. The sequencing data can be compared with the known amount and the known locations of the plurality of test analytes to determine whether the spatial analysis workflow accurately detects the presence, amount, location, or combinations thereof, of the test analyte, thereby determining process bias of the spatial analysis workflow.

III. General Spatial Cell-Based Analytical Methodology

(a) Barcoding a Biological Sample

In some embodiments, provided herein are methods and materials for attaching and/or introducing a molecule (e.g., a peptide, a lipid, or a nucleic acid molecule) having a barcode (e.g., a spatial barcode) to a biological sample (e.g., to a cell in a biological sample) for use in spatial analysis. In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis.

Figure 18:
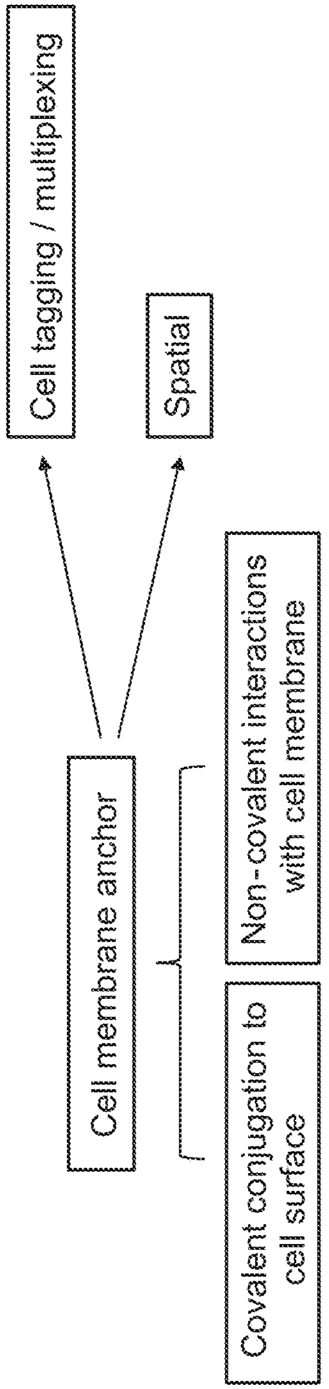
FIG. 18 is a schematic depicting cell tagging using either covalent conjugation of the analyte binding moiety to the cell surface or non-covalent interactions with cell membrane elements.

FIG. 18 is a schematic diagram depicting cell tagging using either covalent conjugation of an analyte binding moiety to a cell surface or non-covalent interactions with cell membrane elements. FIG. 18 lists non-exhaustive examples of a covalent analyte binding moiety/cell surface interactions, including protein targeting, amine conjugation using NHS chemistry, cyanuric chloride, thiol conjugation via maleimide addition, as well as targeting glycoproteins/glycolipids expressed on the cell surface via click chemistry. Non-exhaustive examples of non-covalent interactions with cell membrane elements include lipid modified oligos, biocompatible anchor for cell membrane (BAM, e.g., oleyl-PEG-NHS), lipid modified positive neutral polymer, and antibody to membrane proteins. A cell tag can be used in combination with an analyte capture agent and cleavable or non-cleavable spatially-barcoded capture probes for spatial and multiplexing applications.

In some embodiments, a plurality of molecules (e.g., a plurality of lipid or nucleic acid molecules) having a plurality of barcodes (e.g., a plurality of spatial barcodes) are introduced to a biological sample (e.g., to a plurality of cells in a biological sample) for use in spatial analysis, wherein the plurality of molecules are introduced to the biological sample in an arrayed format. In some embodiments, a plurality of molecules (e.g., a plurality of lipid or nucleic acid molecules) having a plurality of barcodes are provided on a substrate (e.g., any of the variety of substrates described herein) in any of the variety of arrayed formats described herein, and the biological sample is contacted with the molecules on the substrate such that the molecules are introduced to the biological sample. In some embodiments, the molecules that are introduced to the biological sample are cleavably attached to the substrate, and are cleaved from the substrate and released to the biological sample when contacted with the biological sample. In some embodiments, the molecules introduced to the biological sample are covalently attached to the substrate prior to cleavage. In some embodiments, the molecules that are introduced to the biological sample are non-covalently attached to the substrate (e.g., via hybridization), and are released from the substrate to the biological sample when contacted with the biological sample.

In some embodiments, a plurality of molecules (e.g., a plurality of lipid or nucleic acid molecules) having a plurality of barcodes (e.g., a plurality of spatial barcodes) are migrated or transferred from a substrate to cells of a biological sample. In some embodiments, migrating a plurality of molecules from a substrate to cells of a biological sample includes applying a force (e.g., mechanical, centrifugal, or electrophoretic) to the substrate and/or the biological sample to facilitate migration of the plurality of molecules from the substrate to the biological sample.

In some embodiments of any of the spatial analysis methods described herein, physical force is used to facilitate attachment to or introduction of a molecule (e.g., a nucleic acid molecule) having a barcode (e.g., a spatial barcode) into a biological sample (e.g., a cell present in a biological sample). As used herein, "physical force" refers to the use of a physical force to counteract the cell membrane barrier in facilitating intracellular delivery of molecules. Examples of physical force instruments and methods that can be used in accordance with materials and methods described herein include the use of a needle, ballistic DNA, electroporation, sonoporation, photoporation, magnetofection, hydroporation, and combinations thereof.

(i) Introducing a Cell-Tagging Agent to the Surface of a Cell

In some embodiments, biological samples (e.g., cells in a biological sample) can be labelled using cell-tagging agents where the cell-tagging agents facilitate the introduction of the molecules (e.g., nucleic acid molecules) having barcodes (e.g., spatial barcodes) into the biological sample (e.g., into cells in a biological sample). As used herein, the term "cell-tagging agent" refers to a molecule having a moiety that is capable of attaching to the surface of a cell (e.g., thus attaching the barcode to the surface of the cell) and/or penetrating and passing through the cell membrane (e.g., thus introducing the barcode to the interior of the cell). In some embodiments, a cell-tagging agent includes a barcode (e.g., a spatial barcode). The barcode of a barcoded cell-tagging agent can be any of the variety of barcodes described herein. In some embodiments, the barcode of a barcoded cell-tagging agent is a spatial barcode. In some embodiments, a cell-tagging agent comprises a nucleic acid molecule that includes the barcode (e.g., the spatial barcode). In some embodiments, the barcode of a barcoded cell-tagging agent identifies the associated molecule, where each barcode is associated with a particular molecule. In some embodiments, one or more molecules are applied to a sample. In some embodiments, a nucleic acid molecule that includes the barcode is covalently attached to the cell-tagging agent. In some embodiments, a nucleic acid molecule that includes the barcode is non-covalently attached to the cell-tagging agent. A non-limiting example of non-covalent attachment includes hybridizing the nucleic acid molecule that includes the barcode to a nucleic acid molecule on the cell-tagging agent (which nucleic acid molecule on the cell-tagging agent can be bound to the cell-tagging agent covalently or non-covalently). In some embodiments, a nucleic acid molecule attached to a cell-tagging agent that includes a barcode (e.g., a spatial barcode) also includes one or more additional domains. Such additional domains include, without limitation, a PCR handle, a sequencing priming site, a domain for hybridizing to another nucleic acid molecule, and combinations thereof.

In some embodiments, a cell-tagging agent attaches to the surface of a cell. When the cell-tagging agent includes a barcode (e.g., a nucleic acid that includes a spatial barcode), the barcode is also attached to the surface of the cell. In some embodiments of any of the spatial analysis methods described herein, a cell-tagging agent attaches covalently to the cell surface to facilitate introduction of the spatial analysis reagents. In some embodiments of any of the spatial analysis methods described herein, a cell-tagging agent attaches non-covalently to the cell surface to facilitate introduction of the spatial analysis reagents.

In some embodiments, once a cell or cells in a biological sample is spatially tagged with a cell-tagging agent(s), spatial analysis of analytes present in the biological sample is performed. In some embodiments, such spatial analysis includes dissociating the spatially-tagged cells of the biological sample (or a subset of the spatially-tagged cells of the biological sample) and analyzing analytes present in those cells on a cell-by-cell basis. Any of a variety of methods for analyzing analytes present in cells on a cell-by-cell basis can be used. Non-limiting examples include any of the variety of methods described herein and methods described in PCT Application Publication No. WO 2019/113533A1, the content of which is incorporated herein by reference in its entirety. For example, the spatially-tagged cells can be encapsulated with beads comprising one or more nucleic acid molecules having a barcode (e.g., a cellular barcode) (e.g., an emulsion). The nucleic acid present on the bead can have a domain that hybridizes to a domain on a nucleic acid present on the tagged cell (e.g., a domain on a nucleic acid that is attached to a cell-tagging agent), thus linking the spatial barcode of the cell to the cellular barcode of the bead. Once the spatial barcode of the cell and the cellular barcode of the bead are linked, analytes present in the cell can be analyzed using capture probes (e.g., capture probes present on the bead). This allows the nucleic acids produced (using these methods) from specific cells to be amplified and sequenced separately (e.g., within separate partitions or droplets).

In some embodiments, once a cell or cells in a biological sample is spatially tagged with a cell-tagging agent(s), spatial analysis of analytes present in the biological sample is performed in which the cells of the biological sample are not dissociated into single cells. In such embodiments, various methods of spatial analysis such as any of those provided herein can be employed. For example, once a cell or cells in a biological sample is spatially tagged with a cell-tagging agent(s), analytes in the cells can be captured and assayed. In some embodiments, cell-tagging agents include both a spatial barcode and a capture domain that can be used to capture analytes present in a cell. For example, cell-tagging agents that include both a spatial barcode and a capture domain can be introduced to cells of the biological sample in a way such that locations of the cell-tagging agents are known (or can be determined after introducing them to the cells). One non-limiting example of introducing cell-tagging agents to a biological sample is to provide the cell-tagging agents in an arrayed format (e.g., arrayed on a substrate such as any of the variety of substrates and arrays provided herein), where the positions of the cell-tagging agents on the array are known at the time of introduction (or can be determined after introduction). The cells can be permeabilized as necessary (e.g., using permeabilization agents and methods described herein), reagents for analyte analysis can be provided to the cells (e.g., a reverse transcriptase, a polymerase, nucleotides, etc., in the case where the analyte is a nucleic acid that binds to the capture probe), and the analytes can be assayed. In some embodiments, the assayed analytes (and/or copies thereof) can be released from the substrate and analyzed. In some embodiments, the assayed analytes (and/or copies thereof) are assayed in situ.

Non-limiting examples of cell-tagging agents and systems that attach to the surface of a cell (e.g., thus introducing the cell-tagging agent and any barcode attached thereto to the exterior of the cell) that can be used in accordance with materials and methods provided herein for spatially analyzing an analyte or analytes in a biological sample include: lipid tagged primers/lipophilic-tagged moieties, positive or neutral oligo-conjugated polymers, antibody-tagged primers, streptavidin-conjugated oligonucleotides, dye-tagged oligonucleotides, click-chemistry, receptor-ligand systems, covalent binding systems via amine or thiol functionalities, and combinations thereof.

(ii) Introducing a Cell-Tagging Agent to the Interior of a Cell

Non-limiting examples of cell-tagging agents and systems that penetrate and/or pass through the cell membrane (e.g., thus introducing the cell-tagging agent and any barcode attached thereto to the interior of the cell) that can be used in accordance with materials and methods provided herein for spatially profiling an analyte or analytes in a biological sample include: a cell-penetrating agent (e.g., a cell-penetrating peptide), a nanoparticle, a liposome, a polymersome, a peptide-based chemical vector, electroporation, sonoporation, lentiviral vectors, retroviral vectors, and combinations thereof.

In some embodiments, a cell-tagging agent comprises a cell-penetrating agent (described below). In some embodiments, a cell-penetrating agent transports the cell-tagging agent into the cells of a biological sample. When a cell-tagging agent comprises a barcode (e.g., a nucleic acid that includes a spatial barcode), the barcode also penetrates into the cell. In some embodiments, a plurality of cell-tagging agents are cleaved (e.g., photocleaved) from an array via a cleavage domain, thus freeing the cell-tagging agents from the array and allowing at least one capture probe of the plurality to penetrate a cell. The cell-tagging agent can then interact with an intracellular biological analyte via the capture domain. In some embodiments, the plurality of capture probes is migrated from the array into cells of the biological sample via cell-penetrating agents. In some embodiments, migrating a plurality of capture probes from the array to cells of the biological sample includes applying a force (e.g., mechanical, centrifugal, or electrophorectic) to the biological sample.

In some embodiments, the biological sample is treated with one or more reagents to facilitate migration of a plurality of freed (e.g., cleaved) capture probes into cells of a biological sample. In one embodiment, an organic solvent (e.g., methanol or acetone) may be used to permeabilize cells of a biological sample. In another embodiment, a detergent (e.g., saponon, Triton X-100™, or Tween-20™) may be used to permeabilize cells of a biological sample. In yet another embodiment, an enzyme (e.g., trypsin) may be used to permeabilize cells of a biological sample. Any suitable method of cell permeabilization may be used to practice the methods disclosed herein. In some embodiments, the biological sample can be incubated with a cellular permeabilization reagent after contacting the array with the biological sample. In some embodiments, the biological sample can be fixed according to methods described herein.

In some embodiments, migrating a plurality of freed (e.g., cleaved) capture probes into cells of a biological sample includes passive migration (e.g., diffusion). In some embodiments, migrating a plurality of freed (e.g. cleaved) capture probes into cells of a biological sample includes active migration (e.g., electrophoretic migration). In some embodiments, migrating a plurality of freed (e.g., cleaved) capture probes into cells of a biological sample comprises antibodies. In some embodiments, migrating a plurality of freed (e.g., cleaved) capture probes into cells of a biological sample comprises transfection (e.g., chemical, biological, physical, viral vectors).

Figure 19:
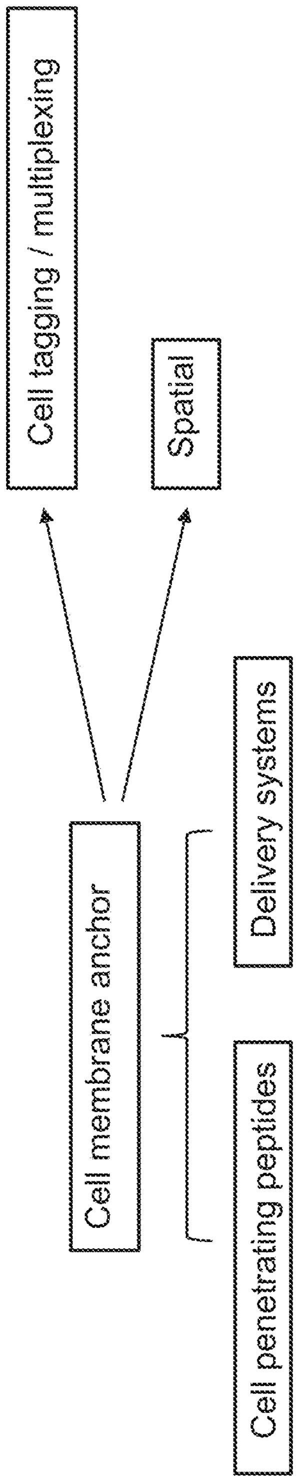
FIG. 19 is a schematic depicting cell tagging using either cell-penetrating peptides or delivery systems.

FIG. 19 is a schematic showing an exemplary cell tagging method. Non-exhaustive examples of oligo delivery vehicles may include a cell penetrating peptide or a nanoparticle. Non-exhaustive examples of the delivery systems can include lipid-based polymeric and metallic nanoparticles or oligos that can be conjugated or encapsulated within the delivery system. The cell tag can be used in combination with a capture agent barcode domain and a cleavable or non-cleavable spatially-barcoded capture probes for spatial and multiplexing applications.

Non-limiting methods and compositions for introducing a cell-tagging agent to the interior of a cell are disclosed in WO 2020/047010 A2; WO 2020/047004 A2; WO 2020/047007 A2; WO 2020/047005 A2; WO 2020/047002 A1; PCT/US2019/065077; PCT/US2019/065048; PCT/US2019/064987; PCT/US2019/065013; PCT/US2019/065100; PCT/US2019/065072; PCT/US2019/065081; PCT/US2019/065096; and PCT/US2019/065041; each of which is incorporated by reference in its entirety.

1. Cell-Penetrating Agent

In some embodiments of any of the spatial profiling methods described herein, identification of a biological analyte by a molecule (e.g., a nucleic acid molecule) having a barcode (e.g., a spatial barcode) and a capture domain is facilitated by a cell-penetrating agent. In some embodiments, a molecule (e.g., a nucleic acid molecule) having a barcode (e.g., a spatial barcode) and a capture domain is coupled to a cell-penetrating agent, and the cell-penetrating agent allows the molecule to interact with an analyte inside the cell. A "cell-penetrating agent" as used herein can refer to an agent capable of facilitating the introduction of a molecule (e.g., a nucleic acid molecule) having a barcode (e.g., a spatial barcode) and a capture domain into a cell of a biological sample (see, e.g., Lovatt et al. Nat Methods. 2014 February; 11(2):190-6, which is incorporated herein by reference in its entirety). In some embodiments, a cell-penetrating agent is a cell-penetrating peptide. A "cell-penetrating peptide" as used herein refers to a peptide (e.g., a short peptide, e.g., a peptide not usually exceeding 30 residues) that has the capacity to cross cellular membranes. In some embodiments, cell-penetrating agents or cell penetrating peptides may be covalently or non-covalently coupled to a molecule (e.g., a barcoded nucleic acid molecule), likely at the 5' end of the molecule. A cell-penetrating peptide may direct the barcoded nucleic acid molecule to a specific organelle.

In some embodiments of any of the spatial profiling methods described herein, a cell-penetrating peptide coupled to a molecule (e.g., a nucleic acid molecule) having a barcode (e.g., a spatial barcode) and a capture domain can cross a cellular membrane using an energy dependent or an energy independent mechanism. For example, a cell-penetrating peptide can cross a cellular membrane through direct translocation through physical perturbation of the plasma membrane, endocytosis (e.g., mediated via clathrin), adaptive translocation, pore-formation, electroporation-like permeabilization, and/or entry at microdomain boundaries. Non-limiting examples of a cell-penetrating peptide include: penetratin, tat peptide, pVEC, transportan, MPG, Pep-1, a polyarginine peptide, MAP, R6W3, (D-Arg)9, Cys(Npys)-(D-Arg)9, Anti-BetaGamma (MPS—Phosducin-like protein C terminus), Cys(Npys) antennapedia, Cys(Npys)-(Arg)9, Cys(Npys)-TAT (47-57), HIV-1 Tat (48-60), KALA, mastoparan, penetratin-Arg, pep-1-cysteamine, TAT(47-57) GGG-Cys(Npys), Tat-NR2Bct, transdermal peptide, SynB1, SynB3, PTD-4, PTD-5, FHV Coat-(35-49), BMV Gag-(7-25), HTLV-II Rex-(4-16), R9-tat, SBP, FBP, MPG, MPG (ANLS), Pep-2, MTS, plsl, and a polylysine peptide (see, e.g., Bechara et al. FEBS Lett. 2013 Jun. 19; 587(12):1693-702, which is incorporated by reference herein in its entirety).

In some embodiments, there could be two orientations for cell-penetrating peptide (CPP) conjugation. For example, one orientation can be (N-terminus)-CPP-Cys-(C-terminus)-linker-NH2C6-5'-oligo-3'; 3'-oligo-5'-NH2C6-linker-(N-terminus)-Cys-CPP-(C-terminus). The methods herein can be performed with other CPP conjugations and orientations.

In some embodiments, cell-tagging agents further comprise a cell-penetration tag. A "cell-penetration tag" as used herein refers to an agent that can be detected as inside a cell. In some embodiments, a cell penetration tag includes a fluorophore. In some embodiments, a cell penetration tag is selected from the group consisting of: Cy2, Cy3, Cy3B, Cy3.5, Cy5, Cy5.5, Cy7, fluorescein (6-FAM), DyLight, Alexa Fluor®, and tetramethylrhodamine (TAMRA) azide.

In some embodiments, a cell penetration tag is detected. In some embodiments, a cell penetration tag is detected after releasing a plurality of capture probes from the array and removing the array from the biological sample. In some embodiments, introduction of a cell-tagging agent into the cell is determined by detecting the presence of the cell penetration tag in the cell.

In some embodiments, cell-tagging agents can optionally include an intracellular cleavage domain, wherein one or more segments or regions of the capture probe (e.g., capture domains, spatial barcodes, and/or UMIs) can be releasably or cleavably bound to the cell-penetrating agent, such that the capture domain, spatial barcode, and/or UMI can be released. In some embodiments, the cleavage of the linkage between the capture domain, spatial barcode, and/or UMI and the cell-penetrating agent is induced in an intracellular environment (e.g., the intracellular cleavage domain is cleaved after the cell-tagging agent is introduced into the cell). In some embodiments, the intracellular cleavage domain comprises a disulfide bond. For example, the intracellular cleavage domain can be a disulfide bond cleaved by reducing conditions in the cell. Any other suitable linker can be used to release or cleave the intracellular cleavage domain of the capture probe.

(iii) Other Barcodes

Additional barcodes disclosed herein feature barcodes with lipid tagged primers/lipophilic-tagged moieties, barcodes with one or more intracellular cleavage domain, barcodes coupled to positive or neutral oligo-conjugated polymers, barcodes coupled to a bifunctional NHS linker, barcodes coupled to an antibody or antigen binding fragment thereof in a manner that facilitates attachment of the molecule (e.g., a nucleic acid molecule) having a barcode to the surface of a cell; barcodes attached to the surface of a cell using biotin-streptavidin (or biotin-avidin); barcodes directly linked to a detectable label; barcodes coupled to click-chemistry moieties; barcodes coupled to a ligand, wherein the ligand is part of a receptor-ligand interaction on the surface of a cell; barcodes that incorporate reactive functional groups at sites within the molecule (e.g., with a nucleic acid sequence); barcodes coupled to an azide group on a cell surface; or barcodes coupled to a lectin that facilitates attachment of the molecule (e.g., a nucleic acid molecule) having a barcode (e.g., a spatial barcode) to a cell surface. Exemplary barcodes are disclosed in WO 2020/047010 A2; WO 2020/047004 A2; WO 2020/047007 A2; WO 2020/047005 A2; WO 2020/047002 A1; PCT/US2019/065077; PCT/US2019/065048; PCT/US2019/064987; PCT/US2019/065013; PCT/US2019/065100; PCT/US2019/065072; PCT/US2019/065081; PCT/US2019/065096; and PCT/US2019/065041; each of which is incorporated by reference in its entirety.

(b) Methods for Separating a Sample into Single Cells or Cell Groups

Some embodiments of any of the methods described herein can include separating a biological sample into single cells, cell groups, types of cells, or a region or regions of interest. For example, a biological sample can be separated into single cells, cell groups, types of cells, or a region or regions of interest before being contacted with one or more capture probes. In other examples, a biological sample is first contacted with one or more capture probes, and then separated into single cells, cell groups, types of cells, or a region or regions of interest.

In some embodiments, a biological sample can be separated into chucks using pixelation. Pixelation can include the steps of providing a biological sample, and punching out one or more portions of the biological sample. The punched out portions of the biological sample can then be used to perform any of the methods described herein. In some embodiments, the punched-out portions of the biological sample can be in a random pattern or a designed pattern. In some embodiments, the punched-out portions of the biological sample can be focused on a region of interest or a subcellular structure in the biological sample.

Figure 20A:
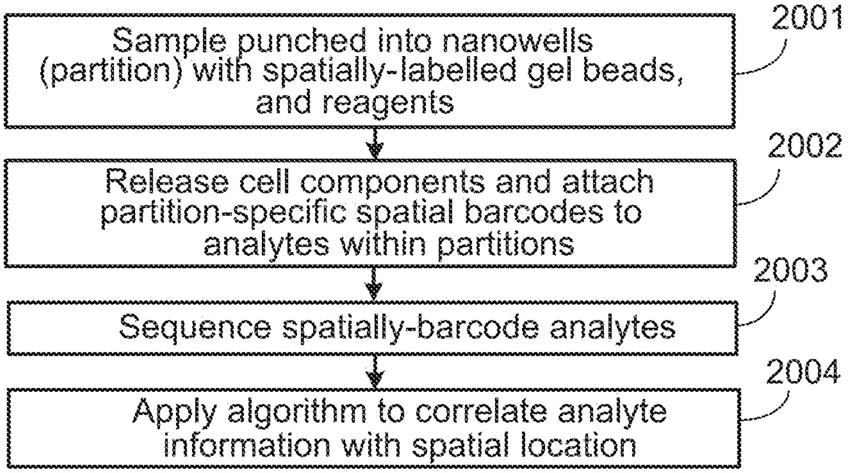
FIG. 20A is a workflow schematic illustrating exemplary, non-limiting, non-exhaustive steps for "pixelating" a sample, wherein the sample is cut, stamped, microdissected, or transferred by hollow-needle or microneedle, moving a small portion of the sample into an individual partition or well.

FIG. 20A is a workflow schematic illustrating exemplary, non-limiting, non-exhaustive steps for "pixelating" a sample, wherein the sample is cut, stamped, microdissected, or transferred by hollow-needle or microneedle, moving a small portion of the sample into an individual partition or well.

Figure 20B:
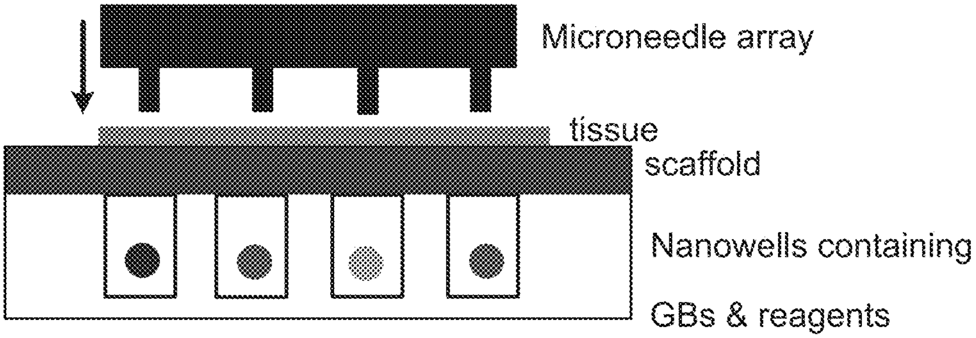
FIG. 20B is a schematic depicting multi-needle pixilation, wherein an array of needles punched through a sample on a scaffold and into nanowells containing gel beads and reagents below. Once the needle is in the nanowell, the cell(s) are ejected.

FIG. 20B is a schematic depicting multi-needle pixelation, wherein an array of needles is punched through a sample on a scaffold, into nanowells containing beads (e.g., gel beads) and reagents. Once the needle is in the nanowell, the cell(s) are ejected.

In some embodiments, a biological sample (e.g., a tissue sample or tissue section) is divided into smaller portions as compared to the original biological sample size ("chunks") before performance of any of the spatial analysis methods described herein. In some embodiments, the methods can include spatial barcoding of FFPE "chunks" via barcodes applied in a spatially well-defined pattern (e.g., array printing). In order to associate a spatial barcode with a particular "chunk" of biological sample, the barcode (e.g., a spatial barcode) can be of a sufficient length to prevent diffusion of the barcode in subsequent steps, or the spatial barcode can be covalently applied to the FFPE sample. In some embodiments, the spatial barcode is unique to each FFPE chunk. In some embodiments, spatial barcodes can be embedded onto an FFPE slide (e.g., within a matrix, such as a wax or a hydrogel). In some embodiments, the FFPE slide is heated (e.g., wax is heated) prior to addition of the spatial barcodes. In some embodiments, after addition of the spatial barcodes, the FFPE slide can be cooled and cut or dissociated into chunks. Methods of chunking (e.g., cutting) biological samples are known in the art. For example, in a non-limiting example, chunking of biological samples can be done in various ways such as laser microdissection, mechanical means, acoustic (e.g., sonication) means, or any other method described herein. In some embodiments, fluorophores/Qdots, etc. can be embedded in the chunk to preserve spatial information about the biological sample. Barcoding at this step enables massively parallel encapsulation of chunks while retaining local spatial information (e.g., tumor versus normal/healthy cells). In some embodiments, chunking of a biological sample (e.g., a tissue section) can result in single-cell chunks of the biological sample. In other embodiments, chunking of a biological sample can be performed to obtain chunks that correspond to diseased portions of the biological sample. In another embodiment, chunking of biological samples can be performed to obtain discrete chunks of the biological sample that correspond to diseased or healthy portions of the biological sample. In some embodiments, chunking of biological samples can be performed to obtain chunks that correspond to specific cell types (e.g., chunking based on fluorescent or chemiluminescent imaging of antibodies bound to target proteins) in the biological sample.

In some embodiments, the spatially-barcoded chunks can be further processed. For example, the spatially-barcoded chunk can be individually encapsulated (e.g., a matrix, emulsion, or hydrogel). In some embodiments, the spatially-barcoded chunk can be encapsulated in a partition (e.g., a well, droplet, channel, or vesicle). In some embodiments, the spatially-barcoded chunk can be encapsulated in a vesicle. In some embodiments, the vesicle can comprise a lipid bilayer. In some embodiments, the spatially-barcoded FFPE chunk can be encapsulated with a uniquely barcoded bead. In some embodiments, the uniquely barcoded bead can have a functional domain, a cleavage domain, a unique molecular identifier, and a capture domain, or combinations thereof. In some embodiments, the encapsulated spatially-barcoded FFPE chunk and the uniquely barcoded bead can be heated to deparaffinize the FFPE sample. In some embodiments, the encapsulated spatially-barcoded FFPE chunk and the uniquely barcoded bead can be treated with xylene to deparaffinize the FFPE sample. In some embodiments, the deparaffinized sample can be treated to de-crosslink methylene bridges in a single step. In some embodiments, additional steps can be performed when, for example, de-crosslinking chemistry is incompatible with barcoding or library preparation steps. In some embodiments, after de-crosslinking methylene bridges, the nucleic acids originating or present in the chunk can bind to the uniquely barcoded bead. In some embodiments, after the spatial barcode binds the uniquely barcoded bead, the encapsulation can be disrupted (e.g., lysed, melted, or removed) and the barcoded beads can be collected. In some embodiments, the collected barcoded beads can be washed and re-encapsulated. In some embodiments, the nucleic acids associated with the bead (e.g., spatial barcode, unique barcode, analyte transcript) can be amplified (e.g., PCR amplified) and processed (e.g., sequenced) according to any of the methods described herein.

In some embodiments, a biological sample can be divided or portioned using laser capture microdissection (e.g., highly-multiplexed laser capture microdissection).

(c) Release and Amplification of Analytes

In some embodiments, lysis reagents can be added to the sample to facilitate release of analyte(s) from a sample. Examples of lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes. Other lysis agents can additionally or alternatively be co-partitioned with the biological sample to cause the release of the sample's contents into the partitions. In some embodiments, surfactant-based lysis solutions can be used to lyse cells, although these can be less desirable for emulsion-based systems where the surfactants can interfere with stable emulsions. Lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of biological materials that can be in addition to or in place of droplet partitioning, where any pore volume of the encapsulate is sufficiently small to retain nucleic acid fragments of a given size, following cellular disruption.

In addition to the permeabilization agents, other reagents can also be added to interact with the biological sample, including, for example, DNase and RNase inactivating agents or inhibitors or chelating agents, such as EDTA, and other reagents to allow for subsequent processing of analytes from the sample. In other embodiments, nucleases, such as DNase or RNAse, or proteases, such as pepsin or proteinase K, are added to the sample.

Further reagents that can be added to a sample, include, for example, endonucleases to fragment DNA, DNA polymerase enzymes, and dNTPs used to amplify nucleic acids. Other enzymes that can also be added to the sample include, but are not limited to, polymerase, transposase, ligase, proteinase K, and DNAse, etc. Additional reagents can also include reverse transcriptase enzymes, including enzymes with terminal transferase activity, primers, and switch oligonucleotides. In some embodiments, template switching can be used to increase the length of a cDNA, e.g., by appending a predefined nucleic acid sequence to the cDNA.

If a tissue sample is not permeabilized sufficiently, the amount of analyte captured on the substrate can be too low to enable adequate analysis. Conversely, if the tissue sample is too permeable, the analyte can diffuse away from its origin in the tissue sample, such that the relative spatial relationship of the analytes within the tissue sample is lost. Hence, a balance between permeabilizing the tissue sample enough to obtain good signal intensity while still maintaining the spatial resolution of the analyte distribution in the tissue sample is desired.

In some embodiments, where the biological sample includes live cells, permeabilization conditions can be modified so that the live cells experience only brief permeabilization (e.g., through short repetitive bursts of electric field application), thereby allowing one or more analytes to migrate from the live cells to the substrate while retaining cellular viability.

In some embodiments, after contacting a biological sample with a substrate that include capture probes, a removal step is performed to remove all or a portion of the biological sample from the substrate. In some embodiments, the removal step includes enzymatic or chemical degradation of the permeabilized cells of the biological sample. For example, the removal step can include treating the biological samples with an enzyme (e.g., proteinase K) to remove at least a portion of the biological sample from the first substrates. In some embodiments, the removal step can include ablation of the tissue (e.g., laser ablation).

In some embodiments, where RNA is captured from cells in a sample, one or more RNA species of interest can be selectively enriched. For example, one or more species of RNA of interest can be selected by addition of one or more oligonucleotides. One or more species of RNA can be selectively down-selected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved RNA capture due to the reduction in non-specific RNA present in the sample. In some embodiments, the additional oligonucleotide is a sequence used for priming a reaction by a polymerase. For example, one or more primer sequences with sequence complementarity to one or more RNAs of interest, can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. In one non-limiting example, biotinylated oligonucleotides with sequence complementary to one or more cDNA of interest binds to the cDNA and can be selected using biotinylation-strepavidin affinity in any number of methods known to the field (e.g., streptavidin beads).

In some embodiments, any of the spatial analysis methods described herein can include modulating the rate of interaction between biological analytes from the biological sample and the capture probes on the array. In some embodiments, modulating the rate of interaction can occur by modulating the biological sample (e.g., modulating temperature or pH). In some embodiments, modulating the rate of interaction includes using external stimuli. Non-limiting examples of external stimuli that can be used to modulate the rate of interaction include light, temperature, small molecules, enzymes, and/or an activating reagent. In one example, light can be used to activate a polymerase in a nucleic acid extension reaction. In another example, temperature can be used to modulate hybridization between two complementary nucleic acid molecules.

Nucleic acid analytes can be amplified using a polymerase chain reaction (e.g., digital PCR, quantitative PCR, or real time PCR), isothermal amplification, or any nucleic acid amplification or extension reactions described herein, or known in the art.

(d) Partitioning

As discussed above, in some embodiments, the sample can optionally be separated into single cells, cell groups (e.g., based on cell sub-type or gene expression profile), or other fragments/pieces that are smaller than the original sample. Each of these smaller portions of the sample can be analyzed to obtain spatially-resolved analyte information from the sample. Non-limiting partitioning methods are described herein.

For samples that have been separated into smaller fragments—and particularly, for samples that have been disaggregated, dissociated, or otherwise separated into individual cells—one method for analyzing the fragments involves partitioning the fragments into individual partitions (e.g., fluid droplets), and then analyzing the contents of the partitions. In general, each partition maintains separation of its own contents from the contents of other partitions. For example, the partition can be a droplet in an emulsion.

The methods described herein provide for the compartmentalization or partitioning of a cell (e.g., a cell) from a sample into discrete compartments or voxels. As used herein, each "voxel" represents a 3-dimensional volumetric unit. In some embodiments, a voxel maintains separation of its own contents from the contents of other voxels. A voxel can be one partition of an array of partitions of volume. For example, a voxel can be one partition of an array of discrete partitions into which a 3-dimensional object is divided. As another example, members of a plurality of photo-crosslinkable polymer precursors can be cross-linked into voxels that are part of an array of the photo-crosslinked polymer covering the substrate or a portion of the substrate. Unique identifiers, e.g., barcodes, may be previously, subsequently, or concurrently delivered to the cell, in order to allow for the later attribution of the characteristics of the cell to the particular voxel. In some embodiments, a voxel has defined dimensions. In some embodiments, a voxel comprises a single cell.

For example, a substrate can be coated with a DTT-sensitive hydrogel and then contacted with a biological sample. Optionally, capture probes attached to the substrate are released from the substrate such that the released capture probes are introduced into the biological sample and at least one released capture probe interacts with at least one biological analyte present in the biological sample via the capture domain. The biological sample and substrate can be assembled into a flow-cell and a photo-crosslinkable polymer precursor added. The cells of the biological sample can be then crosslinked into hydrogel-voxels of defined dimensions using a light source. The flow-cell can be dismantled and washed to remove unpolymerized polymer precursors. The coating can be treated with DTT to yield single-cell partitions for use in downstream applications. The capture probes/biological analytes can be analyzed, and the spatial information of the spatially-barcoded features can be used to determine the spatial location of the captured biological analytes in the biological sample.

In addition to analytes, a partition can include additional components, and in particular, one or more beads. A partition can include a single gel bead, a single cell bead, or both a single cell bead and single gel bead.

A partition can also include one or more reagents. Unique identifiers, such as barcodes, can be injected into the droplets previous to, subsequent to, or concurrently with droplet generation, such as via a microcapsule (e.g., bead). Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids.

The partitions can be flowable within fluid streams. The partitions can include, for example, micro-vesicles that have an outer barrier surrounding an inner fluid center or core. In some cases, the partitions can include a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions can be provided in a water-in-oil emulsion or oil-in-water emulsion. A variety of different vessels are described in, for example, U.S. Patent Application Publication No. 2014/0155295, the entire contents of which are incorporated herein by reference. Emulsion systems for creating stable droplets in non-aqueous or oil continuous phases are described, for example, in U.S. Patent Application Publication No. 2010/0105112, the entire contents of which are incorporated herein by reference.

For droplets in an emulsion, allocating individual particles to discrete partitions can be accomplished, for example, by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters can be adjusted to control the occupancy of the resulting partitions (e.g., number of analytes per partition, number of beads per partition, etc.) For example, partition occupancy can be controlled by providing the aqueous stream at a certain concentration and/or flow rate of analytes.

To generate single analyte partitions, the relative flow rates of the immiscible fluids can be selected such that, on average, the partitions can contain less than one analyte per partition to ensure that those partitions that are occupied are primarily singly occupied. In some cases, partitions among a plurality of partitions can contain at most one analyte. In some embodiments, the various parameters (e.g., fluid properties, particle properties, microfluidic architectures, etc.) can be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The channel segments described herein can be coupled to any of a variety of different fluid sources or receiving components, including reservoirs, tubing, manifolds, or fluidic components of other systems. As will be appreciated, the microfluidic channel structure can have a variety of geometries. For example, a microfluidic channel structure can have one or more than one channel junction. As another example, a microfluidic channel structure can have 2, 3, 4, or 5 channel segments each carrying particles that meet at a channel junction. Fluid can be directed to flow along one or more channels or reservoirs via one or more fluid flow units. A fluid flow unit can include compressors (e.g., providing positive pressure), pumps (e.g., providing negative pressure), actuators, and the like to control flow of the fluid. Fluid can also or otherwise be controlled via applied pressure differentials, centrifugal force, electrokinetic pumping, vacuum, capillary, and/or gravity flow.

A partition can include one or more unique identifiers, such as barcodes. Barcodes can be previously, subsequently, or concurrently delivered to the partitions that hold the compartmentalized or partitioned biological particle. For example, barcodes can be injected into droplets previous to, subsequent to, or concurrently with droplet generation. The delivery of the barcodes to a particular partition allows for the later attribution of the characteristics of the individual biological particle to the particular partition. Barcodes can be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can include a bead.

In some embodiments, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus can disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some embodiments, one more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well.

Figure 21:
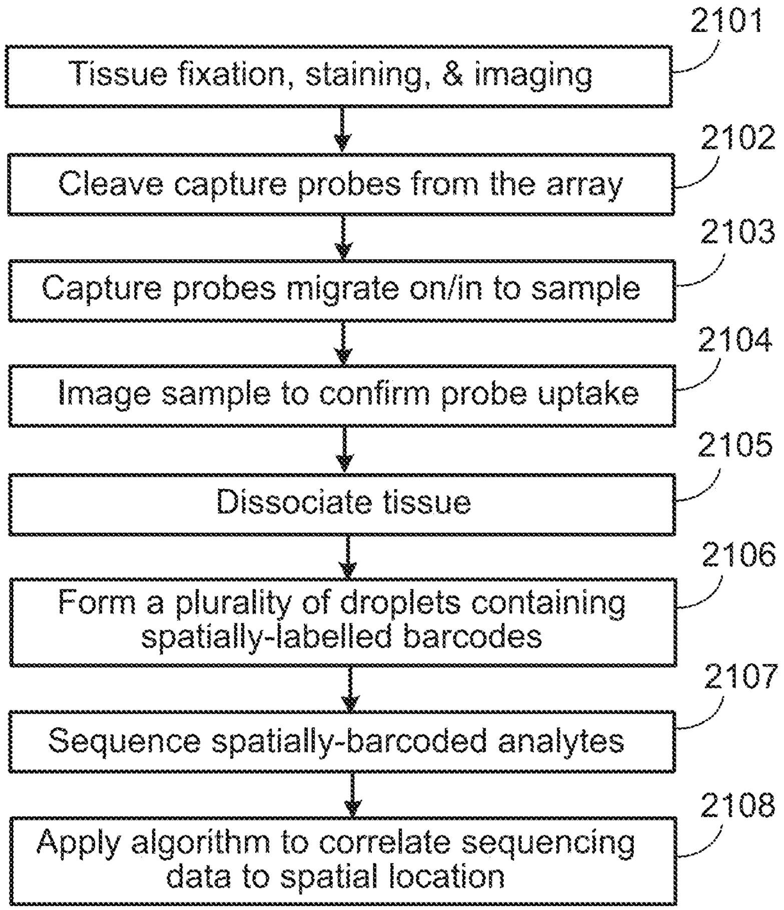
FIG. 21 shows a workflow schematic illustrating exemplary, non-limiting, non-exhaustive steps for dissociating a spatially-barcoded sample for analysis via droplet or flow cell analysis methods.
Figure 22A:
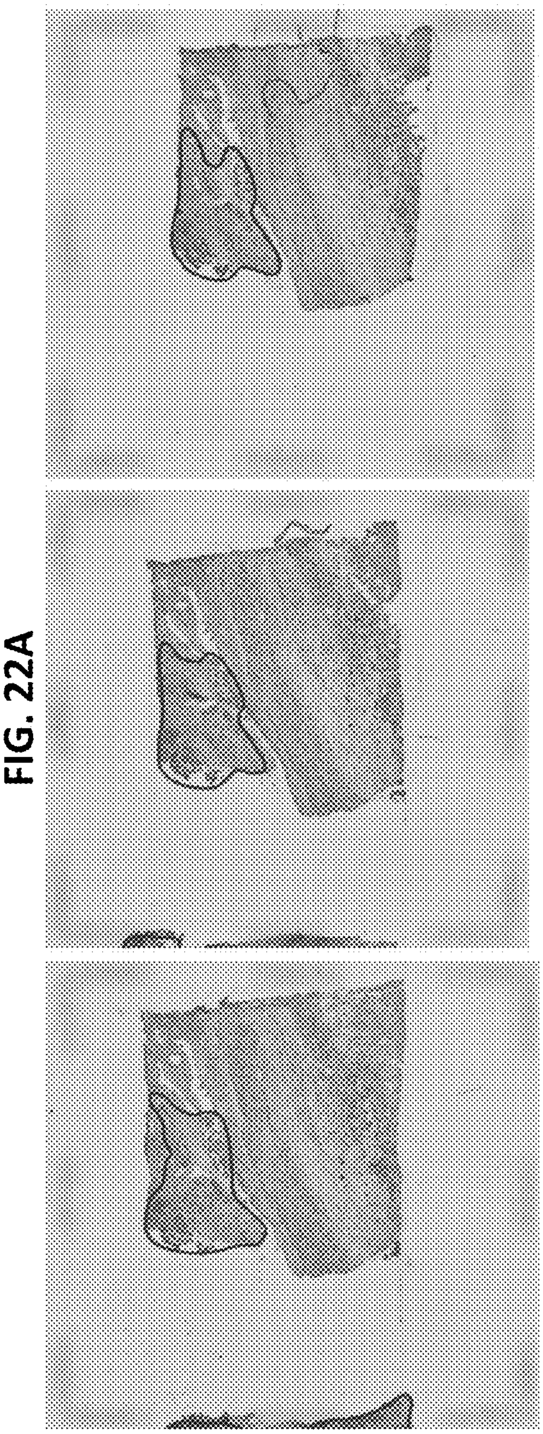
FIG. 22A shows serial Haemotoxylin and Eosin (H&E) stained serial sections of ovarian cancer biological samples.
Figure 22B:
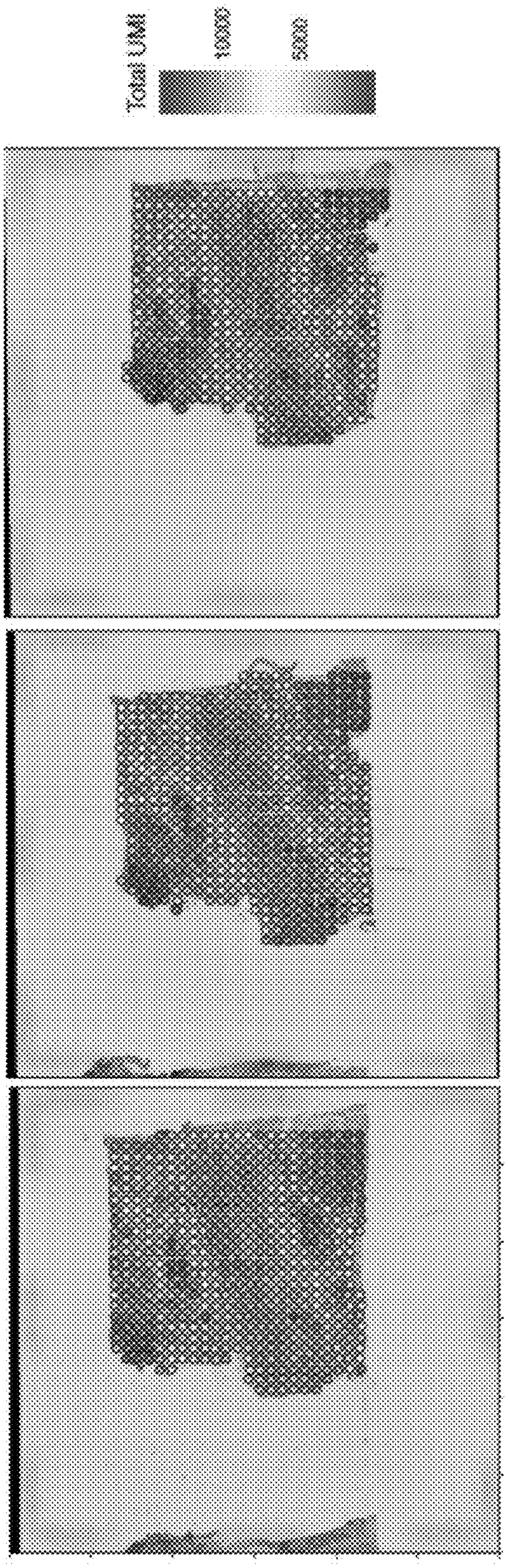
FIG. 22B shows a heat map of total unique molecular identifiers per spot in the biological samples in FIG. 22A.
Figure 22C:
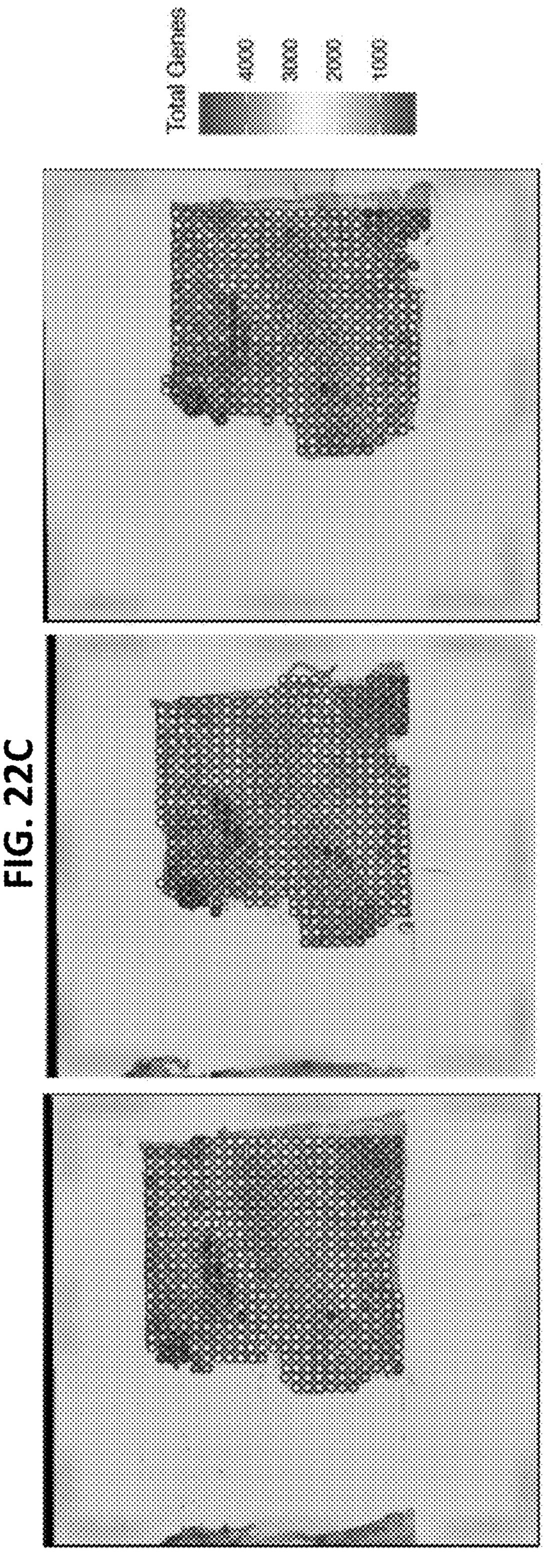
FIG. 22C shows a heat map of total genes detected per spot in the biological samples in FIG. 22A.
Figure 22D:
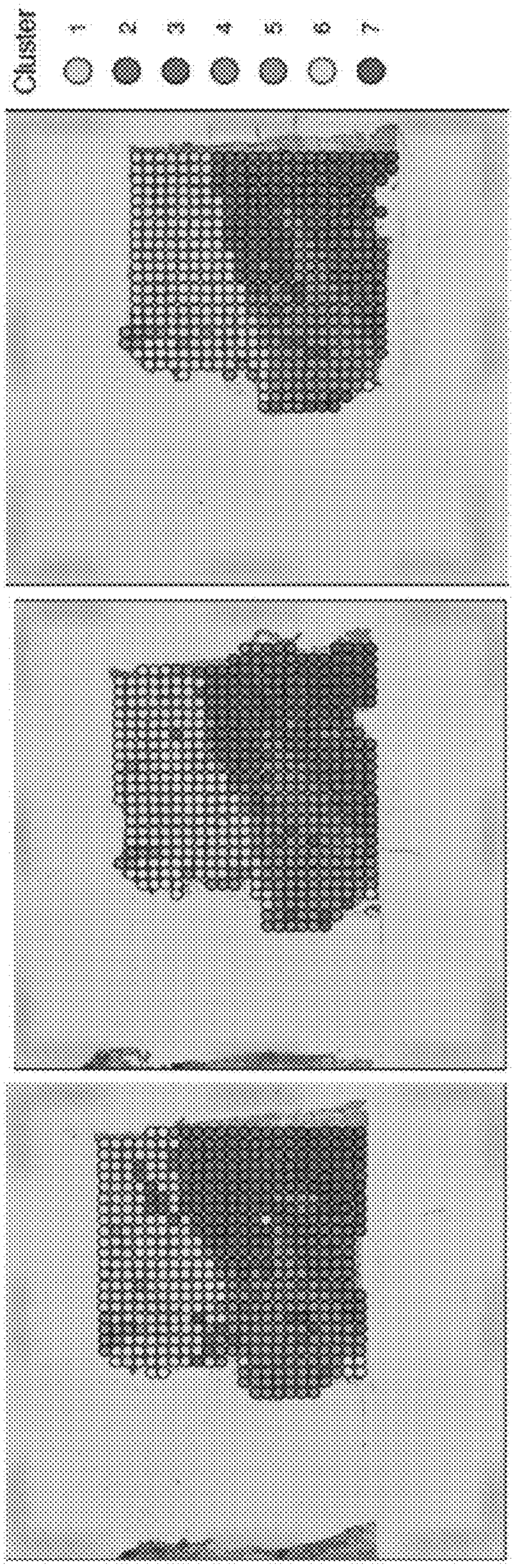
FIG. 22D shows expression of Clusters 1-7 in the biological samples in FIG. 22A.

FIG. 21 depicts an exemplary workflow, where a sample is contacted with a spatially-barcoded capture probe array and the sample is fixed, stained, and imaged 2101, as described elsewhere herein. The capture probes can be cleaved from the array 2102 using any method as described herein. The capture probes can diffuse toward the cells by either passive or active migration as described elsewhere herein. The capture probes may then be introduced to the sample 2103 as described elsewhere herein, wherein the capture probe is able to gain entry into the cell in the absence of cell permeabilization, using one of the cell penetrating peptides or lipid delivery systems described herein. The sample can then be optionally imaged in order to confirm probe uptake, via a reporter molecule incorporated within the capture probe 2104. The sample can then be separated from the array and undergo dissociation 2105, wherein the sample is separated into single cells or small groups of cells. Once the sample is dissociated, the single cells can be introduced to an oil-in water droplet 2106, wherein a single cell is combined with reagents within the droplet and processed so that the spatial barcode that penetrated the cell labels the contents of that cell within the droplet. Other cells undergo separately partitioned reactions concurrently. The contents of the droplet is then sequenced 2107 in order to associate a particular cell or cells with a particular spatial location within the sample 2108.

As described above, FIG. 16 shows an example of a microfluidic channel structure for partitioning individual analytes (e.g., cells) into discrete partitions. FIGS. 17A and 17C also show other examples of microfluidic channel structures that can be used for delivering beads to droplets.

A variety of different beads can be incorporated into partitions as described above. In some embodiments, for example, non-barcoded beads can be incorporated into the partitions. For example, where the biological particle (e.g., a cell) that is incorporated into the partitions carries one or more barcodes (e.g., spatial barcode(s), UMI(s), and combinations thereof), the bead can be a non-barcoded bead.

In some embodiments, a barcode carrying bead can be incorporated into partitions. For example, a nucleic acid molecule, such as an oligonucleotide, can be coupled to a bead by a releasable linkage, such as, for example, a disulfide linker. The same bead can be coupled (e.g., via releasable linkage) to one or more other nucleic acid molecules. The nucleic acid molecule can be or include a barcode. As noted elsewhere herein, the structure of the barcode can include a number of sequence elements.

The nucleic acid molecule can include a functional domain that can be used in subsequent processing. For example, the functional domain can include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule can include a barcode sequence for use in barcoding the sample (e.g., DNA, RNA, protein, etc.). In some cases, the barcode sequence can be bead-specific such that the barcode sequence is common to all nucleic acid molecules coupled to the same bead. Alternatively or in addition, the barcode sequence can be partition-specific such that the barcode sequence is common to all nucleic acid molecules coupled to one or more beads that are partitioned into the same partition. The nucleic acid molecule can include a specific priming sequence, such as an mRNA specific priming sequence (e.g., poly (T) sequence), a targeted priming sequence, and/or a random priming sequence. The nucleic acid molecule can include an anchoring sequence to ensure that the specific priming sequence hybridizes at the sequence end (e.g., of the mRNA). For example, the anchoring sequence can include a random short sequence of nucleotides, such as a 1-mer, 2-mer, 3-mer or longer sequence, which can ensure that a poly(T) segment is more likely to hybridize at the sequence end of the poly(A) tail of the mRNA.

The nucleic acid molecule can include a unique molecular identifying sequence (e.g., unique molecular identifier (UMI)). In some embodiments, the unique molecular identifying sequence can include from about 5 to about 8 nucleotides. Alternatively, the unique molecular identifying sequence can include less than about 5 or more than about 8 nucleotides. The unique molecular identifying sequence can be a unique sequence that varies across individual nucleic acid molecules coupled to a single bead.

In some embodiments, the unique molecular identifying sequence can be a random sequence (e.g., such as a random N-mer sequence). For example, the UMI can provide a unique identifier of the starting mRNA molecule that was captured, in order to allow quantitation of the number of original expressed RNA.

In general, an individual bead can be coupled to any number of individual nucleic acid molecules, for example, from one to tens to hundreds of thousands or even millions of individual nucleic acid molecules. The respective barcodes for the individual nucleic acid molecules can include both common sequence segments or relatively common sequence segments and variable or unique sequence segments between different individual nucleic acid molecules coupled to the same bead.

Within any given partition, all of the cDNA transcripts of the individual mRNA molecules can include a common barcode sequence segment. However, the transcripts made from the different mRNA molecules within a given partition can vary at the unique molecular identifying sequence segment (e.g., UMI segment). Beneficially, even following any subsequent amplification of the contents of a given partition, the number of different UMIs can be indicative of the quantity of mRNA originating from a given partition. As noted above, the transcripts can be amplified, cleaned up, and sequenced to identify the sequence of the cDNA transcript of the mRNA, as well as to sequence the barcode segment and the UMI segment. While a poly(T) primer sequence is described, other targeted or random priming sequences can also be used in priming the reverse transcription reaction. Likewise, although described as releasing the barcoded oligonucleotides into the partition, in some cases, the nucleic acid molecules bound to the bead can be used to hybridize and capture the mRNA on the solid phase of the bead, for example, in order to facilitate the separation of the RNA from other cell contents.

In some embodiments, precursors that include a functional group that is reactive or capable of being activated such that it becomes reactive can be polymerized with other precursors to generate gel beads that include the activated or activatable functional group. The functional group can then be used to attach additional species (e.g., disulfide linkers, primers, other oligonucleotides, etc.) to the gel beads. For example, some precursors featuring a carboxylic acid (COOH) group can co-polymerize with other precursors to form a bead that also includes a COOH functional group. In some cases, acrylic acid (a species comprising free COOH groups), acrylamide, and bis(acryloyl)cystamine can be co-polymerized together to generate a bead with free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMT-MM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead. In some embodiments, a degradable bead can be introduced into a partition, such that the bead degrades within the partition and any associated species (e.g., oligonucleotides) are released within the droplet when the appropriate stimulus is applied. The free species (e.g., oligonucleotides, nucleic acid molecules) can interact with other reagents contained in the partition. For example, a polyacrylamide bead featuring cystamine and linked, via a disulfide bond, to a barcode sequence, can be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet with a bead-bound barcode sequence in basic solution can also result in bead degradation and release of the attached barcode sequence into the aqueous, inner environment of the droplet.

Any suitable number of species (e.g., primer, barcoded oligonucleotide) can be associated with a bead such that, upon release from the bead, the species (e.g., primer, e.g., barcoded oligonucleotide) are present in the partition at a pre-defined concentration. Such pre-defined concentration can be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

A degradable bead can include one or more species with a labile bond such that, when the bead/species is exposed to the appropriate stimulus, the bond is broken and the bead degrades. The labile bond can be a chemical bond (e.g., covalent bond, ionic bond) or can be another type of physical interaction (e.g., van der Waals interactions, dipole-dipole interactions, etc.). In some embodiments, a cross-linker used to generate a bead can include a labile bond. Upon exposure to the appropriate conditions, the labile bond can be broken and the bead degraded. For example, upon exposure of a polyacrylamide gel bead that includes cystamine cross-linkers to a reducing agent, the disulfide bonds of the cystamine can be broken and the bead degraded.

A degradable bead can be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a barcode sequence can be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above description, while referred to as degradation of a bead, in many embodiments, degradation can refer to the disassociation of a bound or entrained species from a bead, both with and without structurally degrading the physical bead itself. For example, entrained species can be released from beads through osmotic pressure differences due to, for example, changing chemical environments. By way of example, alteration of bead pore volumes due to osmotic pressure differences can generally occur without structural degradation of the bead itself. In some cases, an increase in pore volume due to osmotic swelling of a bead can permit the release of entrained species within the bead. In some embodiments, osmotic shrinking of a bead can cause a bead to better retain an entrained species due to pore volume contraction.

Numerous chemical triggers can be used to trigger the degradation of beads within partitions. Examples of these chemical changes can include, but are not limited to pH-mediated changes to the integrity of a component within the bead, degradation of a component of a bead via cleavage of cross-linked bonds, and depolymerization of a component of a bead.

In some embodiments, a bead can be formed from materials that include degradable chemical cross-linkers, such as BAC or cystamine. Degradation of such degradable cross-linkers can be accomplished through a number of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof. A reducing agent can degrade the disulfide bonds formed between gel precursors forming the bead, and thus, degrade the bead.

In certain embodiments, a change in pH of a solution, such as an increase in pH, can trigger degradation of a bead. In other embodiments, exposure to an aqueous solution, such as water, can trigger hydrolytic degradation, and thus degradation of the bead. In some cases, any combination of stimuli can trigger degradation of a bead. For example, a change in pH can enable a chemical agent (e.g., DTT) to become an effective reducing agent.

Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In other cases, heat can increase the internal pressure of the bead components such that the bead ruptures or explodes. Heat can also act upon heat-sensitive polymers used as materials to construct beads.

In addition to beads and analytes, partitions that are formed can include a variety of different reagents and species. For example, when lysis reagents are present within the partitions, the lysis reagents can facilitate the release of analytes within the partition. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St. Louis, MO), as well as other commercially available lysis enzymes. Other lysis agents can additionally or alternatively be co-partitioned to cause the release analytes into the partitions. For example, in some cases, surfactant-based lysis solutions can be used to lyse cells, although these can be less desirable for emulsion based systems where the surfactants can interfere with stable emulsions. In some embodiments, lysis solutions can include non-ionic surfactants such as, for example, TritonX-100 and Tween 20. In some embodiments, lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of analytes that can be in addition to or in place of droplet partitioning, where any pore volume of the encapsulate is sufficiently small to retain nucleic acid fragments of a given size, following cellular disruption.

Examples of other species that can be co-partitioned with analytes in the partitions include, but are not limited to, DNase and RNase inactivating agents or inhibitors or chelating agents, such as EDTA, and other reagents employed in removing or otherwise reducing negative activity or impact of different cell lysate components on subsequent processing of nucleic acids. Additional reagents can also be co-partitioned, including endonucleases to fragment DNA, DNA polymerase enzymes and dNTPs used to amplify nucleic acid fragments and to attach the barcode molecular tags to the amplified fragments.

Additional reagents can also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some embodiments, template switching can be used to increase the length of a cDNA. Template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., poly(C), to the cDNA in a template independent manner. Switch oligos can include sequences complementary to the additional nucleotides, e.g., poly(G). The additional nucleotides (e.g., poly(C)) on the cDNA can hybridize to the additional nucleotides (e.g., poly(G)) on the switch oligo, whereby the switch oligo can be used by the reverse transcriptase as template to further extend the cDNA.

Template switching oligonucleotides can include a hybridization region and a template region. The hybridization region can include any sequence capable of hybridizing to the target. In some cases, the hybridization region includes a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos can include deoxyribonucleic acids; ribonucleic acids; modified nucleic acids including 2-Aminopurine, 2,6-Diaminopurine (2-Amino-dA), inverted dT, 5-Methyl dC, 2'-deoxylnosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), and combinations of the foregoing.

In some embodiments, beads that are partitioned with the analyte can include different types of oligonucleotides bound to the bead, where the different types of oligonucleotides bind to different types of analytes. For example, a bead can include one or more first oligonucleotides (which can be capture probes, for example) that can bind or hybridize to a first type of analyte, such as mRNA for example, and one or more second oligonucleotides (which can be capture probes, for example) that can bind or hybridize to a second type of analyte, such as gDNA for example. Partitions can also include lysis agents that aid in releasing nucleic acids from the co-partitioned cell, and can also include an agent (e.g., a reducing agent) that can degrade the bead and/or break covalent linkages between the oligonucleotides and the bead, releasing the oligonucleotides into the partition. The released barcoded oligonucleotides (which can also be barcoded) can hybridize with mRNA released from the cell and also with gDNA released from the cell.

Barcoded constructs thus formed from hybridization can include a first type of construct that includes a sequence corresponding to an original barcode sequence from the bead and a sequence corresponding to a transcript from the cell, and a second type of construct that includes a sequence corresponding to the original barcode sequence from the bead and a sequence corresponding to genomic DNA from the cell. The barcoded constructs can then be released/removed from the partition and, in some embodiments, further processed to add any additional sequences. The resulting constructs can then be sequenced, the sequencing data processed, and the results used to spatially characterize the mRNA and the gDNA from the cell.

In another example, a partition includes a bead that includes a first type of oligonucleotide (e.g., a first capture probe) with a first barcode sequence, a poly(T) priming sequence that can hybridize with the poly(A) tail of an mRNA transcript, and a UMI barcode sequence that can uniquely identify a given transcript. The bead also includes a second type of oligonucleotide (e.g., a second capture probe) with a second barcode sequence, a targeted priming sequence that is capable of specifically hybridizing with a third barcoded oligonucleotide (e.g., an analyte capture agent) coupled to an antibody that is bound to the surface of the partitioned cell. The third barcoded oligonucleotide includes a UMI barcode sequence that uniquely identifies the antibody (and thus, the particular cell surface feature to which it is bound).

In this example, the first and second barcoded oligonucleotides include the same spatial barcode sequence (e.g., the first and second barcode sequences are the same), which permits downstream association of barcoded nucleic acids with the partition. In some embodiments, however, the first and second barcode sequences are different. The partition also includes lysis agents that aid in releasing nucleic acids from the cell and can also include an agent (e.g., a reducing agent) that can degrade the bead and/or break a covalent linkage between the barcoded oligonucleotides and the bead, releasing them into the partition. The first type of released barcoded oligonucleotide can hybridize with mRNA released from the cell and the second type of released barcoded oligonucleotide can hybridize with the third type of barcoded oligonucleotide, forming barcoded constructs.

The first type of barcoded construct includes a spatial barcode sequence corresponding to the first barcode sequence from the bead and a sequence corresponding to the UMI barcode sequence from the first type of oligonucleotide, which identifies cell transcripts. The second type of barcoded construct includes a spatial barcode sequence corresponding to the second barcode sequence from the second type of oligonucleotide, and a UMI barcode sequence corresponding to the third type of oligonucleotide (e.g., the analyte capture agent) and used to identify the cell surface feature. The barcoded constructs can then be released/removed from the partition and, in some embodiments, further processed to add any additional sequences. The resulting constructs are then sequenced, sequencing data processed, and the results used to characterize the mRNA and cell surface feature of the cell.

The foregoing discussion involves two specific examples of beads with oligonucleotides for analyzing two different analytes within a partition. More generally, beads that are partitioned can have any of the structures described previously, and can include any of the described combinations of oligonucleotides for analysis of two or more (e.g., three or more, four or more, five or more, six or more, eight or more, ten or more, 12 or more, 15 or more, 20 or more, 25 or more, 30 or more, 40 or more, 50 or more) different types of analytes within a partition. Examples of beads with combinations of different types of oligonucleotides (e.g., capture probes) for concurrently analyzing different combinations of analytes within partitions include, but are not limited to: (a) genomic DNA and cell surface features (e.g., using the analyte capture agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites; (f) a barcoded analyte capture agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein). In some embodiments, a perturbation agent can be a small molecule, an antibody, a drug, an aptamer, a nucleic acid (e.g., miRNA), a physical environmental (e.g., temperature change), or any other known perturbation agents.

(e) Sequencing Analysis

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g., sequencing), i.e., can directly take part in the sequence analysis reaction or process (e.g., the sequencing reaction or sequencing process, or be the molecule which is sequenced or otherwise identified). Alternatively, the barcoded nucleic acid molecule can be subjected to a step of second strand synthesis or amplification before sequence analysis (e.g., sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g., barcoded nucleic acid molecules) can be analyzed (e.g., sequenced). To perform single molecule sequencing, the nucleic acid strand can be modified at the 3' end.

In some embodiments, massively parallel pyrosequencing techniques can be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., *Anal. Biochem.* 242(1), 84-9 (1996); Ronaghi, *Genome Res.* 11(1), 3-11 (2001); Ronaghi et al. *Science* 281 (5375), 363 (1998); and U.S. Pat. Nos. 6,210,891, 6,258,568, and 6,274,320, the entire contents of each of which are incorporated herein by reference.

Massively parallel sequencing techniques can be used for sequencing nucleic acids, as described above. In one embodiment, a massively parallel sequencing technique can be based on reversible dye-terminators. As an example, DNA molecules are first attached to primers on, e.g., a glass or silicon substrate, and amplified so that local clonal colonies are formed (e.g., by bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, sequencing can be performed in situ. In situ sequencing methods are particularly useful, for example, when the biological sample remains intact after analytes on the sample surface (e.g., cell surface analytes) or within the sample (e.g., intracellular analytes) have been barcoded. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343(6177), 1360-1363, the entire contents of each of which are incorporated herein by reference.

In addition, examples of methods and systems for performing in situ sequencing are described in PCT Patent Application Publication Nos. WO2014/163886, WO2018/045181, WO2018/045186, and in U.S. Pat. Nos. 10,138,509 and 10,179,932, the entire contents of each of which are incorporated herein by reference. Example techniques for in situ sequencing include, but are not limited to, STARmap (described for example in Wang et al., (2018) *Science,* 361(6499) 5691), MERFISH (described for example in Moffitt, (2016) *Methods in Enzymology,* 572, 1-49), and FISSEQ (described for example in U.S. Patent Application Publication No. 2019/0032121). The entire contents of each of the foregoing references are incorporated herein by reference.

For analytes that have been barcoded via partitioning, barcoded nucleic acid molecules or derivatives thereof (e.g., barcoded nucleic acid molecules to which one or more functional sequences have been added, or from which one or more features have been removed) can be pooled and processed together for subsequent analysis such as sequencing on high throughput sequencers. Processing with pooling can be implemented using barcode sequences. For example, barcoded nucleic acid molecules of a given partition can have the same barcode, which is different from barcodes of other spatial partitions. Alternatively, barcoded nucleic acid molecules of different partitions can be processed separately for subsequent analysis (e.g., sequencing).

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte (e.g., reverse transcription and polymerase amplification of RNA). In some embodiments, analyte analysis uses direct sequencing of one or more captured analytes, such as direct sequencing of hybridized RNA. In some embodiments, direct sequencing is performed after reverse transcription of hybridized RNA. In some embodiments direct sequencing is performed after amplification of reverse transcription of hybridized RNA.

In some embodiments, direct sequencing of captured RNA is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid features are present in a double stranded form these can be processed to provide single stranded nucleic acid templates using methods well known in the art, for example by denaturation, cleavage, etc. The sequencing primers which are hybridized to the nucleic acid template and used for primer extension are preferably short oligonucleotides, for example, 15 to 25 nucleotides in length. The sequencing primers can be greater than 25 nucleotides in length as well. For example, sequencing primers can be about 20 to about 60 nucleotides in length, or more than 60 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010,251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., *Trends Biotechnol.* 18, 14 7-151 (2000); Deamer et al., *Acc. Chem. Res.* 35:817-825 (2002); Li et al., *Nat. Mater.* 2:611-615 (2003); Soni et al., *Clin. Chem.* 53, 1996-2001 (2007); Healy et al., *Nanomed.* 2, 459-481 (2007); Cockroft et al., *J. Am. Chem. Soc.* 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina© sequencing (e.g., flow cell-based sequencing techniques), sequencing by synthesis using modified nucleotides (such as commercialized in TruSeq™ and HiSeq™ technology by Illumina, Inc., San Diego, CA), HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA), and sequencing of DNA nanoballs (Complete Genomics, Inc., Mountain View, CA).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes. The entire contents of each of the foregoing references are incorporated herein by reference.

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181. The entire contents of each of the foregoing references are herein incorporated by reference.

IV. Multiplexing

(a) Multiplexing Generally

In various embodiments of spatial analysis as described herein, features can include different types of capture probes for analyzing both intrinsic and extrinsic information for individual cells. For example, a feature can include one or more of the following: 1) a capture probe featuring a capture domain that binds to one or more endogenous nucleic acids in the cell; 2) a capture probe featuring a capture domain that binds to one or more exogenous nucleic acids in the cell (e.g., nucleic acids from a microorganism (e.g., a virus, a bacterium)) that infects the cell, nucleic acids introduced into the cell (e.g., such as plasmids or nucleic acid derived therefrom), nucleic acids for gene editing (e.g., CRISPR-related RNA such as crRNA, guide RNA); 3) a capture probe featuring a capture domain that binds to an analyte capture agent (e.g., an antibody coupled to a oligonucleotide that includes a capture agent barcode domain having an analyte capture sequence that binds the capture domain), and 4) a capture moiety featuring a domain that binds to a protein (e.g., an exogenous protein expressed in the cell, a protein from a microorganism (e.g., a virus, a bacterium)) that infects the cell, or a binding partner for a protein of the cell (e.g., an antigen for an immune cell receptor).

In some embodiments of any of the spatial analysis methods as described herein, spatial profiling includes concurrent analysis of two different types of analytes. A feature can be a gel bead, which is coupled (e.g., reversibly coupled) to one or more capture probes. The capture probes can include a spatial barcode sequence and a poly(T) priming sequence that can hybridize with the poly(A) tail of an mRNA transcript. The capture probe can also include a UMI sequence that can uniquely identify a given transcript. The capture probe can also include a spatial barcode sequence and a random N-mer priming sequence that is capable of randomly hybridizing with gDNA. In this configuration, capture probes can include the same spatial barcode sequence, which permits association of downstream sequencing reads with the feature.

In some embodiments of any of the spatial analysis methods as described herein, a feature can be a gel bead, which is coupled (e.g., reversibly coupled) to capture probes. The Capture probe can include a spatial barcode sequence and a poly(T) priming sequence that can hybridize with the poly(A) tail of an mRNA transcript. The capture probe can also include a UMI sequence that can uniquely identify a given transcript. The capture probe can include a spatial barcode sequence and a capture domain that is capable of specifically hybridizing with an analyte capture agent. The analyte capture agent can includes an oligonucleotide that includes an analyte capture sequence that interacts with the capture domain coupled to the feature. The oligonucleotide of the analyte capture agent can be coupled to an antibody that is bound to the surface of a cell. The oligonucleotide includes a barcode sequence (e.g., an analyte binding moiety barcode) that uniquely identifies the antibody (and thus, the particular cell surface feature to which it is bound). In this configuration, the capture probes include the same spatial barcode sequence, which permit downstream association of barcoded nucleic acids with the location on the spatial array. In some embodiments of any of the spatial profiling methods described herein, the analyte capture agents can be can be produced by any suitable route, including via example coupling schemes described elsewhere herein.

In some embodiments of any of the spatial analysis methods described herein, other combinations of two or more biological analytes that can be concurrently measured include, without limitation: (a) genomic DNA and cell surface features (e.g., via analyte capture agents that bind to a cell surface feature), (b) mRNA and a lineage tracing construct, (c) mRNA and cell methylation status, (d) mRNA and accessible chromatin (e.g., ATAC-seq, DNase-seq, and/or MNase-seq), (e) mRNA and cell surface or intracellular proteins and/or metabolites, (f) mRNA and chromatin (spatial organization of chromatin in a cell), (g) an analyte capture agent (e.g., any of the MHC multimers described herein) and a V(D)J sequence of an immune cell receptor (e.g., T-cell receptor), (h) mRNA and a perturbation agent (e.g., a CRISPR crRNA/sgRNA, TALEN, zinc finger nuclease, and/or antisense oligonucleotide as described herein), (i) genomic DNA and a perturbation agent, (j) an analyte capture agent and a perturbation agents, (k) accessible chromatin and a perturbation agent, (1) chromatin (e.g., spatial organization of chromatin in a cell) and a perturbation agent, and (m) cell surface or intracellular proteins and/or metabolites and a perturbation agent (e.g., any of the perturbation agents described herein), or any combination thereof.

In some embodiments of any of the spatial analysis methods described herein, the first analyte can include a nucleic acid molecule with a nucleic acid sequence (e.g., mRNA, complementary DNA derived from reverse transcription of mRNA) encoding at least a portion of a V(D)J sequence of an immune cell receptor (e.g., a TCR or BCR). In some embodiments, the nucleic acid molecule with a nucleic acid sequence encoding at least a portion of a V(D)J sequence of an immune cell receptor is cDNA first generated from reverse transcription of the corresponding mRNA, using a poly(T) containing primer. The cDNA that is generated can then be barcoded using a primer, featuring a spatial barcode sequence (and optionally, a UMI sequence) that hybridizes with at least a portion of the cDNA that is generated. In some embodiments, a template switching oligonucleotide in conjunction a terminal transferase or a reverse transcriptase having terminal transferase activity can be employed to generate a priming region on the cDNA to which a barcoded primer can hybridize during cDNA generation. Terminal transferase activity can, for example, add a poly(C) tail to a 3' end of the cDNA such that the template switching oligonucleotide can bind via a poly(G) priming sequence and the 3' end of the cDNA can be further extended. The original mRNA template and template switching oligonucleotide can then be denatured from the cDNA and the barcoded primer comprising a sequence complementary to at least a portion of the generated priming region on the cDNA can then hybridize with the cDNA and a barcoded construct comprising the barcode sequence (and any optional UMI sequence) and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described, for example, in PCT Patent Application Publication No. WO 2018/075693, and in U.S. Patent Application Publication No. 2018/0105808, the entire contents of each of which are incorporated herein by reference.

In some embodiments, V(D)J analysis can be performed using methods similar to those described herein. For example, V(D)J analysis can be completed with the use of one or more analyte capture agents that bind to particular surface features of immune cells and are associated with barcode sequences (e.g., analyte binding moiety barcodes). The one or more analyte capture agents can include an MHC or MHC multimer. A barcoded oligonucleotide coupled to a bead that can be used for V(D)J analysis. The oligonucleotide is coupled to a bead by a releasable linkage, such as a disulfide linker. The oligonucleotide can include functional sequences that are useful for subsequent processing, such as functional sequence, which can include a sequencer specific flow cell attachment sequence, e.g., a P5 sequence, as well as functional sequence, which can include sequencing primer sequences, e.g., a R1 primer binding site. In some embodiments, the sequence can include a P7 sequence and a R2 primer binding site. A barcode sequence can be included within the structure for use in barcoding the template polynucleotide. The functional sequences can be selected for compatibility with a variety of different sequencing systems, e.g., Ion Torrent Proton or PGM, Illumina sequencing instruments, etc., and the requirements thereof. In some embodiments, the barcode sequence, functional sequences (e.g., flow cell attachment sequence) and additional sequences (e.g., sequencing primer sequences) can be common to all of the oligonucleotides attached to a given bead. The barcoded oligonucleotide can also include a sequence to facilitate template switching (e.g., a poly(G) sequence). In some embodiments, the additional sequence provides a unique molecular identifier (UMI) sequence segment, as described elsewhere herein.

In an exemplary method of cellular polynucleotide analysis using a barcode oligonucleotide, a cell is co-partitioned along with a bead bearing a barcoded oligonucleotide and additional reagents such as a reverse transcriptase, primers, oligonucleotides (e.g., template switching oligonucleotides), dNTPs, and a reducing agent into a partition (e.g., a droplet in an emulsion). Within the partition, the cell can be lysed to yield a plurality of template polynucleotides (e.g., DNA such as genomic DNA, RNA such as mRNA, etc.).

A reaction mixture featuring a template polynucleotide from a cell and (i) the primer having a sequence towards a 3' end that hybridizes to the template polynucleotide (e.g., poly(T)) and (ii) a template switching oligonucleotide that includes a first oligonucleotide towards a 5' end can be subjected to an amplification reaction to yield a first amplification product. In some embodiments, the template polynucleotide is an mRNA with a poly(A) tail and the primer that hybridizes to the template polynucleotide includes a poly(T) sequence towards a 3' end, which is complementary to the poly(A) segment. The first oligonucleotide can include at least one of an adaptor sequence, a barcode sequence, a unique molecular identifier (UMI) sequence, a primer binding site, and a sequencing primer binding site or any combination thereof. In some cases, a first oligonucleotide is a sequence that can be common to all partitions of a plurality of partitions. For example, the first oligonucleotide can include a flow cell attachment sequence, an amplification primer binding site, or a sequencing primer binding site and the first amplification reaction facilitates the attachment the oligonucleotide to the template polynucleotide from the cell. In some embodiments, the first oligonucleotide includes a primer binding site. In some embodiments, the first oligonucleotide includes a sequencing primer binding site.

The sequence towards a 3' end (e.g., poly(T)) of the primer hybridizes to the template polynucleotide. In a first amplification reaction, extension reaction reagents, e.g., reverse transcriptase, nucleoside triphosphates, co-factors (e.g., $Mg^{2+}$ or $Mn^{2+}$), that are also co-partitioned, can extend the primer sequence using the cell's nucleic acid as a template, to produce a transcript, e.g., cDNA, having a fragment complementary to the strand of the cell's nucleic acid to which the primer annealed. In some embodiments, the reverse transcriptase has terminal transferase activity and the reverse transcriptase adds additional nucleotides, e.g., poly(C), to the cDNA in a template independent manner.

The template switching oligonucleotide, for example a template switching oligonucleotide which includes a poly (G) sequence, can hybridize to the cDNA and facilitate template switching in the first amplification reaction. The transcript, therefore, can include the sequence of the primer, a sequence complementary to the template polynucleotide from the cell, and a sequence complementary to the template switching oligonucleotide.

In some embodiments of any of the spatial analysis methods described herein, subsequent to the first amplification reaction, the first amplification product or transcript can be subjected to a second amplification reaction to generate a second amplification product. In some embodiments, additional sequences (e.g., functional sequences such as flow cell attachment sequence, sequencing primer binding sequences, barcode sequences, etc.) are attached. The first and second amplification reactions can be performed in the same volume, such as for example in a droplet. In some embodiments, the first amplification product is subjected to a second amplification reaction in the presence of a barcoded oligonucleotide to generate a second amplification product having a barcode sequence. The barcode sequence can be unique to a partition, that is, each partition can have a unique barcode sequence. The barcoded oligonucleotide can include a sequence of at least a segment of the template switching oligonucleotide and at least a second oligonucleotide. The segment of the template switching oligonucleotide on the barcoded oligonucleotide can facilitate hybridization of the barcoded oligonucleotide to the transcript, e.g., cDNA, to facilitate the generation of a second amplification product. In addition to a barcode sequence, the barcoded oligonucleotide can include a second oligonucleotide such as at least one of an adaptor sequence, a unique molecular identifier (UMI) sequence, a primer binding site, and a sequencing primer binding site, or any combination thereof.

In some embodiments of any of the spatial analysis methods described herein, the second amplification reaction uses the first amplification product as a template and the barcoded oligonucleotide as a primer. In some embodiments, the segment of the template switching oligonucleotide on the barcoded oligonucleotide can hybridize to the portion of the cDNA or complementary fragment having a sequence complementary to the template switching oligonucleotide or that which was copied from the template switching oligonucleotide. In the second amplification reaction, extension reaction reagents, e.g., polymerase, nucleoside triphosphates, co-factors (e.g., $Mg^{2+}$ or $Mn^{2+}$), that are also co-partitioned, can extend the primer sequence using the first amplification product as template. The second amplification product can include a second oligonucleotide, a sequence of a segment of the template polynucleotide (e.g., mRNA), and a sequence complementary to the primer.

In some embodiments of any of the spatial analysis methods described herein, the second amplification product uses the barcoded oligonucleotide as a template and at least a portion of the first amplification product as a primer. The segment of the first amplification product (e.g., cDNA) having a sequence complementary to the template switching oligonucleotide can hybridize to the segment of the barcoded oligonucleotide comprising a sequence of at least a segment of the template switching oligonucleotide. In the second amplification reaction, extension reaction reagents, e.g., polymerase, nucleoside triphosphates, co-factors (e.g., $Mg^{2+}$ or $Mn^{2+}$), that are also co-partitioned, can extend the primer sequence (e.g., first amplification product) using the barcoded oligonucleotide as template. The second amplification product can include the sequence of the primer, a sequence which is complementary to the sequence of the template polynucleotide (e.g., mRNA), and a sequence complementary to the second oligonucleotide.

In some embodiments of any of the spatial analysis methods described herein, three or more classes of biological analytes can be concurrently measured. For example, a feature can include capture probes that can participate in an assay of at least three different types of analytes via three different capture domains. A bead can be coupled to a barcoded oligonucleotide that includes a capture domain that includes a poly(T) priming sequence for mRNA analysis; a barcoded oligonucleotide that includes a capture domain that includes a random N-mer priming sequence for gDNA analysis; and a barcoded oligonucleotide that includes a capture domain that can specifically bind a an analyte capture agent (e.g., an antibody with a spatial barcode), via its analyte capture sequence.

In some embodiments of any of the spatial analysis methods described herein, other combinations of three or more biological analytes that can be concurrently measured include, without limitation: (a) mRNA, a lineage tracing construct, and cell surface and/or intracellular proteins and/or metabolites; (b) mRNA, accessible chromatin (e.g., ATAC-seq, DNase-seq, and/or MNase-seq), and cell surface and/or intracellular proteins and/or metabolites; (c) mRNA, genomic DNA, and a perturbation reagent (e.g., a CRISPR crRNA/sgRNA, TALEN, zinc finger nuclease, and/or antisense oligonucleotide as described herein); (d) mRNA, accessible chromatin, and a perturbation reagent; (e) mRNA, an analyte capture agent (e.g., any of the MHC multimers described herein), and a perturbation reagent; (f) mRNA, cell surface and/or intracellular proteins and/or metabolites, and a perturbation agent; (g) mRNA, a V(D)J sequence of an immune cell receptor (e.g., T-cell receptor), and a perturbation reagent; (h) mRNA, an analyte capture agent, and a V(D)J sequence of an immune cell receptor; (i) cell surface and/or intracellular proteins and/or metabolites, a an analyte capture agent (e.g., the MHC multimers described herein), and a V(D)J sequence of an immune cell receptor; (j) methylation status, mRNA, and cell surface and/or intracellular proteins and/or metabolites; (k) mRNA, chromatin (e.g., spatial organization of chromatin in a cell), and a perturbation reagent; (1) a V(D)J sequence of an immune cell receptor, chromatin (e.g., spatial organization of chromatin in a cell); and a perturbation reagent; and (m) mRNA, a V(D)J sequence of an immune cell receptor, and chromatin (e.g., spatial organization of chromatin in a cell), or any combination thereof.

In some embodiments of any of the spatial analysis methods described herein, four or more classes biological analytes can be concurrently measured. A feature can be a bead that is coupled to barcoded primers that can each participate in an assay of a different type of analyte. The feature is coupled (e.g., reversibly coupled) to a capture probe that includes a capture domain that includes a poly(T) priming sequence for mRNA analysis and is also coupled (e.g., reversibly coupled) to capture probe that includes a capture domain that includes a random N-mer priming sequence for gDNA analysis. Moreover, the feature is also coupled (e.g., reversibly coupled) to a capture probe that binds an analyte capture sequence of an analyte capture agent via its capture domain. The feature can also be coupled (e.g., reversibly coupled) to a capture probe that can specifically bind a nucleic acid molecule that can function as a perturbation agent (e.g., a CRISPR crRNA/sgRNA, TALEN, zinc finger nuclease, and/or antisense oligonucleotide as described herein), via its capture domain.

In some embodiments of any of the spatial analysis methods described herein, each of the various spatially-barcoded capture probes present at a given feature or on a given bead include the same spatial barcode sequence. In some embodiments, each barcoded capture probe can be released from the feature in a manner suitable for analysis of its respective analyte. For example, barcoded constructs A, B, C and D can be generated as described elsewhere herein and analyzed. Barcoded construct A can include a sequence corresponding to the barcode sequence from the bead (e.g., a spatial barcode) and a DNA sequence corresponding to a target mRNA. Barcoded construct B can include a sequence corresponding to the barcode sequence from the bead (e.g., a spatial barcode) and a sequence corresponding to genomic DNA. Barcoded construct C can include a sequence corresponding to the barcode sequence from the bead (e.g., a spatial barcode) and a sequence corresponding to barcode sequence associated with an analyte capture agent (e.g., an analyte binding moiety barcode). Barcoded construct D can include a sequence corresponding to the barcode sequence from the bead (e.g., a spatial barcode) and a sequence corresponding to a CRISPR nucleic acid (which, in some embodiments, also includes a barcode sequence). Each construct can be analyzed (e.g., via any of a variety of sequencing methods) and the results can be associated with the given cell from which the various analytes originated. Barcoded (or even non-barcoded) constructs can be tailored for analyses of any given analyte associated with a nucleic acid and capable of binding with such a construct.

In some embodiments of any of the spatial analysis methods described herein, other combinations of four or more biological analytes that can be concurrently measured include, without limitation: (a) mRNA, a lineage tracing construct, cell surface and/or intracellular proteins and/or metabolites, and gDNA; (b) mRNA, accessible chromatin (e.g., ATAC-seq, DNase-seq, and/or MNase-seq), cell surface and/or intracellular proteins and/or metabolites, and a perturbation agent (e.g., a CRISPR crRNA/sgRNA, TALEN, zinc finger nuclease, and/or antisense oligonucleotide as described herein); (c) mRNA, cell surface and/or intracellular proteins and/or metabolites, an analyte capture agent (e.g., the MHC multimers described herein), and a V(D)J sequence of an immune cell receptor (e.g., T-cell receptor); (d) mRNA, genomic DNA, a perturbation reagent, and accessible chromatin; (e) mRNA, cell surface and/or intracellular proteins and/or metabolites, an analyte capture agent (e.g., the MHC multimers described herein), and a perturbation reagent; (f) mRNA, cell surface and/or intracellular proteins and/or metabolites, a perturbation reagent, and a V(D)J sequence of an immune cell receptor (e.g., T-cell receptor); (g) mRNA, a perturbation reagent, an analyte capture agent (e.g., the MHC multimers described herein), and a V(D)J sequence of an immune cell receptor (e.g., T-cell receptor); (h) mRNA, chromatin (e.g., spatial organization of chromatin in a cell), and a perturbation reagent; (i) a V(D)J sequence of an immune cell receptor, chromatin (e.g., spatial organization of chromatin in a cell); and a perturbation reagent; (j) mRNA, a V(D)J sequence of an immune cell receptor, chromatin (e.g., spatial organization of chromatin in a cell), and genomic DNA; (k) mRNA, a V(D)J sequence of an immune cell receptor, chromatin (e.g., spatial organization of chromatin in a cell), and a perturbation reagent, or any combination thereof.

(b) Construction of Spatial Arrays for Multi-Analyte Analysis

This disclosure also provides methods and materials for constructing a spatial array capable of multi-analyte analysis. In some embodiments, a spatial array includes a plurality of features on a substrate where one or more members of the plurality of features include a plurality of oligonucleotides having a first type functional sequence and oligonucleotides having a second, different type of functional sequence. In some embodiments, a feature can include oligonucleotides with two types of functional sequences. A feature can be coupled to oligonucleotides comprising a TruSeq functional sequence and also to oligonucleotides comprising a Nextera functional sequence. In some embodiments, a functional sequence can include can include a sequencer specific flow cell attachment sequence, e.g., a P5 sequence, as well as functional sequence, which can include sequencing primer sequences, e.g., a R1 primer binding site. In some embodiments, one or more members of the plurality of features comprises both types of functional sequences. In some embodiments, one or more members of the plurality features includes a first type of functional sequence. In some embodiments, one or more members of the plurality of features includes a second type of functional sequence. In some embodiments, an additional oligonucleotide can be added to the functional sequence to generate a full oligonucleotide where the full oligonucleotide includes a spatial barcode sequence, an optional UMI sequence, a priming sequence, and a capture domain. Attachment of these sequences can be via ligation (including via splint ligation as is described in U.S. Patent Application Publication No. 20140378345, the entire contents of which are incorporated herein by reference), or any other suitable route. As discussed herein, oligonucleotides can be hybridized with splint sequences that can be helpful in constructing complete full oligonucleotides (e.g., oligonucleotides that are capable of spatial analysis).

In some embodiments, the oligonucleotides that hybridize to the functional sequences (e.g., TruSeq and Nextera) located on the features include capture domains capable of capturing different types of analytes (e.g., mRNA, genomic DNA, cell surface proteins, or accessible chromatin). In some examples, oligonucleotides that can bind to the TruSeq functional sequences can include capture domains that include poly(T) capture sequences. In addition to the poly (T) capture sequences, the oligonucleotides that can bind the TruSeq functional groups can also include a capture domain that includes a random N-mer sequence for capturing genomic DNA (e.g., or any other sequence or domain as described herein capable of capturing any of the biological analytes described herein). In such cases, the spatial arrays can be constructed by applying ratios of TruSeq-poly(T) and TruSeq-N-mer oligonucleotides to the features comprising the functional TruSeq sequences. This can produce spatial arrays where a portion of the oligonucleotides can capture mRNA and a different portion of oligonucleotides can capture genomic DNA. In some embodiments, one or more members of a plurality of features include both TruSeq and Nextera functional sequences. In such cases, a feature including both types of functional sequences is capable of binding oligonucleotides specific to each functional sequence. For example, an oligonucleotide capable of binding to a TruSeq functional sequence could be used to deliver an oligonucleotide including a poly(T) capture domain and an oligonucleotide capable of binding to a Nextera functional sequence could be used to deliver an oligonucleotide including an N-mer capture domain for capturing genomic DNA. It will be appreciated by a person of ordinary skill in the art that any combination of capture domains (e.g., capture domains having any of the variety of capture sequences described herein capable of binding to any of the different types of analytes as described herein) could be combined with oligonucleotides capable of binding to TruSeq and Nextera functional sequences to construct a spatial array.

In some embodiments, an oligonucleotide that includes a capture domain (e.g., an oligonucleotide capable of coupling to an analyte) or an analyte capture agent can include an oligonucleotide sequence that is capable of binding or ligating to an assay primer. The adapter can allow the capture probe or the analyte capture agent to be attached to any suitable assay primers and used in any suitable assays. The assay primer can include a priming region and a sequence that is capable of binding or ligating to the adapter. In some embodiments, the adapter can be a non-specific primer (e.g., a 5' overhang) and the assay primer can include a 3' overhang that can be ligated to the 5' overhang. The priming region on the assay primer can be any primer described herein, e.g., a poly (T) primer, a random N-mer primer, a target-specific primer, or an analyte capture agent capture sequence.

In some examples, an oligonucleotide can includes an adapter, e.g., a 5' overhang with 10 nucleotides. The adapter can be ligated to assay primers, each of which includes a 3' overhang with 10 nucleotides that complementary to the 5' overhang of the adapter. The capture probe can be used in any assay by attaching to the assay primer designed for that assay.

Adapters and assay primers can be used to allow the capture probe or the analyte capture agent to be attached to any suitable assay primers and used in any suitable assays. A capture probe that includes a spatial barcode can be attached to a bead that includes a poly(dT) sequence. A capture probe including a spatial barcode and a poly(T) sequence can be used to assay multiple biological analytes as generally described herein (e.g., the biological analyte includes a poly(A) sequence or is coupled to or otherwise is associated with an analyte capture agent comprising a poly (A) sequence as the analyte capture sequence).

A splint oligonucleotide with a poly(A) sequence can be used to facilitate coupling to a capture probe that includes a spatial barcode and a second sequence that facilitates coupling with an assay primer. Assay primers include a sequence complementary to the splint oligo second sequence and an assay-specific sequence that determines assay primer functionality (e.g., a poly(T) primer, a random N-mer primer, a target-specific primer, or an analyte capture agent capture sequence as described herein).

In some embodiments of any of the spatial profiling methods described herein, a feature can include a capture probe that includes a spatial barcode comprising a switch oligonucleotide, e.g., with a 3' end 3rG. For example, a feature (e.g., a gel bead) with a spatial barcode functionalized with a 3rG sequence can be used that enables template switching (e.g., reverse transcriptase template switching), but is not specific for any particular assay. In some embodiments, the assay primers added to the reaction can determine which type of analytes are analyzed. For example, the assay primers can include binding domains capable of binding to target biological analytes (e.g., poly (T) for mRNA, N-mer for genomic DNA, etc.). A capture probe (e.g., an oligonucleotide capable of spatial profiling) can be generated by using a reverse transcriptase enzyme/polymerase to extend, which is followed by template switching onto the barcoded adapter oligonucleotide to incorporate the barcode and other functional sequences. In some embodiments, the assay primers include capture domains capable of binding to a poly(T) sequence for mRNA analysis, random primers for genomic DNA analysis, or a capture sequence that can bind a nucleic acid molecule coupled to an analyte binding moiety (e.g., a an analyte capture sequence of an analyte capture agent) or a nucleic acid molecule that can function in as a perturbation reagent (e.g., a CRISPR crRNA/sgRNA, TALEN, zinc finger nuclease, and/or antisense oligonucleotide as described herein).

VI. Methods of Immune and Tumor Clustering

(a) Introduction

In the United States approximately 22,000 women receive a new diagnosis and 14,000 women die from ovarian cancer (OC) each year, making the disease the fifth most deadly cancer among women. Like many cancers, OC can be genetically heterogeneous making studies difficult to plan, execute, and interpret. Bulk methods such as whole-genome and whole-transcriptome sequencing are limited in their ability to resolve fine grain molecular signatures which limit their utility in dissecting the underlying biology of individual tumors.

Disclosed herein are methods of identifying areas of a biological sample as expressing one or more different clusters of genes. This disclosure is based on the understanding that various areas of a biological sample (e.g., a tissue section) have differential expression of transcripts and other methods which can identify distinct areas in a biological sample (e.g., H&E) do not provide differential transcript resolution. In some instances, the biological sample utilized in the methods described herein includes tumor cells. In some instances, the biological sample includes immunocellular infiltrates (e.g., immune cells, genes expressed by immune cells). In some instances, the biological sample includes both a tumor area in an immunocellular infiltrate area. In some instances, the spatial methods disclosed herein (e.g., permeabilizing a cell; cDNA synthesis; barcoding; library construction; sequencing and data analysis) is combined with gene clustering to identify areas of a sample that include a tumor, immunocellular infiltrates or immune cells, or both.

In some instances, within a particular area (e.g., a tumor) of a biological sample there can be regions of genetic heterogeneity. For example, a tumor can have at least 1, 2, 3, 4, 5, 6, 7, 8, or more distinct genetic expression patterns which can be elucidated using gene enrichment clusters as described herein. Understanding the genetic heterogeneity of a biological sample provides information that aids in determining the best course of treatment by providing improved diagnostic and therapeutic options for a subject having the tumor.

In some instances, a cluster includes detection of expression of mannan binding lectin serine peptidase 1 (MASP1; NCBI Gene ID: 5648) and hemoglobin subunit gamma-1 (HBG1; NCBI Gene ID: 3047). In some instances, a cluster includes up-regulation (e.g., over expression) of MASP1 and down-regulation (i.e., under expression) of HBG1 compared to expression of the same genes in other areas of the same biological sample. In some instances, a cluster comprising overexpression of MASP1 and under expression of HBG1 is called Cluster 1 in this disclosure.

In some instances, a cluster includes detection of expression of carbonic anhydrase 1 (CA1; NCBI Gene ID: 759) and scavenger receptor class A member 5 (SCARA5; NCBI Gene ID: 286133). In some instances, a cluster includes up-regulation (e.g., over expression) of CA1 and down-regulation (i.e., under expression) of SCARA5 compared to expression of the same genes in other areas of the same biological sample. In some instances, a cluster comprising overexpression of CA1 and under expression of SCARA5 is called Cluster 2 in this disclosure.

In some instances, a cluster includes detection of expression of AC009495.1 (e.g., GenBank number: AC009495.5) and mitogen-activated protein kinase 15 (MAPK15; NCBI Gene ID: 225689). In some instances, a cluster includes up-regulation (e.g., over expression) of AC009495.1 and down-regulation (i.e., under expression) of MAPK15 compared to expression of the same genes in other areas of the same biological sample. In some instances, a cluster comprising overexpression of AC009495.1 and under expression of MAPK15 is called Cluster 3 in this disclosure.

In some instances, a cluster includes detection of expression of small nucleolar RNA, C/D box 69 (SNORD69; NCBI Gene ID: 692109) and C-X-C motif chemokine ligand 3 (CXCL3; NCBI Gene ID: 2921). In some instances, a cluster includes up-regulation (e.g., over expression) of SNORD69 and down-regulation (i.e., under expression) of CXCL3 compared to expression of the same genes in other areas of the same biological sample. In some instances, a cluster comprising overexpression of SNORD69 and under expression of CXCL3 is called Cluster 4 in this disclosure.

In some instances, a cluster includes detection of expression of long intergenic non-protein coding RNA 2202 (LINC02202; NCBI Gene ID: 101927740) and long intergenic non-protein coding RNA 2614 (LINC02614; NCBI Gene ID: 101927056). In some instances, a cluster includes up-regulation (e.g., over expression) of LINC02202 and down-regulation (i.e., under expression) of LINC02614 compared to expression of the same genes in other areas of the same biological sample. In some instances, a cluster comprising overexpression of RNA 2202 and under expression of RNA 2614 is called Cluster 5 in this disclosure.

In some instances, a cluster includes detection of expression of gap junction protein beta 5 (GJB5; NCBI Gene ID: 2709) and matrix metallopeptidase 12 (MMP12; NCBI Gene ID: 4321). In some instances, a cluster includes up-regulation (e.g., over expression) of GJB5 and down-regulation (i.e., under expression) of MMP12 compared to expression of the same genes in other areas of the same biological sample. In some instances, a cluster comprising overexpression of GJB5 and under expression of MMP12 is called Cluster 6 in this disclosure.

In some instances, a cluster includes detection of expression of AL445433.1; (Ensembl Gene ID: ENSG00000227034) and A-Raf proto-oncogene, serine/threonine kinase (ARAF; NCBI Gene ID: 369). In some instances, a cluster includes up-regulation (e.g., over expression) of AL445433.1 and down-regulation (i.e., under expression) of ARAF compared to expression of the same genes in other areas of the same biological sample. In some instances, a cluster comprising overexpression of AL445433.1 and under expression of ARAF is called Cluster 7 in this disclosure.

In some instances, the methods disclosed herein include defining an area of a biological sample as having a tumor or a region of interest. In some instances, the methods disclosed herein include determining heterogeneity of a tumor or a region of interest in a biological sample. In some instances, the methods include contacting the biological sample with a plurality of probes, wherein a probe of the plurality of probes comprises a spatial barcode and a capture domain that binds specifically to a nucleic acid in the biological sample, wherein the nucleic acid is associated with an immune cell or a cancer cell. In some instances, the methods further include determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample. In some instances, after the contacting and determining steps, the methods include defining the area of the biological sample as having the tumor or the region of interest based on the location of the nucleic acid associated with the immune cell or the cancer cell in the biological sample.

In some instances, the biological sample (e.g., a tissue sample) disclosed herein includes one or more types of cells. In some instances, areas of a biological sample are identified by a trained pathologist. In some instances, areas of a biological sample include areas that include tumor cells. In some instances, areas of a biological sample include areas that include immunocellular infiltrates or immune cells. Thus, in some instances, the sample can be identified as heterogeneous, or having heterogeneity. As used herein, heterogeneity includes, but is not limited to, differences in cell types, percentage of a particular cell type, differences in gene expression among cells in a biological sample, and/or amount of infiltrating cells (e.g., immune cells) in a biological sample. As such, a sample can be "heterogeneous" when some areas of the sample include one type of cell while another area includes a different type of cell. Without limitation and for example, a biological sample can be heterogeneous or have heterogeneity if one area of the biological sample includes tumor cells and another area of the biological sample includes immune cells. Differences in heterogeneity can further include abundance of cell types in a particular area. Further, a biological sample can be heterogeneous or have heterogeneity with respect to nucleic acid (DNA or RNA) detection or expression.

In some embodiments, the methods disclosed herein include determining the type and/or percentage of a particular cell in a biological sample. In determining the heterogeneity of a cell, one can then identify a particular disease state (e.g., cancer) and/or determine a method of treatment. In some embodiments, the methods disclosed herein include determining expression of a particular gene or set of genes in a biological sample. A set of expressed genes can include but is not limited to genes expressed in a particular cellular pathway or genes dysregulated in a particular disease state, such as cancer. Also provided herein are methods that combine determining heterogeneity of the biological sample with the spatial technology disclosed herein.

Methods disclosed herein can be performed on any type of sample. In some embodiments, the sample is a fresh tissue. In some embodiments, the sample is a frozen sample. In some embodiments, the sample was previously frozen. In some embodiments, the sample is a fixed sample, for example a formalin-fixed, paraffin embedded (FFPE) sample. Nucleic acids in FFPE samples generally are heavily cross-linked and fragmented, and therefore this type of sample allows for limited RNA recovery using conventional detection techniques. In certain embodiments, methods of targeted RNA capture provided herein are less affected by RNA degradation associated with FFPE fixation than other methods (e.g., methods that take advantage of oligo-dT capture and reverse transcription of mRNA). In some instances, the biological sample can be stained prior to targeted nucleic acid capture, using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the biological sample is affixed to a slide. In some embodiments, the sample is stained prior to detection of one or more genes of interest. In some instances, the sample is imaged using any method disclosed herein. In some instances, imaging is done using a brightfield microscope. In some instances, the biological sample is stained using H&E and then imaged using a brightfield microscope.

In some instances, the biological sample is examined for detection of one or more immune infiltrates. In some instances, detection of one or more immune infiltrates is performed on a biological sample that has been stained using H&E. In some instances, the one or more immune infiltrates includes detection of $CD3^+$, $CD4^+$, $CD8^+$, $CD20^+$, $CD68^+$, $FOXP3^+$, or combinations thereof. See e.g., Nederlof et al. *Breast Cancer Res* 21, 151 (2019), which is incorporated by reference in its entirety.

In some embodiments, the methods described herein can be used in conjunction with any type of cell aggregate or tumor cell. For example, the methods of the invention can identify cancer types or sarcomas. Specific cancers that can be examined and identified using the method of the present invention include, but are not limited to, breast cancer, ovarian cancer, colon cancer, pancreatic cancer, prostate cancer, squamous cell cancer, cervical cancer, lung cancer, small cell lung cancer, kidney cancer, liver cancer, brain tumor, skin cancer, and bladder cancer. In some instances, cancers are derived from xenografts of human cancer cells removed from humans or non-human mammals (e.g., mice).

In some embodiments, disclosed are methods that include assessing, scoring, or defining a tumor or cancer in a biological sample. Examples of cancer that can be treated in accordance with the methods described herein include, but are not limited to, B cell lymphomas (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

In some instances, the cancer is breast cancer.

In some instances, the cancer is ovarian cancer.

In some embodiments, one or more probes (e.g., from a cluster of cancer-specific probes or a cluster of immune-specific probes) are hybridized to analytes in the biological sample. In some embodiments, the probes include a capture domain that is substantially complementary to an analyte of interest and a spatial barcode that provides the location of the probe and analyte.

In some embodiments, the one or more probes is 40 nucleotides long. In some embodiments, the one or more probes is between 40 and 160 nucleotides long. In some embodiments, the one or more probes is between 40 and 120 nucleotides long. In some embodiments, the one or more probes is about 40, about 41, about 42, about 43, about 44, about 45, about 46, about 47, about 48, about 49, about 50, about 51, about 52 about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, or about 160 nucleotides long.

In some embodiments, the analyte from the biological sample is associated with a disease or condition (e.g., cancer). In some embodiments, the analyte from the biological sample comprises a mutation. In some embodiments, the analyte from the biological sample comprises a single nucleotide polymorphism (SNP). In some embodiments, the analyte from the biological sample comprises a trinucleotide repeat. In some embodiments, the analyte from the biological sample comprises an insertion, deletion or translocation.

In some embodiments, the domain of the one or more probes hybridizes to a particular exon of a transcript (i.e., an mRNA molecule). For example, a transcript can be processed such that an exon that would otherwise be excised during a normal setting is included in the mature mRNA product in a different setting (e.g., a pathological setting such as cancer). In some embodiments, the domain of the one or more probes identifies (e.g., hybridizes to) one or more isoforms or an analyte, but not others. In some embodiments, one or more probes hybridizes to a particular exon that is detected in a pathological setting (e.g., cancer).

In some embodiments, the one or more probes is fully complementary (i.e., 100% complementary) to a portion of a target analyte. In some embodiments, one or more probes is partially complementary (i.e., less than 100% complementary) to a portion of a target analyte. In some embodiments, the one or more probes has at least 75%, at least 80%, at least 85%, at least 90%, at least 91%, at least 92%, at least 93%, at least 94%, at least 95%, at least 96%, at least 97%, at least 98%, or at least 99% sequence identity to a portion of a target analyte.

In some embodiments, one or more probes are included in one or more cohorts. Cohorts include groups of one or more probes that target a particular cohort of analytes. For example, a cohort can include a set of one or more probes that is particular to a pathological setting (e.g., cancer). In some embodiments, more than one cohort can be used to selectively detect analytes. For example, in some embodiments, at least 1, at least 2, at least 3, at least 4, at least 5, at least 6, at least 7, at least 8, or more cohorts (e.g., set of probes) can be used to target analyte detection. In some embodiments, a cohort includes probes that hybridize and detect analytes dysregulated in cancer (e.g., a cancer cohort or immune cell cohort). In some embodiments, the cohort allows for quantitative analysis of analytes aberrantly expressed in the cancer transcriptome while avoiding the excess costs and time associated with sequencing an entire exome.

As disclosed herein, an area of a sample can be assessed, scored, or defined based on expression of one or more clusters of genes. In some instances, scoring can be performed by combining the expression of one or more clusters of genes with a pathologist's determination of identifying distinct areas of a biological sample.

(b) Immune Cluster Profiling

Disclosed herein are methods of profiling the transcriptome of a biological sample (e.g., a tissue) by using clustering data to determine one or more cell types in a sample. In some embodiments, immunological markers (e.g., immune checkpoint genes, cytokines) are profiled in a biological sample. After profiling the transcriptome, one can determine the percentage and/or relative abundance of a particular type of cells in a biological sample (relative to other biological samples). In some embodiments, the methods include determining the percentage and/or amount of a particular type of genes associated with a particular phenotype (e.g., cancer) in a biological sample. In some embodiments, the methods include determining the percentage and/or amount of a particular type of immune infiltrate associated with a particular phenotype (e.g., cancer) in a biological sample.

In some instances, the immune cells identified using the methods disclosed herein include, but are not limited to, naïve B cells, memory B cells, plasma cells, CD8 T cells, CD4 naïve T cells, CD4 memory-resting T cells, CD4 memory-activated T cells, follicular helper T cells, regulatory T cells (Tregs), gamma-delta T cells, resting NK cells, activated NK cells, monocytes, M0 macrophages, M1 macrophages, M2 macrophages, resting dendritic cells, activated dendritic cells, resting mast cells, activated mast cells, eosinophils, neutrophils and any combinations thereof. In some instances, particular combinations of immune cells are used to differentiate areas of heterogeneous samples.

In some embodiments described herein, the methods are used to detect and/or identify immune cell profiles in a biological sample by selective detection of immune cells. Immune cells express various adaptive immunological receptors relating to immune function, such as T cell receptors (TCRs) and B cell receptors (BCRs). T cell receptors and B cell receptors play a part in the immune response by specifically recognizing and binding to antigens and aiding in their destruction. In some instances, immune cell infiltrates are detected. Immune cell infiltrates include but are not limited to one or more immune cells that are detected in a biological sample. Immune cells that infiltrate a biological sample include but are not limited to regulatory B cells; dendritic cells; germinal center B cells; cells expressing interferon gamma (IFNγ); cells expressing immunoglobulins; cells expressing one or more of interleukin 4 (IL4), interleukin 10 (IL10), interleukin 17 (IL17), and/or interleukin 21 (IL21); macrophages; myeloid derived suppressor cells; neutrophils; natural killer (NK) cells; natural killer T (NKT) cells; follicular B helper T cells; helper CD4+ T cells; cells expressing transforming growth factor beta (TGFβ); tumor-infiltrating lymphocytes regulatory T cells; or any combination thereof.

In some embodiments, the biological sample is a cell. In some embodiments, the biological sample is a tissue. In some embodiments, the biological sample is a tissue section. In some embodiments, the tissue section is a fixed tissue section, for example an FFPE tissue section. In some embodiments, a tissue section is fixed with, for example, PFA, acetone, methanol, etc. In some embodiments, the cell type is a normal (i.e., non-cancerous) cell. In some embodiments, the cell type is a cancer cell.

In some instances, an immune score of a biological sample is determined. An immune score as used herein refers to quantifying the density and location of immune cells in a biological sample (e.g., near or within a tumor in the biological sample). In some instances, the immune score is determined by identifying the intratumoral immune infiltrates in the biological sample. In some instances, the immune score is determined by identifying the invasive margin (at, near, or adjacent to the tumor) of immune infiltrates in the biological sample. In some instances, the immune score is determined by identifying the immune infiltrates in an area of the biological sample distinct from an area of a sample comprising a tumor. See e.g., Mlecinik et al., *J Clin Oncol.* (2011) 29(6):610-8; Galon et al., *J Transl Med.* (2012) 10:1, each of which is incorporated by reference in its entirety.

In some instances, immune status or inflammatory status of a biological sample is determined. Immune status as used herein refers the ability of the subject to demonstrate an immune response or to defend itself against disease or foreign substances. Immune status can be related to the relative abundance of immune cells or immune cell infiltrates detected in the biological sample (e.g., compared to a reference individual or biological sample). In such embodiments, the immune or inflammatory status can be a relative determination by quantifying the expression of one, at least two, at least three, at least four, at least five, at least six, at least seven, at least eight, at least nine, at least ten, or more cytokines or chemokines. For example, the immune or inflammatory status is increased when the abundance of cytokines or chemokines have quantity in the tumor sample at a level above a reference sample. In some instance, the reference sample includes a sample (or area of a sample) not identified as including a tumor. In some instance, the reference sample includes a sample (or area of a sample) identified as including a tumor but lacking expression of a cytokine or chemokine expressed in an area of interest.

Examples of cytokines detected using the methods disclosed herein include but are not limited to IL-1, IL-2, IL-3, IL-4, IL-5, IL-6, IL-7, IL-8, IL-10 IL-12, IL-15, IL-18, IL-21, IL-23, IFN-α, IFN-7, M-CSF, GM-CSF, TNF-α, MIF, TGF-β, Fas-Fas ligand, and combinations thereof.

In some instances, the cytokine is a ligand that binds to a Type I Cytokine Receptor. Examples of ligands that bind to a Type I Cytokine Receptors disclosed herein include IL-2, IL-3, IL-4, IL-5, IL-6, IL-7, IL-9, IL-11, IL-12, IL-13, IL-15, IL-21, IL-23, IL-27, erythropoietin, GM-CSF, G-CSF, growth hormone, prolactin, oncostatin M, and leukemia inhibitory factor. In some instances, the cytokine detected is a ligand that binds to a Type II Cytokine Receptor. Examples of ligands that bind to a Type II Cytokine Receptors disclosed herein include IFN-α/β, IFN-γ, IL-10, IL-20, IL-22, and IL-28. In some instances, the cytokine is a ligand that binds to an Immunoglobulin Superfamily Receptor. Examples of ligands that bind to an Immunoglobulin Superfamily Receptors disclosed herein include IL-1, CSF1, c-kit, and IL-18. In some instances, the cytokine is a ligand that binds to an IL-17 Receptor. Examples of ligands that bind to an IL-17 Receptors disclosed herein include IL-17, IL-17B, IL-17C, IL-17D, IL-17E, IL-17F.

In some instances, the cytokine is a ligand that binds to a G Protein-Coupled Receptors (GPCR). Examples of ligands that bind to a G Protein-Coupled Receptor (GPCR) disclosed herein include IL-8, CC chemokines disclosed herein, and CXC chemokines disclosed herein. In some instances, the cytokine is a ligand that binds to a TGF-β receptor. Examples of ligands that bind to a TGF-β receptor disclosed herein include TGF-β. In some instances, the cytokine is a ligand that binds to a Tumor Necrosis Factor Receptors (TNFR). Examples of ligands that bind to a Tumor Necrosis Factor Receptors (TNFR) disclosed herein include CD27, CD30, CD40, CD120, and Lymphotoxin-β. See Lee and Margolin, *Cancers* (*Basel*), (2011) 3(4): 3856-3893, which is incorporated by reference in its entirety.

Examples of chemokines that are detected using the methods disclosed herein include chemokines that promote neovascularization and escape immunosurveillance via recruitment of immunosuppressive cells, such as T regulatory cells, NK T cells, macrophages and immature dendritic cells (iDCs) or by promoting metastasis. In some instances, the chemokine detected includes IL-8, CXCL8, CXCL9, CXCL10, CXCL12, MIP-1α, CCL3, CCL17, CCL22, CCL19, CCL21, MDC, MIG, IP-10, SDF-1, SLC, ELC, TARC, and combinations thereof.

In some instances, inflammatory cell concentration in the biological sample is determined. In some instances, particular inflammatory markers are used to determine the presence and relative expression (e.g., concentration) of one or more inflammatory cells. In some instances, the inflammatory markers include but are not limited to markers that detect $CD3^+$, $CD8^+$, $CD68^+$, $CD83^+$, $FoxP3^+$ cells, neutrophils, mast cells, $CD1a^+$ immature dendritic cells, or combinations thereof.

In some embodiments, the methods disclosed herein rely on information provided for a purified cell type. In some embodiments, gene expression of individual types of cell (e.g., lymphocytes, monocytes, polymorphonuclear leukocytes) can be determined, creating a database of one or more transcriptome profiles for each cell type. In some embodiments, data sources that include gene signatures (e.g., expression matrices) for various samples and cell types are used to create one or more transcriptome profiles. In some embodiments, the resulting characterization can also be used to identify a gene signature/matrix (e.g., inflammatory gene signature/matrix, e.g., a gene signature/matrix including one or more of CCL5, CD27, CD274, CD276, CD8A, CMKLR1, CXCL9, CXCR6, HLA-DQA1, HLA-DRB1, HLA-E, IDO1, LAG3, NKG7, PDCD1LG2, PSMB10, STAT1, and TIGIT) or a tumor profile of a tumor (e.g., across the entire tumor or a region of interest in the tumor), heterogeneity (e.g., protein expression heterogeneity, immune cell heterogeneity, inflammatory status/level/score/cluster profile heterogeneity, gene expression heterogeneity, and/or genetic mutation heterogeneity) of a tumor (e.g., across the entire tumor or a region of interest in a tumor), immune status of a tumor (e.g., across the entire tumor or a region of a tumor), inflammatory status of a tumor (e.g., across the entire tumor or a region of interest in a tumor), and an inflammatory score of a tumor (e.g., across the entire tumor or a region of interest in a tumor).

An inflammatory score as used herein includes a histopathologic scoring tool by which semi-quantitative data can be obtained from a biological sample. Any method to quantify and produce an inflammatory score in a biological sample can be used herein. In some instances, the relative abundance of immune cell infiltrates in a biological sample is quantified relative to a reference sample. See Gibson-Corley et al., *Vet Pathol.* 2013 November; 50(6). An inflammation score also refers to comparative ratios of values determined using the Glasgow prognostic score, including modified Glasgow Prognostic Score (mGPS), neutrophil-to-lymphocyte ratio (NLR), platelet-to-lymphocyte ratio (PLR), lymphocyte-to-monocyte ratio (LMR), Prognostic Nutritional Index (PNI), platelet count, and combination of platelet count and neutrophil to lymphocyte ratio (COP-NLR), See e.g., Bugada et al., *Biomed Res Int.* 2014; 2014:142425; Nakagawa et al., *Pancreatology,* 2019 July; 19(5):722-728; Lin et al., *Mol Med Rep.* 2015 April; 11(4): 2421-2428, each of which is incorporated by reference in its entirety. In some instances, an inflammation score is assessed and quantified by detecting inflammatory markers using immunohistochemistry, immunofluorescence, or any method of detection described herein. In some instances, an inflammation score is assessed and quantified using, for example, molecular markers (e.g., cyclooxygenase-2 (COX-2), inducible nitric oxide synthase (iNOS), matrix metallopeptidase-9 (MMP-9), mammalian target of rapamycin (mTOR), phosphorylated 40S ribosomal protein S6 (Phos-S6)).

The methods provided herein can also be used to determine a relative level of inflammation in a subject (e.g., determine an inflammatory score) or a subject's response to treatment or the development of resistance to treatment, or relapse after a treatment regimen. The methods described herein can also be used to identify candidate targets for potential therapeutic intervention and/or to identify biomarkers associated with different disease states in a subject.

In some instances, the gene expression associated with an immune response in or around a tumor can be examined to develop a spatially resolved inflammation score for each section from each subject. In some instances, genes that are involved in an immune response and are examined here include CCL5, HLA-DRB1, CD27, HLA-E, CD274, IDO1, CD276, LAG3, CD8A, NKG7, CMKLR1, PDCD1LG2, CXCL9, PSMB10, CXCR6, STAT1, HLA-DQA1, TIGIT, and any combination thereof. Further expression profiles of cells involved in an immune response can be identified and utilized in methods disclosed herein from data sources including but not limited to sequence-based sources such as the FANTOM5 project, the ENCODE project, and Blueprint epigenomics; and array-based sources such as Gene Expression Omnibus (GEO) as described in Aran et al. *Genome Biology,* 18:220 (2017), which is herein incorporated by reference in its entirety.

Using methods disclosed herein, the local inflammatory cell concentration of a biological sample can be assessed. Local inflammatory cell concentration refers to the abundance of a particular immune cell (e.g., any immune cell described herein) in an entire biological sample or a region of interest of the biological sample. Methods of measuring inflammatory cell concentration include histological methods as well as methods that utilize gene expression methods disclosed herein.

In some embodiments, one or more transcriptome profiles is determined from the same tissue or organ (e.g., breast) sample. For example a tissue can have multiple types of cell types and cell phenotypes (e.g., cancerous). In some embodiments, a transcriptome profile allows a user to detect a particular type of cell in a biological sample. In some embodiments, a transcriptome profile allows a user to measure the percentage of a total biological sample (e.g., the percentage of the area) that a particular cell type occupies based on the transcriptome expression of the cell type in the biological sample. In some embodiments, a transcriptome profile as disclosed herein includes different types of cells from blood. In some embodiments, a transcriptome profile includes blood (e.g., leukocyte) infiltration into an organ.

In some embodiments, the one or more transcriptome profiles created are grouped into clusters of multiple transcriptome profiles based on gene expression and cell type. For example, cells can be clustered into lymphoid cells, stem cells, myeloid cells, and stromal cells. In some embodiments, the methods disclosed herein provide steps to bifurcate the type of cell further into individual cell types, based on gene expression. In some embodiments, transcriptome profiles are generated by determining genes that are overexpressed in a particular cell type as compared to a reference sample. In some embodiments, an overexpressed gene is one that is expressed at least 1.5-fold more, 2.0-fold more, 3.0 fold more, 4.0-fold more, 5.0-fold more, or more compared to a reference sample. In some embodiments, transcriptome profiles are generated by determining genes that are underexpressed in a particular cell type as compared to a reference sample. In some embodiments, an underexpressed gene is one that is expressed at least 1.5-fold less, 2.0-fold less, 3.0 fold less, 4.0-fold less, 5.0-fold less, or less compared to a reference sample.

In some embodiments, the methods disclosed herein include generating an expression matrix. As used herein, an expression matrix is a cohort of expression of analytes (e.g., DNA, RNA, protein) for a biological sample or an individual cell type. In some instances, the expression matrix includes at least 2, at least 3, at least 4, at least 5, at least 6, at least 7, at least 8, at least 9, at least 10, at least 20, at least 30, at least 40, at least 50, at least 60, at least 70, at least 80, at least 90, at least, 100, at least 200, at least 300, at least 400, at least 500, at least 600, at least 700, at least 800, at least 900, at least 1000 or more analytes. In some instances, the analytes detected in the expression matrix are associated with one or more disease states. For example, the expression matrix in some instances is associated with a particular type of cancer (e.g., any cancer described herein). In some instances, the expression matrix is associated with infiltration of one or more immune cells. In some instances, the expression matrix in the biological sample can be determined and then compared to one or more individual cell types to determine the abundance and type of cell types in the biological sample. In some instances, the expression matrix in the biological sample can be determined and then compared to one or more individual cell types to determine the abundance and type of cancer cells present in the biological sample. In some instances, the expression matrix in the biological sample can be determined and then compared to one or more individual cell types to determine the abundance and type of immune cells present in the biological sample. In some instances, the methods disclosed herein identify the most reliable gene expression matrix from an individual cell to use as a reference. In some instances, a subset of the cell types can be used to create a reference transcriptome for comparison to a test or unknown tissue sample transcriptome profile.

In some embodiments, many (e.g., thousands) of gene signatures of different cell types are created. In some embodiments, of all gene signatures created, a subset of gene signatures are used. That is, in some embodiments, for example, relative scores of a cell type are computed and compared to scores of all other samples, generating a raw score. In some embodiments, the raw score can be converted to an adjusted score. After isolation and purification of total RNA from the biological sample, a subset of RNA transcripts can be identified (e.g., using one or more of the clusters described herein).

In some embodiments, to identify clusters, linear support vector regression is used, as described in Newman et al. *Nat Methods,* 12(5):453-7 (2015), which is herein incorporated by reference in its entirety. Linear support vector regression implements a machine learning approach, called support vector regression (SVR), that improves deconvolution performance through a combination of feature selection and robust mathematical optimization techniques. In particular, the methods disclosed herein rely on particular features identified in the one or more transcriptome profiles to determine the presence and relative amount (i.e., percentage amount) of a particular cell type in a mixed population of cells (e.g., a tissue). In some embodiments, single-sample gene set enrichment analysis (ssGSEA) is used to score each sample based on cluster expression of gene signatures. ssGSEA is a method for determining a single aggregate score of the enrichment of a set of genes in the top of a ranked gene expression profile. See, e.g., Barbie et al. *Nature,* 462:108-12 (2009), which is incorporated by reference in its entirety.

In some embodiments, gene transcripts associate with inflammation are evaluated in a transcriptome profile. In some embodiments, gene transcripts associated with an immune response are evaluated in a transcriptome profile. In some embodiments, the biological sample is from a subject who is undergoing treatment for a disease (e.g., a particular type of cancer). In some embodiments, biological samples can be taken before, during, and after the course of treatment. In some embodiments, a transcriptome profile is generated at different time points (e.g., before, during, and after the course of treatment). In some embodiments, the transcriptome profile provides information that allows one to determine whether a subject will be responsive, is response, or has been responsive to a particular treatment. In some embodiments, a transcriptome profile provides information for determining whether a subject was responsive to a particular treatment regimen but has relapsed and is no longer responsive to that treatment regimen.

In some embodiments, immune signaling factors are analyzed in a sample. In the setting of cancer, for example, evaluating immune signal factors in a sample provides information that can be translated into cancer progression, progression-free survival (PFS), and/or overall survival (OS). In some embodiments, generating and evaluating a transcriptome profile predicts a response to a type of treatment. See e.g., Ayers et al. *J Clin Invest.;* 127(8):2930-2940 (2017), which is incorporated by reference in its entirety.

Figure 27A:
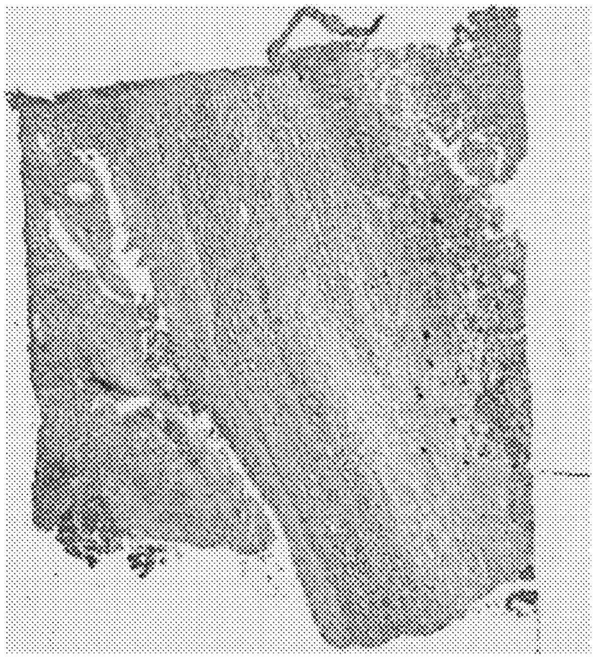
FIG. 27A shows an H&E stain of an ovarian cancer sample comprising a tumor.
Figure 27B:
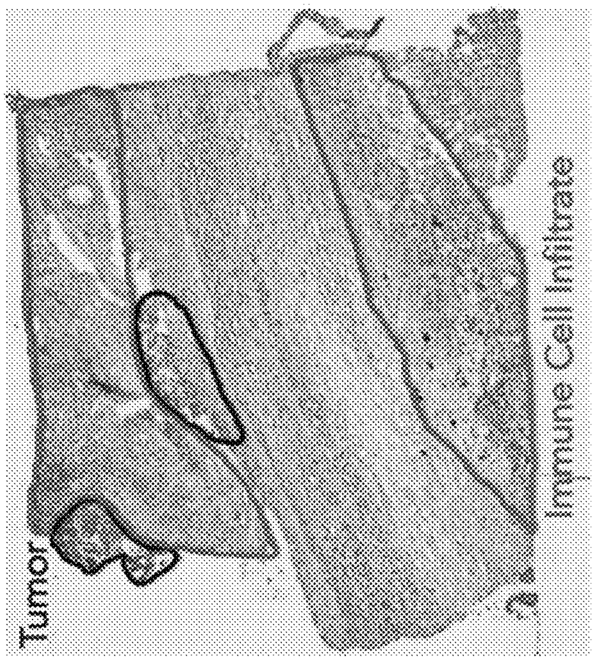
FIG. 27B shows the same H&E stain of FIG. 27A with histological boundaries of tumor or areas having immune cell infiltrates identified.
Figure 27C:
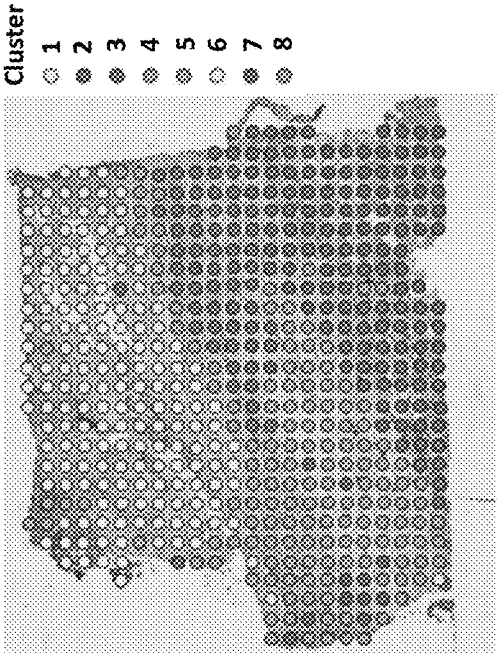
FIG. 27C shows differential expression patterns of eight different gene clusters in areas of the biological sample of FIG. 27A. Overlap of cluster expression and phenotype is shown. For example, cluster 6 associates with the tumor; cluster 1 is a macrophage region near the tumor; cluster 2 is expressed in immune cell infiltrate areas.

In some embodiments, more than one cluster of immune infiltrates can be analyzed in a particular sample. In some embodiments, serial sections of a tumor can be analyzed for expression of different cluster groups. For example, various clusters can be detected at different spatial sections of a biological sample. See e.g., FIG. 27C. In addition, areas of a two-dimensional sample (e.g., a tissue section) can be analyzed for distinct profiles. In some embodiments, at least 2, at least 3, at least 4, at least 5, at least 6, at least 7, at least 8, at least 9, at least 10, or more distinct immune cluster profiles can be determined.

(c) Tumor Cluster Profiling

In some embodiments, the methods disclosed herein include profiling a tumor based on expression of genes or a group of genes. In some instances, disclosed herein are methods used to detect the presence, level, and/or activity of mRNA(s), genomic DNA, and/or protein(s) in the tumor or the region of interest in the tumor. In some embodiments, the methods include examining the expression profile of the entire genome in a tissue sample. In some embodiments, the methods include examining the expression profile of the set of genes having a common pathways or having co-expression patterns based on prior biological knowledge. Pathways that are commonly dysregulated in tumors include but are not limited to the RTK/RAS pathway, the Wnt pathway, the Hippo pathway, the p53 pathway, the Myc pathway, the Nrf2 pathway, the TGFβ pathway, the PI3K pathway, the Notch pathway, and pathways involving cell cycle. See e.g., Sanchez-Vega et al., *Cell* 173, 321-337 (2018), which is incorporated by reference in its entirety.

In some instances, the methods disclosed herein include detecting one or more genomic mutations in an area of a biological sample. In some instances, the genomic mutation is a gene amplification, a gene deletion, insertion or inactivation, a mutation that results in increased transcription of a gene, a mutation that results in the expression of an protein having increased activity, a mutation that results in decreased transcription of a gene, a mutation that results in the expression of a protein having decreased activity as compared to a wildtype genome, or a combination thereof. In some instances, the one or more genomic mutations contribute to resistance of the tumor or a region of interest in the tumor to treatment with a therapeutic agent.

In some instances, disclosed herein are methods of identifying or diagnosing the type of cancer based on the assessment, scoring, and/or determined heterogeneity in the tumor or the region of interest in a tumor through tumor cluster profiling. In some embodiments, tumor cluster profiling is achieved using methods of pathway determinations, including pathway analysis (e.g., Ingenuity Pathway Analysis, Qiagen IPA). In some embodiments, a pathway associated with a particular cancer is used to analyze the transcriptome of a sample. In some embodiments, a transcript can be identified and can be associated with a pre-identified pathway associated with a phenotype (e.g., a disease state such as cancer). In some embodiments, the transcript was not previously identified as associated with a pre-identified pathway. In some embodiments, a pathway can be identified based on expression patterns of a set of genes. In some embodiments, multiple (related or unrelated) pathways can be combined during analysis of a tumor.

In some embodiments, the methods include Gene Set Enrichment Analysis (GSEA), as disclosed in Subramanian et al., *Proc Natl Acad Sci USA.;* 102(43):15545-50 (2005), which is incorporated by reference in its entirety. Compared to single-gene analysis, GSEA features ease the interpretation of a large-scale experiment by identifying pathways and processes, allows detection of modest changes in individual genes associated with a pathway or process, and can help define gene subsets to elucidate cellular pathways and processes.

In some embodiments, the methods of GSEA include calculating an enrichment score. See Subramanian et al. *Proc Natl Acad Sci USA*, (2005) 102(43):15545-50 (incorporated by reference in its entirety) for examples of a calculation as disclosed herein. There are three key elements of the GSEA method. Briefly, step 1 includes calculation of an Enrichment ScoreA calculated enrichment score (ES) that reflects the degree to which a set of genes is overrepresented at the extremes (top or bottom) of an entire ranked list. The score is calculated by walking down the list, increasing a running-sum statistic when a gene is encountered in the set and decreasing it when genes not in the set are encountered. The magnitude of the increment depends on the correlation of the gene with the phenotype. The enrichment score is the maximum deviation from zero encountered in the random walk. In some instances, the methods of calculating ES include estimation of significance level of the ES. Finally, in some instances, calculating the GSEA includes adjustment for multiple hypothesis testing as disclosed in Subramanian et al. In some embodiments, after determining the extremes of an entire genome, the level of significance of the enrichment score can be estimated.

In some embodiments, more than one cancer pathway (e.g., a cluster of genes) or sets of genes can be analyzed in a particular sample. In some embodiments, serial sections of a tumor can be analyzed for expression of different cluster groups. For example, various clusters can be detected at different spatial sections of a biological sample. See e.g., FIG. 30C. In addition, areas of a two-dimensional sample (e.g., a tissue section) can be analyzed for distinct profiles. In some embodiments, at least 2, at least 3, at least 4, at least 5, at least 6, at least 7, at least 8, at least 9, at least 10, or more distinct tumor cluster profiles can be determined.

(d) Methods of Identifying Subjects for Treatment

Provided herein is a method of identifying whether a patient is in need of treating a cancer using a therapeutic composition (e.g., a pharmaceutical composition) described herein. The disclosure features methods for identifying whether a patient is in need of a therapeutic composition (e.g., a pharmaceutical composition) for the prevention and/or treatment of a cancer.

In some instances, the methods disclosed herein include identifying a patient as having an increased likelihood of being responsive to the treatment for cancer. In some instances, the subject is previously identified as having an increased likelihood of being responsive to the treatment for cancer by contacting a biological sample obtained from the subject (i.e., a patient) with a plurality of probes, wherein a probe of the plurality of probes comprises a spatial barcode and a capture domain that binds specifically to a nucleic acid in the biological sample, wherein the nucleic acid is associated with an immune cell or a cancer cell; determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample; and identifying a subject having the nucleic acid associated with an immune cell or a cancer cell in the biological sample as having an increased likelihood of being responsive to the treatment for cancer.

In some instances, disclosed herein are methods of scoring, assessing, or defining areas of a sample based on immune clustering or tumor clustering which can aide in determining whether a patient is in need of a therapeutic composition for the treatment of cancer or other disease. The methods of scoring, assessing, or defining areas of a sample based on immune clustering or tumor clustering as described herein can be useful for identifying the need for treating a cancer in a subject. The methods of scoring, assessing, or defining areas of a sample based on immune clustering or tumor clustering as described herein can also be useful for identifying potential preventative measures for preventing cancer from developing in a subject. Thus, provided herein are methods of determining a course for treating a cancer in a subject in need thereof, comprising aiding in identifying a therapeutic regimen for the subject, for example aiding in determining a therapeutically effective amount of a therapeutic composition which might benefit a subject based on the results of scoring, assessing, or defining areas of the sample. Also provided herein are methods of preventing a cancer in a subject in need thereof, comprising helping in determining a therapeutically effective amount of a therapeutic composition which can be administered to a subject based on the results of scoring, assessing, or defining areas of the sample.

In some instances, the subject is a human. In some instances, the subject is an animal. In some embodiments, the subject is a mammal such as a non-primate (e.g., cow, pig, horse, cat, dog, rat, etc.) or a primate (e.g., monkey or human).

In some instances, the cancer is a hematologic cancer. In some instances, the cancer is a solid organ cancer. In some instances, the cancer is ovarian cancer. In some instances, the cancer is epithelial ovarian cancer. In some instances, the cancer is Stage I ovarian cancer. In some instances, the cancer is Stage II ovarian cancer. In some instances, the cancer is Stage III ovarian cancer. In some instances, the cancer is Stage IV ovarian cancer.

In some instances, the cancer is breast cancer. In some instances, the breast cancer is epithelial in origin. In some instances, the breast cancer is ductal carcinoma in situ (DCIS). In some instances, the breast cancer is invasive ductal carcinoma (IDC). In some instances, the breast cancer is invasive lobular carcinoma (ILC). In some instances, the breast cancer is triple negative breast cancer. In some instances, the breast cancer is inflammatory breast cancer (IBC). In some instances, the breast cancer is metastatic breast cancer. In some instances, the breast cancer is breast cancer that develops during pregnancy. In some instances, the breast cancer is medullary carcinoma. In some instances, the breast cancer is tubular carcinoma. In some instances, the breast cancer is mucinous carcinoma. In some instances, the breast cancer is stromal in origin. In some instances, stromal, or connective tissue, cells that may be cancerous include myofibroblasts or blood vessel cells which can lead to phyllodes tumors, fibrosarcomas and angiosarcomas.

In some instances, the methods disclosed herein include selecting a treatment for cancer. In some instances, the methods of selection include selecting a treatment for cancer for a subject previously identified as having an increased likelihood of being responsive to the treatment for cancer. In some instances, the methods of selection include selecting a treatment for cancer for a subject previously identified as having an increased likelihood of being responsive to the treatment for cancer include contacting a biological sample obtained from the subject with a plurality of probes, wherein a probe of the plurality of probes comprises a spatial barcode and a capture domain that binds specifically to a nucleic acid in the biological sample, wherein the nucleic acid is associated with an immune cell or a cancer cell; determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample; and identifying a subject having the nucleic acid associated with an immune cell or a cancer cell in the biological sample as having an increased likelihood of being responsive to the treatment for cancer.

In some instances, the methods of selecting a treatment for cancer for a subject previously identified as having an increased likelihood of being responsive to the treatment for cancer using a method comprising the steps of contacting a biological sample obtained from the subject with a plurality of probes, wherein a probe of the plurality of probes comprises a spatial barcode and a capture domain that binds specifically to a nucleic acid in the biological sample, wherein the nucleic acid is associated with an immune cell or a cancer cell; determining (i) all or a part of a sequence corresponding to the spatial barcode or a complement thereof, and (ii) all or a part of a sequence corresponding to the nucleic acid associated with the immune cell or the cancer cell, or a complement thereof, and using the determined sequences of (i) and (ii) to identify a location of the nucleic acid associated with the immune cell or the cancer cell in the biological sample; determining heterogeneity of a tumor or a region of interest in the biological sample based on the location of the nucleic acid associated with the immune cell or the cancer cell in the biological sample; and identifying a subject determined to have heterogeneity of the tumor or the region of interest in the biological sample as having an increased likelihood of being responsive to the treatment for cancer.

(e) Diagnostic Methods

Provided herein is a method of diagnosing a subject as having cancer using one or more of the methods of scoring, assessing, or defining areas of a sample based on immune clustering or tumor clustering as described herein. Moreover, the disclosure additionally provides a method for predicting and/or tracking the efficacy of treatment of a therapeutic composition for a subject having cancer using the methods of scoring, assessing, or defining areas of a sample based on immune clustering or tumor clustering as described herein.

In some instances, the methods can include, for example, selecting a subject having a cancer; evaluating (e.g., detecting) the expression and/or activity of one or more genes associated with a cancer described herein); and, if expression and/or activity of one or more genes associated with a cancer is detected, providing the subject with a personalized treatment regimen that includes administering an effective amount of one or more therapeutic compositions as disclosed herein to the subject.

In some instances, the methods include selecting a subject having cancer; detecting the presence and/or level of one or more of the cluster of genes disclosed herein; and, if one or more of the cluster of genes is detected, providing the subject with a personalized treatment regimen that includes administering an effective amount of a therapeutic composition as disclosed herein to the subject. In some embodiments, the method includes administering the therapeutic composition as disclosed herein to the subject under conditions and for a period of time sufficient to treat the subject.

EXAMPLES

Figure 26:
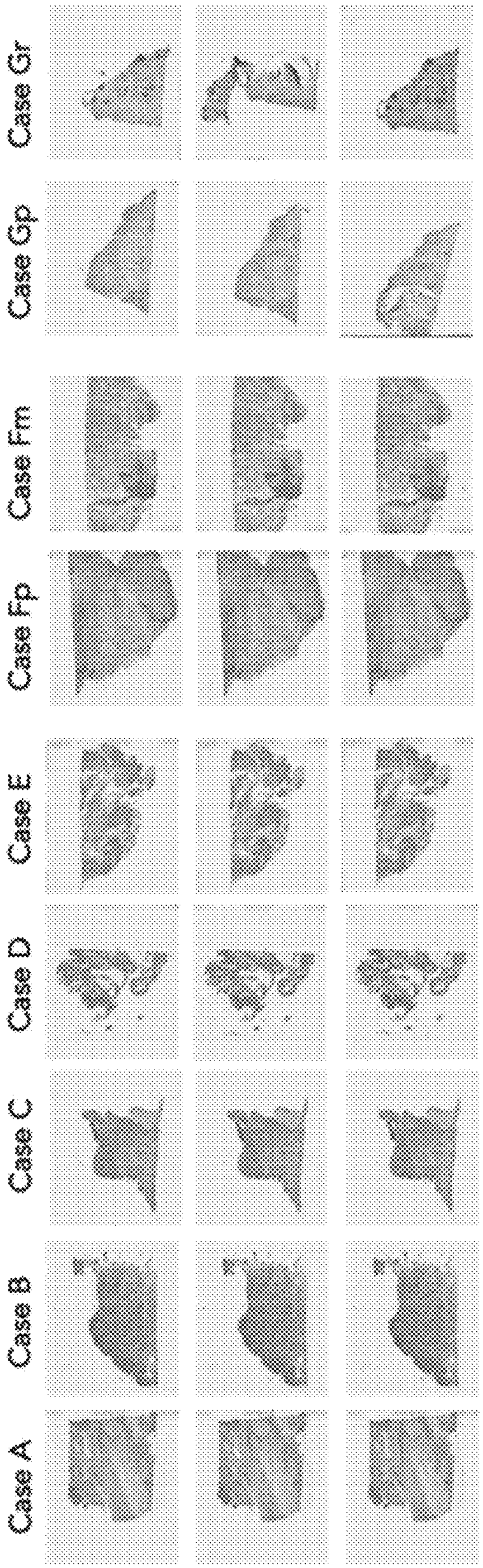
FIG. 26 shows Haemotoxylin and Eosin (H&E) stain of ovarian cancer biological samples.

Example 1. Structurally Resolved Immune Profiling in Ovarian Carcinoma Using Whole-Transcriptome Spatial Sequencing Investigation of 11 subjects, previously diagnosed with ovarian cancer (OC), was performed using whole-transcriptome spatial sequencing on the 10× Genomics Spatial Transcriptomics platform which requires no tissue dissociation keeping fragile cell types intact. Serial tissue sections were cut and stained for H&E. FIG. 26. Using serial sections of solid tumors from each subject the tissue was profiled at 100 Tm resolution and spatial resolution of the gene expression signatures (e.g., matrices) and cluster regions of tissue based on these signatures (e.g., matrices) (FIGS. 22A-22D and 27A-27C) was determined. Next, the transcriptional profiles of serial sections were aggregated from each case increasing the power to cluster similar regions and identify differentially expressed genes within these tissues.

Figure 28:
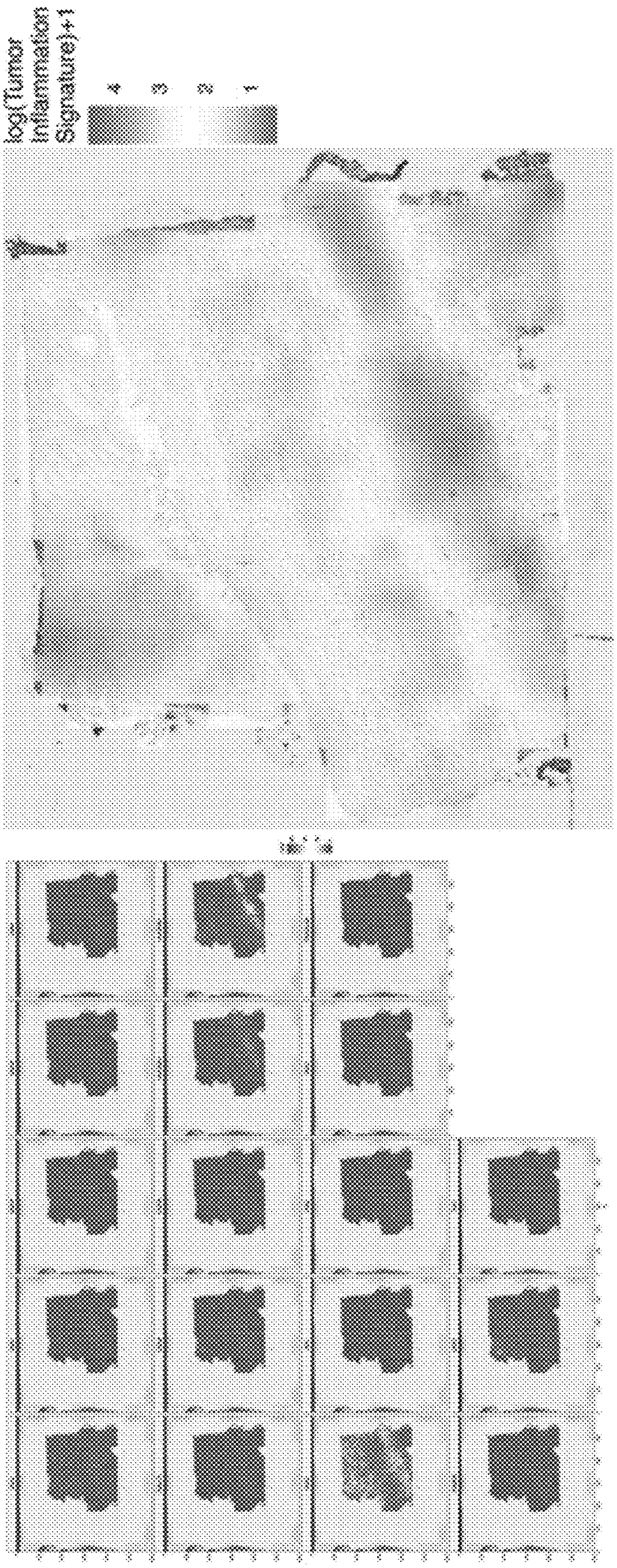
FIG. 28 shows a tumor inflammation signature of the biological sample of FIG. 27A.

Using spatial gene expression signatures, a refined analysis of 18 key genes known to play an important role in the immune response of OC was conducted for use in developing a spatially resolved inflammation score for each section from each subject. The 18 key genes identified as playing a role in an immune response of OC include CCL5, HLA-DRB1, CD27, HLA-E, CD274, IDO1, CD276, LAG3, CD8A, NKG7, CMKLR1, PDCD1LG2, CXCL9, PSMB10, CXCR6, STAT1, HLA-DQA1, and TIGIT. A statistically-significant regionalized inflammation score was observed within each subject (see FIGS. 22E and 28 for representative slides (e.g., Case A in FIG. 26)). Further, an inflammation score was quantified among serial slides. As shown in FIG. 22F, no significant difference was identified when calculating tumor inflammation score (TIS) among serial slides. However, when examining TIS among spots identified by one of the seven different clusters as differentially expressed, each slide showed spatially-resolved TIS. FIG. 22G. Thus, clusters can be used to disambiguate inflammatory and noninflammatory regions (see e.g., FIGS. 27A-27C) in order to identify individually enriched biochemical pathways in each region which highlight the intra-subject heterogeneity of OC in the study.

Further, clear transcriptional substructure was observed in some tumors, where different tumor regions were defined by molecular pathways that are associated with tumorigenesis (i.e. UV Response, Epithelial to Mesenchymal Transition, and Estrogen Response pathways), regions defined by immune populations (B cells, Macrophages, and CD4+ T cells), and molecular pathways that are associated with immune infiltration (i.e. complement, IL2, and IL6 signaling pathways).

Next, clustering of expression of dysregulated genes was performed. In particular, at least 7 Clusters were identified. In Cluster 1, MASP1 is upregulated and HBG1 is downregulated. In Cluster 2, CA1 is upregulated and SCARA5 is downregulated. In Cluster 3, AC009495.1 is upregulated and MAPK15 is downregulated. In Cluster 4, SNORD69 is upregulated and CXCL3 is downregulated. In Cluster 5, LINC02202 is upregulated and LINC02614 is downregulated. In Cluster 6, GJB5 is upregulated and MMP12 is downregulated. In Cluster 7, AL445433.1 is upregulated and ARAF is downregulated.

Figure 23A:
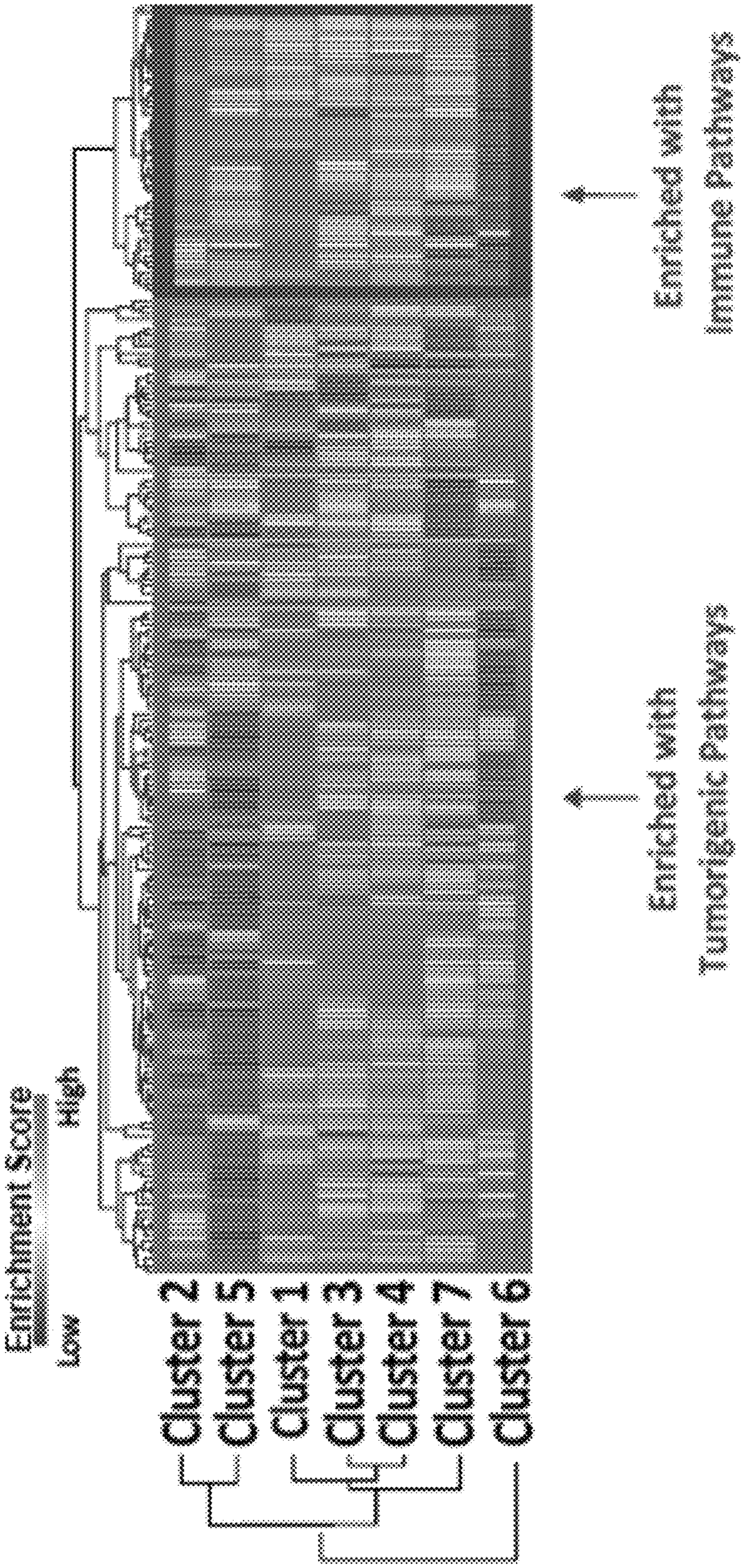
FIG. 23A shows differentially expressed genes from each aggregated cluster were assessed. X-axis represents the gene sets investigated. Y-axis is each cluster of differentially expressed genes. Branching represents hierarchical clustering of Biocarta's 289 tumorigenic and immune related gene sets.
Figure 23B:
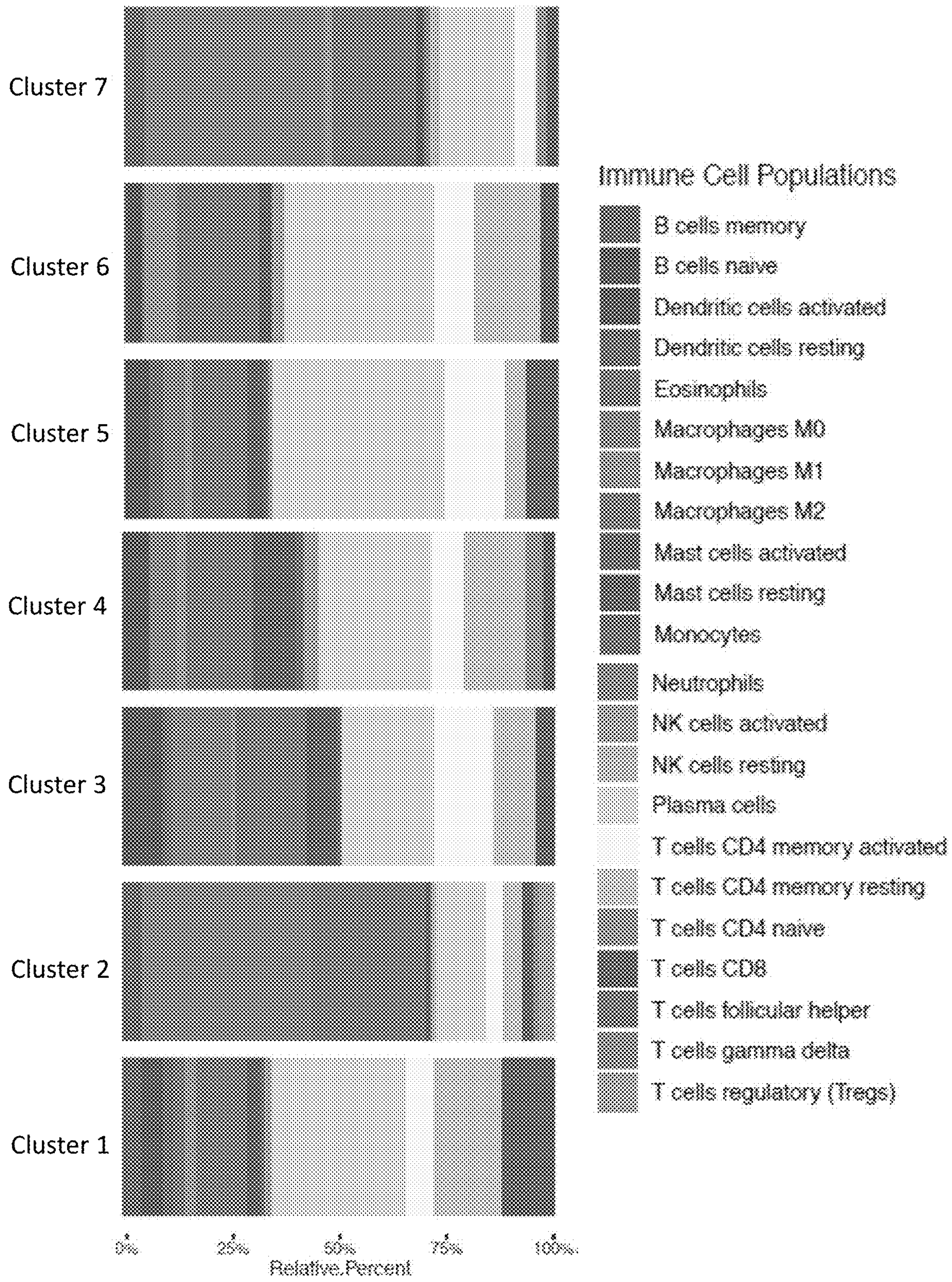
FIG. 23B shows analysis of 22 immune cell subsets. Rows represent gene expression signatures within spatial clusters and reveal dynamic spatial distribution and localization of immune cell subtypes.

Using Biocarta Pathways (Rouillard A D, The harmonizome: a collection of processed datasets gathered to serve and mine knowledge about genes and proteins. Database (Oxford) (2016)), differentially expressed genes from each aggregated Cluster were assessed. Differential enrichment scores were determined in each cluster. See FIG. 23A. Finally, using Cibersort (Newman et al., *Nat Methods*, (2015) 12(5):453-7), Immune cell populations of each cluster was determined. FIG. 23B.

Figure 29:
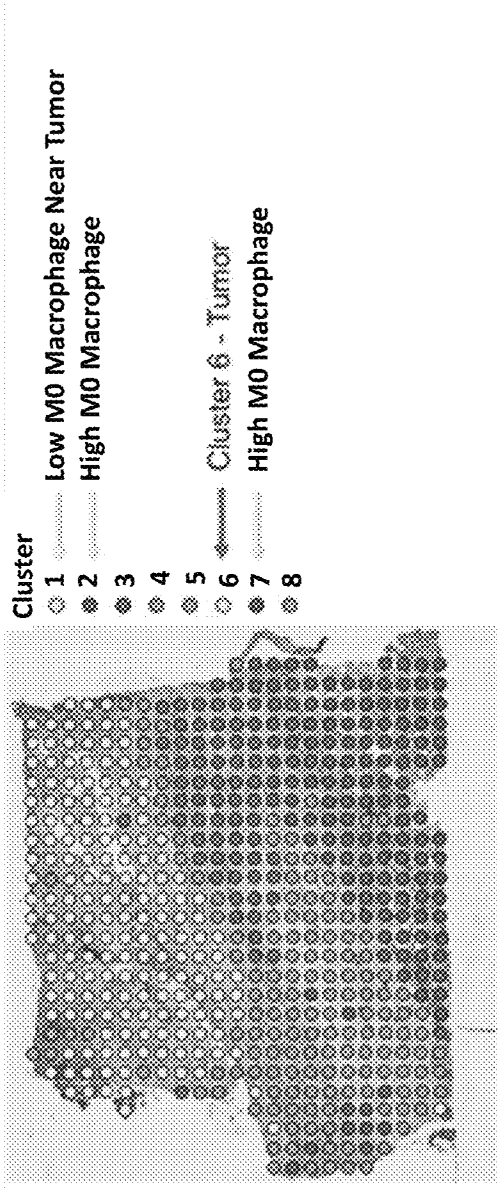
FIG. 29 shows differential expression patterns of eight gene clusters in areas of the biological sample of FIG. 27A.

Further, as shown in FIG. 29 and Table 2, Cluster 1 showed enhanced expression near the region identified as having a tumor. After generating an expression matrix using Cluster 1, it was determined that cells identified with Cluster 1 included low levels of naïve M0 macrophages near the tumor (cluster 6). Cluster 2 showed enhanced expression near the region identified as near an area of immune cell infiltrates. After generating an expression matrix using Cluster 2, it was identified that cells identified with Cluster 2 included high levels of naïve M0 macrophages. High levels of naïve M0 macrophages also were identified in Cluster 7. Finally, detection of Cluster 6 expression was identified in regions of the tumor.

This approach highlights the power of using spatial whole-transcriptome sequencing in solid tumor studies to help unravel the complexity of heterogeneous cancers.

Example 2. Single Cell Genomics and Spatial Transcriptomics Enables Novel Approaches to Dissect Tumor Heterogeneity Tumor heterogeneity is a hallmark of cancer where the molecular and cellular interactions within the tumor microenvironment can dictate a cancer's fate. To understand tumor heterogeneity in a cancer sample, a detailed molecular characterization of ovarian cancers (OC) using single cell DNA sequencing was performed, and novel spatial transcriptomic methods were used to assess tumor heterogeneity and the tumor microenvironment in a spatially resolved manner.

Fresh-frozen OCT-embedded specimens from 11 high grade OC cases were used for this study. See FIG. 26. Single nuclei from 100-micron sections were used to perform 10× Genomics Chromium single cell copy number variation (scCNV) assay, 1000 nuclei per sample were targeted. For spatial transcriptomics, three serial 5-micron sections were placed on spatial array slides and processed using manufacturer specifications (10× Genomics). Libraries were sequenced on the Illumina NovaSeq 6000 system and data was processed using the 10× Genomics CellRanger and Loupe Browser software. scCNV analysis of OC revealed varying degrees of tumor heterogeneity. Defined tumor clonal populations were observed within some cases that showed both unique and overlapping regions of copy number variation (CNV) suggesting that these populations arose from a common progenitor. However, other cases exhibited CNV heterogeneity with no clear overlap in copy number profiles suggesting that these may represent completely independent cancers occupying the same tumor bed. Somatic events in known cancer genes, including PTEN and CDKN2A homozygous deletions in individual tumors, were also identified.

Figure 30A:
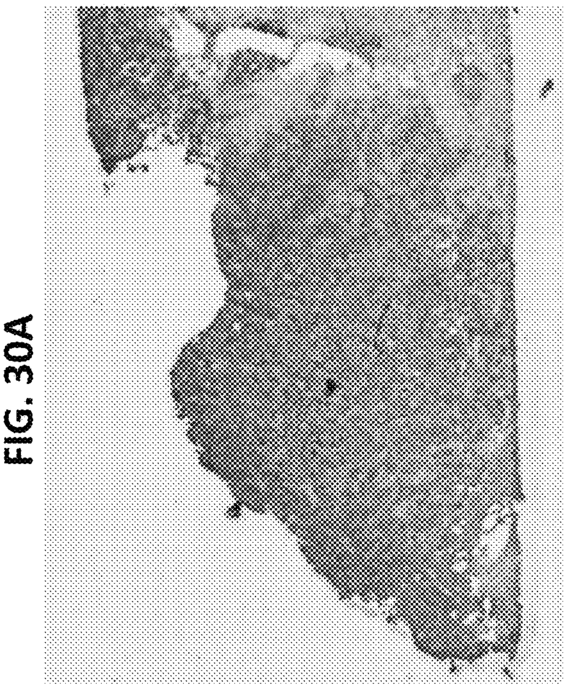
FIG. 30A shows an H&E stain of a biological sample comprising an ovarian cancer tumor.
Figure 30B:
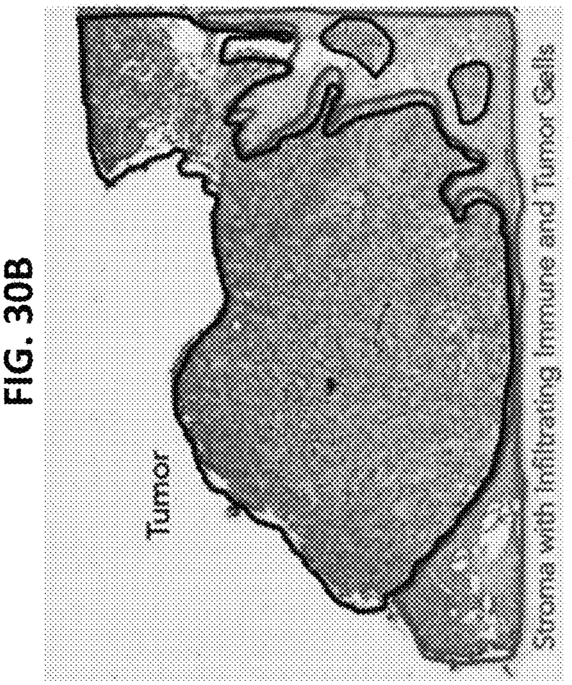
FIG. 30B shows the same H&E stain of FIG. 30A with histological boundaries of tumor or areas having immune cell infiltrates identified.
Figure 30C:
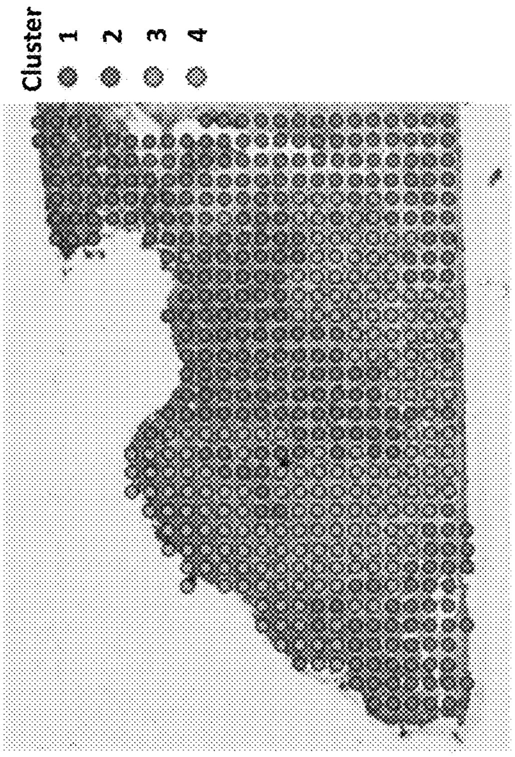
FIG. 30C shows differential expression patterns of four different gene clusters in areas of the biological sample of FIG. 30A. Distinct gene expression profiles in the tumor were identified using three different clusters (clusters 1, 3, and 4). A distinct gene expression profile was observed in stroma with infiltrating immune and tumor cells (cluster 2).
Figure 31:
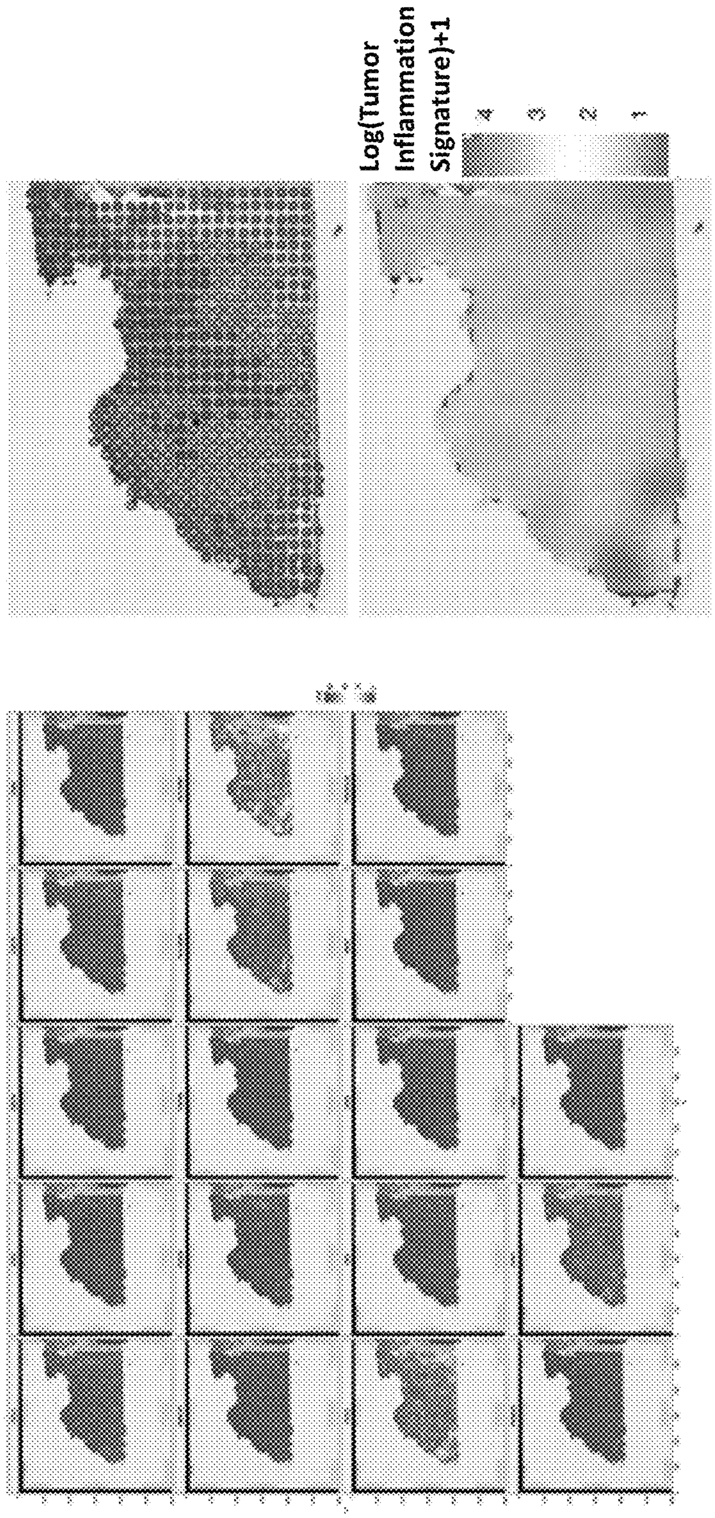
FIG. 31 shows a tumor inflammation signature of the biological sample of FIG. 30A.

Spatial transcriptomic data from each section were analyzed to create spatially defined cellular clusters at 100-micron resolution. Using the sample identified as Case B in FIG. 26, spatial transcriptomic assay results revealed cellular heterogeneity across the entirety of the tumor microenvironment in an anatomically resolved manner. FIGS. 30A-30C. Regions of the sample from Case B were identified as tumor or stroma with infiltrating immune and tumor cells. See FIG. 30B. Detection of the genes associated with Clusters 1-4 were determined (FIG. 30C), and spatial heat maps of the inflammatory microenvironment at the single gene level and for gene profiles that define specific inflammatory signals and immune cell profiles were created (FIG. 31).

Figure 32:
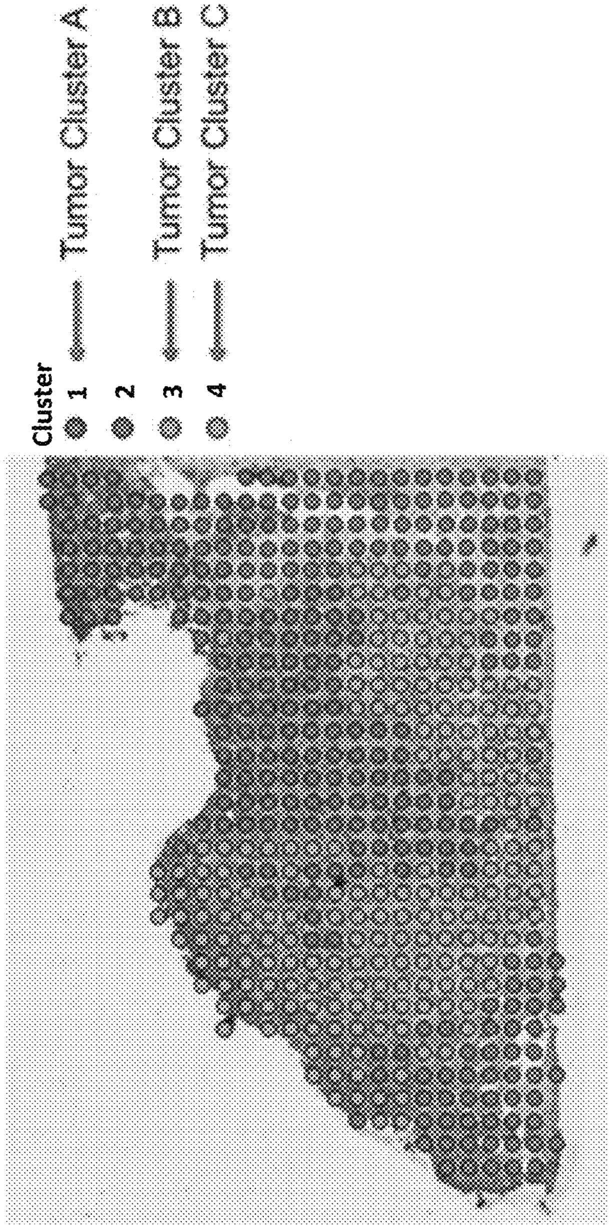
FIG. 32 shows differential expression patterns of four gene clusters in areas of the biological sample of FIG. 30A.

As shown in FIG. 32 and Table 3., Clusters 1, 3, and 4 were expressed in different areas of the tissue section as were defined as tumor (designated as Tumor Clusters A, B, and C). Importantly, these data also revealed clear transcriptional substructure in some tumors, where different tumor regions were defined by unique gene sets associated with different molecular processes known to be related to tumorigenesis. Integrated analysis was also performed to determine if specific DNA copy number events (PTEN deletion, CDKN2A deletion) derived from scCNV analysis could be detected spatially at the RNA level, and if these genomic alterations were associated with specific spatial transcriptional features of the tumor microenvironment.

TABLE 2

Immune cell detection using Clusters 1-8.

| Input Sample | B cells Naïve | B cells memory | Plasma Cells | T cells CD8 | T cells CD4 naïve | T cells CD4 memory resting | T cells CD4 memory activated | T cells follicular helper | T cells regulatory (Tregs) | T cells gamma delta | NK cells resting | NK cells activated |
|---|---|---|---|---|---|---|---|---|---|---|---|---|
| Cluster 1 | 0 | 0.059 | *0.32* | *0.088* | 0 | *0.137* | *0.055* | 0 | 0 | 0 | 0 | *0.002* |
| Cluster 2 | 0.004 | 0.011 | *0.30* | 0.042 | 0 | 0 | 0.036 | 0 | *0.028* | 0 | *0.002* | 0 |
| Cluster 3 | 0.001 | 0.015 | *0.35* | 0.007 | 0 | *0.09* | *0.095* | 0 | 0 | 0 | *0.022* | 0 |
| Cluster 4 | 0 | 0.049 | *0.34* | 0 | 0.003 | *0.14* | 0.031 | 0 | 0 | 0 | 0 | *0.037* |
| Cluster 5 | 0 | 0.044 | *0.34* | *0.051* | 0 | 0.022 | *0.106* | 0 | 0 | 0 | 0 | *0.005* |
| Cluster 6 | 0 | 0.036 | *0.35* | 0.041 | 0.021 | *0.076* | 0.046 | 0 | 0 | 0 | 0 | *0.017* |
| Cluster 7 | 0 | 0.008 | *0.33* | 0.007 | 0.005 | *0.065* | 0.026 | 0 | 0 | *0.003* | *0.018* | 0 |
| Cluster 8 | 0.019 | 0.005 | *0.34* | 0.043 | 0 | 0.012 | 0.007 | 0 | 0 | *0.004* | 0 | 0.049 |

| Input Sample | Monocytes | Macrophages M0 | Macrophages M1 | Macrophages M2 | Dendritic cells resting | Dendritic cells activated | Mast cells resting | Mast cells activated | Eosinophils | Neutrophils | p-value | Pearson Correlation |
|---|---|---|---|---|---|---|---|---|---|---|---|---|
| Cluster 1 | 0.008 | 0 | 0.019 | *0.113* | 0.002 | 0.006 | 0.014 | 0 | 0.006 | 0 | 0.000 | 0.612 |
| Cluster 2 | 0 | *0.29* | 0 | *0.225* | 0.004 | 0 | 0.011 | 0 | 0 | 0.006 | 0.001 | 0.399 |
| Cluster 3 | 0.004 | *0.105* | 0.011 | *0.175* | 0.018 | 0 | *0.063* | 0 | 0.003 | 0.005 | 0.000 | 0.553 |

TABLE 2-continued

Immune cell detection using Clusters 1-8.

| | | | | | | | | | | | | |
|---|---|---|---|---|---|---|---|---|---|---|---|---|
| Cluster 4 | 0 | *0.058* | 0.039 | *0.188* | 0 | 0.002 | *0.046* | 0 | 0.004 | 0 | 0.000 | 0.576 |
| Cluster 5 | 0.001 | *0.051* | 0.007 | *0.159* | 0.002 | 0.005 | 0.024 | 0 | 0.004 | 0 | 0.000 | 0.613 |
| Cluster 6 | 0 | 0.024 | 0.045 | *0.102* | 0 | 0.004 | 0.011 | 0 | 0 | 0 | 0.000 | 0.612 |
| Cluster 7 | 0 | *0.29* | 0 | *0.177* | 0 | 0 | 0.005 | 0 | 0.003 | 0.017 | 0.001 | 0.403 |
| Cluster 8 | 0 | *0.072* | 0.007 | *0.195* | 0.014 | 0.003 | *0.092* | 0 | 0.015 | 0.014 | 0.000 | 0.575 |

In Table 2, italicized values indicate increases in cell type; underlined values indicate decreases in cell type.

TABLE 3

Immune cell detection using Clusters 1-4.

| Input Sample | B cells Naïve | B cells memory | Plasma Cells | T cells CD8 | T cells CD4 naïve | T cells CD4 memory resting | T cells CD4 memory activated | T cells follicular helper | T cells regulatory (Tregs) | T cells gamma delta | NK cells resting | NK cells activated |
|---|---|---|---|---|---|---|---|---|---|---|---|---|
| Cluster 1 | 0 | *0.087* | 0.022 | 0 | 0 | *0.182* | 0 | 0.022 | 0.029 | 0 | 0 | *0.113* |
| Cluster 2 | 0 | 0.026 | *0.206* | *0.066* | 0 | *0.048* | 0 | 0.007 | 0.026 | 0 | 0 | *0.053* |
| Cluster 3 | 0 | *0.069* | 0.016 | 0 | 0 | *0.206* | 0 | 0.01 | 0.011 | 0 | 0 | *0.098* |
| Cluster 4 | 0 | *0.109* | *0.083* | 0.024 | 0 | *0.109* | 0 | 0 | 0 | 0 | 0.014 | 0 |

| Input Sample | Monocytes | Macrophages M0 | Macrophages M1 | Macrophages M2 | Dendritic cells resting | Dendritic cells activated | Mast cells resting | Mast cells activated | Eosinophils | Neutrophils | p-value | Pearson Correlation | RMSE |
|---|---|---|---|---|---|---|---|---|---|---|---|---|---|
| Cluster 1 | 0 | *0.246* | *0.09* | *0.172* | 0 | 0 | 0 | 0.031 | 0 | 0.006 | 0.014 | 0.256 | 0.990 |
| Cluster 2 | 0.009 | *0.118* | *0.06* | *0.258* | 0.007 | 0 | 0.017 | 0 | 0 | 0.001 | 0.003 | 0.350 | 0.942 |
| Cluster 3 | 0 | *0.298* | *0.056* | *0.16* | 0 | 0.017 | 0 | 0.06 | 0 | 0 | 0.013 | 0.264 | 0.988 |
| Cluster 4 | 0 | *0.278* | *0.101* | *0.016* | 0.004 | 0.012 | 0 | 0.014 | 0 | 0 | 0.009 | 0.311 | 0.972 |

In Table 3, italicized values indicate increases in cell type; underlined values indicate decreases in cell type.

These approaches highlight the power of novel spatial whole-transcriptomic approaches in solid tumor studies to help unravel the complexity of heterogeneous cancers.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining a location of an mRNA expressed in an ovarian tissue sample, the method comprising:

(a) contacting the ovarian tissue sample obtained from a subject with an array comprising a plurality of capture probes, wherein a capture probe of the plurality of capture probes comprises a spatial barcode and a capture domain, wherein a plurality of the capture probes hybridize to a mRNA expressed by a tumor cell in the ovarian tissue sample, and wherein the mRNA expressed by the tumor cell is GJB5 and/or MMP12, wherein GJB5 mRNA expression is increased in the tumor cell and MMP12 is decreased in the tumor cell as compared to GJB5 mRNA expression and MMP12 mRNA expression in non-tumor cells of the ovarian tissue sample;

(b) hybridizing the mRNAs expressed by the ovarian tissue sample to the plurality of capture probes;

(c) extending the plurality of capture probes, thereby generating a plurality of extended capture probes, wherein a 3' end of the capture probe uses the mRNA as a template to generate an extended capture probe; and (d) sequencing (i) all or part of the plurality of extended capture probes, (ii) the spatial barcode or a complement thereof, and (iii) all or part of a sequence corresponding to the mRNA expressed by the ovarian tissue sample, or a complement thereof, and using the determined sequences of (ii) and (iii) to identify the location of the mRNA expressed in the ovarian tissue sample.

2. The method of claim 1, further comprising comparing expression of the mRNA in the ovarian tissue sample to expression of mRNA in a reference sample.

3. The method of claim 2, wherein the reference sample comprises a non-cancerous sample from a different subject, a cancerous sample from a different subject, a non-cancerous sample from the subject, or a cancerous sample from the subject.

4. The method of claim 2, wherein the reference sample is a non-tumor sample from a different subject or a non-tumor sample from the subject.

5. The method of claim 1, wherein the capture probe further comprises one or more functional domains, a unique molecular identifier, a cleavage domain, or combinations thereof.

6. The method of claim 1, wherein the capture domain comprises a poly-uridine sequence or a poly-thymidine sequence.

7. The method of claim 1, further comprising generating a nucleic acid that is complementary to all or a part of the extended capture probe.

8. The method of claim 1, wherein the ovarian tissue sample is permeabilized with a permeabilization agent prior to step (b).

9. The method of claim 8, wherein the permeabilization agent comprises trypsin or a protease.

10. The method of claim 8, wherein the permeabilization agent comprises pepsin or proteinase K.

11. The method of claim 1, further comprising amplifying the extended capture probe, or a complement thereof.

12. The method of claim 1, further comprising determining a location of one or more additional mRNAs expressed by one or more immune cells in the ovarian tissue sample.

13. The method of claim 1, wherein the mRNA expressed by the tumor cell comprises at least one mutation.

14. The method of claim 13, wherein the at least one mutation is selected from a substitution, a deletion, a translocation, and an insertion.

15. The method of claim 1, wherein the ovarian tissue sample is a frozen tissue sample, a fresh tissue sample, or a fixed tissue sample.

16. The method of claim 15, wherein the fixed tissue sample is a formalin-fixed, paraffin-embedded tissue sample.

17. The method of claim 1, further comprising, prior to step (a), fixing the ovarian tissue sample.

18. The method of claim 1, wherein the ovarian tissue sample comprises a fresh-frozen tissue section or a formalin fixed paraffin embedded tissue section.

19. The method of claim 1, wherein the ovarian tissue sample is stained by hematoxylin and eosin, immunohistochemistry, and/or immunofluorescence.

20. The method of claim 1, wherein the subject is a human subject.

* * * * *